US009315872B2

(12) United States Patent
Franchino et al.

(10) Patent No.: US 9,315,872 B2
(45) Date of Patent: Apr. 19, 2016

(54) MAJOR QTLS CONFERRING RESISTANCE OF CORN TO FIJIVIRUS

(71) Applicants: E I DU PONT DE NEMOURS AND COMPANY, Wilmington, DE (US); PIONEER HI BRED INTERNATIONAL INC, Johnston, IA (US)

(72) Inventors: Jose Alejandro Franchino, Pergamino (AR); Enrique Domingo Kreff, Pergamino (AR); Stanley Luck, Wilmington, DE (US); Teresita Martin, Pergamino (AR); Ana Maria Procopiuk, Pergamino (AR); Guoping Shu, Shenzhen (CN); Adriana Tomas, Newark (DE)

(73) Assignees: PIONEER HI BRED INTERNATIONAL INC., Johnston, IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/487,236

(22) Filed: Sep. 16, 2014

(65) Prior Publication Data
US 2015/0143575 A1 May 21, 2015

Related U.S. Application Data

(63) Continuation of application No. 14/035,009, filed on Sep. 24, 2013, now Pat. No. 8,841,510, which is a continuation-in-part of application No. 12/740,140, filed as application No. PCT/US2008/012327 on Oct. 31, 2008, now abandoned.

(60) Provisional application No. 61/001,455, filed on Nov. 1, 2007.

(51) Int. Cl.
*A01H 1/02* (2006.01)
*C12Q 1/68* (2006.01)
*C12Q 1/70* (2006.01)
*C12N 15/82* (2006.01)

(52) U.S. Cl.
CPC .............. *C12Q 1/6895* (2013.01); *A01H 1/02* (2013.01); *C12N 15/8283* (2013.01); *C12Q 1/701* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 6,872,874 | B1 | 3/2005 | Colbert et al. |
| 2005/0250938 | A1 | 11/2005 | Kriz et al. |
| 2006/0041954 | A1 | 2/2006 | Lu et al. |
| 2007/0192909 | A1 | 8/2007 | Salmeron et al. |

FOREIGN PATENT DOCUMENTS

AR P20030100125 1/2005

OTHER PUBLICATIONS

Collard et al. (Euphytica, (2005) 142: pp. 169-196).*
Mohan et al., Molecular Breeding, 1997, vol. 3, pp. 87-103.
Marzachi et all, (Seminars in Virology), 1995, vol. 6, pp. 103-108.
Alvarez, M., et al., "Marcadores moleculares y tolerancia a Mal de Rio IV (MRCV) en maiz (Zea mays L.) analisis preliminar", VII Congreso Nacional de Maiz, Nov. 7-9, 2001.
Citron, B.A., et al., "Sequences of the Saccharomyces Gal region and its transcription in vivo", J. Bacteriol., vol. 158, pp. 269-278 (1984).
Di Renzo, M.A., et al., "Microsatellite markers linked to QTL for resistance to Mal de Rio Cuarto disease in Zea mays L", J. Agri. Science, vol. 142, pp. 289-295 (2004).
Distephano, et al., "Sequence analysis of genome segments S4 and S8 of Mal de Rio Cuarto virus (MRCV) . . . ", Arch. Virol. vol. 147, pp. 1699-1709 (2002).
Kreff, E.D., "Genetica de la tolerancia al Mal de Rio Cuarto en maiz . . . ", Tesis para optar al grado de Magister Scientiae, Universidad Nacional de Rosario-INTA, p. 84 (2004).
Mayor, P.J., "Identification de marcadores microsatellites ligados . . . ", Tesis para optar al grado de Magister Scientiae, Universidad Nacional de Rosario-INTA, p. 87 (2004).
Remington, D.L., et al., "Structure of linkage disequilibrium and phenotypic associations in the maize genome", Proc. Natl. Acad. Sci., vol. 98, pp. 11479-11484 (2001).
Rodriguez, P.E., et al., "Wheat: A new natural host for the Mal de Rio Cuarto virus in the endemic disease area, Rio Cuarto . . . ", Plant Dis., vol. 82, pp. 149-152 (1998).
Sala, C., et al., "Combinacion de alelos de tres loci de rasgos cuantitativos . . . ", Boletin de patentes No. 238, p. 23, http://www.inpi.gov.ar/pdf/patentes/p120105.pdf (2005).
International Search Report and Written Opinion in international application No. PCT/US08/12327, mailed Feb. 3, 2009.

* cited by examiner

*Primary Examiner* — David T Fox
*Assistant Examiner* — Jared Shapiro

(57) ABSTRACT

The invention relates to methods and compositions for identifying maize plants that have newly conferred resistance or enhanced resistance to, or are susceptible to, a *Fijivirus*, particularly Mal de Río Cuarto Virus (MRCV) and/or Maize Rough Dwarf Virus (MRDV). The methods use molecular genetic markers to identify, select and/or construct resistant plants or identify and counter-select susceptible plants. Maize plants that display newly conferred resistance or enhanced resistance to a *Fijivirus* that are generated by the methods of the invention are also a feature of the invention.

6 Claims, 17 Drawing Sheets

FIG. 13A

```
SEQ ID NO:211   CATCGCCGTTCCTTCCTGGCGATCGCGCCTCCTAGCTATCCGGTGTGCCAAAGACACGGC   60
SEQ ID NO:212   CATCGTCGTTCCTTCCTGGCGATCGCCGCCTCCTAGCTATCCGGTGTGCCAAAGACACGGC   60
                ***** ***************** ************************************

SEQ ID NO:211   TAGTGGTAGGCTCGAGCGAGACGAGCTCTTGCTGAAGAGAGAATGAATGTAACGTTACCG   120
SEQ ID NO:212   TAGTGGTAGGCTCGAGTGAGACGAGCTCTTGCTGAAGAGAGAATGAATGTAACGTTACCG   120
                **************** *******************************************

SEQ ID NO:211   CCTCCTGGTCGTAGG---------------------------------------GGTGT   140
SEQ ID NO:212   CCTCCTGGTCGTAGGTGTAATAAGTTGTAACGCGAGCGTCGTTAGCAAGCACAAGGGTTT   180
                ***************                                       ***  *

SEQ ID NO:211   GTGTATGTGAGGACAAGAGGAGCGAGAGGAGAGCCAGAGCCGCAGAGCTGCGGGAAGGAG   200
SEQ ID NO:212   GTGTATGTGAGGACAAGAGGAGCGAGAGGAGAGCCAGAGCCGCAGAGCGTGCGGGAAGGAG   240
                ***********************************************  ***********

SEQ ID NO:211   GGCCGTCATGTGTCCGAGGAATCTAGGACCGACCACTTCTTGGCA----------GCTGGGGCCGGGGGT   253
SEQ ID NO:212   GGCGTCATGTGTCCGAGGAATCTAGGAATCTAGGACGACTTAGGACGACTTGTTGGCACTTGGCCAGCTGGGCCACTTGGCCGGGGGT   300
                *** ***************************  **** *** * **          ***  ** * * * *

SEQ ID NO:211   GCCGTGCGAGAATGCAAGCAAGAACAAAAGGCGACGGGCATCTCGGCTCGGCCACGCCTTCCAA   313
SEQ ID NO:212   GCCGTGCGAGAATGCAAGCAAGAACAAAAGCCGACGGGCAT---------CACGCCTCCAG   350
                ******************************  ********         ******* ***
```

FIG. 13B

```
SEQ ID NO:211   GTCCATCCCGGGGCGCGCACTCGGCGCGGCTCATTGAGGCCCAGGCGCCAAGACGGCGG   373
SEQ ID NO:212   GTCCAACCCGGGGGCGCCCCACTCGGCGCCCCGTCATTGAGGCCCAAGGCCAAGACGGCGG  410
                ***** ******** ** ****** ***** * *******************  *******

SEQ ID NO:211   CTCCACCCAGTCACAATTGGCAACAAGAAGCACACGGCTGGGACGCGTCGAAT         433
SEQ ID NO:212   CTCCACCCACATCACAATTGGCAACAAGAAGCACACGGCGGCTGGGACGCGGTCGGAT    470
                ********* ************************************  ********

SEQ ID NO:211   TTTTCACCAGAAAATACCCTCTGATCTCTGGCGTTTCGT--------GAACG          476
SEQ ID NO:212   TTTTCACCAGAAAATACCCTCTGATCCGTTGGCGTTCGTCAGATGCTACGTGAACG       530
                ************************** **********        ****

SEQ ID NO:211   GCAAAACCTAGCAGCAGCAGCAGCATTC---------------------TTTGCGTG   504
SEQ ID NO:212   GCAAAACCTAGCAGCAGCAGCAGCACTCAGACTGGACACAAGAGGGAAATCTTTGCGTG    590
                ************************* *

SEQ ID NO:211   -----------CACGGGTCGGATGAC-----ATATCATATCCTCGTGCCGGAGCGGACT   546
SEQ ID NO:212   GGAACCCAAACTGAACGACGAGTCGGATGACATATCGACATATCCTCGTCCGGACCGGACT  650
                           *** *   ***** * *     *   ***  *

SEQ ID NO:211   CTACGGCGAGTCCAGTCGCTGTGGCTGGGAATATTCCGGCGGAAGCGCGGGAGCGGACGG  606
SEQ ID NO:212   CGACCGCGCAGTCCAGTCGCTGCCGCAATATTCCGGCCGGAAGCCGGGAGCGGACGG     710
                *  * *** ************  *   ***********  ***** ***** *****
```

FIG. 13C

```
SEQ ID NO:211   CGGCCTCCGGTGGGACCCGGGGCGAAGATGTGGGCTGATGT   666
SEQ ID NO:212   CGGCCTCCGGTGGGACCCGGGGCGAAGATGTGCGGCTGATGT   770
                ****************************************

SEQ ID NO:211   CGCTGGAATATTCGCGGCCAGCTGTGGCTGCCGTGCGACCTG   726
SEQ ID NO:212   CGCTGGAATATTCGCGGCCAGCTGTGGCTGCCGTGCGACCTG   830
                ****************************************

SEQ ID NO:211   GCAGTGGCCACCGCTCTCCTCTGCTG----------------   786
SEQ ID NO:212   GCAGTGGCCACCGCCTCC------------------------   850
                **************  **

SEQ ID NO:211   CAACATCCATCACAGAGATTGGCGGACGGATTAGCCGAGACTA   846
SEQ ID NO:212   -----ATCACAGAGATTCCGCCGACGATTAGCCGAGACTA   902
                     ******* *** ** *  ******************

SEQ ID NO:211   TAAAACCGTACGTGCAAAATGCTAAGGGGCCGTT   880
SEQ ID NO:212   TAAAACCGTGCCGTGCAGAATGCTAAGGGCCGGTT   936
                ******** * ***** ************ * **
```

MAJOR QTLS CONFERRING RESISTANCE OF CORN TO FIJIVIRUS

CROSS-REFERENCE TO RELATED APPLICATION

This application is a Continuation of U.S. application Ser. No. 14/035,009, filed Sep. 24, 2013, now U.S. Pat. No. 8,841, 510, which is a Continuation-in-part of U.S. application Ser. No. 12/740,140, filed Oct. 31, 2008, which is a 371 of International Application No. PCT/US08/12327, filed Oct. 31, 2008, which claims the benefit of U.S. Provisional Application No. 61/001,455, filed Nov. 1, 2007, which is incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20140910_BB1966USCNT2_SeqLst.txt created on Sep. 10, 2014 and having a size of 174 kilobytes and is filed concurrently with the specification. The sequence listing contained in this ASCII formatted document is part of the specification and is herein incorporated by reference in its entirety.

FIELD OF THE INVENTION

The present disclosure relates to compositions and methods useful in creating or enhancing Fijivirus, particularly Mal de Río Cuarto Virus and/or Maize Rough Dwarf Virus, resistance in plants. Additionally, the invention relates to plants that have been genetically transformed with the compositions of the invention.

BACKGROUND OF THE INVENTION

The disease caused by Mal de Río Cuarto Virus (MRCV) is a major corn disease in Argentina, accounting for yield losses of greater than 70% in years of severe outbreak (Rodriguez P E et al. (1998) *Plant Dis.* 82:149-52). The disease is a member of Serogroup 2 of *Fijivirus*, which includes other viruses such as maize rough dwarf virus, rice black streaked dwarf virus, and pangola stunt virus (Uyeda I & Milne R G (1995) *Semin. Virol.* 6:85-88). The main vector for MRCV is *Delphacodes kuscheli*, but other *Delphacodes* species, such as *D. haywardi* and *D. tigrinus*, and *Toya propinqua* have been shown to carry the virus. The virus does not appear to be transmitted to progeny via seeds. Distéfano et al., Arch. Virol. 147:1699-1709 (2002), analyzed the MRCV sequence and proposed that it is a new *Fijivirus* species related to MRDV (Maize Rough Dwarf Virus). MRDV is found in several European countries (e.g., the Czech Republic, France, Italy, Norway, Spain, Sweden) and in China, while MRCV has been also detected in Uruguay (Ornaghi J. A., Beviacqua J. E., Aguirrezabala D. A., March G. J. and Lenardón S. L. 1999. Detection of Mal de Río Cuarto virus in Uruguay. Fitopatologia Brasileira 24: 471).

MRCV infection causes abnormal maize development and significantly reduces crop yields. The susceptible phenotype includes stunting, shortening of internodes, multiple ears with scattered grain, deformed tassel with no anthers, presence of small enations in the back of the leaves, reduced roots, cut and reduced leaves. Plants symptoms depend on phenological stage of the plant, plant genotype, and environment (Lenardón et al., "Virus del Mal de Río Cuarto en maíz", in Proyecto de Investigaciones en Fitovirologia (Lenardón ed.), 2:10 (1999). Most severe symptoms occur when infected at the coleoptile—first leaf stage.

In the severe MRCV outbreak of 1996-1997, over 300,000 hectares of maize in Argentina were affected, resulting in losses totaling approximately $120 million. Increased populations of *Delphacodes kuscheli* in 2006 apparently led to a reoccurrence of the viral disease in Argentinean corn plants, which significantly affected the 2007 harvesting. Susceptible genotypes were strongly affected by MRCV at the endemic region (Córdoba Province) and moderately affected at other maize regions.

The development of molecular genetic markers has facilitated mapping and selection of agriculturally important traits in maize. Markers tightly linked to disease resistant genes are an asset in the rapid identification of resistant maize lines on the basis of genotype by the use of marker assisted selection (MAS). Introgressing disease resistance genes into a desired cultivar would also be facilitated by using suitable DNA markers.

SUMMARY OF THE INVENTION

Compositions and methods for identifying maize plants or germplasm with newly conferred or enhanced resistance to *fijivirus* are provided. Methods of making maize plants or germplasm that are resistant to *fijivirus*, e.g., through introgression of desired resistance marker alleles and/or by transgenic production methods, as well as plants and germplasm made by these methods, are also provided. Systems and kits for selecting resistant plants and germplasm are also a feature of the invention.

In some aspects, the invention provides methods for identifying a first maize plant or germplasm (e.g., a line or variety) that has newly conferred resistance, enhanced resistance, or susceptibility to MRCV. In the methods, at least one allele of one or more marker locus (e.g., a plurality of marker loci) that is associated with the newly conferred resistance, enhanced resistance, or susceptibility are detected in the first maize plant or germplasm. The marker loci can be selected from the loci provided in Tables 1 and 2, including MZA625, MZA16656, MZA15451, MZA15490, MZA2038, MZA11826, and MZA9105, as well as any other marker that is linked to these QTL markers (e.g., within about 10 cM of these loci). Tables 1 and 2 show maize markers demonstrating linkage disequilibrium with the MRCV resistance phenotype as determined by association mapping analysis and QTL interval mapping (including single marker regression analysis) methods. The table indicates the genomic-SSR or EST-SSR marker type (all simple sequence repeats) or SNP or MZA markers, the chromosome on which the marker is located and its approximate genetic map position relative to other known markers, given in cM, with position zero being the first (most distal) marker on the chromosome. Also shown are the maize populations used in the analysis and the statistical probability of random segregation of the marker and the resistance/susceptibility phenotype given as an adjusted probability taking into account the variability and false positives of multiple tests. Probability values from single marker regression are also shown.

The invention also provides chromosomal QTL intervals that correlate with MRCV. These intervals are located on linkage group 2. Any marker located within these intervals also finds use as a marker for MRCV resistance and is also a feature of the invention. These intervals include:

(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

A plurality of marker loci can be selected in the same plant. Which QTL markers are selected in combination is not particularly limited. The QTL markers used in combinations can be any of the markers listed in Tables 1 and 2, any other marker that is linked to the markers in Tables 1 and 2 (e.g., the linked markers determined from the MaizeGDB resource), or any marker within the QTL intervals described herein.

TABLE 1

| Marker | Relative Map Position (cM). PHD v1.4 | Method of Identification | Gene Pool Analyzed/ Mapping Population | Adjusted Probability | | | | |
|---|---|---|---|---|---|---|---|---|
| | | | | Structured association | | | Not structured association | Association |
| | | | | Association analysis Myriad Argentine inbreds | Association analysis I Myriad SS inbreds | Association analysis II Myriad SS inbreds | Association analyisis set 1 (SS) inbreds | analysis SNPs at MRCV1. Argentine inbreds |
| MZA7588 | 63.17 | Association analysis, identity by descent | Broad Pioneer germplasm | 0.12 | 0.341 | 0.742 | 0.000676917 | |
| MZA8381 | 63.47 | Association analysis, identity by descent | Broad Pioneer germplasm | 0.002 | 0.0037 | 0.0044 | 0.000198191 | less than 0.001 |
| MZA3105 | 63.55 | Association analysis, identity by descent | Broad Pioneer germplasm | 0.0412 | | | | 0.064 |
| MZA482 | 63.64 | Association analysis, identity by descent | Broad Pioneer germplasm | 0.551 | 0.0958 | 0.197 | 0.002172499 | |
| MZA16531 | 63.83 | Association analysis, identity by descent | Broad Pioneer germplasm | | 0.174 | 0.0282 | 0.055088894 | |
| MZA14553 | 64.1 | Association analysis, identity by descent | Broad Pioneer germplasm | | | | | |
| MZA4305 | 64.1 | Association analysis, identity by descent | Broad Pioneer germplasm | 0.644 | 0.0394 | 0.066 | 0.331615457 | |
| MZA625 | 64.1 | Association analysis, identity by descent, QTL mapping | Broad Pioneer germplasm | 0.0476 | 0.685 | 0.74 | 0.000136376 | |
| MZA625-30-A | 64.1 | Identity by descent, QTL mapping | Broad Pioneer germplasm | | | | | less than 0.001 |
| MZA625-29-A | 64.1 | Identity by descent, QTL mapping | Broad Pioneer germplasm | | | | | less than 0.001 |
| MZA15451 | 65.3 | Association analysis, identity by descent | Broad Pioneer germplasm | 0.0105 | 0.0438 | 0.0612 | 0.51165696 | |
| MZA9105 | 65.4 | Association analysis, identity by descent | Broad Pioneer germplasm | 0.0226 | 0.436 | 0.453 | 0.003621576 | |
| MZA9105-8-A | 65.4 | Identity by descent, QTL mapping | Broad Pioneer germplasm | | | | | less than 0.001 |
| MZA9105-6-A | 65.4 | Identity by descent, QTL mapping | Broad Pioneer germplasm | | | | | 0.066 |
| MZA11826 | 66.0 | Association analysis, identity by descent, QTL mapping | Broad Pioneer germplasm | 0.0201 | 0.16 | 0.486 | 1.79182E−06 | |
| MZA11826-803-A | 66.0 | Identity by descent, QTL mapping | Broad Pioneer germplasm | | | | | 0.014 |
| MZA11826-801-A | 66.0 | Identity by descent, QTL mapping | Broad Pioneer germplasm | | | | | 0.034 |
| MZA11826-27-A | 66.0 | Identity by descent, QTL mapping | Broad Pioneer germplasm | | | | | 0.04 |

TABLE 1-continued

| Marker | Relative Map Position (cM). PHD v1.4 | Method of Identification | Gene Pool Analyzed/ Mapping Population | Adjusted Probability | | | | |
|---|---|---|---|---|---|---|---|---|
| | | | | Structured association | | | | Not structured association Association |
| | | | | Association analysis Myriad Argentine inbreds | Association analysis I Myriad SS inbreds | Association analysis II Myriad SS inbreds | Association analyisis set 1 (SS) inbreds | analysis SNPs at MRCV1. Argentine inbreds |
| MZA15490 | 66.0 | Association analysis, identity by descent | Broad Pioneer germplasm | 0.0079 | 0.186 | 0.523 | 0.4067326 | |
| MZA15490-801-A | 66.0 | Identity by descent, QTL mapping | Broad Pioneer germplasm | | | | | less than 0.001 |
| MZA15490-138-A | 66.0 | Identity by descent, QTL mapping | Broad Pioneer germplasm | | | | | less than 0.001 |
| MZA15490-137-A | 66.0 | Identity by descent, QTL mapping | Broad Pioneer germplasm | | | | | less than 0.001 |
| MZA16656 | 66.0 | Association analysis, identity by descent, QTL mapping | Broad Pioneer germplasm | 0.000194 | 0.452 | 0.474 | 0.011514162 | |
| MZA16656-8-A | 66.0 | Identity by descent, QTL mapping | Broad Pioneer germplasm | | | | | less than 0.001 |
| MZA16656-19-A | 66.0 | Identity by descent, QTL mapping | Broad Pioneer germplasm | | | | | less than 0.001 |
| MZA2038 | 66.0 | Association analysis, identity by descent | Broad Pioneer germplasm | 0.0035 | 0.104 | 0.391 | 2.66345E−06 | |
| MZA2038-76-A | 66.0 | Identity by descent, QTL mapping | Broad Pioneer germplasm | | | | | 0.161 |
| MZA2038-71-A | 66.0 | Identity by descent, QTL mapping | Broad Pioneer germplasm | | | | | 0.298 |
| MZA2803 | 66.0 | Association analysis, identity by descent | Broad Pioneer germplasm | 0.404 | 0.0728 | 0.0916 | 0.116318398 | |
| MZA18224 | 68.8 | Association analysis, identity by descent, QTL mapping | Broad Pioneer germplasm | 0.000066 | 0.039 | 0.041 | 0.003921924 | |
| MZA18224-801-A | 68.8 | Identity by descent, QTL mapping | Broad Pioneer germplasm | | | | | 0.052 |
| MZA2349 | 68.8 | Association analysis, identity by descent | Broad Pioneer germplasm | 0.0498 | 0.238 | 0.185 | 0.001262359 | 0.277 |
| MZA564 | 68.8 | Association analysis, identity by descent | Broad Pioneer germplasm | 0.756 | 0.167 | 0.0524 | 0.000254878 | |
| MZA11066 | 70.7 | Association analysis, identity by descent | Broad Pioneer germplasm | 0.617 | 0.819 | 0.786 | 0.330400979 | |
| MZA18180 | 71.3 | Association analysis, identity by descent | Broad Pioneer germplasm | 0.0272 | 0.0201 | 0.0204 | 0.091180064 | 0.005 |
| MZA8442 | 71.4 | Association analysis, identity by descent | Broad Pioneer germplasm | 0.000234 | 0.0358 | 0.0402 | 0.000598737 | |
| MZA15563 | 71.5 | Association analysis, identity by descent | Broad Pioneer germplasm | 0.0754 | 0.0079 | 0.0079 | 0.114427854 | 0.524 |
| MZA18036 | 71.8 | Association analysis, identity by descent | Broad Pioneer germplasm | 0.000138 | 0.112 | 0.0474 | 0.008370189 | 0.007 |
| MZA15264 | 71.9 | Association analysis, identity by descent | Broad Pioneer germplasm | 0.794 | 0.608 | 0.664 | 0.207135606 | |
| MZA10384 | 72.2 | Association analysis, identity by descent | Broad Pioneer germplasm | 0.706 | 0.133 | 0.0442 | 0.001530899 | |

TABLE 1-continued

| Marker | Relative Map Position (cM). PHD v1.4 | Method of Identification | Gene Pool Analyzed/ Mapping Population | Adjusted Probability | | | | |
|---|---|---|---|---|---|---|---|---|
| | | | | Structured association | | | Not structured association | |
| | | | | Association analysis Myriad Argentine inbreds | Association analysis I Myriad SS inbreds | Association analysis II Myriad SS inbreds | Association analyisis set 1 (SS) inbreds | Association analysis SNPs at MRCV1. Argentine inbreds |
| MZA12874 | 72.3 | Association analysis, identity by descent | Broad Pioneer germplasm | 0.829 | 0.141 | 0.215 | 0.009463312 | 0.059 |
| MZA12454 | 72.4 | Association analysis, identity by descent | Broad Pioneer germplasm | 0.000064 | 0.126 | 0.088 | 5.75703E−05 | |
| MZA8926 | 72.9 | Association analysis, identity by descent | Broad Pioneer germplasm | 0.0089 | | | 0.641842316 | |
| MZA5057 | 73.0 | Association analysis, identity by descent | Broad Pioneer germplasm | 4.5231E−05 | 0.0246 | 0.0098 | 0.050959299 | less than 0.001 |
| BNLG1327 | 66.9 | Link between Pioneer and public maps | Extrapolation by map position | | | | | |
| BNLG1458B | | Link between Pioneer and public maps | Extrapolation by map position | | | | | |
| UMC1261 | 70.0 | Link between Pioneer and public maps | Extrapolation by map position | | | | | |
| UMC1262 | 70.2 | Link between Pioneer and public maps | Extrapolation by map position | | | | | |

TABLE 2

| | QTL mapping | | | | |
|---|---|---|---|---|---|
| Marker | PH7WTxPH3DT mapping pop | PH9TJxPH890 mapping pop | PH7WTxPH3DT BC3F3 by MAS | MEPS populations (adjusted probability) | Notes |
| MZA625 MZA15451 MZA9105 MZA11826 MZA15490 MZA16656 MZA2038 MZA2803 | QTL position extrapolated from LOD score peak. >6 Position 65.8; flanking markers umc1756-umc1518 | QTL position extrapolated from LOD score peak. >20; Position 65.99-68.8; flanking markers MZA625-MZA18224 | QTL position corresponding to the highest associated markers. LOD score peak: >10 | less than 0.05 | QTL position by using the information across different association analysis, QTL mapping studies and Identity by descent information. |
| BNLG1327 BNLG1458B UMC1261 UMC1262 | | | | | Markers to extrapolate the QTL position to public maps |

The markers that are linked to the QTL markers of Tables 1 and 2 can be closely linked, for example, within about 10 cM from the Tables 1 and 2 QTL markers. In some embodiments, the linked locus displays a genetic recombination distance of 9 centiMorgans, 8, 7, 6, 5, 4, 3, 2, 1, 0.75, 0.5 or 0.25, or less from the QTL marker.

In some embodiments, preferred QTL markers are selected from MZA625, MZA16656, MZA15451, MZA15490, MZA2038, MZA11826, and MZA9105. Most preferred are QTL markers selected from MZA15490 and MZA2038.

In some embodiments, the germplasm is a maize line or variety. In some aspects, the newly conferred resistance, enhanced resistance, or susceptibility of a maize plant to MRCV can be quantitated using any suitable means, for example 1 to 9 scale (MRCV score), where 1, represents a highly susceptible genotype and 9, a completely resistant genotype; 4 represents a genotype with the minimum level of resistance to generate a commercial hybrid.

A second way of evaluating MRCV resistance is by evaluating the percentage of highly susceptible plants on a specific genotype. For example, a field experiment where the genotypes are arranged on a randomly completely block design and each experimental unit is represented by a field row of 4 meters and approximately 20 plants are planted on each row. The MRCV enhanced resistance is evaluated by observing each experimental unit and assigning a field score (1 to 9 scale). At the same time, the percentage of highly susceptible plants on each experimental unit is assayed.

Any of a variety of techniques can be used to identify a marker allele. It is not intended that the method of allele detection be limited in any way. Methods for allele detection typically include molecular identification methods such as amplification and detection of the marker amplicon. For example, an allelic form of a polymorphic simple sequence repeat (SSR) or of a single nucleotide polymorphism (SNP) can be detected, e.g., by an amplification based technology. In these and other amplification based detection methods, the marker locus or a portion of the marker locus is amplified (e.g., via PCR, LCR or transcription using a nucleic acid isolated from a maize plant of interest as a template), and the resulting amplified marker amplicon is detected. In one example of such an approach, an amplification primer or amplification primer pair is admixed with genomic nucleic acid isolated from the first maize plant or germplasm, wherein the primer or primer pair is complementary or partially complementary to at least a portion of the marker locus, and is capable of initiating DNA polymerization by a DNA polymerase using the maize genomic nucleic acid as a template. The primer or primer pair (e.g., a primer pair provided in Table 3) is extended in a DNA polymerization reaction having a DNA polymerase and a template genomic nucleic acid to generate at least one amplicon.

MRCV resistance phenotype (directly or by extrapolation from the genetic map). Table 3 provides the sequences of the left and right PCR primers used in the SSR marker locus genotyping analysis. Also shown is the pigtail sequence used on the 5' end of the right primer, and the number of nucleotides in the tandem repeating element in the SSR.

In any case, data representing the detected allele(s) can be transmitted (e.g., electronically or via infrared, wireless or optical transmission) to a computer or computer readable medium for analysis or storage. In some embodiments, plant RNA is the template for the amplification reaction. In other embodiments, plant genomic DNA is the template for the amplification reaction. In some embodiments, the QTL marker is a SNP type marker, and the detected allele is a SNP allele (see, e.g., Table 4 (showing SNP markers at QTL position and the specific PH7WT (=630=PH14J) and PH9TJ haplotypes)), and the method of detection is allele specific hybridization (ASH).

TABLE 3

| Marker Name | Left Primer Sequence | Right Primer Sequence | Repeat | Also Known As (AKA) |
|---|---|---|---|---|
| BNLG1327 | SEQ ID NO: 49 | SEQ ID NO: 50 | CT(25) | bmc1327, A4615G09, p-bnlg1327, A4615G10, bnlg1327, LGI456705 |
| BNLG1458B | SEQ ID NO: 51 | SEQ ID NO: 52 | — | bnlg1458, p-bnlg1458, A4651C06, bmc1458, A4651C05 |
| UMC1261 | SEQ ID NO: 53 | SEQ ID NO: 54 | (TG)8 | AI987278 |
| UMC1262 | SEQ ID NO: 55 | SEQ ID NO: 56 | (GTC)4 | AI987278 |

Table 3 lists genomic and SSR markers, including those markers that demonstrated linkage disequilibrium with the

TABLE 4

| QTL | | | | | MRCV1 | | | |
|---|---|---|---|---|---|---|---|---|
| STARS | PASS | PASS | PASS | PASS | PASS | PASS | PASS | PASS |
| Ctg Pos | 745 | 745 | 897 | 897 | | | | 897 |
| Ctg | 203 | 203 | 203 | 203 | | | | 203 |
| PHD | 64.1 | 64.1 | 66.0 | 66.0 | 66.0 | 66.0 | 66.0 | 66.0 |
| Chromosome | 2 | 2 | 2 | 2 | 2 | 2 | 2 | 2 |
| Sample Name | MZA-625-29-A | MZA625-30-A | MZA16656-8-A | MZA16656-19-A | MZA15490-137-A | MZA15490-138-A | MZA15490-801-A | MZA2038-71-A |
| PH7WT | C | T | C | G | C | G | G | A |
| PH9TJ | C | T | T | A | A | C | C | T |

| QTL | | | | MRCV1 | | | |
|---|---|---|---|---|---|---|---|
| STARS | PASS | PASS | PASS | PASS | PASS | PASS | PASS |
| Ctg Pos | 930 | 930 | 930 | 930 | 930 | 1018 | 1018 |
| Ctg | 203 | 203 | 203 | 203 | 203 | 203 | 203 |
| PHD | 66.0 | 66.0 | 66.0 | 66.0 | 66.0 | 65.4 | 65.4 |
| Chromosome | 2 | 2 | 2 | 2 | 2 | 2 | 2 |
| Sample Name | MZA2038-76-A | C00081-01-A | MZA11826-27-A | MZA11826-801-A | MZA11826-803-A | MZA9105-6-A | MZA9105-8-A |
| PH7WT | T | P | C | A | C | G | A |
| PH9TJ | C | X | T | G | T | G | A |

In some embodiments, the allele that is detected is a favorable allele that positively correlates with newly conferred resistance or enhanced resistance. Alternatively, the allele that is detected can be an allele that correlates with disease susceptibility or reduced disease resistance, and that allele is counter-selected. For example, alleles that can be selected for (favorable alleles, e.g., PH7WT and PH9TJ (see Table 5)) or against (unfavorable alleles, e.g., PH3DT, PH890, and PH6KW (see Table 5)).

Similarly, in other embodiments, if an allele is correlated with newly conferred resistance or enhanced resistance to MRCV, the method can include introgressing the allele into a second maize plant or germplasm to produce an introgressed maize plant or germplasm. In some embodiments, the second maize plant or germplasm will typically display reduced resistance to MRCV as compared to the first maize plant or germplasm, while the introgressed maize plant or germplasm will display an increased resistance to MRCV as compared to

TABLE 5

| QTL | | | | | MRCV1 | | | |
|---|---|---|---|---|---|---|---|---|
| STARS | PASS | PASS | PASS | PASS | PASS | PASS | PASS | PASS |
| Ctg Pos | 745 | 745 | 897 | 897 | | | | 897 |
| Ctg | 203 | 203 | 203 | 203 | | | | 203 |
| PHD | 64.1 | 64.1 | 66.0 | 66.0 | 66.0 | 66.0 | 66.0 | 66.0 |
| Chromosome | 2 | 2 | 2 | 2 | 2 | 2 | 2 | 2 |
| Sample Name | MRCV1 | MZA-625-29-A | MZA625-30-A | MZA16656-8-A | MZA16656-19-A | MZA15490-137-A | MZA15490-138-A | MZA15490-801-A | MZA2038-71-A |
| PH7WT | Positive Effect | C | T | C | G | C | G | G | A |
| PH9TJ | Positive Effect | C | T | T | A | A | C | C | T |
| PH3DT | Negative Effect | T | C | T | A | A | C | C | T |
| PH890 | Negative Effect | T | C | C | A | A | C | C | T |
| PH6KW | Negative Effect | T | C | T | A | A | C | C | A |

| QTL | | | | | MRCV1 | | | |
|---|---|---|---|---|---|---|---|---|
| STARS | PASS | PASS | PASS | PASS | PASS | PASS | PASS |
| Ctg Pos | 930 | 930 | 930 | 930 | 930 | 1018 | 1018 |
| Ctg | 203 | 203 | 203 | 203 | 203 | 203 | 203 |
| PHD | 66.0 | 66.0 | 66.0 | 66.0 | 66.0 | 65.4 | 65.4 |
| Chromosome | 2 | 2 | 2 | 2 | 2 | 2 | 2 |
| Sample Name | MRCV1 | MZA2038-76-A | C00081-01-A | MZA11826-27-A | MZA11826-801-A | MZA11826-803-A | MZA9105-6-A | MZA9105-8-A |
| PH7WT | Positive Effect | T | P | C | A | C | G | A |
| PH9TJ | Positive Effect | C | X | T | G | T | G | A |
| PH3DT | Negative Effect | C | X | T | G | T | A | G |
| PH890 | Negative Effect | C | X | T | G | T | A | G |
| PH6KW | Negative Effect | T | P | C | A | C | G | A |

In the case where more than one marker is selected, an allele is selected for each of the markers; thus, two or more alleles are selected. In some embodiments, it can be the case that a marker locus will have more than one advantageous allele, and in that case, either allele can be selected.

It will be appreciated that the ability to identify QTL marker loci that correlate with newly conferred resistance, enhanced resistance, or susceptibility to MRCV provides a method for selecting plants that have favorable marker loci as well. That is, any plant that is identified as comprising a desired marker locus (e.g., a marker allele that positively correlates with resistance) can be selected for, while plants that lack the locus, or that have a locus that negatively correlates with resistance, can be selected against. Thus, in one method, subsequent to identification of a marker locus, the methods include selecting (e.g., isolating) the first maize plant or germplasm, or selecting a progeny of the first plant or germplasm. In some embodiments, the resulting selected first maize plant or germplasm can be crossed with a second maize plant or germplasm (e.g., an elite or exotic maize, depending on characteristics that are desired in the progeny).

the second maize plant or germplasm. An introgressed maize plant or germplasm produced by these methods is also a feature of the invention. (In some embodiments, the favorable introgressed allele is PH7WT/PH9TJ, see Table 5).

In other aspects, various mapping populations are used to determine the linked markers of the invention. In one embodiment, the mapping population used is the population derived from the cross PH7WTxPH3DT or PH9TJxPH890. In other embodiments, other populations can be used. In other aspects, various software is used in determining linked marker loci. For example, TASSEL, MapManager-QTX, and GeneFlow all find use with the invention. In some embodiments, such as when software is used in the linkage analysis, the detected allele information (i.e., the data) is electronically transmitted or electronically stored, for example, in a computer readable medium.

In other aspects, various mapping populations are used to determine the linked markers that find use in constructing the transgenic plant. In one embodiment, the mapping population used is the population derived from the cross PH7WTxPH3DT or PH9TJxPH890. In other embodiments, other populations can be used. In other aspects, various software is used in determining linked marker loci used to construct the transgenic plant. For example, TASSEL, MapManager-QTX, and GeneFlow all find use with the invention.

Systems for identifying a maize plant predicted to have newly conferred resistance or enhanced resistance to MRCV are also a feature of the invention. Typically, the systems include a set of marker primers and/or probes configured to detect at least one favorable allele of one or more marker locus associated with newly conferred resistance or enhanced resistance to MRCV, wherein the marker locus or loci are selected from: MZA7588, MZA8381, MZA3105, MZA482, MZA16531, MZA14553, MZA4305, MZA625, MZA15451, MZA9105, MZA11826, MZA15490, MZA16656, MZA2038, MZA2803, MZA18224, MZA2349, MZA564, MZA11066, MZA18180, MZA8442, MZA15563, MZA18036, MZA15264, MZA10384, MZA12874, MZA12454, MZA8926, and MZA5057, as well as any other marker that is linked (or in some embodiments, closely linked, e.g., demonstrating not more than 10% recombination frequency) to these QTL markers; and furthermore, any marker locus that is located within the chromosomal QTL intervals including:
  (i) MZA8381 and MZA18180;
  (ii) MZA4305 and MZA2803;
  (iii) MZA15490 and MZA2038;
  (iv) bnlg1458b and umc1261a;
  (v) bnlg1458b and umc1262a;
  (vi) bnlg1327 and umc1261a; and
  (viii) bnlg1327 and umc1262a.

In some embodiments, preferred QTL markers used are selected from MZA625, MZA16656, MZA15451, MZA15490, MZA2038, MZA11826, and MZA9105.

Where a system that performs marker detection or correlation is desired, the system can also include a detector that is configured to detect one or more signal outputs from the set of marker probes or primers, or amplicon thereof, thereby identifying the presence or absence of the allele and/or system instructions that correlate the presence or absence of the favorable allele with the predicted resistance. The precise configuration of the detector will depend on the type of label used to detect the marker allele. Typical embodiments include light detectors, radioactivity detectors, and the like. Detection of the light emission or other probe label is indicative of the presence or absence of a marker allele. Similarly, the precise form of the instructions can vary depending on the components of the system, e.g., they can be present as system software in one or more integrated unit of the system, or can be present in one or more computers or computer readable media operably coupled to the detector. In one typical embodiment, the system instructions include at least one look-up table that includes a correlation between the presence or absence of the favorable allele and predicted newly conferred resistance, enhanced resistance, or susceptibility.

In some embodiments, the system can be comprised of separate elements or can be integrated into a single unit for convenient detection of markers alleles and for performing marker-resistance trait correlations. In some embodiments, the system can also include a sample, for example, genomic DNA, amplified genomic DNA, cDNA, amplified cDNA, RNA, or amplified RNA from maize or from a selected maize plant tissue.

Kits are also a feature of the invention. For example, a kit can include appropriate primers or probes for detecting resistance-associated marker loci and instructions in using the primers or probes for detecting the marker loci and correlating the loci with predicted MRCV resistance. The kits can further include packaging materials for packaging the probes, primers or instructions, controls such as control amplification reactions that include probes, primers or template nucleic acids for amplifications, molecular size markers, or the like.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

The term "allele" refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., resistance to MRCV, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene or marker is located. Thus, for example, a "gene locus" is a specific chromosome location in the genome of a species where a specific gene can be found.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele", alternatively an "allele of a marker locus", is one of a plurality of polymorphic nucleotide sequences found at a marker locus in a population that is polymorphic for the marker locus. In some aspects, the present invention provides marker loci correlating with resistance to MRCV in maize. Each of the identified markers is expected to be in close physical and genetic proximity (resulting in physical and/or genetic linkage) to a genetic element, e.g., a QTL, that contributes to resistance.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

As used herein, the term "linkage" is used to describe the degree with which one marker locus is "associated with" another marker locus or some other locus (for example, a resistance locus).

As used herein, "linkage equilibrium" describes a situation where two markers independently segregate, i.e., sort among progeny randomly. Markers that show linkage equilibrium are considered unlinked (whether or not they lie on the same chromosome).

As used herein, "linkage disequilibrium" describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. A marker locus can be associated with (linked to) a trait, e.g., a marker locus can be associated with newly conferred resistance or enhanced resistance to a plant pathogen when the marker locus is in linkage disequilibrium with the resistance trait. The degree of linkage of a molecular marker to a phenotypic trait is measured, e.g., as a statistical probability of co-segregation of that molecular marker with the phenotype.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "disease caused by Mal de Río Cuarto Virus" or "disease caused by MRCV" refers to the plant disease caused by an infection of the plant with MRCV.

"Newly conferred resistance" or "enhanced resistance" in a maize plant to MRCV is an indication that the maize plant is less affected with respect to yield and/or survivability or other relevant agronomic measures, upon introduction of the causative agents of that disease. Resistance is a relative term, indicating that the infected plant produces better yield of maize than another, similarly treated, more susceptible plant. That is, the conditions cause a reduced decrease in maize survival and/or yield in a resistant maize plant, as compared to a susceptible maize plant.

One of skill will appreciate that maize plant resistance to MRCV varies widely, can represent a spectrum of more resistant or less resistant phenotypes, and can vary depending on the severity of the infection. However, by simple observation, one of skill can determine the relative resistance or susceptibility of different plants, plant lines or plant families to MRCV, and furthermore, will also recognize the phenotypic gradations of "resistant" (an exemplary scoring system is presented in Example 7 below). As used in the art, "resistance" is sometimes referred to as "general resistance", "rate-reducing resistance", or "partial resistance".

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite strain" is an agronomically superior line that has resulted from many cycles of breeding and selection for superior agronomic performance. Numerous elite lines are available and known to those of skill in the art of maize breeding. An "elite population" is an assortment of elite individuals or lines that can be used to represent the state of the art in terms of agronomically superior genotypes of a given crop species, such as maize. Similarly, an "elite germplasm" or elite strain of germplasm is an agronomically superior germplasm, typically derived from and/or capable of giving rise to a plant with superior agronomic performance, such as an existing or newly developed elite line of maize.

In contrast, an "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from its natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference.

The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection", "transformation", and "transduction".

As used herein, the term "vector" is used in reference to polynucleotide or other molecules that transfer nucleic acid segment(s) into a cell. The term "vehicle" is sometimes used interchangeably with "vector". A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Positional cloning" is a cloning procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as sub-cloning or sequencing can be used to identify and/or isolate subsequences of the clone that are located near the marker.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome segment.

The terms "phenotype", or "phenotypic trait" or "trait" refers to one or more trait of an organism. The phenotype can be observable to the naked eye, or by any other means of evaluation known in the art, e.g., microscopy, biochemical analysis, genomic analysis, or an assay for a particular disease resistance. In some cases, a phenotype is directly controlled by a single gene or genetic locus, i.e., a "single gene trait". In other cases, a phenotype is the result of several genes.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

A "set" of markers or probes refers to a collection or group of markers or probes, or the data derived therefrom, used for a common purpose, e.g., identifying maize plants with a desired trait (e.g., resistance to MRCV). Frequently, data corresponding to the markers or probes, or data derived from their use, is stored in an electronic medium. While each of the members of a set possess utility with respect to the specified purpose, individual markers selected from the set as well as subsets including some, but not all, of the markers are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer and the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

BRIEF DESCRIPTION OF THE DRAWINGS AND SEQUENCES

FIG. 1A shows a structured association analysis of an Argentinean group. Note: significant region (p-value: less than 0.00005) from position 65.99 to 85.84. X axis: Distance expressed on cM from the extreme of Chr 2. Y axis: probability value. FIG. 1B shows a structured association analysis for an SS group. Note: main significant marker at MRCV1, MZA1525 at position 54.62 and MZA11826 at position 65.99. X axis: Distance expressed on cM from the extreme of chromosome 2. Y axis: probability value. FIG. 1C shows a structured association analysis for another SS group. Note: The highest associated marker on the short arm of chromosome 2 was MZA12899 at position 53.83 (p=0.000298). X axis: Distance expressed on cM from the extreme of chromosome 2. Y axis: probability value.

FIG. 2 shows an interval mapping for the PH3DTxPH7WT cross. Chromosome 2, LOD score peak: position 65.89, 46% of phenotypic variation.

FIG. 3A shows a graphic of genotypes at the QTL region and averaged phenotypes (MRCVSC) for a group of recombinants of the high resolution mapping BC5F3 population from the cross PH3DTxPH7WT. The piece of the resistant parent into the susceptible background and the region of recombination is shown. The region includes the recombinants located between MZA1525-98-A and MZA10094-9-A. FIG. 3B shows a graphic of genotypes at the QTL region and averaged phenotypes (MRCVSC) for a group of recombinants of the high resolution mapping BC5F3 population from the cross PH3DTxPH7WT. The piece of the resistant parent into the susceptible background and the region of recombination is shown. The region includes the recombinants located between MZA15490 and MZA18224. It also includes three recombinants in the interval MZA11826 to MZA9105 genetically characterized. Phenotype is indicated by the circles at the right of the graphic (black circles: susceptible; white circles: resistant; diagonal lined circle: mix of resistant and susceptible; gray circles: unknown).

FIG. 4 shows an interval mapping for the PH3DTxPH7WT cross. Chromosome 2, LOD score peak: position 65.99 (MZA2038). MZA11826 and MZA9105 were not included in the analysis because there were not recombinants respects to MZA2038 in this specific population. Note: the genetic map was adapted to permit interval mapping at 65.99 position; markers MZA16656, MZA15490 and MZA2038 are highly linked on distances below 0.5 cM, but they were artificially positioned at distances of 0.5 cM for this specific analysis.

FIG. 5 shows an interval mapping analysis for the PH9TJxPH890 cross on specific QTL regions on Chr 2 and Chr 5. Chromosome 2, LOD score peak: position 65.99-68.8. There were no recombinants between the preferred markers and markers at position 68.8; thus, only MZA9105 was included as representative of preferred markers for this analysis.

Figure 8:
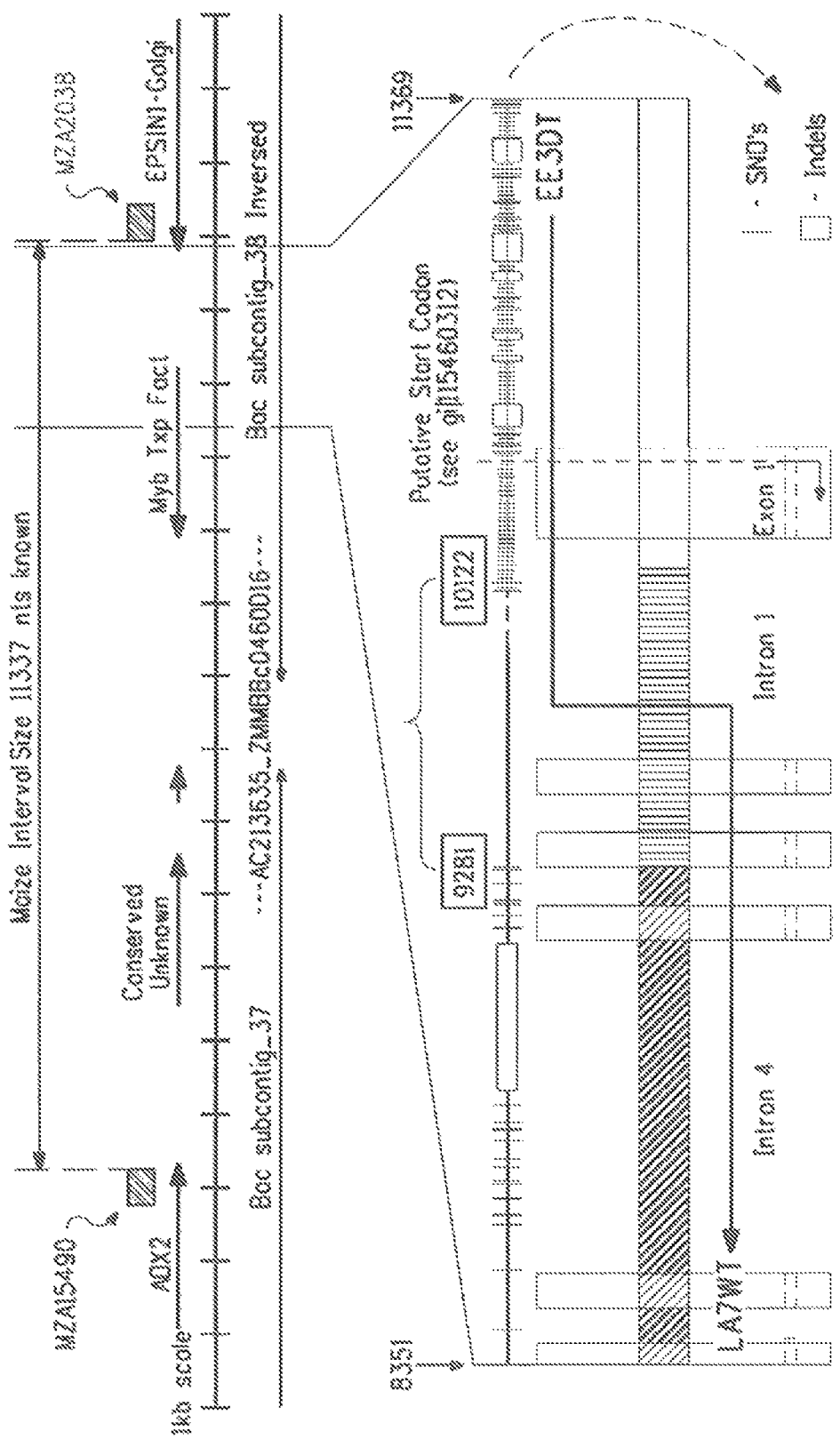

FIG. 8 shows a graphic description of a recombinant at the MZA15490 to MZA2038 interval. The point of recombination was located inside PCO644442, generating a quimeric gene from resistant (PH7WT) and susceptible (PH3DT) parents. The position of SNPs and indels is indicated in the sequenced region.

Figure 9:
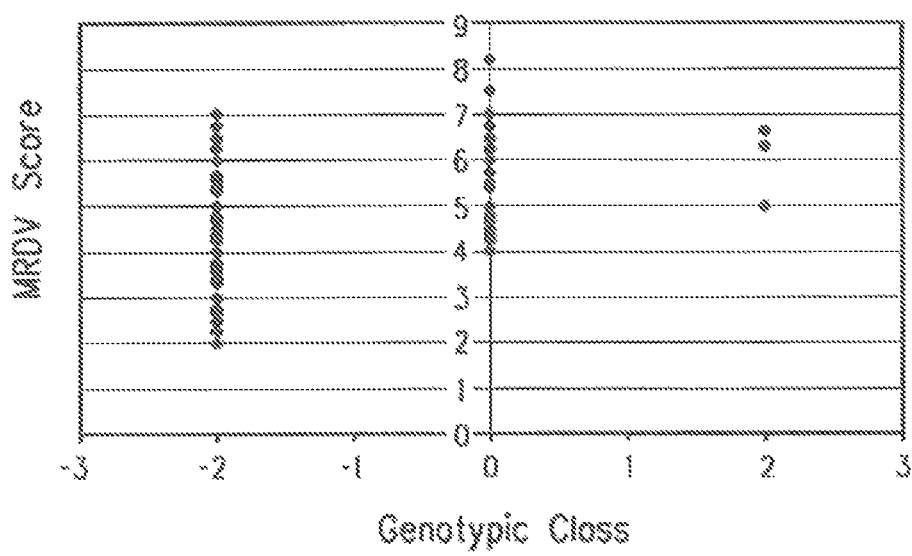

FIG. 9 shows the performance (MRDV score) of maize hybrids under MRDV infection across genotypic classes for the region of preferred markers. "-2", "0" and "2" in the X coordinate (genotypic class) represent the genotypic classes of susceptible haplotype, heterozygous haplotype and homozygous resistant haplotype, respectively.

Figure 10:
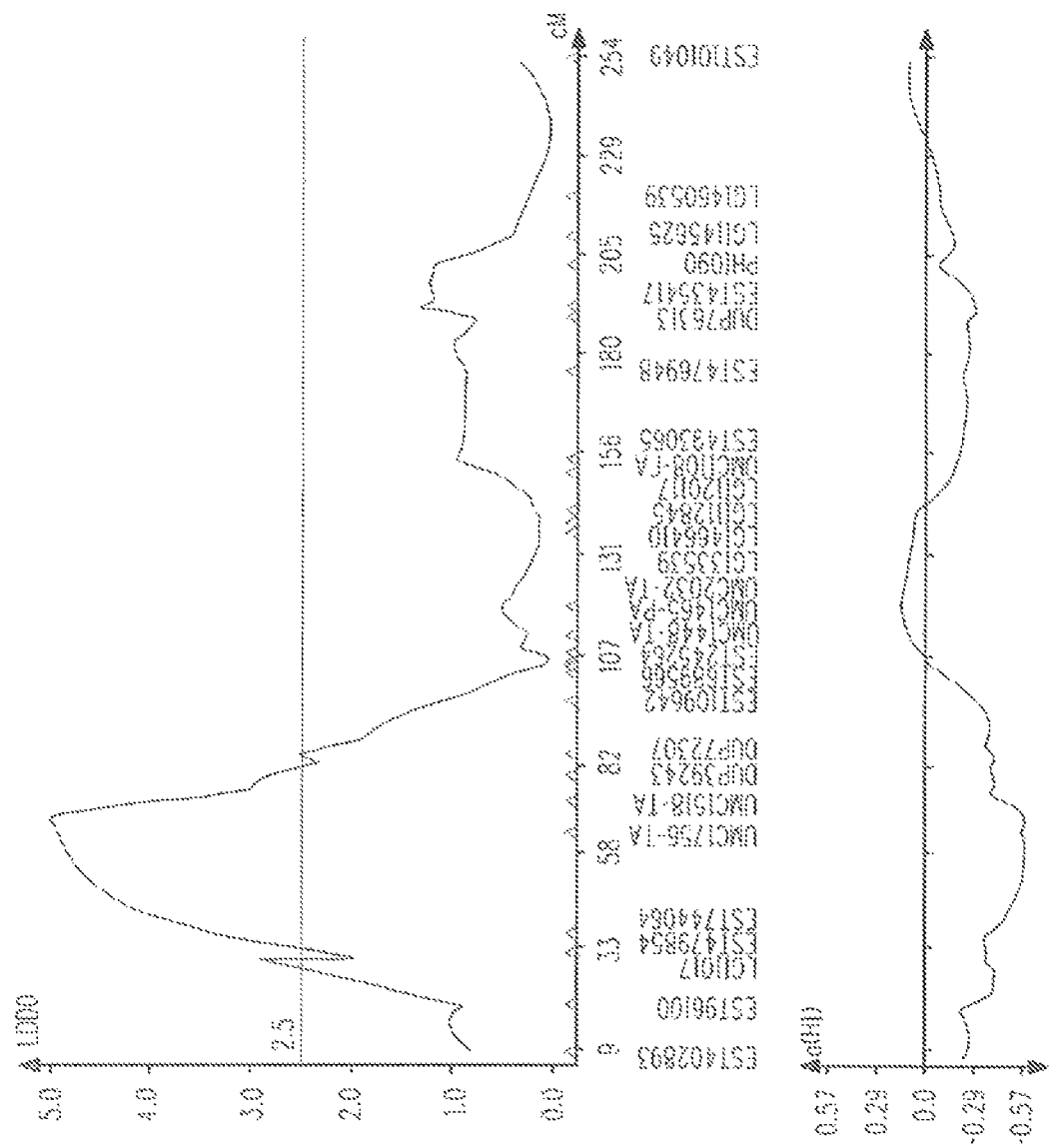

FIG. 10 is an interval map of mean phenotypic scores across three crop seasons for the PH7WTxPH3DT mapping population. Note that the LOD score peak is close to umc1756.

Figure 11:
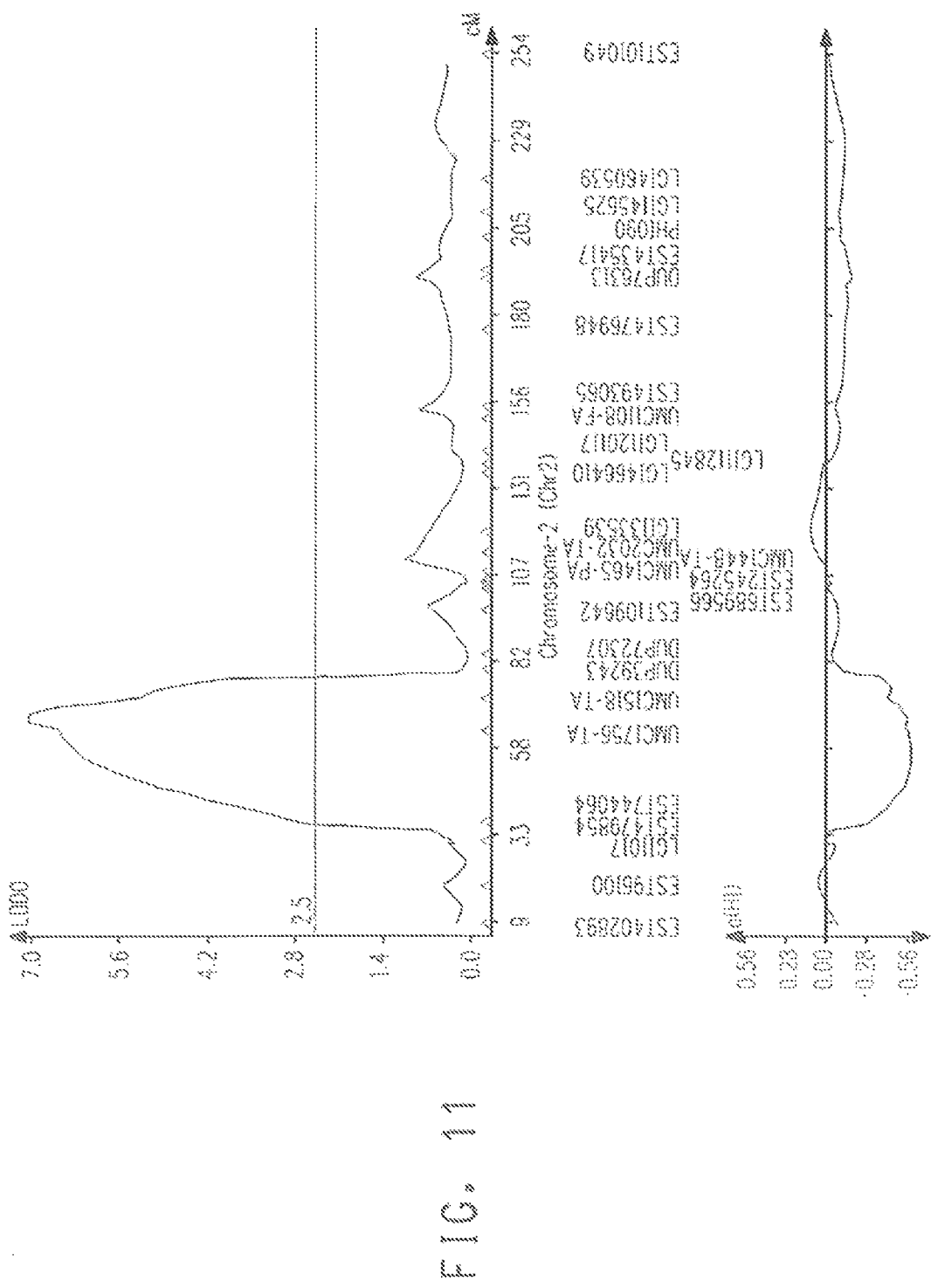

FIG. 11 is a composite interval map of mean phenotypic scores across three crop seasons for the PH7WTxPH3DT mapping population. Note that the LOD score peak is close to the umc1756-umc1518 interval.

Figure 12:
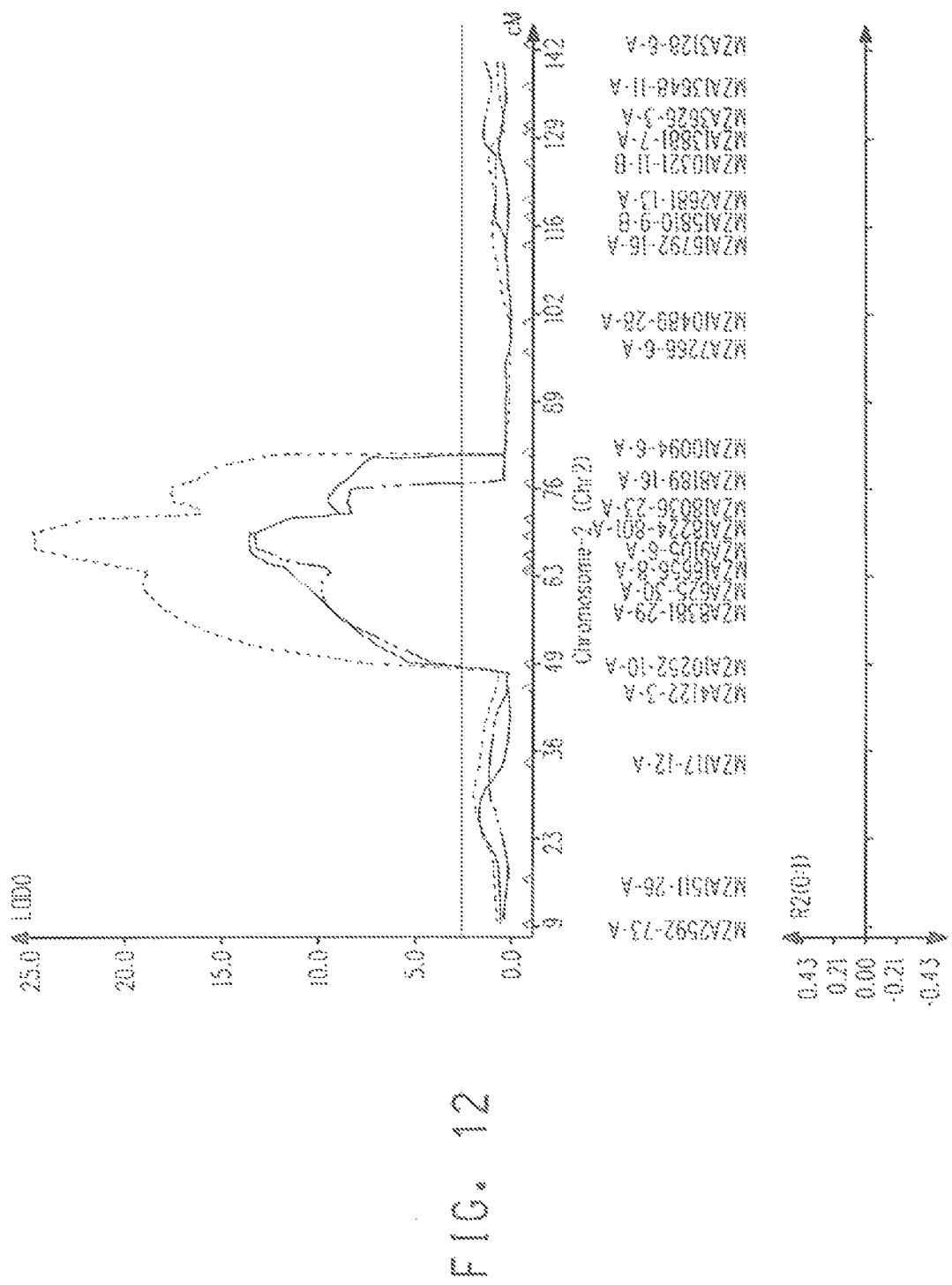

FIG. 12 is a composite interval map of the PH9TJxPH890 mapping population. The LOD score peak for the MRCV1 QTL was located at position 65.99-68.8.

FIGS. 13A-13C represent a ClustalW sequence alignment between SEQ ID NO:211 (pco644442 promoter from PH7WT) and SEQ ID NO:212 (pco644442 promoter from PH3DT).

The following sequence descriptions summarize the Sequence Listing attached hereto. The Sequence Listing contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

SEQ ID NOs: 1-5, 8-11, 14, 15, 18, 21, 25, 29, 30, 32, 34-37, 39, and 42-48 are consensus sequences for the MZA markers found in Table 6.

SEQ ID NOs: 6, 7, 12, 13, 16, 17, 19, 20, 22-24, 26-28, 31, 33, 38, 40, and 41 are SNP consensus sequences for the SNP markers found in Table 7.

SEQ ID NOs: 49-56 are left and right primer sequences for the public markers found in Table 3.

SEQ ID NOs: 57-172 are forward external, forward internal, reverse internal, and reverse external primers for the MZA markers found in Table 6.

SEQ ID NOs: 173-210 are forward and reverse primers for the SNP markers found in Table 7.

SEQ ID NO:211 is the PCO644442 promoter region of maize inbred line PH7WT.

SEQ ID NO:212 is the PCO644442 promoter region of maize inbred line PH3DT.

SEQ ID NO:213 is the sequence region including MRQV_08351 and MRQV_10673 for maize inbred line PH3DT.

SEQ ID NO:214 is the sequence region including MRQV_08351 and MRQV_10673 for maize inbred line AP19506160.

SEQ ID NO:215 is the sequence region including MRQV_08351 and MRQV_10673 for maize inbred line AP19506157.

SEQ ID NO:216 is the sequence region including MRQV_08351 and MRQV_10673 for maize inbred line AP19506156.

SEQ ID NO:217 is the sequence region including MRQV_08351 and MRQV_10673 for maize inbred line PH7WT.

SEQ ID NO:218 is the sequence region including MRQV_08351 and MRQV_10673 for maize inbred line 630.

SEQ ID NO:219 is the sequence region including MRQV_08351 and MRQV_10673 for maize inbred line PHG63.

SEQ ID NO:220 is the sequence region including MRQV_08351 and MRQV_10673 for maize inbred line PHK09.

SEQ ID NO:221 is the sequence region including MRQV_08351 and MRQV_10673 for maize inbred line PHR33.

SEQ ID NO:222 is the sequence region including MRQV_08351 and MRQV_10673 for maize inbred line 501.

SEQ ID NO:223 is the sequence region including MRQV_08351 and MRQV_10673 for maize inbred line 157.

SEQ ID NO:224 is the sequence region including MRQV_08351 and MRQV_10673 for maize inbred line PHK56.

SEQ ID NO:225 is the sequence region including MRQV_08351 and MRQV_10673 for maize inbred line 661.

SEQ ID NO:226 is the sequence region including MRQV_08351 and MRQV_10673 for maize inbred line PHR03.

SEQ ID NO:227 is the sequence region including MRQV_08351 and MRQV_10673 for maize inbred line 1047.

SEQ ID NO:228 is the sequence region including MRQV_08351 and MRQV_10673 for maize inbred line PHJ40.

SEQ ID NO:229 is the sequence region including MRQV_08351 and MRQV_10673 for maize inbred line 274.

SEQ ID NO:230 is the sequence region including MRQV_08351 and MRQV_10673 for maize inbred line 165.

SEQ ID NO:231 is the sequence region including MRQV_08351 and MRQV_10673 for maize inbred line B73.

SEQ ID NO:232 is the sequence region including MRQV_08351 and MRQV_10673 for maize inbred line PHN47.

SEQ ID NO:233 is the sequence region including MRQV_08351 and MRQV_10673 for maize inbred line PH26N.

SEQ ID NO:234 is the sequence region including MRQV_08351 and MRQV_10673 for maize inbred line PHDG9.

SEQ ID NO:235 is the sequence region including MRQV_08351 and MRQV_10673 for maize inbred line ST10H60.

SEQ ID NO:236 is the sequence region including MRQV_08351 and MRQV_10673 for maize inbred line PHKP5.

DETAILED DESCRIPTION OF THE INVENTION

The identification and selection of maize plants that show resistance to MRCV using MAS can provide an effective and environmentally friendly approach to overcoming losses caused by this disease. The present invention provides maize marker loci that demonstrate statistically significant co-segregation with MRCV resistance. Detection of these loci or additional linked loci can be used in marker assisted maize breeding programs to produce resistant plants, or plants with improved resistance to MRCV or a related *fijivirus*. The linked SSR and SNP markers identified herein are provided in Tables 1 and 2. These markers include MZA625, MZA16656, MZA15451, MZA15490, MZA2038, MZA11826, and MZA9105.

Each of the SSR-type markers display a plurality of alleles that can be visualized as different sized PCR amplicons. The PCR primers that are used to generate the SSR-marker amplicons are provided in Table 3. The alleles of SNP-type markers are determined using an allele-specific hybridization protocol, as known in the art. The PCR primers used to amplify the SNP domain, and the allele-specific probes used to genotype the locus, are provided in Tables 6 and 7.

TABLE 6

MZA primers

| MZA Marker | Forward/external | Forward/internal | Reverse/internal | Reverse/external | MZA consensus |
|---|---|---|---|---|---|
| MZA7588 | SEQ ID NO: 57 | SEQ ID NO: 58 | SEQ ID NO: 59 | SEQ ID NO: 60 | SEQ ID NO: 1 |
| MZA8381 | SEQ ID NO: 61 | SEQ ID NO: 62 | SEQ ID NO: 63 | SEQ ID NO: 64 | SEQ ID NO: 2 |
| MZA3105 | SEQ ID NO: 65 | SEQ ID NO: 66 | SEQ ID NO: 67 | SEQ ID NO: 68 | SEQ ID NO: 3 |
| MZA482 | SEQ ID NO: 69 | SEQ ID NO: 70 | SEQ ID NO: 71 | SEQ ID NO: 72 | SEQ ID NO: 4 |
| MZA16531 | SEQ ID NO: 73 | SEQ ID NO: 74 | SEQ ID NO: 75 | SEQ ID NO: 76 | SEQ ID NO: 5 |
| MZA625 | SEQ ID NO: 77 | SEQ ID NO: 78 | SEQ ID NO: 79 | SEQ ID NO: 80 | SEQ ID NO: 8 |
| MZA4305 | SEQ ID NO: 81 | SEQ ID NO: 82 | SEQ ID NO: 83 | SEQ ID NO: 84 | SEQ ID NO: 9 |
| MZA14553 | SEQ ID NO: 85 | SEQ ID NO: 86 | SEQ ID NO: 87 | SEQ ID NO: 88 | SEQ ID NO: 10 |
| MZA15451 | SEQ ID NO: 89 | SEQ ID NO: 90 | SEQ ID NO: 91 | SEQ ID NO: 92 | SEQ ID NO: 11 |
| MZA9105 | SEQ ID NO: 93 | SEQ ID NO: 94 | SEQ ID NO: 95 | SEQ ID NO: 96 | SEQ ID NO: 14 |
| MZA2803 | SEQ ID NO: 97 | SEQ ID NO: 98 | SEQ ID NO: 99 | SEQ ID NO: 100 | SEQ ID NO: 15 |
| MZA2038 | SEQ ID NO: 101 | SEQ ID NO: 102 | SEQ ID NO: 103 | SEQ ID NO: 104 | SEQ ID NO: 18 |
| MZA16656 | SEQ ID NO: 105 | SEQ ID NO: 106 | SEQ ID NO: 107 | SEQ ID NO: 108 | SEQ ID NO: 21 |
| MZA15490 | SEQ ID NO: 109 | SEQ ID NO: 110 | SEQ ID NO: 111 | SEQ ID NO: 112 | SEQ ID NO: 25 |
| MZA11826 | SEQ ID NO: 113 | SEQ ID NO: 114 | SEQ ID NO: 115 | SEQ ID NO: 116 | SEQ ID NO: 29 |
| MZA564 | SEQ ID NO: 117 | SEQ ID NO: 118 | SEQ ID NO: 119 | SEQ ID NO: 120 | SEQ ID NO: 30 |
| MZA2349 | SEQ ID NO: 121 | SEQ ID NO: 122 | SEQ ID NO: 123 | SEQ ID NO: 124 | SEQ ID NO: 32 |
| MZA18224 | SEQ ID NO: 125 | SEQ ID NO: 126 | SEQ ID NO: 127 | SEQ ID NO: 128 | SEQ ID NO: 34 |
| MZA11066 | SEQ ID NO: 129 | SEQ ID NO: 130 | SEQ ID NO: 131 | SEQ ID NO: 132 | SEQ ID NO: 35 |
| MZA18180 | SEQ ID NO: 133 | SEQ ID NO: 134 | SEQ ID NO: 135 | SEQ ID NO: 136 | SEQ ID NO: 36 |
| MZA8442 | SEQ ID NO: 137 | SEQ ID NO: 138 | SEQ ID NO: 139 | SEQ ID NO: 140 | SEQ ID NO: 37 |
| MZA15563 | SEQ ID NO: 141 | SEQ ID NO: 142 | SEQ ID NO: 143 | SEQ ID NO: 144 | SEQ ID NO: 39 |
| MZA18036 | SEQ ID NO: 145 | SEQ ID NO: 146 | SEQ ID NO: 147 | SEQ ID NO: 148 | SEQ ID NO: 42 |
| MZA15264 | SEQ ID NO: 149 | SEQ ID NO: 150 | SEQ ID NO: 151 | SEQ ID NO: 152 | SEQ ID NO: 43 |
| MZA10384 | SEQ ID NO: 153 | SEQ ID NO: 154 | SEQ ID NO: 155 | SEQ ID NO: 156 | SEQ ID NO: 44 |
| MZA12874 | SEQ ID NO: 157 | SEQ ID NO: 158 | SEQ ID NO: 159 | SEQ ID NO: 160 | SEQ ID NO: 45 |
| MZA12454 | SEQ ID NO: 161 | SEQ ID NO: 162 | SEQ ID NO: 163 | SEQ ID NO: 164 | SEQ ID NO: 46 |
| MZA8926 | SEQ ID NO: 165 | SEQ ID NO: 166 | SEQ ID NO: 167 | SEQ ID NO: 168 | SEQ ID NO: 47 |
| MZA5057 | SEQ ID NO: 169 | SEQ ID NO: 170 | SEQ ID NO: 171 | SEQ ID NO: 172 | SEQ ID NO: 48 |

TABLE 7

| SNP Marker | SNP primers Forward | SNP primers Reverse | SNP alleles SNP | SNP consensus |
|---|---|---|---|---|
| MZA625-30-A | SEQ ID NO: 173 | SEQ ID NO: 174 | T/C | SEQ ID NO: 6 (SNP at position 186) |
| MZA625-29-A | SEQ ID NO: 175 | SEQ ID NO: 176 | T/C | SEQ ID NO: 7 (SNP at position 165) |
| MZA9105-8-A | SEQ ID NO: 177 | SEQ ID NO: 178 | G/A | SEQ ID NO: 12 (SNP at position 123) |
| MZA9105-6-A | SEQ ID NO: 179 | SEQ ID NO: 180 | G/A | SEQ ID NO: 13 (SNP at position 98) |
| MZA2038-76-A | SEQ ID NO: 181 | SEQ ID NO: 182 | T/C | SEQ ID NO: 16 (SNP at position 277) |
| MZA2038-71-A | SEQ ID NO: 183 | SEQ ID NO: 184 | T/A | SEQ ID NO: 17 (SNP at position 258) |
| MZA16656-8-A | SEQ ID NO: 185 | SEQ ID NO: 186 | T/C | SEQ ID NO: 19 (SNP at position 85) |
| MZA16656-19-A | SEQ ID NO: 187 | SEQ ID NO: 188 | G/A | SEQ ID NO: 20 (SNP at position 218) |
| MZA15490-801-A | SEQ ID NO: 189 | SEQ ID NO: 190 | G/C | SEQ ID NO: 22 (SNP at position 96) |
| MZA15490-138-A | SEQ ID NO: 191 | SEQ ID NO: 192 | G/C | SEQ ID NO: 23 (SNP at position 96) |
| MZA15490-137-A | SEQ ID NO: 193 | SEQ ID NO: 194 | C/A | SEQ ID NO: 24 (SNP at position 84) |
| MZA11826-803-A | SEQ ID NO: 195 | SEQ ID NO: 196 | C/T | SEQ ID NO: 27 (SNP at position 701) |
| MZA11826-801-A | SEQ ID NO: 197 | SEQ ID NO: 198 | A/G | SEQ ID NO: 26 (SNP at position 89) |
| MZA11826-27-A | SEQ ID NO: 199 | SEQ ID NO: 200 | T/C | SEQ ID NO: 28 (SNP at position 222) |
| MZA2349-71-A | SEQ ID NO: 201 | SEQ ID NO: 202 | T/C | SEQ ID NO: 31 (SNP at position 133) |
| MZA18224-801-A | SEQ ID NO: 203 | SEQ ID NO: 204 | A/G | SEQ ID NO: 33 (SNP at position 188) |
| MZA15563-12-A | SEQ ID NO: 205 | SEQ ID NO: 206 | T/A | SEQ ID NO: 38 (SNP at position 601) |
| MZA18036-9-A | SEQ ID NO: 207 | SEQ ID NO: 208 | A/G | SEQ ID NO: 40 (SNP at position 90) |
| MZA18036-23-A | SEQ ID NO: 209 | SEQ ID NO: 210 | A/G | SEQ ID NO: 41 (SNP at position 285) |

Tables 6 and 7 list the SNP markers that demonstrated linkage disequilibrium with the MRCV resistance phenotype. These tables provide the sequences of the PCR primers used to generate a SNP-containing amplicon, and the allele-specific probes that were used to identify the SNP allele in an allele-specific hybridization assay (ASH assay).

As recognized in the art, any other marker that is linked to a QTL marker (e.g., a disease resistance marker) also finds use for that same purpose. Examples of additional markers that are linked to the disease resistance markers recited herein are provided. For example, a linked marker can be determined from the closely linked markers provided in Table 8.

TABLE 8

| Linked Markers |
|---|
| pco061820a, pco116928a, sog0930a, pco102443, sog5467ac, cl7211__1l, k4-14p, pco135612a, pco101521, si687005h09c, si707023g07c, cl15901__1a, pco134907, si660032f12i, cl7048__1b, cl2578__1, cl5312__1a, pco094715, sog5829a, cl30__1e, pco125905, sog0690, cl36282__1b, pco118508, gpm636, pco066747a, pco083425q, sog5844av, bnlg1458b, si606065e12a, cl22018__1, pco091058, si946053g10, sog1265, sog0743c, cl9862__1, pco114887, bnlg1327, sog5587a, cl1488__-4a, pco085208a, sog1295c, sog5609b, sog0912a, tel7sc1ah, si66060d11b, cl10933__1d, cl37019__1a, sog1856ae, pco117007l, |

TABLE 8-continued Linked Markers cl40761__1a, siaf099388e, pco137067a, sog2274m, cl31185__3a, pco098939a, pco151039r, cl11825__1a, pco122145b, cl24291__1a, si618065b03a, si707029g03a, sog1495a, IDP4006, umc1262a, umc1261a, sog5758o It is not intended, however, that linked markers finding use with the invention be limited to those recited in Table 8.

The invention also provides chromosomal QTL intervals that correlate with MRCV resistance. These intervals are located on linkage group 2. Any marker located within these intervals finds use as a marker for MRCV resistance. These intervals include:

(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

Methods for identifying maize plants or germplasm that carry preferred alleles of resistance marker loci are a feature of the invention. In these methods, any of a variety of marker detection protocols are used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

Although particular marker alleles can show co-segregation with a disease resistance or susceptibility phenotype, it is important to note that the marker locus is not necessarily part of the QTL locus responsible for the resistance or susceptibility. For example, it is not a requirement that the marker polynucleotide sequence be part of a gene that imparts disease resistance (for example, be part of the gene open reading frame). The association between a specific marker allele with the resistance or susceptibility phenotype is due to the original "coupling" linkage phase between the marker allele and the QTL resistance or susceptibility allele in the ancestral maize line from which the resistance or susceptibility allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the genetic marker can be used to monitor segregation of the phenotype. It only changes which marker allele is considered favorable in a given segregating population.

Identification of maize plants or germplasm that include a marker locus or marker loci linked to a resistance trait or traits provides a basis for performing marker assisted selection of maize. Maize plants that comprise favorable markers or favorable alleles are selected for, while maize plants that comprise markers or alleles that are negatively correlated with resistance can be selected against. Desired markers and/or alleles can be introgressed into maize having a desired (e.g., elite or exotic) genetic background to produce an introgressed resistant maize plant or germplasm. In some aspects, it is contemplated that a plurality of resistance markers are sequentially or simultaneous selected and/or introgressed. The combinations of resistance markers that are selected for in a single plant is not limited, and can include any combination of markers recited in Tables 1 and 2, any markers linked to the markers recited in Tables 1 and 2, or any markers located within the QTL intervals defined herein.

As an alternative to standard breeding methods of introducing traits of interest into maize (e.g., introgression), transgenic approaches can also be used. In these methods, exogenous nucleic acids that encode traits linked to markers are introduced into target plants or germplasm. For example, a nucleic acid that codes for a resistance trait is cloned, e.g., via positional cloning and introduced into a target plant or germplasm.

Verification of resistance can be performed by available resistance protocols (see, e.g., Example 10). Resistance assays are useful to verify that the resistance trait still segregates with the marker in any particular plant or population, and, of course, to measure the degree of resistance improvement achieved by introgressing or recombinantly introducing the trait into a desired background.

Systems, including automated systems for selecting plants that comprise a marker of interest and/or for correlating presence of the marker with resistance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also a feature of the invention. For example, a kit can include appropriate primers or probes for detecting resistance-associated marker loci and instructions in using the primers or probes for detecting the marker loci and correlating the loci with predicted MRCV resistance. The kits can further include packaging materials for packaging the probes, primers or instructions, controls such as control amplification reactions that include probes, primers or template nucleic acids for amplifications, molecular size markers, or the like.

Resistance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in maize, 1 cM correlates, on average, to about 2,140,000 base pairs (2.14 Mbp).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The markers herein, as described in Tables 1 and 2, e.g., MZA625, MZA16656, MZA15451, MZA15490, MZA2038, MZA11826, and MZA9105, as well as any of the chromosome intervals
  (i) MZA8381 and MZA18180;
  (ii) MZA4305 and MZA2803;
  (iii) MZA15490 and MZA2038;
  (iv) bnlg1458b and umc1261a;
  (v) bnlg1458b and umc1262a;
  (vi) bnlg1327 and umc1261a; and
  (viii) bnlg1327 and umc1262a;
have been found to correlate with newly conferred resistance, enhanced resistance, or susceptibility to MRCV in maize. This means that the markers are sufficiently proximal to a resistance trait that they can be used as a predictor for the resistance trait. This is extremely useful in the context of marker assisted selection (MAS), discussed in more detail herein. In brief, maize plants or germplasm can be selected for markers or marker alleles that positively correlate with resistance, without actually raising maize and measuring for newly conferred resistance or enhanced resistance (or, contrarily, maize plants can be selected against if they possess markers that negatively correlate with newly conferred resistance or enhanced resistance). MAS is a powerful shortcut to selecting for desired phenotypes and for introgressing desired traits into cultivars of maize (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the most preferred QTL markers are a subset of the markers provided in Tables 1 and 2. For example, the most preferred markers are MZA15490 and MZA2038.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

A favorable allele of a marker is that allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of resistant maize lines. Optionally, one, two, three or more favorable allele(s) of different markers are identified in, or introgressed into a plant, and can be selected for or against during MAS. Desirably, plants or germplasm are identified that have at least one such favorable allele that positively correlates with newly conferred or enhanced resistance.

Alternatively, a marker allele that co-segregates with disease susceptibility also finds use with the invention, since that allele can be used to identify and counter select disease-susceptible plants. Such an allele can be used for exclusionary purposes during breeding to identify alleles that negatively correlate with resistance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles from more than one resistance marker, or alternatively, favorable alleles from more than one resistance marker are introgressed into a desired maize germplasm. One of skill in the art recognizes that the simultaneous selection of favorable alleles from more than one disease resistance marker in the same plant is likely to result in an additive (or even synergistic) protective effect for the plant.

One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in maize populations other than the populations used or described herein is well within the scope of the invention.

Amplification primers for amplifying SSR-type marker loci are a feature of the invention. Another feature of the invention is primers specific for the amplification of SNP domains (SNP markers), and the probes that are used to genotype the SNP sequences. Tables 6 and 7 provide specific primers for marker locus amplification and probes for detecting amplified marker loci. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook et al., *Molecular Cloning—A Laboratory Manual* ($3^{rd}$ Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel") and *PCR Protocols A Guide to Methods and Applications* (Innis et al. eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc. ("Croy").

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the figures and tables herein are either SSR or SNP (ASH) markers, any of the aforementioned marker types can be employed in the context of the invention to identify chromosome segments encompassing genetic element that contribute to superior agronomic performance (e.g., newly conferred resistance or enhanced resistance).

QTL Chromosome Intervals

In some aspects, the invention provides QTL chromosome intervals, where a QTL (or multiple QTL) that segregate with MRCV resistance are contained in those intervals. A variety of methods well known in the art are available for identifying chromosome intervals (also as described in detail in Examples 1 and 2). The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for disease resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The present invention provides maize chromosome intervals, where the markers within that interval demonstrate co-segregation with resistance to MRCV. Thus, each of these intervals comprises at least one MRCV resistance QTL as shown in Table 9.

TABLE 9

| Flanking Markers | Method(s) of Identification |
|---|---|
| MZA8381 and MZA1810 | Association analysis, identity by descent |
| MZA4305 and MZA2803 | Association analysis, identity by descent |
| MZA15490 and MZA2038 | Association analysis, identity by descent |
| bnlg1458b and umc1261a | Linkage to a preferred marker |
| bnlg1458b and umc1262a | Linkage to a preferred marker |
| bnlg1327 and umc1261a | Linkage to a preferred marker |
| bnlg1327 and umc1262a | Linkage to a preferred marker |

Each of the intervals described above shows a clustering of markers that co-segregate with MRCV resistance. This clustering of markers occurs in relatively small domains on the linkage groups, indicating the presence of one or more QTL in those chromosome regions. QTL intervals were drawn to encompass the markers that co-segregate with resistance. The intervals are defined by the markers on their termini, where the interval encompasses all the markers that map within the interval as well as the markers that define the termini.

In some cases, an interval can be drawn where the interval is defined by linkage to a preferred marker. For example, an interval on chromosome 2 is defined where any marker that is linked to the marker MZA16656 is a member of that interval. For example, as used here, linkage is defined as any marker that is within 25 cM from MZA16656. This interval on chromosome 2 is further illustrated in Table 8. The markers that are linked to MZA16656 (e.g., within 5 cM of MZA16656) as determined by any suitable genetic linkage map (for example, the IBM2 2005 Neighbors Frame 2 map found on the MaizeGDB website). These markers are shown in genetic order. Each of the markers listed, including the terminal markers pco061820a and sog5758o, are members of the interval. The pco061820a and sog5758o markers are known in the art.

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown. The invention provides a variety of means for defining a chromosome interval, for example, in the lists of linked markers of Table 8, and in references cited herein.

Linked Markers

From the present disclosure and widely recognized in the art, it is clear that any genetic marker that has a significant probability of co-segregation with a phenotypic trait of interest (e.g., in the present case, a newly conferred resistance or enhanced resistance trait) can be used as a marker for that trait. A list of useful QTL markers provided by the present invention is provided in Tables 1 and 2.

In addition to the QTL markers noted in Tables 1 and 2, additional markers linked to (showing linkage disequilibrium with) the QTL markers can also be used to predict the newly conferred resistance or enhanced resistance trait in a maize plant. In other words, any other marker showing less than 50% recombination frequency (separated by a genetic distance less than 50 cM) with a QTL marker of the invention (e.g., the markers provided in Tables 1 and 2) is also a feature of the invention. Any marker that is linked to a QTL marker can also be used advantageously in marker-assisted selection for the particular trait.

Genetic markers that are linked to QTL markers (e.g., QTL markers provided in Tables 1 and 2) are particularly useful when they are sufficiently proximal (e.g., closely linked) to a given QTL marker so that the genetic marker and the QTL marker display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more prefer-ably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

In some aspects, linked markers (including closely linked markers) of the invention are determined by review of a genetic map, for example, the integrated genetic maps found on the MaizeGDB website. For example, it is shown herein that the linkage group 2 markers MZA625, MZA16656, MZA15451, MZA15490, MZA2038, MZA11826, and MZA9105 correlate with at least one MRCV resistance QTL. Markers that are linked to MZA625, MZA16656, MZA15451, MZA15490, MZA2038, MZA11826, and MZA9105 can be determined from the list provided in Table 8 (see also Table 11, which shows Rice Locus and Working Maize Gene ID of genetic markers between MZA625 and MZA9105).

TABLE 11

| PHD Chr | PHD Map Pos | UC7 PCO Vs. Myriad Amplicons | Locus Order | Rice Locus | Working Maize Gene ID | Annotation Summary |
|---|---|---|---|---|---|---|
| 2 | 64.05 | MZA625 | Loc_029 | LOC_Os04g51320 | AC191302_5part | Transcription Factor |
| | | | Loc_028 | LOC_Os04g51310 | AC191302_3 | Putrescine-binding protein; Hypothetical protein |
| | | | Loc_027 | LOC_Os04g51300 | pco600856 | Putative L-ascorbate peroxidase |
| | | | Loc_025 | LOC_Os04g51280 | pco530474 | Plastid development protein; DAG |
| | | | Loc_024 | LOC_Os04g51270 | pco593067 | Hypothetical protein; Vacuolar ATP synthase subunit? |
| | | | Loc_023 | LOC_Os04g51260 | AC191302_6 | Hypothetical protein |
| | | | Loc_022 | LOC_Os04g51250 | Inferred by rice and *sorghum* | Hypothetical protein |
| | | | Loc_021 | LOC_Os04g51240 | pco641713 | Hypothetical protein |
| | | | Loc_016 | LOC_Os04g51190 | pco591841 | Growth regulating factor |
| | | | Loc_015 | LOC_Os04g51180 | Genomic_PCO622600_PCO666161 | G protein-coupled receptor 89C (*Homo sapiens*) |

TABLE 11-continued

| PHD Chr | PHD Map Pos | UC7 PCO Vs. Myriad Amplicons | Locus Order | Rice Locus | Working Maize Gene ID | Annotation Summary |
|---|---|---|---|---|---|---|
| 2 | 65.99 | MZA166656 | Loc_014 | LOC_Os04g51172 | pco638426 | Major intrinsic protein; NIP; *BREVIS RADIX* like 1 |
|  |  |  | Loc_013 | LOC_Os04g51166 | pco514627 | Hypothetical protein |
| 2 | 65.30 | MZA15451 | Loc_012 | LOC_Os04g51160 LOC_Os04g51150 | pco588936 | Alternative oxidase AOX3 |
|  |  |  | Loc_010 | LOC_Os04g51140 | Inferred by rice and *sorghum* | Hypothetical protein |
|  |  |  | Loc_009 | LOC_Os04g51130 | pco644442 | Myb-like; 2-component response regulator |
| 2 | 65.99 | MZA2038 | Loc_008 | LOC_Os04g51120 | pco641455 | Clathrin interactor; Epsin; Hypothetical protein |
|  |  |  | Loc_007 | LOC_Os04g51110 | pco640541 | CDC20 WD-repeat protein |
|  |  |  | Loc_006 | LOC_Os04g51100 | pco651091 | Cobalamin synthesis protein |
|  |  |  | Loc_005 | LOC_Os04g51090 | pco571541 | Hypothetical protein |
|  |  |  | Loc_004 | LOC_Os04g51080 | pco525409 | Scramblase |
|  |  |  | Loc_003 | LOC_Os04g51070 | pco553755 | Hypothetical protein |
|  |  |  | Loc_002 | LOC_Os04g51060 | pco644099 | Hypothetical protein |
| 2 | 65.44 | MZA9105 | Loc_001 | LOC_Os04g51050 | pco588179 | Receptor protein kinase |

For example, markers on linkage group 2 that are linked to MZA625, MZA16656, MZA15451, MZA15490, MZA2038, MZA11826, and MZA9105 include those listed in Table 12.

TABLE 12

| Marker | Map Position |
|---|---|
| pco061820a | 148.07 |
| pco116928a | 148.07 |
| sog0930a | 148.07 |
| pco102443 | 148.07 |
| pco133385a | 148.07 |
| sog5467ac | 148.07 |
| cl7211_1l | 148.08 |
| K4-14p | 148.08 |
| pco135612a | 148.08 |
| si687005h09c | 148.08 |
| si707023g07c | 148.08 |
| cl15901_1a | 148.08 |
| pco134907 | 148.08 |
| si660032f12i | 148.08 |
| cl7048_1b | 148.08 |
| cl2578_1 | 148.09 |
| cl5312_1a | 148.09 |
| pco094715 | 148.09 |
| sog5829a | 148.09 |
| cl30_1e | 148.09 |
| pco125905 | 148.09 |
| sog0690 | 148.09 |
| cl36282_1b | 148.09 |
| pco118508 | 148.09 |
| gpm636 | 148.09 |
| pco066747a | 148.09 |
| pco083425q | 148.09 |
| sog5844av | 148.09 |
| bnlg1458b | 148.09 |
| si606065e12a | 148.09 |
| cl22018_1 | 148.09 |
| pco091058 | 148.09 |
| si946053g10 | 148.10 |
| sog1265 | 148.10 |
| sog0743c | 148.10 |
| cl9862_1 | 148.10 |
| pco114887 | 148.10 |
| bnlg1327 | 148.10 |
| sog5587a | 148.10 |
| cl1488_-4a | 148.11 |
| pco085208a | 148.11 |
| sog1295c | 148.11 |
| sog5609b | 148.11 |
| sog0912a | 148.11 |

TABLE 12-continued

| Marker | Map Position |
| --- | --- |
| tel7sc1ah | 148.11 |
| si660060d11b | 148.11 |
| cl10933_1d | 148.11 |
| cl37019_1a | 148.11 |
| sog1856ae | 148.11 |
| pco117007l | 148.11 |
| cl40761_1a | 148.11 |
| siaf099388e | 148.11 |
| pco137067a | 148.11 |
| sog2274m | 148.11 |
| cl31185_3a | 148.11 |
| pco098939a | 148.11 |
| pco150139r | 148.11 |
| cl11825_1a | 148.11 |
| pco122145b | 148.11 |
| cl24291_1a | 148.11 |
| si618065g03a | 148.11 |
| si707029g03a | 148.11 |
| sog1495a | 148.75 |
| umc1262a | 153.10 |
| umc1261a | 154.60 |
| sog5758o | 154.71 |

Similarly, linked markers (including closely linked markers) of the invention can be determined by review of any suitable maize genetic map. For example, integrated genetic maps can be found on the MaizeGDB website resource.

It is not intended that the determination of linked or closely linked markers be limited to the use of any particular maize genetic map. Indeed, a large number of maize genetic maps is available and are well known to one of skill in the art. Alternatively, the determination of linked and closely linked markers can be made by the generation of an experimental dataset and linkage analysis.

It is also not intended that the identification of markers that are linked (e.g., within about 50 cM or within about 10 cM) to the MRCV resistance QTL markers identified herein be limited to any particular map or methodology. The integrated genetic maps provided on the MaizeGDB website serve only as example for identifying linked markers. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any maize genetic map can be used to determine markers that are linked and closely linked to the QTL markers of the present invention.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype, to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly maize plants, that have newly conferred resistance or enhanced resistance to, or are susceptible to, MRCV by identifying plants having a specified allele at one of those loci, e.g., MZA625, MZA16656, MZA15451, MZA15490, MZA2038, MZA11826, or MZA9105. In one embodiment, identified resistant plants have the haplotype: C at MRQV_08351-173, A at MRQV_08351-262, G at MRQV_08351-280, G at MRQV_08351-323, C at MRQV_08351-369, C at MRQV_08351-372.

Similarly, by identifying plants lacking the desired marker locus, susceptible or less resistant plants can be identified and, e.g., eliminated from subsequent crosses. Similarly, these marker loci can be introgressed into any desired genomic background, germplasm, plant, line, variety, etc., as part of an overall MAS breeding program designed to enhance maize yield. In one embodiment, identified susceptible plants have the haplotype: T at MRQV_08351-173, T at MRQV_08351-262, A at MRQV_08351-280, C at MRQV_08351-323, T at MRQV_08351-369, T at MRQV_08351-372.

The invention also provides chromosome QTL intervals that find equal use in MAS to select plants that demonstrate newly conferred or enhanced MRCV resistance. Similarly, the QTL intervals can also be used to counter-select plants that are susceptible or have reduced resistance MRCV. Any marker that maps within the QTL interval (including the termini of the intervals) finds use with the invention. These intervals are defined by the following pairs of markers:
  (i) MZA8381 and MZA18180;
  (ii) MZA4305 and MZA2803;
  (iii) MZA15490 and MZA2038;
  (iv) bnlg1458b and umc1261a;
  (v) bnlg1458b and umc1262a;
  (vi) bnlg1327 and umc1261a; and
  (viii) bnlg1327 and umc1262a.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence of a desired allele in the QTL marker. The most preferred markers (or marker alleles) are those that have the strongest association with the resistance trait.

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired resistance phenotype, typically called marker-assisted selection (MAS). In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "TECHNIQUES FOR MARKER DETECTION". After the presence (or absence) of a particular marker allele in the biological sample is verified, the plant is selected (e.g., used to make progeny plants by selective breeding).

Maize plant breeders desire combinations of resistance loci with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to resistance loci, provide an effective method for selecting resistant varieties in breeding programs. For example, one advantage of marker-assisted selection over field evaluations for resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in resistance, or multiple loci each involved in resistance to different diseases, the efficiency of MAS compared to phenotypic screening becomes even greater, because all the loci can be evaluated in the lab together from a single sample of DNA. In the present instance, the MZA625, MZA16656, MZA15451, MZA15490, MZA2038, MZA11826, and MZA9105 markers, as well as any of the chromosome intervals
 (i) MZA8381 and MZA18180;
 (ii) MZA4305 and MZA2803;
 (iii) MZA15490 and MZA2038;
 (iv) bnlg1458b and umc1261a;
 (v) bnlg1458b and umc1262a;
 (vi) bnlg1327 and umc1261a; and
 (viii) bnlg1327 and umc1262a;
can be assayed simultaneously or sequentially from a single sample or a population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable resistance marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to MRCV.

The presence and/or absence of a particular genetic marker or allele, e.g., MZA625, MZA16656, MZA15451, MZA15490, MZA2038, MZA11826, and MZA9105 markers, as well as any of the chromosome intervals
 (i) MZA8381 and MZA18180;
 (ii) MZA4305 and MZA2803;
 (iii) MZA15490 and MZA2038;
 (iv) bnlg1458b and umc1261a;
 (v) bnlg1458b and umc1262a;
 (vi) bnlg1327 and umc1261a; and
 (viii) bnlg1327 and umc1262a;
in the genome of a plant is made by any method noted herein. If the nucleic acids from the plant are positive for a desired genetic marker allele, the plant can be self fertilized to create a true breeding line with the same genotype, or it can be crossed with a plant with the same marker or with other desired characteristics to create a sexually crossed hybrid generation.

Introgression of Favorable Alleles—Efficient Backcrossing of Resistance Markers into Elite Lines One application of MAS, in the context of the present invention is to use the newly conferred resistance or enhanced resistance markers to increase the efficiency of an introgression or backcrossing effort aimed at introducing a resistance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of maize varieties with the desired complement (set) of allelic forms of chromosome segments associated with superior agronomic performance (resistance, along with any other available markers for yield, etc.). Any of the disclosed marker alleles can be introduced into a maize line via introgression, by traditional breeding (or introduced via transformation, or both), to yield a maize plant with superior agronomic performance. The number of alleles associated with resistance that can be introduced or be present in a maize plant of the present invention ranges from 1 to the number of alleles disclosed herein, each integer of which is incorporated herein as if explicitly recited.

The present invention also extends to a method of making a progeny maize plant and these progeny maize plants, per se. The method comprises crossing a first parent maize plant with a second maize plant and growing the female maize plant under plant growth conditions to yield maize plant progeny. Methods of crossing and growing maize plants are well within the ability of those of ordinary skill in the art. Such maize plant progeny can be assayed for alleles associated with resistance and, thereby, the desired progeny selected. Such progeny plants or seed can be sold commercially for maize production, used for food, processed to obtain a desired constituent of the maize, or further utilized in subsequent rounds of breeding. At least one of the first or second maize plants is a maize plant of the present invention in that it comprises at least one of the allelic forms of the markers of the present invention, such that the progeny are capable of inheriting the allele.

A method of the present invention can be applied to at least one related maize plant such as from progenitor or descendant lines in the subject maize plant's pedigree such that inheritance of the desired resistance allele can be traced. The number of generations separating the maize plants being subject to the methods of the present invention will generally be from 1 to 20, commonly 1 to 5, and typically 1, 2, or 3 generations of separation, and quite often a direct descendant or parent of the maize plant will be subject to the method (i.e., one generation of separation).

Introgression of Favorable Alleles—Incorporation of "Exotic" Germplasm while Maintaining Breeding Progress Genetic diversity is important for long term genetic gain in any breeding program. With limited diversity, genetic gain will eventually plateau when all the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite×exotic maize lines by subjecting the segregating progeny to MAS to maintain major yield alleles, along with the resistance marker alleles herein.

Positional Cloning

The molecular marker loci and alleles of the present invention, e.g., MZA625, MZA16656, MZA15451, MZA15490, MZA2038, MZA11826, and MZA9105 markers, as well as any of the chromosome intervals
(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a;
can be used, as indicated previously, to identify a resistance QTL, which can be cloned by well established procedures, e.g., as described in detail in Ausubel, Berger and Sambrook, herein.

These resistance clones are first identified by their genetic linkage to markers of the present invention. Isolation of a nucleic acid of interest is achieved by any number of methods as discussed in detail in such references as Ausubel, Berger and Sambrook, herein, and Clark, Ed. (1997) *Plant Molecular Biology: A Laboratory Manual* Springer-Verlag, Berlin.

For example, "positional gene cloning" uses the proximity of a resistance marker to physically define an isolated chromosomal fragment containing a resistance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the ORF is identified by successive rounds of screening and isolation of clones which together comprise a contiguous sequence of DNA, a process termed "chromosome walking", resulting in a "contig" or "contig map". Protocols sufficient to guide one of skill through the isolation of clones associated with linked markers are found in, e.g., Berger, Sambrook and Ausubel, all herein.

Generation of Transgenic Cells and Plants

The present invention also relates to host cells and organisms which are transformed with nucleic acids corresponding to resistance QTL identified according to the invention. For example, such nucleic acids include chromosome intervals (e.g., genomic fragments), ORFs and/or cDNAs that encode a newly conferred resistance or enhanced resistance trait. Additionally, the invention provides for the production of polypeptides that provide newly conferred resistance or enhanced resistance by recombinant techniques.

General texts which describe molecular biological techniques for the cloning and manipulation of nucleic acids and production of encoded polypeptides include Berger, Sambrook, and Ausubel supra. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Methods for MRCV Resistant Maize Plants

Experienced plant breeders can recognize resistant maize plants in the field and can select the resistant individuals or populations for breeding purposes or for propagation. In this context, the plant breeder recognizes "resistant" and "non-resistant", or "susceptible", maize plants.

Such plant breeding practitioners will appreciate that plant resistance is a phenotypic spectrum consisting of extremes in resistance, susceptibility and a continuum of intermediate resistance phenotypes. Resistance also varies due to environmental effects and the severity of pathogen infection. Evaluation of phenotypes using reproducible assays and resistance scoring methods are of value to scientists who seek to identify genetic loci that impart resistance, conduct marker assisted selection for resistant populations, and for introgression techniques to breed a resistance trait into an elite maize line, for example.

In contrast to fortuitous field observations that classify plants as either "resistant" or "susceptible", various systems are known for scoring the degree of plant resistance or susceptibility. These techniques can be applied to different fields at different times, and provide approximate resistance scores that can be used to characterize a given strain regardless of growth conditions or location.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

The present study was completed by two different association analysis approaches: 1) Population-based Structured association analysis and 2) Pedigree-based association analysis. By identifying such genetic markers, marker assisted selection (MAS) can be used to improve the efficiency of breeding for improved resistance of maize to MRCV infection. Association mapping is known in the art, and is described in various sources, e.g., Jorde (2000) Genome Res. 10:1435-1444; Remington et al. (2001) "Structure of linkage disequilibrium and phenotype associations in the maize genome," Proc Natl Acad Sci USA 98:11479-11484; Weiss and Clark (2002) Trends Genet. 18:19-24; and Shu et al. (2003) "Detection Power of Random, Case-Control, and Case-Parent Control Designs for Association Tests and Genetic Mapping of Complex Traits," Proceedings of 15th Annual KSU Conference on Applied Statistics in Agriculture 15:191-204.

Example 1

Association Mapping Analysis

An association mapping strategy was undertaken to identify maize genetic markers associated with resistance to MRCV infection, which is the causative agent of "Mal de Río Cuarto".

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) “Protective effect of apolipoprotein-E type-2 allele for late-onset Alzheimer-disease,” Nat Genet 7:180-184; Hastbacka et al. (1992) “Linkage disequilibrium mapping in isolated founder populations: diastrophic dysplasia in Finland,” Nat Genet 2:204-211; Kerem et al. (1989) “Identification of the cystic fibrosis gene: genetic analysis,” Science 245:1073-1080) and maize (Remington et al., (2001) “Structure of linkage disequilibrium and phenotype associations in the maize genome,” Proc Natl Acad Sci USA 98:11479-11484; Thornsberry et al. (2001) “Dwarf8 polymorphisms associate with variation in flowering time,” Nat Genet 28:286-289; reviewed by Flint-Garcia et al. (2003) “Structure of linkage disequilibrium in plants,” Annu Rev Plant Biol. 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) “Haplotype blocks and linkage disequilibrium in the human genome,” Nat Rev Genet 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) “Structure of linkage disequilibrium in plants,” Annu Rev Plant Biol. 54:357-374).

Elite breeding lines provide a valuable starting point for association analyses. Association analyses use quantitative phenotypic scores (e.g., disease tolerance rated from one to nine for each maize line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable maize map (for example, a composite map) can optionally be used to help observe distribution of the identified QTL markers and/or QTL marker clustering using previously determined map locations of the markers.

Maize Lines and Phenotypic Scoring

Maize lines were phenotypically scored based on their degree of resistance to MRCV infection (in contrast to simple categorization of “tolerant” or “susceptible”). The plant varieties used in the analysis were from diverse sources, including elite germplasm, commercially released cultivars and other public varieties. The collections comprised 475 maize lines. The lines used in the study had a broad maturity range varying from CRM (comparative relative maturity) 90 to CRM 140, representing the main inbreds of Pioneer germplasm.

The degree of plant resistance to MRCV infection varied widely, as measured using a scale from one (highly susceptible) to nine (highly resistant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains accumulated over multiple locations and multiple years, and an averaged (e.g., consensus) score was ultimately assigned to each line.

Resistance scores for the 475 inbred collection were collected over several growing seasons (394 inbreds were evaluated at the same time in the growing season). Data collection was typically done in one scoring after flowering time.

In assessing the linkage of markers to tolerance, a quantitative approach was used, where a resistance score for each maize line was assessed and incorporated into the association mapping statistical analysis.

Maize Genotyping

A collection of 475 maize lines was analyzed by DNA sequencing at 4000-10000 genes (genetic loci). SNP variation was used to generate specific haplotypes across inbreds at each loci. This data was used for identifying associations between alleles and MRCV resistance at genome level.

Statistical Methods

A structure-based association analysis is conducted using standard association mapping methods where the population structure is controlled by using marker data. The model-based cluster analysis software, Structure, developed by Pritchard et al. was used with haplotype data for 880 elite maize inbreds at two hundred markers to estimate admixture coefficients and assign the inbreds to seven subpopulations (J. K. Pritchard, M. Stephens and P. J. Donnelly (2000) "Inference of population structure using multilocus genotype data," Genetics 155: 945-959). This reduces the occurrence of false positives that can arise due to the effect of population structure on association mapping statistics. Kuiper's statistic for testing whether two distributions are the same is used to test a given marker for association between haplotype and phenotype in a given subpopulation (W. H. Press, S. A. Teukolsky, W. T. Vetterling, B. P. Flannery, 2002; Numerical Recipes in C, second edition, Cambridge University Press, NY).

The Pedigree-based association mapping is conducted using GPA Procedure (General Pedigree-Based Association Analysis), developed by Shu et al. (Guoping Shu, Beiyan Zeng, and Oscar Smith, 2003; Detection Power of Random, Case-Control, and Case-Parent Control Designs for Association Tests and Genetic Mapping of Complex Traits. Proceedings of 15th Annual KSU Conference on Applied Statistics in Agriculture. 15: 191-204). The GPA Procedure is a conditional likelihood-based association mapping software implemented in SAS Computer Language Version 9.0 (2001, SAS Institute, Cary, N.C.).

Results

Tables 1 and 2 provide tables listing the maize markers that demonstrated linkage disequilibrium with the MRCV phenotype using the Association Mapping method, and they were validated on segregating populations. Also indicated in Tables 1 and 2 are the chromosomes on which the markers are located and their approximate map position relative to other known markers, given in cM, with position zero being the first (most distal from centromere) marker known at the beginning of the chromosome. These map positions are not absolute, and represent an estimate of map position. Tables 6 and 7 provide the primer and probe sequences used to type the SNP markers.

The statistical probabilities that the marker allele and disease tolerance phenotype are segregating independently are reflected in the association mapping adjusted probability values in Tables 1 and 2, which is a probability (P) derived from analysis of association between genotype and phenotype. The lower the probability value, the more significant is the association between the marker genotype at that locus and the MRCV infection tolerance phenotype.

Non-structured association analysis for the named SS group revealed the presence of two peaks of probability on chromosome 2, at position 65.99 represented by markers MZA2038 (p=0.00000266) and MZA11826 (p=0.00000179) and at position 127.18-131.13 represented by markers MZA11806 (p=0.000002) and MZA14212 (p=0.00000327). The non-structured analysis also revealed several other associations across the genome. The only consistent association that it was validated by independent approaches corresponded to the position 65.99 on chromosome 2. The non-structured analysis increases the power to evaluate the whole allele variability for a target region but at the same time increase the number of false positive associations because population structure is not corrected by this analysis.

FIG. 1A shows a structured association analysis of a group of argentinian inbreds (or inbreds target for the argentine breeding program) where several markers were significant at 0.0005 p-level at the region from position 65.99 to 85.84, including MZA16656 (P=0.000194), MZA18224 (p=0.000066) and MZA5057 (p=0.000045). FIG. 1B shows a structured association analysis for an SS group where on the short arm of chromosome 2, the most associated markers were MZA1525 at position 54.62 (p=0.00043) and MZA11826 at position 65.99 (p=0.00168). Two additional associations were observed at position 91.19 represented by marker MZA13812 (p=0.000299) and position 154.06 represented by marker MZA10682 (p=0.000024).

FIG. 1C shows a structured association analysis for the SS group with a different set of phenotypic data. The highest associated marker on the short arm of chromosome 2 was MZA12899 at position 53.83 (p=0.000298). There were other associated markers in the long arm of chromosome 2 where the highest associated markers were MZA1067 (Map position: 141.9; p=0.000094) and MZA10832 (Map position: 159.8; p=0.000086).

Example 2

QTL Interval Mapping and Single Marker Regression Analysis

A QTL interval mapping and a single marker regression analysis was undertaken to identify maize chromosome intervals and genetic markers (respectively) that are associated with resistance and allow the plant resistance of maize to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Two main mapping populations for MRCV resistance were created from the crosses of inbreds PH7WT (resistant genotype) and PH3DT (highly susceptible genotype), and PH9TJ (resistant genotype) and PH890 (susceptible genotype). The PH7WTxPH3DT population consisted of 120 F5/F7 families and the PH9TJxPH890 consisted of 212 BC2F4/BC2F5 families.

Phenotypic Scoring

Phenotypic scoring of each of the lines was based on sets of phenotypic data collected from the field on two (PH890xPH9TJ cross) or three different crop seasons (PH7WTxPH3DT).

Maize Genotyping

Maize F5 progeny of PH7WTxPH3DT were genotyped using a total of 246 polymorphic and good quality markers and the BC2F4 progeny of PH890xPH9TJ were genotyped with 167 polymorphic and good quality markers. First round of genotyping included SSR markers. A second round of genotyping with a set of 101 polymorphic and good quality markers was performed on F7 PH7WTxPH3DT progeny. A second round of genotyping was performed on PH890xPH9TJ population by using a set of makers at specific genomic regions.

Windows QTL Cartographer (the most up-to-date version of this software was used according the date of QTL mapping) was used for both the marker regression analysis and QTL interval mapping. LOD scores (logarithm of the odds ratio) were estimated across the genome according the standard QTL mapping procedures. The term "likelihood of odds" is used to describe the relative probability of two or more explanations of the sources of variation in a trait. The probability of these two different explanations (models) can be computed, and the most likely model chosen. If model A is 1000 times more probable than model B, then the ratio of the odds are 1000:1 and the logarithm of the odds ratio is 3.

Both the raw data for individual replications and years, and mean scores, were used in QTL interval mapping. The LOD threshold was 2.5. A confidence interval was estimated for each QTL. The positions obtained are then plotted as a histogram overlaying the interval mapping figure.

Results

QTL Interval Mapping

The present study identified various chromosome intervals that correlate with QTLs that associate with resistance/susceptibility to MRCV infection. The QTLs were identified using the field data. One major, significant QTL was located on linkage group 2 on both mapping crosses (see FIGS. 12-14; see also Table 13, which shows a QTL marker regression analysis for the PH890xPH9TJ cross).

Markers that lie within these intervals are useful for use in MAS, as well as other purposes.

Example 3

QTL Validation by Marker Assisted Selection

A QTL interval mapping and a single marker regression analysis was undertaken to identify maize chromosome intervals and genetic markers (respectively) that are associated with resistance and allow the resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

One main population for validation and mapping of MRCV resistance was created from the cross of inbreds PH7WT and PH3DT. Other populations were generated to validate the effect of this QTL across backgrounds. The

TABLE 13

| Marker | Chrom. | Position | b1 | $F(1, n-2)$ | pr(F) | Rep 1 | b1 | $F(1, n-2)$ | pr(F) | Rep 2 | b1 | $F(1, n-2)$ | pr(F) | Mean Score |
|---|---|---|---|---|---|---|---|---|---|---|---|---|---|---|
| MZA117-12-A | 2 | 34.53 | −0.245 | 4.691 | 0.032 | * | −0.117 | 1.026 | 0.313 | | −0.242 | 7.452 | 0.007 | ** |
| MZA4122-3-A | 2 | 45.60 | −0.354 | 11.881 | 0.001 | *** | −0.383 | 13.637 | 0 | *** | −0.383 | 23.661 | 0 | **** |
| MZA10252-10-A | 2 | 48.85 | −0.389 | 13.624 | 0 | *** | −0.444 | 17.587 | 0 | **** | −0.380 | 21.621 | 0 | **** |
| MZA8381-29-A | 2 | 63.47 | −0.640 | 45.160 | 0 | **** | −0.716 | 58.110 | 0 | **** | −0.640 | 85.828 | 0 | **** |
| MZA625-30-A | 2 | 64.05 | −0.638 | 50.504 | 0 | **** | −0.686 | 58.803 | 0 | **** | −0.622 | 90.530 | 0 | **** |
| MZA16656-8-A | 2 | 65.99 | −0.719 | 66.790 | 0 | **** | −0.727 | 66.005 | 0 | **** | −0.685 | 117.393 | 0 | **** |
| MZA9105-6-A | 2 | 65.44 | −0.719 | 66.790 | 0 | **** | −0.727 | 66.005 | 0 | **** | −0.685 | 117.393 | 0 | **** |
| MZA9510-8-A | 2 | 65.44 | −0.702 | 64.097 | 0 | **** | −0.720 | 65.830 | 0 | **** | −0.673 | 114.098 | 0 | **** |
| MZA18224-801-A | 2 | 68.80 | −0.739 | 69.538 | 0 | **** | −0.730 | 64.530 | 0 | **** | −0.698 | 119.381 | 0 | **** |
| MZA2349-71-A | 2 | 68.80 | −0.694 | 60.777 | 0 | **** | −0.625 | 44.607 | 0 | **** | −0.651 | 100.026 | 0 | **** |
| MZA18036-23-A | 2 | 71.75 | −0.576 | 41.165 | 0 | **** | −0.531 | 32.632 | 0 | **** | −0.543 | 65.053 | 0 | **** |
| MZA8189-16-A | 2 | 76.80 | −0.542 | 37.689 | 0 | **** | −0.538 | 35.626 | 0 | **** | −0.529 | 64.896 | 0 | **** |
| MZA10094-6-A | 2 | 80.90 | −0.501 | 30.686 | 0 | **** | −0.475 | 26.107 | 0 | **** | −0.477 | 48.187 | 0 | **** |
| MZA7266-6-A | 2 | 96.43 | −0.267 | 5.081 | 0.025 | * | −0.169 | 1.955 | 0.164 | | −0.223 | 5.677 | 0.018 | * |
| MZA15573-12-A | 5 | 144.73 | −0.153 | 1.371 | 0.243 | | −0.332 | 6.482 | 0.012 | * | −0.234 | 5.252 | 0.023 | * |
| MZA7908-20-A | 5 | 152.87 | −0.284 | 7.206 | 0.008 | ** | −0.421 | 16.156 | 0 | **** | −0.336 | 17.077 | 0 | **** |
| MZA8726-9-A | 5 | 154.05 | −0.326 | 10.429 | 0.001 | ** | −0.459 | 21.357 | 0 | **** | −0.375 | 23.713 | 0 | **** |
| MZA4599-24-A | 5 | 167.44 | −0.237 | 5.649 | 0.019 | * | −0.235 | 5.380 | 0.022 | * | −0.293 | 14.552 | 0 | *** |
| MZA8048-8-A | 5 | 168.07 | −0.231 | 5.339 | 0.022 | * | −0.234 | 5.305 | 0.022 | * | −0.291 | 14.201 | 0 | *** |
| MZA3899-10-A | 5 | 175.23 | −0.123 | 1.292 | 0.257 | | −0.225 | 4.264 | 0.040 | * | −0.211 | 6.270 | 0.013 | * |

A second QTL was identified on linkage group 5 at position 150-160 (PH890xPH9TJ pop) and another at position 200-220 on linkage group 5 (PH7WTxPH3DT pop). A third QTL was mapped on PH7WTxPH3DT at position 165-185 on chromosome 2.

Single Marker Regression

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on Chr 2 identified by both marker regression and association mapping.

Discussion/Conclusions

This present study has identified chromosome intervals and individual markers that correlate with MRCV resistance.

PH7WTxPH3DT population consisted of 82 BC3F3 families generated by introgress by markers the QTL mapped on chromosome 2 into PH3DT. There were 4 additional BC1F3 populations generated by marker assisted selection that consisted of 24 BC1F3 from the cross PH6KWxPH7WT, 12 BC1F3 from the cross PH6B8xPH7WT, 3 BC1F3 from the cross PHP3P1xPH7WT and 6 BC1F3 from the cross PH6GFxPH7WT. These populations were generated by selfing specific BC3 or BC1 plants and deriving BC3F3 or BC1F3 families with allelic variation at the QTL region.

Phenotypic Scoring

Phenotypic scoring of each of the BC1F3, BC3F3 and parents was based on sets of phenotypic data collected from the field on one crop season.

Maize Genotyping

Maize BC1F2 progeny from the different crosses and BC3F3 from the cross PH7WTxPH3DT were genotyped by using polymorphic SNPs at the QTL region. BC3F3 were subjected to background clean at BC3 stage, especially at chromosome 5 QTL. Markers included SNP markers.

Windows QTL Cartographer (up-to-date version according the date of QTL mapping) was used for both the marker regression analysis and QTL interval mapping. LOD scores (logarithm of the odds ratio) were estimated across the genome according the standard QTL mapping procedures.

Both the raw data for individual replications and mean scores were used in QTL interval mapping. The LOD threshold was 2.5. A confidence interval was estimated for each QTL. The positions obtained are then plotted as a histogram overlaying the interval mapping figure.

As these population were generated by marker assisted selection (not random events of recombination), marker regression analysis was considered as powerful as interval mapping analysis.

Results

QTL Interval Mapping

The present study identified a single chromosome interval that correlated with QTLs associated with resistance/susceptibility to MRCV infection. The QTL were identified using the field data. One major significant QTL was located on linkage group 2 on the main validation BC3F3 population. The main markers at this QTL in the main validation population when checked on the other BC1F3 progenies confirmed the effect of this QTL on resistance/susceptibility to MRCV infection.

Single Marker Regression

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on chromosome 2 identified by both marker regression and association mapping. See FIG. 2 for interval mapping and Table 14 for marker regression analysis for the PH3DTxPH7WT cross. Note that replication #3 was affected by herbicide stress. MRCVSC=MRCV phenotypic score. Inc. Sev. Symp.=frequency of plants with severe symptoms on each experimental unit.

TABLE 14

| Marker | Chrom. | Position | F(1, n − 2) | pr(F) | Rep 1 | F(1, n − 2) | pr(F) | Rep 2 | F(1, n − 2) | pr(F) | Rep 3 | F(1, n − 2) | pr(F) | Mean Score |
|---|---|---|---|---|---|---|---|---|---|---|---|---|---|---|
| | | | Inc sev symptoms | | | Inc sev symptoms | | | Inc sev symptoms | | | Inc sev symptoms | | |
| MZA2592-73-A | 2 | 9.29 | 3.49 | 0.07 | | 4.22 | 0.04 | | 1.19 | 0.28 | | 6.29 | 0.01 | * |
| MZA225-50-A | 2 | 25.51 | 5.57 | 0.02 | * | 3.10 | 0.08 | | 1.38 | 0.24 | | 6.35 | 0.01 | * |
| MZA3334-4-A | 2 | 33.38 | 9.98 | 0 | ** | 2.15 | 0.015 | | 5.60 | 0.02 | * | 10.58 | 0 | ** |
| MZA4122-3-A | 2 | 45.60 | 26.19 | 0 | **** | 9.49 | 0 | ** | 10.21 | 0 | ** | 31.82 | 0 | **** |
| MZA8067-27-A | 2 | 52.77 | 28.10 | 0 | **** | 9.21 | 0 | ** | 9.57 | 0 | ** | 31.56 | 0 | **** |
| MZA5822-15-A | 2 | 53.53 | 30.53 | 0 | **** | 10.77 | 0 | ** | 10.26 | 0 | ** | 35.66 | 0 | **** |
| MZA1525-98-A | 2 | 54.62 | 32.66 | 0 | **** | 12.89 | 0 | *** | 10.85 | 0 | ** | 40.37 | 0 | **** |
| MZA8381-801-A | 2 | 63.47 | 34.31 | 0 | **** | 14.25 | 0 | *** | 11.56 | 0 | ** | 43.52 | 0 | **** |
| MZA625-29-A | 2 | 64.05 | 34.27 | 0 | **** | 13.94 | 0 | *** | 11.91 | 0 | *** | 44.63 | 0 | **** |
| MZA625-30-A | 2 | 65.99 | 34.88 | 0 | **** | 14.21 | 0 | *** | 11.78 | 0 | *** | 44.21 | 0 | **** |
| MZA16656-19-A | 2 | 65.99 | 32.03 | 0 | **** | 13.17 | 0 | *** | 11.08 | 0 | ** | 40.36 | 0 | **** |
| MZA15490-801-A | 2 | 65.99 | 34.31 | 0 | **** | 14.66 | 0 | *** | 11.46 | 0 | ** | 44.16 | 0 | **** |
| MZA2038-71-A | 2 | 65.99 | 34.31 | 0 | **** | 14.66 | 0 | *** | 11.46 | 0 | ** | 44.16 | 0 | **** |
| MZA11826-803-A | 2 | 65.99 | 34.31 | 0 | **** | 14.66 | 0 | *** | 11.46 | 0 | ** | 44.16 | 0 | **** |
| MZA11826-801-A | 2 | 65.99 | 34.31 | 0 | **** | 14.66 | 0 | *** | 11.46 | 0 | ** | 44.16 | 0 | **** |
| MZA9105-8-A | 2 | 65.44 | 34.30 | 0 | **** | 14.67 | 0 | *** | 11.46 | 0 | ** | 44.16 | 0 | **** |
| MZA18224-801-A | 2 | 68.80 | 34.19 | 0 | **** | 14.76 | 0 | *** | 11.39 | 0 | ** | 44.14 | 0 | **** |
| MZA18036-23-A | 2 | 71.75 | 29.40 | 0 | **** | 11.65 | 0 | ** | 9.41 | 0 | ** | 35.80 | 0 | **** |
| MZA15853-10-A | 2 | 77.72 | 23.81 | 0 | **** | 5.97 | 0.02 | * | 6.02 | 0.02 | * | 22.76 | 0 | **** |
| MZA10094-6-A | 2 | 80.90 | 23.24 | 0 | **** | 5.82 | 0.02 | * | 7.91 | 0.01 | ** | 24.05 | 0 | **** |
| MZA15844-19-A | 2 | 82.87 | 19.48 | 0 | **** | 3.67 | 0.06 | | 8.16 | 0.01 | ** | 19.32 | 0 | **** |
| MZA4425-25-A | 2 | 85.68 | 12.42 | 0 | *** | 1.94 | 0.17 | | 6.37 | 0.01 | * | 12.15 | 0 | *** |
| MZA7964-33-A | 2 | 94.40 | 6.24 | 0.02 | * | 2.08 | 0.15 | | 6.23 | 0.02 | * | 7.90 | 0.01 | ** |
| MZA1962-33-A | 2 | 96.01 | 5.32 | 0.02 | * | 2.01 | 0.16 | | 6.93 | 0.01 | * | 7.36 | 0.01 | ** |
| MZA5581-13-A | 2 | 105.99 | 4.91 | 0.03 | * | 1.47 | 0.23 | | 7.99 | 0.01 | ** | 7.70 | 0.01 | ** |
| MZA3439-8-A | 2 | 128.57 | 4.27 | 0.04 | * | 0.90 | 0.35 | | 7.34 | 0.01 | ** | 6.51 | 0.01 | * |
| MZA4564-49-A | 2 | 142.10 | 5.85 | 0.02 | * | 0.66 | 0.42 | | 8.59 | 0 | ** | 7.49 | 0.01 | ** |
| MZA10883-17-A | 2 | 158.98 | 0.20 | 0.66 | | 0.02 | 0.89 | | 2.26 | 0.14 | | 0.24 | 0.63 | |
| MZA12915-19-A | 2 | 170.53 | 0.00 | 0.98 | | 0.01 | 0.91 | | 0.57 | 0.45 | | 0.04 | 0.84 | |
| MZA10488-21-A | 2 | 177.67 | 0.19 | 0.66 | | 0.01 | 0.91 | | 0.11 | 0.74 | | 0.03 | 0.87 | |
| MZA3152-16-A | 2 | 191.27 | 0.15 | 0.70 | | 0.11 | 0.74 | | 0.74 | 0.39 | | 0.00 | 1.00 | |
| MZA505-250-A | 2 | 201.35 | 1.20 | 0.28 | | 2.22 | 0.14 | | 1.53 | 0.22 | | 3.55 | 0.06 | |
| | | | MRCVSC | | | MRCVSC | | | MRCVSC | | | MRCVSC | | |
| MZA2592-73-A | 2 | 9.29 | 2.87 | 0.09 | | 0.86 | 0.36 | | 0.02 | 0.90 | | 1.37 | 0.25 | |
| MZA225-50-A | 2 | 25.51 | 8.89 | 0 | ** | 3.31 | 0.07 | | 1.15 | 0.29 | | 5.63 | 0.02 | * |
| MZA3334-4-A | 2 | 33.38 | 21.58 | 0 | **** | 4.03 | 0.05 | * | 2.48 | 0.12 | | 11.67 | 0 | ** |
| MZA4122-3-A | 2 | 45.60 | 35.56 | 0 | **** | 6.06 | 0.02 | * | 4.90 | 0.03 | * | 20.90 | 0 | **** |
| MZA8067-27-A | 2 | 52.77 | 48.72 | 0 | **** | 9.52 | 0 | ** | 8.85 | 0 | ** | 32.41 | 0 | **** |
| MZA5822-15-A | 2 | 53.53 | 53.73 | 0 | **** | 9.93 | 0 | ** | 9.06 | 0 | ** | 34.53 | 0 | **** |
| MZA1525-98-A | 2 | 54.62 | 58.15 | 0 | **** | 10.12 | 0 | ** | 8.96 | 0 | ** | 35.86 | 0 | **** |
| MZA8381-801-A | 2 | 63.47 | 58.64 | 0 | **** | 12.09 | 0 | *** | 9.52 | 0 | ** | 39.57 | 0 | **** |
| MZA625-29-A | 2 | 64.05 | 63.88 | 0 | **** | 13.29 | 0 | *** | 10.82 | 0 | ** | 40.92 | 0 | **** |
| MZA625-30-A | 2 | 65.99 | 60.02 | 0 | **** | 12.44 | 0 | *** | 9.81 | 0 | ** | 40.33 | 0 | **** |
| MZA16656-19-A | 2 | 65.99 | 59.49 | 0 | **** | 11.23 | 0 | ** | 10.13 | 0 | ** | 38.87 | 0 | **** |
| MZA15490-801-A | 2 | 65.99 | 62.05 | 0 | **** | 13.09 | 0 | *** | 10.51 | 0 | ** | 41.62 | 0 | **** |

TABLE 14-continued

| Marker | Chrom. | Position | F(1, n − 2) | pr(F) | Rep 1 | F(1, n − 2) | pr(F) | Rep 2 | F(1, n − 2) | pr(F) | Rep 3 | F(1, n − 2) | pr(F) | Mean Score |
|---|---|---|---|---|---|---|---|---|---|---|---|---|---|---|
| MZA2038-71-A | 2 | 65.99 | 62.05 | 0 | **** | 13.09 | 0 | *** | 10.51 | 0 | ** | 41.62 | 0 | **** |
| MZA11826-803-A | 2 | 65.99 | 62.05 | 0 | **** | 13.09 | 0 | *** | 10.51 | 0 | ** | 41.62 | 0 | **** |
| MZA11826-801-A | 2 | 65.99 | 62.05 | 0 | **** | 13.09 | 0 | *** | 10.51 | 0 | ** | 41.62 | 0 | **** |
| MZA9105-8-A | 2 | 65.44 | 62.03 | 0 | **** | 13.09 | 0 | *** | 10.50 | 0 | ** | 41.61 | 0 | **** |
| MZA18224-801-A | 2 | 68.80 | 61.77 | 0 | **** | 13.10 | 0 | *** | 10.43 | 0 | ** | 41.50 | 0 | **** |
| MZA18036-23-A | 2 | 71.75 | 47.25 | 0 | **** | 11.83 | 0 | *** | 7.58 | 0.01 | ** | 40.17 | 0 | **** |
| MZA15853-10-A | 2 | 77.72 | 43.32 | 0 | **** | 8.75 | 0 | ** | 6.44 | 0.01 | * | 31.80 | 0 | **** |
| MZA10094-6-A | 2 | 80.90 | 37.87 | 0 | **** | 7.62 | 0.01 | ** | 9.31 | 0 | ** | 31.20 | 0 | **** |
| MZA15844-19-A | 2 | 82.87 | 33.89 | 0 | **** | 4.90 | 0.03 | * | 8.38 | 0.01 | ** | 26.58 | 0 | **** |
| MZA4425-25-A | 2 | 85.68 | 19.92 | 0 | **** | 1.44 | 0.23 | | 5.28 | 0.02 | * | 15.62 | 0 | *** |
| MZA7964-33-A | 2 | 94.40 | 12.94 | 0 | *** | 2.44 | 0.12 | | 7.06 | 0.01 | ** | 13.89 | 0 | *** |
| MZA1962-33-A | 2 | 96.01 | 11.02 | 0 | ** | 2.34 | 0.13 | | 7.63 | 0.01 | ** | 13.26 | 0 | *** |
| MZA5581-13-A | 2 | 105.99 | 8.12 | 0.01 | ** | 1.93 | 0.17 | | 6.48 | 0.01 | * | 14.69 | 0 | *** |
| MZA3439-8-A | 2 | 128.57 | 2.93 | 0.09 | | 1.47 | 0.23 | | 2.82 | 0.10 | | 7.13 | 0.01 | ** |
| MZA4564-49-A | 2 | 142.10 | 2.90 | 0.09 | | 1.47 | 0.23 | | 2.98 | 0.09 | | 6.78 | 0.01 | * |
| MZA10883-17-A | 2 | 158.98 | 0.00 | 0.96 | | 0.86 | 0.36 | | 0.28 | 0.60 | | 1.83 | 0.18 | |
| MZA12915-19-A | 2 | 170.53 | 0.67 | 0.42 | | 0.43 | 0.51 | | 0.16 | 0.69 | | 0.57 | 0.45 | |
| MZA10488-21-A | 2 | 177.67 | 0.21 | 0.65 | | 0.01 | 0.95 | | 0.04 | 0.85 | | 0.01 | 0.91 | |
| MZA3152-16-A | 2 | 191.27 | 0.62 | 0.43 | | 0.32 | 0.57 | | 0.00 | 1.00 | | 0.31 | 0.58 | |
| MZA505-250-A | 2 | 201.35 | 0.66 | 0.42 | | 0.23 | 0.63 | | 0.07 | 0.80 | | 0.80 | 0.37 | |

The effect of MRCV1 allelic variation on several backgrounds was evaluated by the phenotypic data of BC1F3s progeny with allelic variation at MRCV1 region. MRCV1 resistant allele showed a positive effect across another 4 genetic backgrounds (PH6GF, PHP3P1, PH6B8 and PH6KW inbreds). Table 15 below shows the mean phenotypic score for BC1F3 progeny with allelic variation at MRCV1 region.

TABLE 15

| | Inbreds | | | |
|---|---|---|---|---|
| Marker position 65.99 | PH6GF | PHP3P1 | PH6B8 | PH6KW |
| Inbred score | 3.8 | 2.5 | 3 | 3 |
| BC1F3 susceptible allele (AA) | 5.00 | 4.10 | 4.50 | 4.19 |
| BC1F3 heterozygous allele (AB) | — | 3.53 | 5.17 | 4.26 |
| BC1F3 resistant allele (BB) | 6.11 | 6.17 | 5.47 | 5.00 |
| QTL effect | 1.11 | 2.07 | 0.97 | 0.81 |

Discussion/Conclusions

This present study has identified chromosome intervals and individual markers that correlate with MRCV resistance. Markers that lie within these intervals are useful for use in MAS, as well as other purposes.

Example 4

QTL Validation on DH Breeding Populations

A QTL marker regression analysis was undertaken to identify maize chromosome intervals and genetic markers (respectively) that are associated with resistance and allow the resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Marker enhanced pedigree selection (MEPS) populations means the scheme of breeding population populations for MRCV resistance were created from different crosses of inbreds. The crosses included: a) Crosses with MRCV1 fixed: PHKEFxPHBNA, PHKEFxPHS2G, PHKFDxPHS3J, PHKFAxPHBNA, PHKFAxPHKEF, PHS2YxPHKEF, and b) Crosses with MRCV1 segregating: PH3DTxPHKEF, PHKEFxPH9PR, PHKEFxPH9PR, PHKEFxPHKDK, PHKDNxPHKFD, PHKDNxPHS3J, PHKFDxPHCOG, PHKDKxPHKFA, PHKDNxPH9PH.

TABLE 16

| Population | # Ind | MRCV1 |
|---|---|---|
| PHKEF/PHBNA | 9 | Fixed |
| PHKEF/PHS2G | 13 | Fixed |
| PHKFD/PHS3J | 12 | Fixed |
| PHKFA/PHBNA | 12 | Fixed |
| PHKFA/PHKEF | 34 | Fixed |
| PHS2Y/PHKEF | 12 | Fixed |
| PH3DT/PHKEF | 11 | Segregating |
| PHKEF/PH9PR | 12 | Segregating |
| PHKEF/PHKDK | 18 | Segregating |
| PHKDN/PHKFD | 30 | Segregating |
| PHKDN/PHS3J | 11 | Segregating |
| PHKFD/PHC0G | 9 | Segregating |
| PHKDK/PHKFA | 15 | Segregating |
| PHKDN/PH9PH | 8 | Segregating |

These populations were generated by the doubled haploids process. The number of individuals characterized for MRCV resistance were included in Table 16. Fingerprint data at the main QTL region and identity by descent information was used to define QTL segregating and QTL fixed populations.

Phenotypic Scoring

Phenotypic scoring of each of the DH MEPS population was based on sets of phenotypic data collected from the field in one crop season.

Maize Genotyping

Maize DH progeny from the different crosses were genotyped by using a set of 756 SNPs distributed in the maize genome. The positions obtained are then plotted as a histogram overlaying the interval mapping figure.

Results

QTL Marker Analysis

The present study identified a single major chromosome interval that correlated with QTL associated with resistance/susceptibility to MRCV infection when populations from SS crosses Resistant×Susceptible and segregating for MRCV major QTL on chromosome 2 were selected "a priori" 2. The QTL were identified using the field data. One major, significant QTL was located on linkage group 2. Genetic crosses between inbreds harboring the positive allele of the major QTL on chromosome 2 (QTL fixed by parents) showed most of the progenies with a field MRCV score of 4 or higher.

Single Marker Regression

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on chromosome 2 identified by both marker regression and association mapping. On a group of SS inbreds, main association was located at the MZA10538 marker (position 54.5). On a group of NSS inbreds, a major association was located at position 72 cM.

Discussion/Conclusions

This present study has identified chromosome intervals and individual markers that correlate with MRCV resistance. Markers that lie within these intervals are useful for use in MAS, as well as other purposes.

Example 5

Main Inbreds Characterization

A set of key argentine genetic materials were phenotypically and genetically characterized to confirm maize genetic marker loci associated with resistance to MRCV. By identifying such genetic markers, marker assisted selection (MAS) can be used to improve the efficiency of breeding for improved resistance of maize to MRCV.

Maize Lines and Resistance Scoring

The plant varieties used in the analysis were from diverse sources, including elite germplasm, commercially released cultivars and other public lines representing a broad range of germplasm related to the argentine breeding program and including main sources of MRCV resistance.

The groups of maize lines were assembled for the analysis based on their phenotypic responses against MRCV infection, where the plants were sorted into either highly susceptible or highly resistant varieties. The classifications of resistance and susceptible were based solely on observations of fortuitous, naturally occurring disease incidence in field tests over several years. The degree of plant resistance to MRCV infection varied widely, as measured using a scale from one (highly susceptible) to nine (highly tolerant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains accumulated over multiple locations and multiple years, and an averaged (e.g., consensus) score was ultimately assigned to each line.

Data collection was typically done in one scoring time. Scoring time is placed after flowering time.

In assessing association of markers to resistance, a comparison by simple regression approach was used. Allele origin was checked by the identity by descent approach. Using this approach, those maize lines that were considered to be representative of either the resistant or susceptible classes were used for assessing association. A list of resistant lines was constructed, where inbreds having a resistance score of 4 or greater were considered “Resistant”. Similarly, maize lines with scores of three or less were collectively considered susceptible. Only lines that could be reliably placed into the two groups were used. Once a line is included in the “Resistant” or “susceptible” group, it was treated as an equal in that group. The actual quantitative ratings were also used for association test. In addition to this test, the identity by descent information was used to confirm the resistant allele origin at the highest associated markers.

In the study, 85 maize lines were identified that were considered resistant in the phenotypic spectrum; these plants formed the “RESISTANT” group. Also, 35 maize lines were identified that were judged to be susceptible to MRCV; these strains formed the “SUSCEPTIBLE” group.

Maize Genotyping

Each of the tolerant and susceptible lines was genotyped with a set of 63 SNP markers that span the QTL region at Chromosome 2 using techniques well known in the art. The genotyping protocol consisted of collecting young leaf tissue and isolating genomic DNA from pooled tissue of each inbred. The maize genomic DNA was extracted by the CTAB method, as described in Maroof et al. (1984) Proc. Natl. Acad. Sci. (USA) 81:8014-8018.

The isolated genomic DNA was then used in PCR reactions using amplification primers specific for a large number of markers that covered the QTL region. SNP-type markers were genotyped using an ASH protocol.

The underlying logic is that markers with significantly different allele distributions between the resistant and susceptible groups (i.e., non-random distributions) might be associated with the trait and can be used to separate them for purposes of marker assisted selection of maize lines with previously uncharacterized or characterized resistance or susceptibility to MRCV. The present analysis examined one marker locus at a time and determined if the allele distribution within the resistant group is significantly different from the allele distribution within the susceptible group. This analysis compares the plants' phenotypic score with the genotypes at the target loci.

Results

Tables 1 and 2 list maize markers that demonstrated linkage disequilibrium with the MRCV resistant/susceptibility phenotype. Also indicated in those tables is where the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

Tables 6 and 7 provide the PCR primer sequences that were used to genotype these marker loci.

The non-random distribution of alleles between the resistant and susceptible plant groups at the various marker loci in Tables 1 and 2 is good evidence that a QTL influencing MRCV resistance is linked to these marker loci. Considering that most of the inbreds of this set correspond to a specific breeding program (argentine breeding program), it is expected that Appliants have found linkage disequilibrium with other markers on flanking regions of the gene. The highest associated markers corresponded to the previously considered preferred markers.

As well known in the art, the level of association of target markers to a trait of interest will be determined by the level of linkage disequilibrium at the target region on that specific set of genetic materials. Table 17 below shows the level of association across the target region between the genotypic data of SNPs markers and the response to MRCV.

TABLE 17

| Chr | Pos | Marker | b0 | b1 | F(1, n − 2) | pr(F) | MRCV Trait |
|---|---|---|---|---|---|---|---|
| 2 | 64.05 | MZA625-29-A | 1.612 | −0.322 | 95.712 | 0 | **** |
| 2 | 64.05 | MZA625-30-A | 1.602 | −0.326 | 92.373 | 0 | **** |
| 2 | 65.99 | MZA16656-8-A | 1.613 | −0.255 | 44.107 | 0 | **** |
| 2 | 65.99 | MZA16656-19-A | 1.571 | −0.344 | 105.781 | 0 | **** |
| 2 | 65.99 | MZA15490-137-A | 1.724 | −0.189 | 23.834 | 0 | **** |
| 2 | 65.99 | MZA15490-138-A | 1.731 | −0.179 | 20.667 | 0 | **** |
| 2 | 65.99 | MZA15490-801-A | 1.727 | −0.172 | 19.222 | 0 | **** |
| 2 | 65.99 | MZA2038-71-A | 1.702 | −0.045 | 1.095 | 0.298 | |
| 2 | 65.99 | MZA2038-76-A | 1.691 | −0.063 | 1.987 | 0.161 | |
| 2 | 65.99 | MZA11826-801-A | 1.673 | −0.098 | 4.614 | 0.034 | * |
| 2 | 65.99 | MZA11826-27-A | 1.681 | −0.092 | 4.315 | 0.04 | * |
| 2 | 65.99 | MZA11826-803-A | 1.673 | −0.113 | 6.286 | 0.014 | * |
| 2 | 65.44 | MZA9105-8-A | 1.576 | −0.226 | 22.461 | 0 | **** |
| 2 | 65.44 | MZA9105-6-A | 1.681 | −0.081 | 3.452 | 0.066 | |

In order to evaluate the effect of the allelic variation at this QTL at the hybrid level, a set of 371 hybrids (heterogenous genetic backgrounds) was characterized according to the presence of one (heterozygous for the QTL) or two resistant alleles (homozygous for the QTL) from the parent lines. A positive and additive effect of the resistant allele at the major QTL was observed on the hybrid combinations; no maternal effects were observed. Table 18 below shows the field performance of hybrids with different genotypes at the major QTL.

TABLE 18

| Hybrid genotype at major QTL | Number of hybrids | MRCVSC | Category |
|---|---|---|---|
| AA, homozygous susceptible allele | 65 | 3.8 | Susceptible |
| BA, heterozygous, female resistant allele | 121 | 4.41 | Resistant |
| AB, heterozygous, male resistant allele | 96 | 4.46 | Resistant |
| BB, homozygous resistant allele | 89 | 4.76 | Resistant |

Discussion

There are a number of ways to use the information provided in this analysis for the development of improved maize varieties. One application is to use the associated markers (or more based on a higher probability cutoff value) as candidates for mapping QTL in specific populations that are segregating for plants having tolerance to MRCV infection. In this application, one proceeds with conventional QTL mapping in a segregating population, but focusing on the markers that are associated with MRCV infection tolerance, instead of using markers that span the entire genome. This makes mapping efforts more cost-effective by dramatically reducing lab resources committed to the project. For example, instead of screening segregating populations with a large set of markers that spans the entire genome, one would screen with only those few markers that met some statistical cutoff in the allele association study. This will not only reduce the cost of mapping but will also eliminate false leads that will undoubtedly occur with a large set of markers. In any given cross, it is likely that only a small subset of the associated markers will actually be correlated with tolerance to MRCV infection. Once the few relevant markers are identified in any tolerant parent, future marker assisted selection (MAS) efforts can focus on only those markers that are important for that source of tolerance. By pre-selecting lines that have the allele associated with tolerance via MAS, one can eliminate the undesirable susceptible lines and concentrate the expensive field testing resources on lines that have a higher probability of being resistant to MRCV infection.

Example 6

QTL Evaluation on F3 Breeding Populations

Marker associations are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Old scheme of breeding was based on the traditional pedigree based method of making F1 crosses and deriving several self generations (F2, F3, F4, etc.). With the goal of checking the importance of the positive and negative alleles at the major QTL for MRCV resistance in a specific set of argentine breeding materials, these steps were followed: a) Selection of resistant parents whose resistance is expected to be based on the major MRCV1; b) Selecting a total of 2372 F3 families originated from multiple breeding crosses; c) Making two groups of F3 families, a first group, based on crosses between parents without the positive alleles of the major QTL and a second group with both parents harboring the positive allele at the major QTL. Fingerprint data at the main QTL region and identity by descent information was used to define QTL segregating and QTL fixed populations (positive/negative). MZA16656 and/or flanking markers were the key markers to define the presence of MRCV1 positive allele.

The total number of individuals located on these groups was 2372. Fingerprint data at main QTL region and identity by descent information was used to define QTL segregating and QTL fixed populations.

Phenotypic Scoring

Phenotypic scoring of each of the F3 populations was based on sets of phenotypic data collected from the field on one crop season.

Maize Genotyping

Individual F3 families were not genotyped. Genotype at major QTL on each individual F3 was estimated according to the specific alleles on both parents. If both parents in a specific F3 population harbor the positive allele at MRCV1, all the progenies from that cross were considered as having the positive allele. If both parents in a specific F3 population harbor the negative allele at MRCV1, all the progenies from that cross were considered as having the negative allele. Standard software was used to the marker ANOVA analysis.

Results

QTL Marker Analysis

The present study supported the conclusion that a major chromosome interval correlated with QTL associated with resistance/susceptibility to MRCV infection when populations from crosses fixed at MRCV major QTL on chromosome 2 were selected "a priori".

Single Marker ANOVA

Using marker ANOVA, there are a number of markers showing association with the tolerance phenotype at a confidence level of P=0.05 or better, as shown in Tables 1 and 2. Some of the markers identified in the marker ANOVA analysis show a concordance of observations with the association mapping, where the different approaches identify the same markers. For example, there are markers at the region from 55 to 70 cM on chromosome 2 identified by both marker regression and association mapping.

Discussion/Conclusions

This present study has identified chromosome intervals and individual markers that correlate with MRCV resistance. Markers that lie within these intervals are useful for use in MAS, as well as other purposes. In this example, Applicants evaluated the effect on MRCV resistance of the allelic variation at MRCV1, and there was a clear the association between this allelic variation and the expected phenotype on a high number of F3 progenies.

Table 19 below shows the F-test of the model where the Source is QTL and two levels of the source were considered: Level AA: F3 populations with fixed susceptible alleles at target region (position 65.99 or inferred by flanking markers) and Level BB: F3 populations with fixed resistant alleles at target region (position 65.99 or inferred by flanking markers).

TABLE 19

One-Way ANOVA: MRCVSC score versus QTL

| Source | DF | SS | MS | F | P |
|---|---|---|---|---|---|
| QTL | 1 | 1656.41 | 1656.41 | 1383.90 | 0.000 |
| Error | 2370 | 2836.69 | 1.20 | | |
| Total | 2371 | 4493.10 | | | |

S = 1.094; R-Sq = 36.87%; R-Sq(adj) = 36.84%

References:

DF. Degree of freedom.

SS. Square Sum.

MS. Mean square.

F. F value.

P. Probability value.

Table 20 below shows a mean test where level AA and level BB represents the allelic variation at target QTL and according to the model included in Table 19. Phenotypic mean for level AA was 3.42 (MRCV susceptible category) and phenotypic mean for level BB was 5.138 (MRCV resistant category).

TABLE 20

| Level | N | Mean | StDev | Individual 95% Confidence Interval For Mean Based on Pooled StDev ---+---------+---------+---------+------ |
|---|---|---|---|---|
| AA | 1462 | 3.420 | 1.048 | (*-) |
| BB | 910 | 5.138 | 1.164 | (-*) |
| | | | | ---+---------+---------+---------+------ 3.50 4.00 4.50 5.00 |

Pooled StDev = 1.094

References:

N: Number of F3 families.

Mean: Phenotypic mean of each level.

StDev: Standard deviation.

Example 7

High-Resolution Gene Mapping and Near-Isogenic Lines

High-resolution gene mapping by progeny testing of homozygous recombinant plants was undertaken for high resolution positioning of the MRCV resistance genes. QTL interval mapping and a single marker regression analysis were performed to identify maize chromosome intervals and genetic markers (respectively) that are associated with resistance and enhance resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

One main population for high-resolution gene mapping of MRCV resistance was created from the cross of inbreds PH7WT and PH3DT. Another population for fine mapping in an independent source was created from the cross of inbreds PH9TJ and PH890. The PH7WTxPH3DT population consisted of 256 BC5F3 families generated by selfing and fixing selected recombinant BC5 plants from a total of 3000 BC5 plants harboring a heterozygous fragment at the region from 50 to 80 cM on chromosome 2. This strategy permitted coverage with recombinants of the whole QTL region (Tables 7 and 8, and FIG. 3A and FIG. 3B). The PH9TJxPH890 population consisted of 245 BC3F3 families generated by: a) Crossing selected BC2F4 plants homozygous for the major QTL on chromosomes 2 and 5 with PH890 (susceptible parent); b) Making two self generations to advance to fixed BC3F3 families.

Table 21 shows the number of BC5F3s recombinants generated from the cross PH3DTxPH7WT. An expected Kb size for each marker interval is also included. Table 22 shows the number of BC5F3s recombinants generated from the cross PH3DTxPH7WT. A comparison with the first estimation of gene content is included.

TABLE 21

| Marker | Pioneer Genetic Map* | Fingerprint bands** | Estimated size of each interval (sequence data) | Total Recombinants | BC5F3s |
|---|---|---|---|---|---|
| MZA625 | 64.05 | | | | |
| MZA16656 | 65.99 | 152 | Higher than 100 Kb | 76 | 59 |
| MZA15451 | 65.99 | — | 10 Kb | — | — |
| MZA15490 | 65.99 | — | Less than 100 Kb | 3 | 2 |
| MZA2038 | 65.99 | 0 | Less than 20 Kb | 1 | 1 |
| MZA11826 | 65.99 | 33 | Higher than 20 Kb | 0 | 0 |
| MZA9150-8-A | 65.44 | 88 | Higher than 50 Kb | 0 | 0 |
| MZA18224-801-A | 68.80 | 400 | Higher than 165 Kb | 51 | 44 |

*Marker ordered according to sequencing, physical, and recombination. Pioneer genetic map is included only as reference.
**Number of fingerprint bands between pairs of markers.

TABLE 22

| PHD Chr | PHD Map Pos | UC7 PCO Vs. Myriad Amplicons | Locus Order | Working Maize Gene ID | Annotation Summary | Recombinants |
|---|---|---|---|---|---|---|
| 2 | 64.05 | MZA625 | Loc_029 | AC191302_5part | Transcription Factor | 59 |
| | | | Loc_028 | AC191302_3 | Putrescine-binding protein; Hypothetical protein | |
| | | | Loc_027 | pco600856 | Putative L-ascorbate peroxidase | |
| | | | Loc_025 | pco530474 | Plastid development protein; DAG | |
| | | | Loc_024 | pco593067 | Hypothetical protein; Vacuolar ATP synthase subunit? | |
| | | | Loc_023 | AC191302_6 | Hypothetical protein | |
| | | | Loc_022 | Inferred by rice and sorghum | Hypothetical protein | |
| | | | Loc_021 | pco641713 | Hypothetical protein | |
| | | | Loc_016 | pco591841 | Growth regulating factor | |
| | | | Loc_015 | Genomic_PCO622600_PCO666161 | G protein-coupled receptor 89C (Homo sapiens) | |
| 2 | 65.99 | MZA166656 | Loc_014 | pco638426 | Major intrinsic protein; NIP; BREVIS RADIX like 1 | |
| | | | Loc_013 | pco514627 | Hypothetical protein | 2 |
| 2 | 65.30 | MZA15451 | Loc_012 | pco588936 | Alternative oxidase AOX3 | |

TABLE 22-continued

| PHD Chr | PHD Map Pos | UC7 PCO Vs. Myriad Amplicons | Locus Order | Working Maize Gene ID | Annotation Summary | Recombinants |
|---|---|---|---|---|---|---|
| | 65.99 | MZA15490 | | pco642154 | Alternative oxidase AOX2 | |
| | | | Loc_010 | Inferred by rice and *sorghum* | Hypothetical protein | 1 |
| | | | Loc_009 | pco644442 | Myb-like; 2-component response regulator | |
| 2 | 65.99 | MZA2038 | Loc_008 | pco641455 | Clathrin interactor; Epsin; Hypothetical protein | |
| | | | Loc_007 | pco640541 | CDC20 WD-repeat protein | 0 |
| | | | Loc_006 | pco651091 | Cobalamin synthesis protein | |
| | | MZA11826 | | | | |
| | | | Loc_005 | pco571541 | Hypothetical protein | |
| | | | Loc_004 | pco525409 | Scramblase | |
| | | | Loc_003 | pco553755 | Hypothetical protein | |
| | | | Loc_002 | pco644099 | Hypothetical protein | |
| 2 | 65.44 | MZA9105 | Loc_001 | pco588179 | Receptor protein kinase | |
| | | AC208537 (CAP) | | | | 13 |
| | | AC197085 (CAP) | | | | 2 |
| | | MZA18224 | | | | 23 |

BC5F3 near-isogenic lines (NIL) harboring allelic variation at the region of the preferred markers (MZA16656, MZA15451, MZA15490, MZA2038, MZA11826 and MZA9105) were generated by marker assisted selection from the PH7WTxPH3DT cross. The NILs were generated by introgressing the QTL region from PH7WT into PH3DT, cleaning the genetic background, and selecting specific recombinants at the region of the preferred markers. By selfing individual BC5F2 plants harboring a heterozygous fragment at the region of the preferred markers, negative and positive near-isogenic lines were derived, and the QTL was treated as a single Mendelian factor.

Phenotypic Scoring

Phenotypic scoring of each of the BC5F3 families from PH7WTxPH3DT cross and the 245 BC3F3 families from PH9TJxPH890 cross and parents was based on sets of phenotypic data collected from the field (field experiments under natural infection, Córdoba Province, Argentina) on one crop season.

In addition to the phenotyping scoring, the specific isolines at the region of preferred markers were characterized by ELISA test for virus in the Buenos Aires Province, Argentina.

Maize Genotyping

Maize BC5F3 progeny from PH7WTxPH3DT cross and BC3F3 from the PH9TJxPH890 cross were genotyped by using polymorphic SNPs at the QTL region on chromosome 2 (see Example 2). In addition, two CAPS markers were designed and used to genotype the BC5F3 progenies; these two CAPS markers were positioned to the interval MZA9105 to MZA18224. In the case of the PH9TJxPH890 cross, additional markers were positioned on the chromosome 5 QTL. The BC5F3s from PH7WTxPH3DT cross were subjected to background cleaning at BC3 stage, especially at chromosome 5 QTL. The BC3F3s from PH9TJxPH890 cross were subjected to background cleaning at BC2 stage.

Windows QTL Cartographer (up-to-date version according the date of QTL mapping) was used for both the marker regression analysis and QTL interval mapping. LOD scores (logarithm of the odds ratio) were estimated across the target regions according the standard QTL mapping procedures.

Mean scores were used in QTL interval mapping. The LOD threshold was 2.5. A confidence interval was estimated for each QTL. The positions obtained are then plotted as a histogram overlaying the interval mapping figure.

As these population were generated by marker assisted selection (not random events of recombination), marker regression analysis was considered as powerful as interval mapping analysis.

Results

QTL Interval Mapping

The present study identified a single chromosome interval that correlated with QTLs associated with resistance/susceptibility to MRCV infection. The QTL were identified using the field data. One major, significant QTL was located on linkage group 2 at the position of "preferred markers" on the high resolution mapping pops from PH7WTxPH3DT and PH9TJxPH890 crosses. The additional QTL on chromosome 5 from PH9TJxPH890 cross was not significant in this analysis.

Single Marker Regression

Figure 1A:
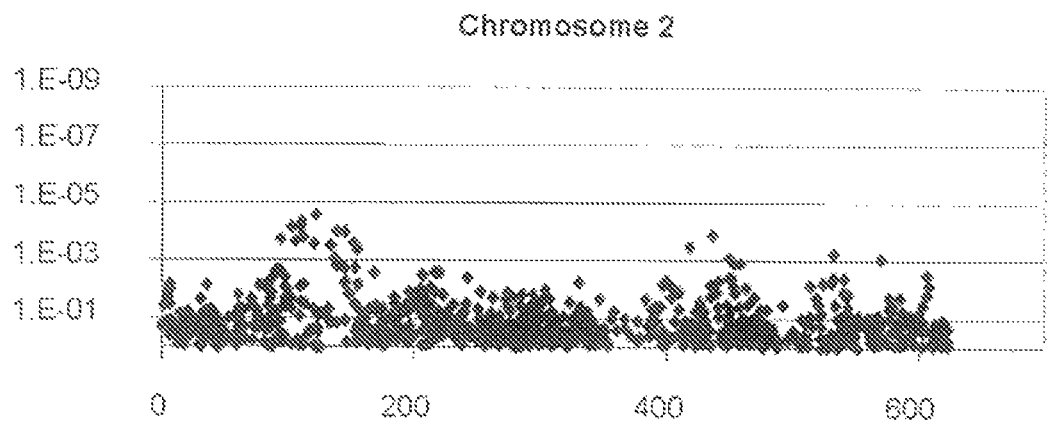
Figure 1B:
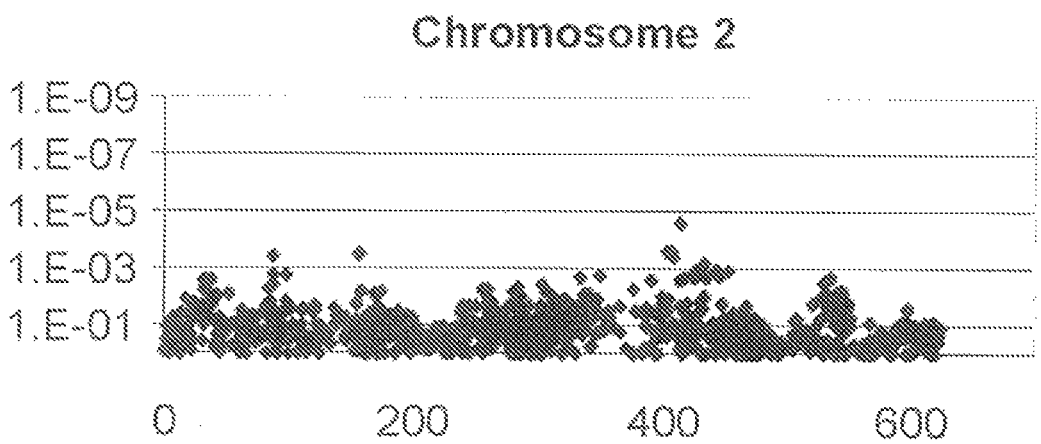
Figure 1C:
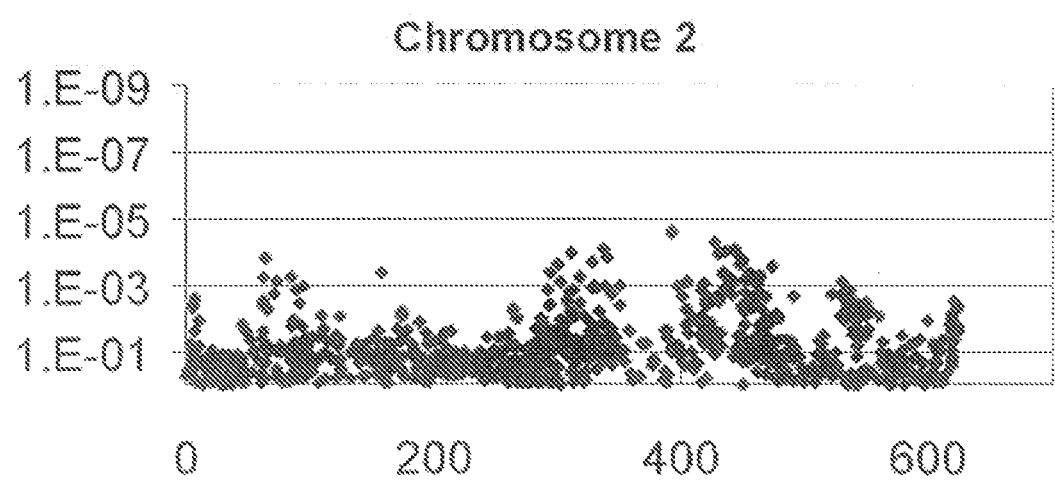
Figure 2:
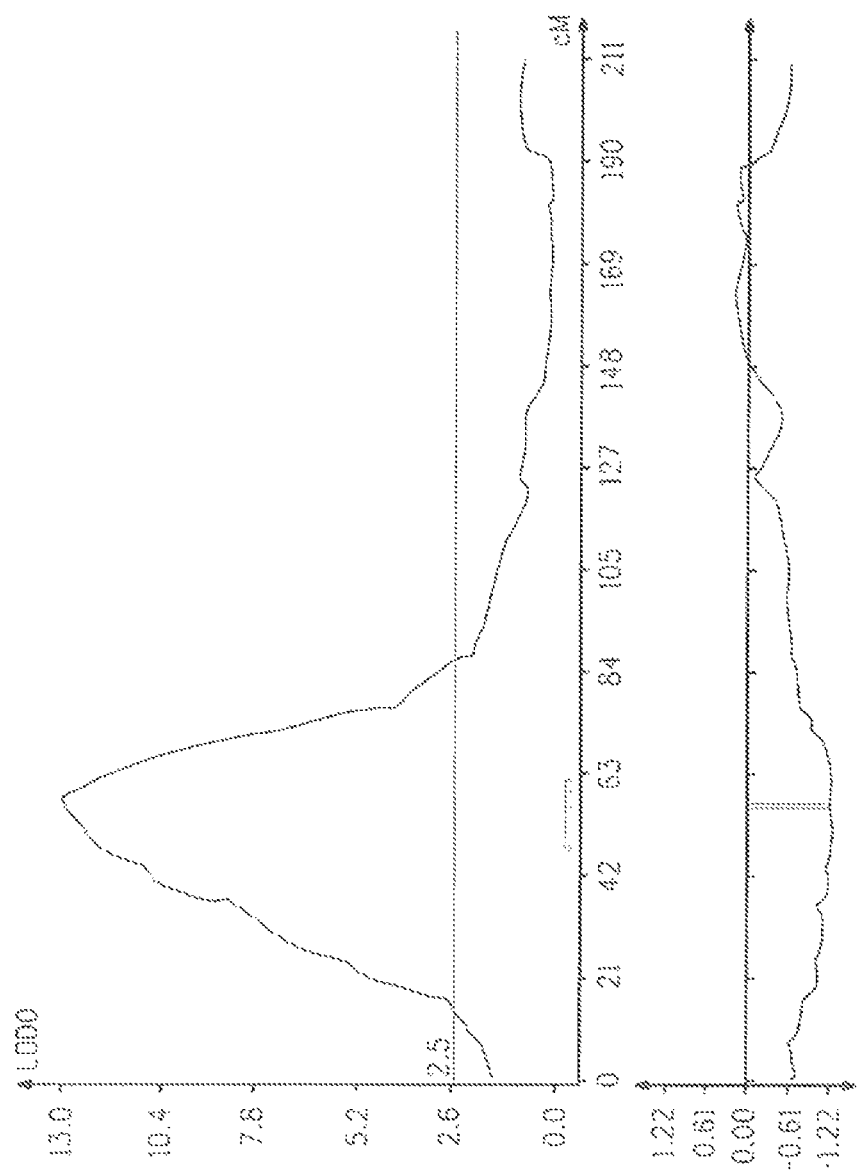
Figure 3A:
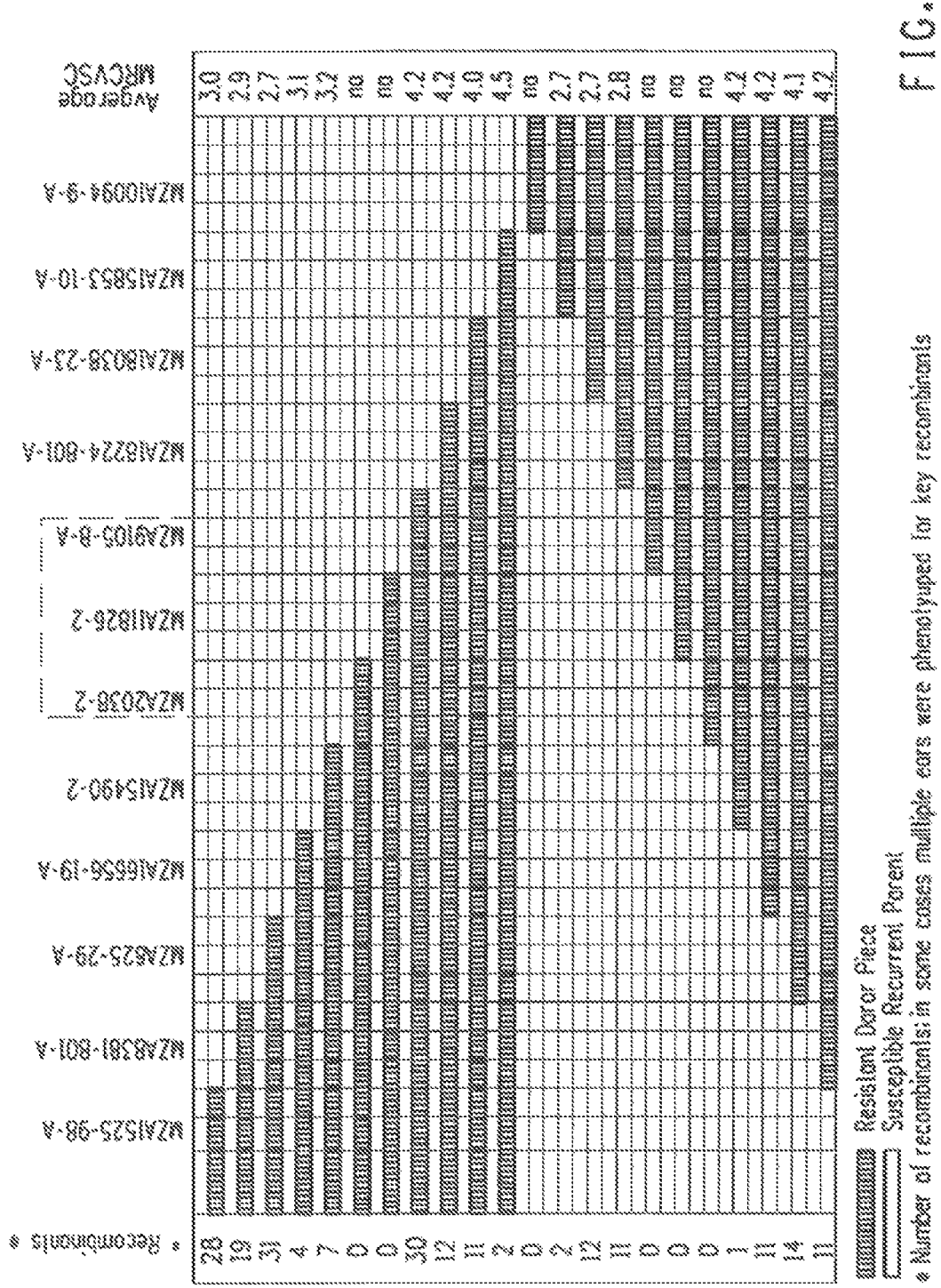
Figure 3B:
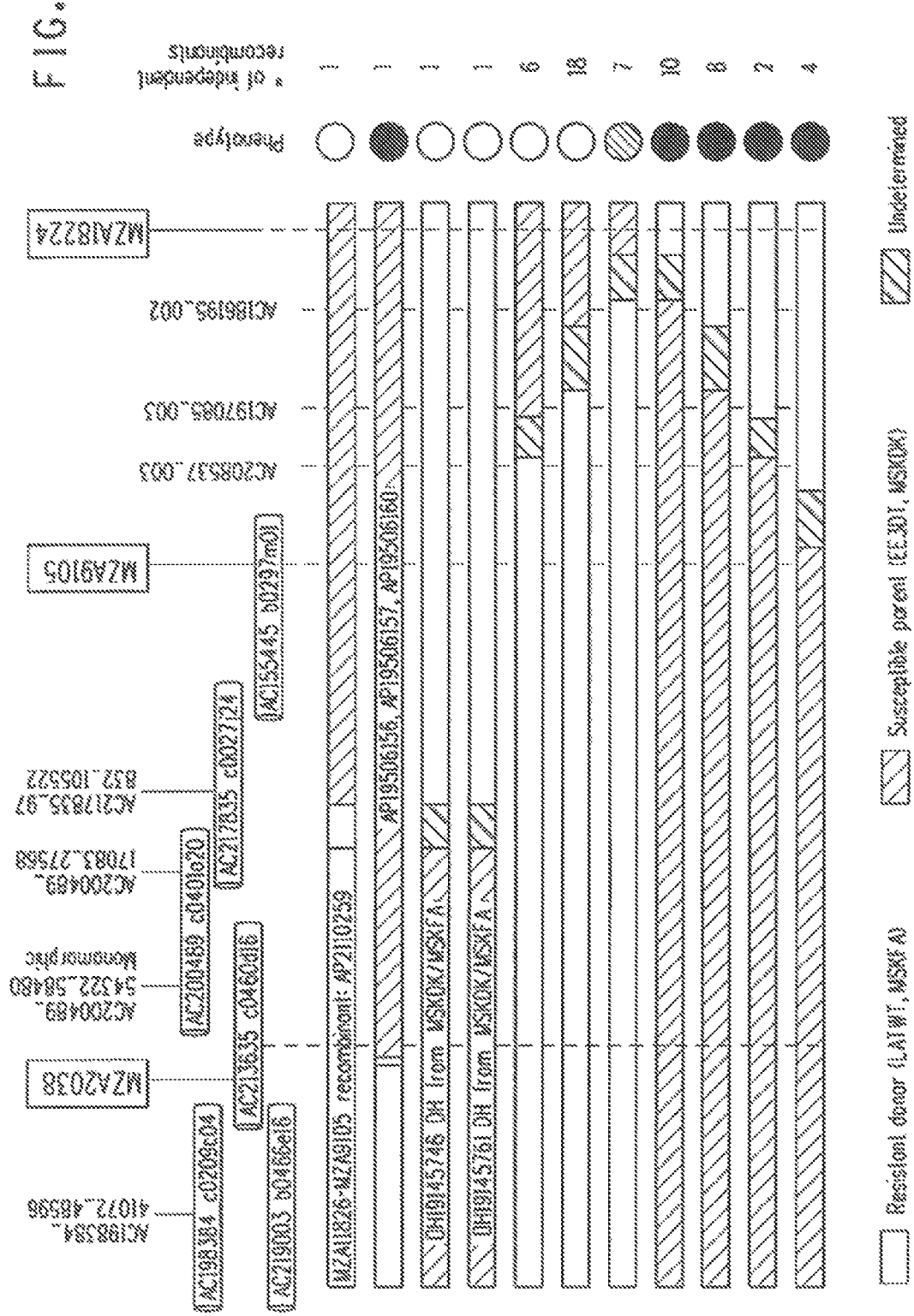
Figure 4:
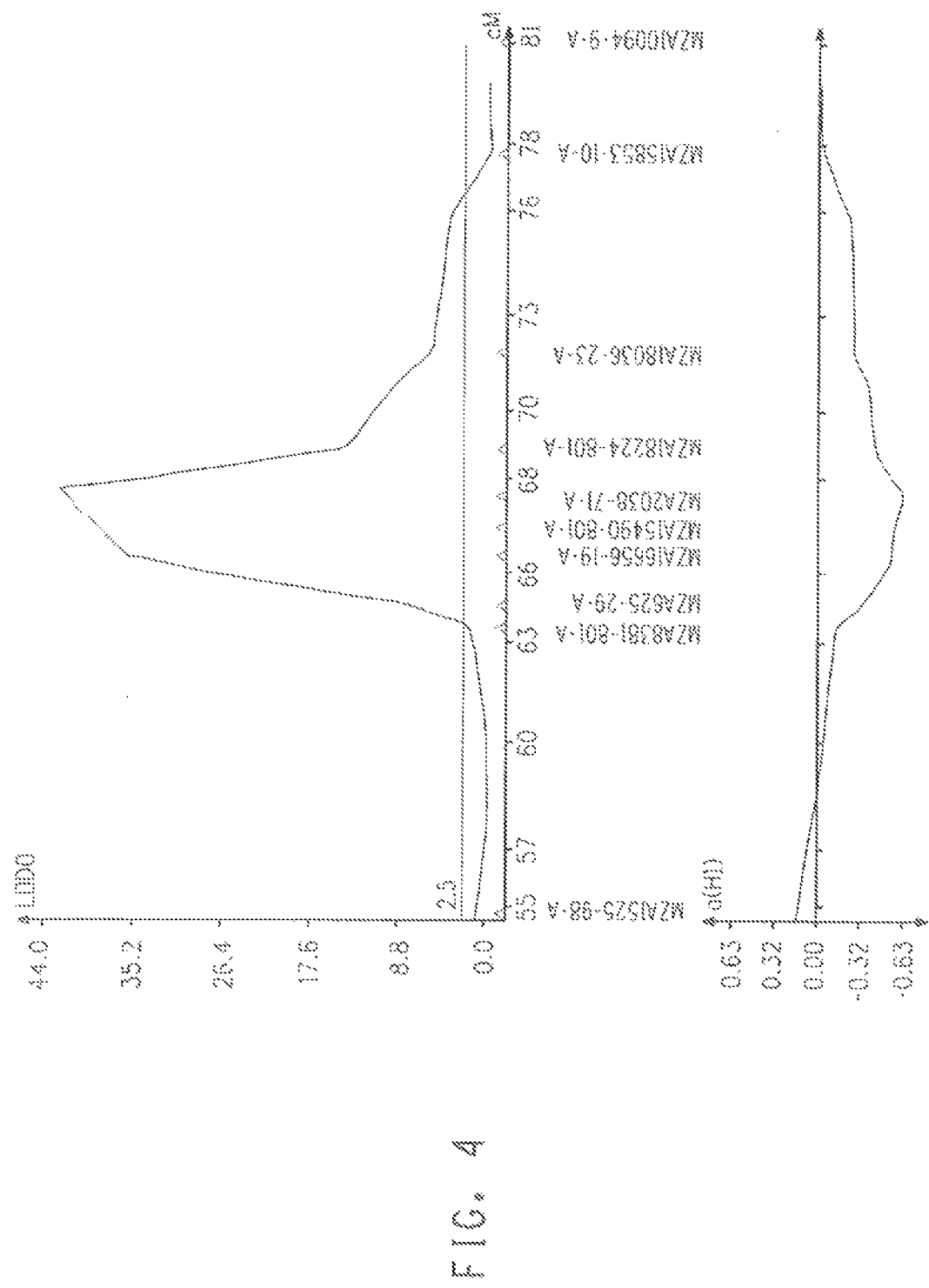
Figure 5:
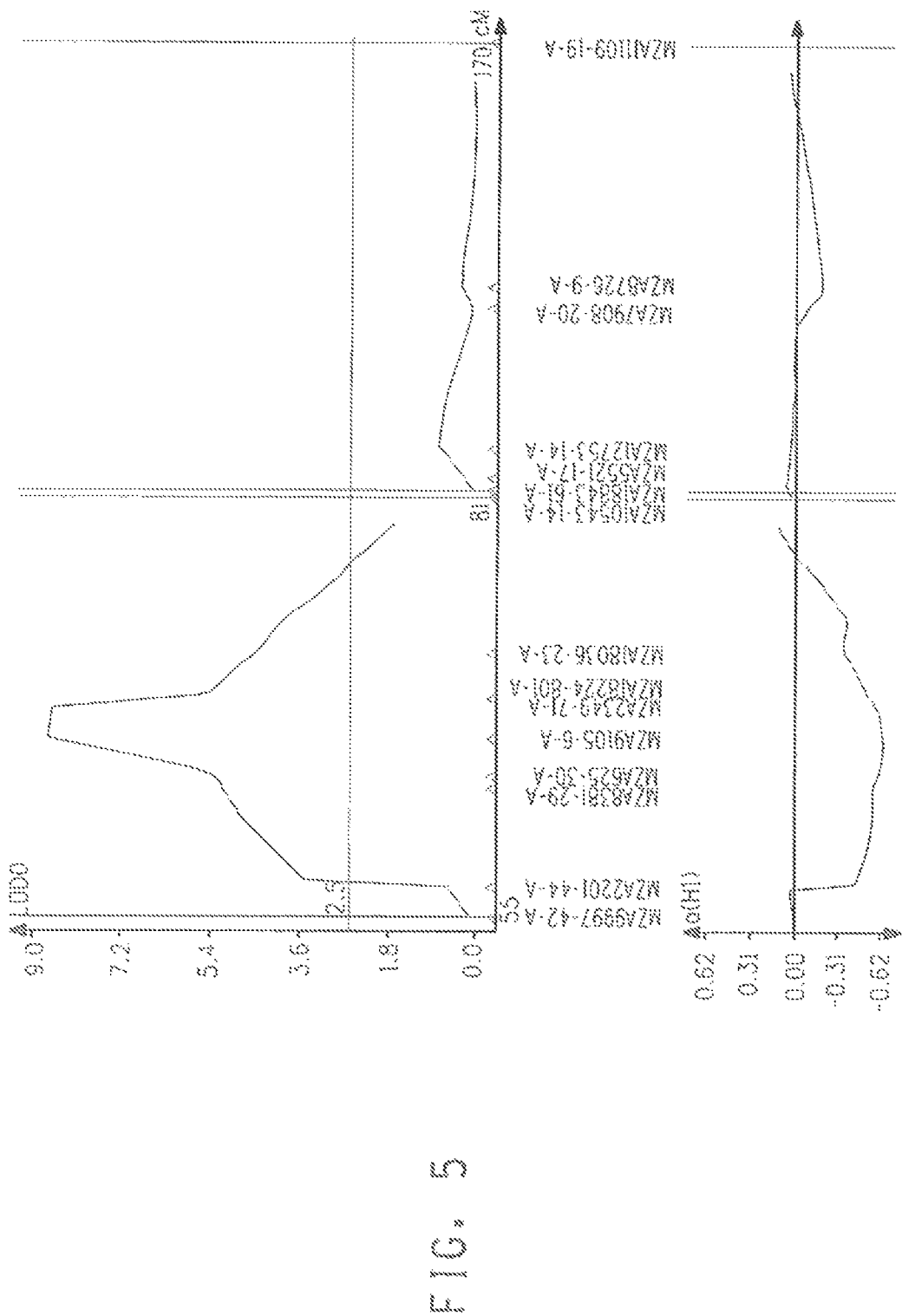

Using single marker regression, there are a number of markers showing association with the resistant phenotype at a confidence level of P=0.05 or better, as shown in Tables 23 and 24. The markers identified in the marker regression analysis show a high resolution gene position for the target QTL, coincident with the position of the preferred markers. See Table 23 for marker regression analysis (MRCVSC=MRCV phenotypic score) and FIG. 4 for interval mapping for the PH7WTxPH3DT cross. See Table 24 for a QTL marker regression analysis for the PH9TJxPH890 cross on specific QTL at chromosomes 2 and 5 (MRCVSC=MRCV phenotypic score) and FIG. 5 for interval mapping for the PH7WTxPH3DT cross.

TABLE 23

| Marker | Position | b0 | b1 | F(1, n − 2) | pr(F) | MRCVSC |
|---|---|---|---|---|---|---|
| MZA1525-98-A | 54.62 | 3.423 | −0.330 | 9.144 | 0.003 | ** |
| MZA8381-801-A | 63.47 | 3.337 | −0.429 | 15.852 | 0 | *** |
| MZA625-29-A | 64.05 | 3.362 | −0.422 | 16.218 | 0 | *** |
| MZA16656-19-A | 65.99 | 3.300 | −0.589 | 38.934 | 0 | **** |
| MZA15490-137-A | 65.99 | 3.331 | −0.597 | 42.193 | 0 | **** |
| MZA2038-71-A | 65.99 | 3.377 | −0.628 | 51.838 | 0 | **** |
| MZA11826-801-A | 65.99 | 3.377 | −0.628 | 51.838 | 0 | **** |
| MZA9105-8-A | 65.44 | 3.377 | −0.628 | 51.838 | 0 | **** |
| AC208537_003 | | 3.448 | −0.257 | 5.276 | 0.025 | * |
| AC197085_003 | | 3.472 | −0.135 | 1.331 | 0.253 | |
| MZA18224-801-A | 68.80 | 3.403 | 0.095 | 0.595 | 0.443 | |

TABLE 24

| Marker | Chr | Pos | b0 | b1 | −2ln(L0/L1) | F(1, n − 2) | pr(F) | MRCVSC |
|---|---|---|---|---|---|---|---|---|
| MZA9997-42-A | 2 | 54.56 | 3.891 | −0.460 | 37.209 | 39.855 | 0 | **** |
| MZA2201-44-A | 2 | 56.95 | 3.828 | −0.334 | 24.549 | 25.610 | 0 | **** |
| MZA8381-29-A | 2 | 63.47 | 3.939 | −0.465 | 33.536 | 35.647 | 0 | **** |
| MZA625-30-A | 2 | 64.05 | 3.907 | −0.485 | 38.029 | 40.803 | 0 | **** |
| MZA9105-6-A | 2 | 66.00 | 3.887 | −0.547 | 51.358 | 56.671 | 0 | **** |
| MZA2349-71-A | 2 | 68.80 | 3.907 | −0.534 | 49.417 | 54.307 | 0 | **** |
| MZA18224-801-A | 2 | 68.80 | 3.902 | −0.531 | 48.959 | 53.751 | 0 | **** |
| MZA18036-23-A | 2 | 71.75 | 3.906 | −0.505 | 43.106 | 46.746 | 0 | **** |
| MZA10543-14-A | 2 | 81.45 | 3.934 | −0.054 | 0.332 | 0.320 | 0.572 | |
| MZA18843-61-A | 5 | 141.08 | 3.897 | 0.004 | 0.003 | 0.003 | 0.958 | |
| MZA5521-17-A | 5 | 141.62 | 3.895 | 0.009 | 0.014 | 0.014 | 0.906 | |
| MZA12753-14-A | 5 | 143.95 | 3.886 | 0.044 | 0.333 | 0.331 | 0.566 | |
| MZA7908-20-A | 5 | 152.87 | 3.903 | −0.046 | 0.311 | 0.309 | 0.579 | |
| MZA8726-9-A | 5 | 154.05 | 3.901 | −0.050 | 0.385 | 0.382 | 0.537 | |
| MZA11109-19-A | 5 | 169.77 | 3.895 | 0.036 | 0.156 | 0.155 | 0.694 | |

Near Isogenic Lines

The near isogenic lines harboring allelic variation at the region of preferred markers showed a significant difference in their response to the disease in Córdoba Province. Table 25 shows the genotype of SNPs at the region of preferred markers for the near isogenic lines (negative isoline=susceptible haplotype; positive isoline=resistant haplotype); the introgressed fragment is represented by the SNP polymorphics at markers from MZA16656-19-A to MZA9105-8-A while flanking monomorphics markers MZA625-30-A and MZA18224-801-A represent the susceptible haplotype on both near isogenic lines. The ELISA test for virus (samples from Buenos Aires Province) showed 0% of plants positive for virus in the isolines harboring the resistant allele, while 38% of plants were positive for virus in the isolines harboring the susceptibility allele.

TABLE 25

| Isoline | MZA625-30-A | MZA16656-19-A | MZA15490-801-A | MZA15490-137-A | MZA2038-71-A | MZA2038-76-A | MZA11826-801-A | MZA11826-803-A | MZA9105-8-A | MZA18224-801-A |
|---|---|---|---|---|---|---|---|---|---|---|
| | 64.05 | 65.99 | 65.99 | 65.99 | 65.99 | 65.99 | 65.99 | 65.99 | 65.44 | 68.8 |
| Negative | C | A | C | A | T | C | G | T | G | A |
| Positive | C | G | G | C | A | T | A | C | A | A |

Note: ELISA test was not performed on materials planted in Córdoba Province (the disease pressure was higher than in Buenos Aires Province). However, the presence of enations (a specific symptom of *Fijivirus*) on both resistant and susceptible materials in Córdoba Province indicates the presence of the virus in the plants.

Discussion/Conclusions

This present study has identified chromosome intervals and individual markers that correlate with MRCV resistance. Markers that lie within these intervals are useful for use in MAS, as well as other purposes. The high resolution gene position facilitates the cloning of the target QTL.

Example 8

Gene Positioning, Sequencing and Candidate Genes

Sequencing, genetic and physical information for the region of the preferred markers was integrated to characterize the target region. Information from independent approaches (recombination data, association analysis and conservative fragments) was used to identify a specific interval for the generation of additional sequencing data.

Maize Lines and Phenotypic Scoring

Maize lines were phenotypically scored based on their degree of resistance to MRCV infection (in contrast to simple categorization of "tolerant" or "susceptible"). The plant varieties used in the analysis were from diverse sources, including elite germplasm, commercially released cultivars and other public varieties. The collections comprised 883 maize lines. The lines used in the study had a broad maturity range varying from CRM (comparative relative maturity) 90 to CRM 140, representing the main inbreds of Pioneer germplasm.

The degree of plant resistance to MRCV infection varied widely, as measured using a scale from one (highly susceptible) to nine (highly resistant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains were accumulated over multiple locations and multiple years, and an averaged (e.g., consensus) score was ultimately assigned to each line.

Resistance scores for part of the 883 inbred collections were collected over several growing seasons (394 inbreds were evaluated at the same time in the growing season). Data collection was typically done in one scoring after flowering time.

Maize Genotyping

A collection of 883 maize lines was analyzed by DNA sequencing at 4000-10000 genes (genetic loci). SNP variation was used to generate specific haplotypes across inbreds at each locus. This data was used for identifying associations between alleles and MRCV resistance at genome level.

Maize Pedigree—Resistance Sources

A Pioneer pedigree database was used to understand the relationship between inbreds and haplotypes. This database contains the pedigree relationship between Pioneer inbreds since 1919. In the case of public inbreds, public information about pedigree and origins was incorporated to understand inbred and haplotype relationship. A list of key founders representing sources of resistance and susceptibility to MRCV in Pioneer germplasm (including public lines) was created by using pedigree, phenotypic and genotypic data. Most of the susceptible inbreds trace back to a specific set of haplotypes from U.S. germplasm (Public lines as B37, B73, B14, OH07, C103 and Pioneer inbreds 165 and 938); an exception is PH26N coming from tropical germplasm.

Gene Positioning

Figure 6:
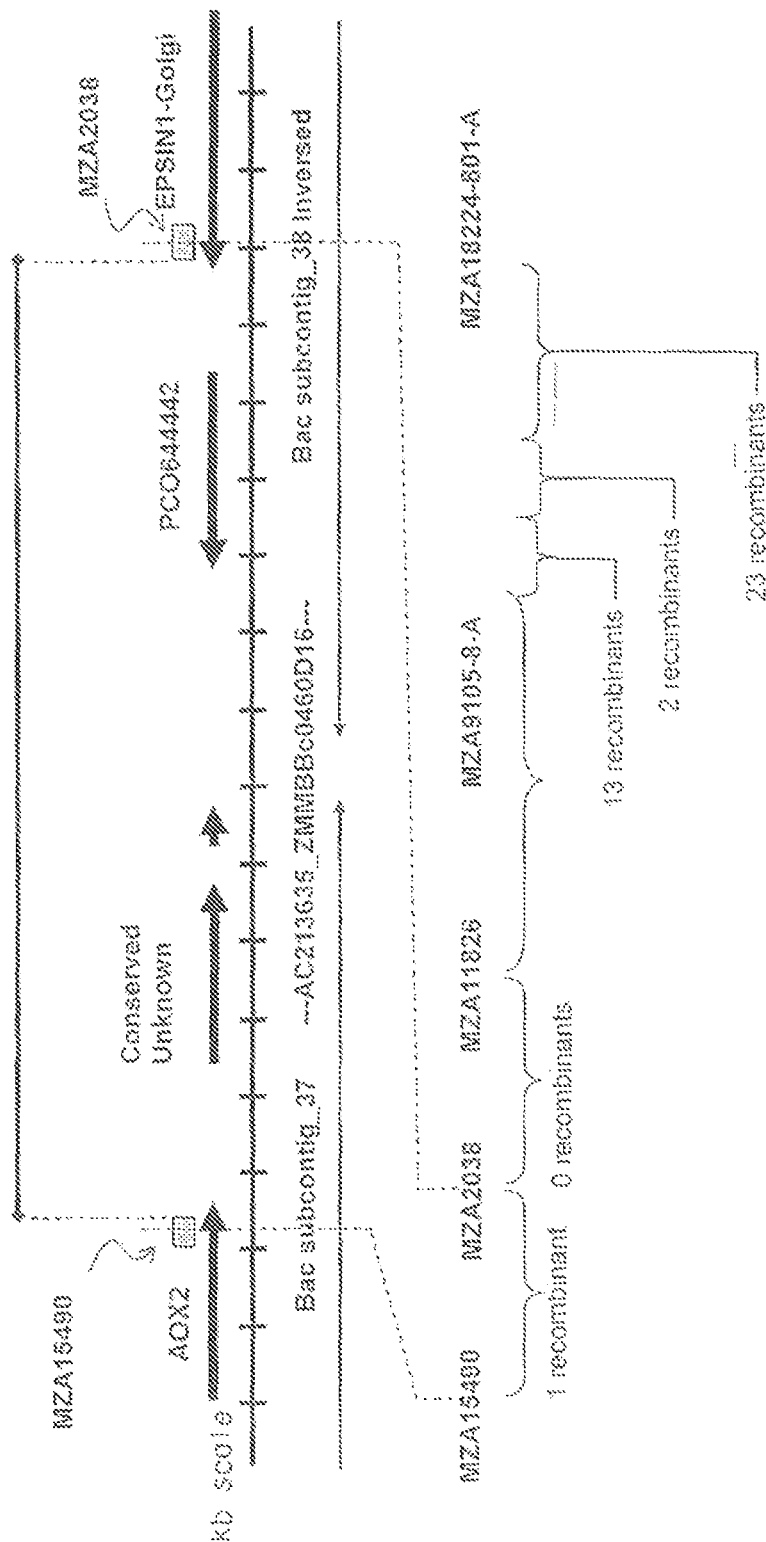
FIG. 6 shows the chromosome 2 QTL region between markers MZA15490 and MZA2038.

The interval between markers MZA15490 and MZA2038 (FIG. 6) was considered as a candidate region for studying the allelic diversity at the resistance gene region. This region was selected by using information from:
a) Recombinants. The positioning by recombinants was showed in Example 7. The phenotypic data for two recombinants at MZA16656 to MZA15490 interval and one recombinant at MZA15490 to MZA2038 interval was used to delimitate the left side of the gene position. From recombination population, there were no available recombinants at the region MZA2038-MZA11826-MZA9105.
b) Genotypic and phenotypic information across inbreds from Pioneer germplasm was used to detect a conservative fragment across resistant/susceptible inbreds. The detection of a conservative fragment was performed inside specific pedigrees and across multiple independent founders when enough conservative SNPs were available across independent founders.

Natural Allelic Diversity and Founder Relationship

The interval MZA15490 to MZA2038 was selected for allelic diversity analysis because of the high probability of harboring a candidate gene or the high linkage disequilibrium with a candidate gene. As the full sequence at MZA15490 to MZA2038 interval is available for B73 (B73=274) line, a group of 13 small sequence fragments were targeted for sequencing in a set of tester's lines. The tester's lines (Table 26) included: a) some of the key resistant and susceptible inbreds and haplotypes; b) the resistant and susceptible parents from the mapping populations PH7WTxPH3DT and PH9TJxPH890; c) key recombinants from the inbred set and recombination population (PHG63 and a recombinant at MZA15490 to MZA2038 interval).

Table 26 shows a list of tester's lines including sources of resistance and susceptibility to MRCV in Pioneer germplasm and a recombinant at MZA15490-MZA2038 interval.

TABLE 26

| Inbred | Phenotype | Expected haplotype | n |
|---|---|---|---|
| PH9TJ | Resistant | PH9TJ | 1 |
| PHJ40 | Resistant | PHJ40 | 5 |
| PHGD3 | — | PHGD3 | 2 |
| 383 | Resistant | — | 1 |
| PHG63 | Resistant | 630 | 14 |
| 630 | Resistant | 630 | 14 |
| PH7WT | Resistant | 630 | 14 |
| PHR33 | Resistant | PHR33 | 1 |
| 501 | — | 501 | — |
| PH467 | Resistant | PH467 | 1 |
| PHDG9 | Resistant | PHDG9 | 1 |
| PHK09 | Resistant | PHK09 | 1 |
| 274 | Susceptible | 274 | 47 |
| 1047 | Susceptible | 1047 | 23 |
| PH26N | Susceptible | PH26N | 1 |
| PH3DT | Susceptible | 274 | 47 |
| PH890 | Susceptible | 1047 | 23 |

TABLE 26-continued

| Inbred | Phenotype | Expected haplotype | n |
|---|---|---|---|
| 165 | Susceptible | 165 | 33 |
| 661 | Susceptible | PHAN0 | 93 |
| PHR03 | Susceptible | PHAN0 | 93 |
| PHK56 | Susceptible | PHAN0 | 93 |
| PHN47 | Susceptible | PHN47 | 1 |
| PHNV8 | Susceptible | PHNV8 | 1 |
| ap19506156 | Susceptible | Recombinant | 1 |
| ap19506157 | Susceptible | Recombinant | 1 |
| ap19506160 | Susceptible | Recombinant | 1 |
| 157 | Susceptible | 625 | 7 |
| 625 | Susceptible | 625 | 7 |
| PHKP5 | — | PHKP5 | 1 |

Figure 7:
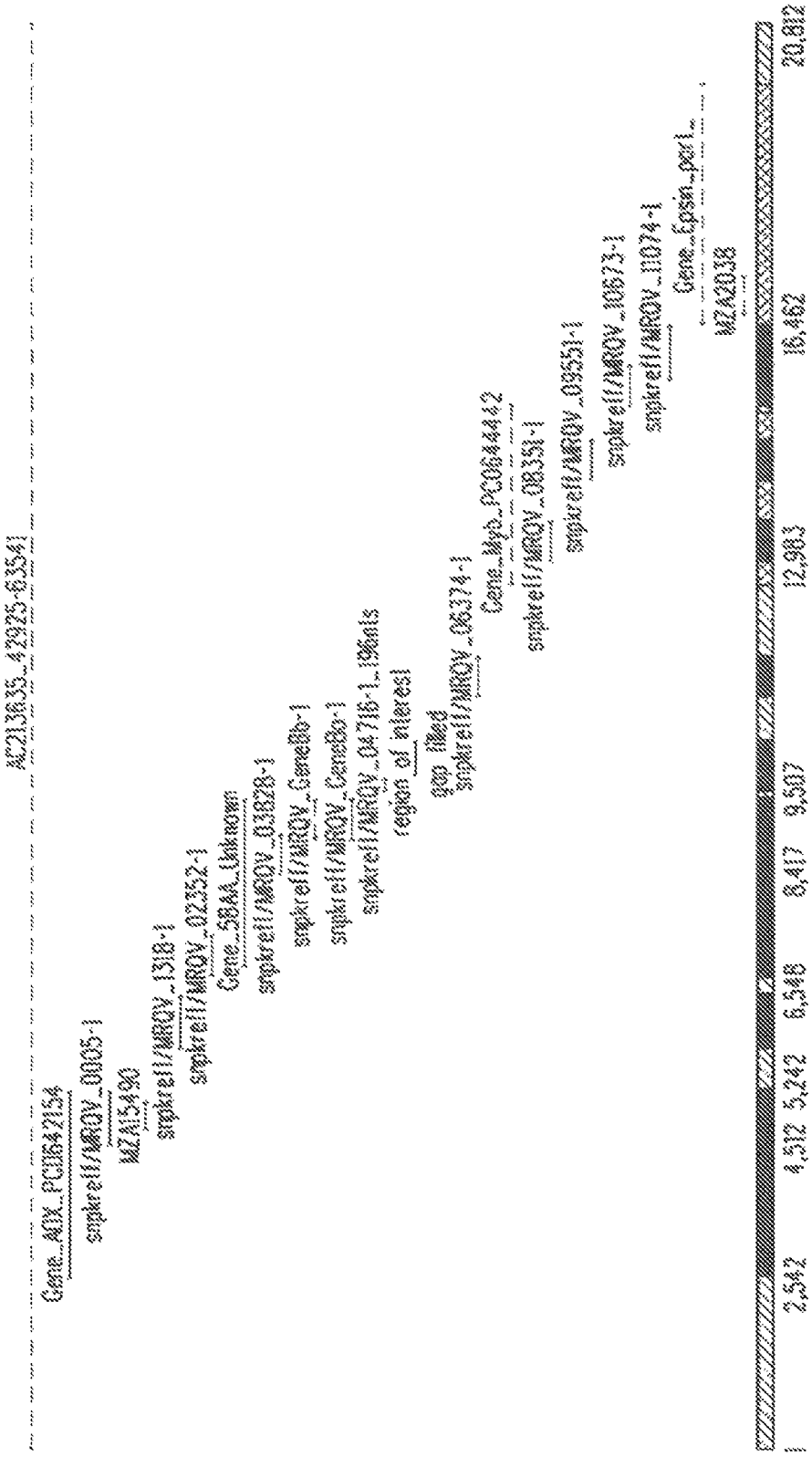
FIG. 7 shows a graphic of the region at the MZA15490 to MZA2038 interval where the position of specific sequenced fragments in a group of representative susceptible and resistant inbreds is indicated.

FIG. 7 shows the position of the targeted fragments in the MZA15490 to MZA2038 interval and the position of candidate genes. Sequencing results were obtained for sequences named: MRQV_00005-1; MRQV_1318-1; MRQV_02352-1; MRQV_03828-1; MRQV_06374-1; MRQV_08351-1; MRQV_09551-1-1; MRQV_10673-1 and MRQV_11074-1. The sequences across the group of tester inbreds for the segments MRQV_08351-1 and MRQV_10673-1 are provided herein, including polymorphic SNPs to characterize haplotypes (see Table 27). The sequence position in the MZA15490 to MZA2038 interval was included in the FIG. 7.

TABLE 27

| | | |
|---|---|---|
| SEQ_ID_NO_213 | TCGCATCTGCAGCTTCTTTTGCACCTGATTACAGACATAAGCACTTGTAGCGTTTATGGA | 60 |
| SEQ_ID_NO_222 | TCGCATCTGCAGCTTCTTTTGCACCTGATTACAGACATAAGCACTTGTAGCGTTTATGGA | 60 |
| SEQ_ID_NO_220 | TCGCATCTGCAGCTTCTTTTGCACCTGATTACAGACATAAGCACTTGTAGCGTTTATGGA | 60 |
| SEQ_ID_NO_235 | TCGCATCTGCAGCTTCTTTTGCACCTGATTACAGACATAAGCACTTGTAGCGTTTATGGA | 60 |
| SEQ_ID_NO_225 | TCGCATCTGCAGCTTCTTTTGCACCTGATTACAGACATAAGCACTTGTAGCGTTTATGGA | 60 |
| SEQ_ID_NO_226 | TCGCATCTGCAGCTTCTTTTGCACCTGATTACAGACATAAGCACTTGTAGCGTTTATGGA | 60 |
| SEQ_ID_NO_228 | TCGCATCTGCAGCTTCTTTTGCACCTGATTACAGACATAAGCACTTGTAGCGTTTATGGA | 60 |
| SEQ_ID_NO_227 | TCGCATCTGCAGCTTCTTTTGCACCTGATTACAGACATAAGCACTTGTAGCGTTTATGGA | 60 |
| SEQ_ID_NO_223 | TCGCATCTGCAGCTTCTTTTGCACCTGATTACAGACATAAGCACTTGTAGCGTTTATGGA | 60 |
| SEQ_ID_NO_215 | TCGCATCTGCAGCTTCTTTTGCACCTGATTACAGACATAAGCACTTGTAGCGTTTATGGA | 60 |
| SEQ_ID_NO_216 | TCGCATCTGCAGCTTCTTTTGCACCTGATTACAGACATAAGCACTTGTAGCGTTTATGGA | 60 |
| SEQ_ID_NO_214 | TCGCATCTGCAGCTTCTTTTGCACCTGATTACAGACATAAGCACTTGTAGCGTTTATGGA | 60 |
| SEQ_ID_NO_233 | TCGCATCTGCAGCTTCTTTTGCACCTGATTACAGACATAAGCACTTGTAGCGTTTATGGA | 60 |
| SEQ_ID_NO_236 | TCGCATCTGCAGCTTCTTTTGCACCTGATTACAGACATAAGCACTTGTAGCGTTTATGGA | 60 |
| SEQ_ID_NO_231 | TCGCATCTGCAGCTTCTTTTGCACCTGATTACAGACATAAGCACTTGTAGCGTTTATGGA | 60 |
| SEQ_ID_NO_229 | TCGCATCTGCAGCTTCTTTTGCACCTGATTACAGACATAAGCACTTGTAGCGTTTATGGA | 60 |
| SEQ_ID_NO_230 | TCGCATCTGCAGCTTCTTTTGCACCTGATTACAGACATAAGCACTTGTAGCGTTTATGGA | 60 |
| SEQ_ID_NO_232 | TCGCATCTGCAGCTTCTTTTGCACCTGATTACAGACATAAGCACTTGTAGCGTTTATGGA | 60 |
| SEQ_ID_NO_234 | TCGCATCTGCAGCTTCTTTTGCACCTGATTACAGACATAAGCACTTGTAGCGTTTATGGA | 60 |
| SEQ_ID_NO_218 | TCGCATCTGCAGCTTCTTTTGCACCTGATTACAGACATAAGCACTTGTAGCGTTTATGGA | 60 |
| SEQ_ID_NO_219 | TCGCATCTGCAGCTTCTTTTGCACCTGATTACAGACATAAGCACTTGTAGCGTTTATGGA | 60 |
| SEQ_ID_NO_217 | TCGCATCTGCAGCTTCTTTTGCACCTGATTACAGACATAAGCACTTGTAGCGTTTATGGA | 60 |
| SEQ_ID_NO_221 | TCGCATCTGCAGCTTCTTTTGCACCTGATTACAGACATAAGCACTTGTAGCGTTTATGGA | 60 |

TABLE 27-continued

| | | |
|---|---|---|
| SEQ_ID_NO_224 | TCGCATCTGCAGCTTCTTTTGCACCTGATTACAGACATAAGCACTTGTAGCGTTTATGGA | 60 |
| | ************************************************************ | |
| SEQ_ID_NO_213 | AGAAAGTTTTGGAGTGCAGATCTCATGACAATGATGTAAATCTATCTTGCCTCAGTTTGT | 120 |
| SEQ_ID_NO_222 | AGAAAGGTTTGGAGTGCAGATCTCATGACAATGATGTAAATCTATCTTGCCTCAGTTTGT | 120 |
| SEQ_ID_NO_220 | AGAAAGTTTTGGAGTGCAGATCTCATGACAATGATGTAAATCTATCTTGCCTCAGTTTGT | 120 |
| SEQ_ID_NO_235 | AGAAAGTTTTGGAGTGCAGATCTCATGACAATGATGTAAATCTATCTTGCCTCAGTTTGT | 120 |
| SEQ_ID_NO_225 | AGAAAGTTTTGGAGTGCAGATCTCATGACAATGATGTAAATCTATCTTGCCTCAGTTTGT | 120 |
| SEQ_ID_NO_226 | AGAAAGTTTTGGAGTGCAGATCTCATGACAATGATGTAAATCTATCTTGCCTCAGTTTGT | 120 |
| SEQ_ID_NO_228 | AGAAAGTTTTGGAGTGCAGATCTCATGACAATGATGTAAATCTATCTTGCCTCAGTTTGT | 120 |
| SEQ_ID_NO_227 | AGAAAGTTTTGGAGTGCAGATCTCATGACAATGATGTAAATCTATCTTGCCTCAGTTTGT | 120 |
| SEQ_ID_NO_223 | AGAAAGTTTTGGAGTGCAAATCTCATGACAATGATGTAAATCTGTCTTGCCTCAGTTTGT | 120 |
| SEQ_ID_NO_215 | AGAAAGTTTTGGAGTGCAAATCTCATGACAATGATGTAAATCTATCTTGCCTCAGTTTGT | 120 |
| SEQ_ID_NO_216 | AGAAAGTTTTGGAGTGCAAATCTCATGACAATGATGTAAATCTATCTTGCCTCAGTTTGT | 120 |
| SEQ_ID_NO_214 | AGAAAGTTTTGGAGTGCAAATCTCATGACAATGATGTAAATCTATCTTGCCTCAGTTTGT | 120 |
| SEQ_ID_NO_233 | AGAAAGTTTTGGAGTGCAGATCTCATGACAATGATGTAAATCTATCTTGCCTCAGTTTGT | 120 |
| SEQ_ID_NO_236 | AGAAAGTTTTGGAGTGCAGATCTCATGACAATGATGTAAATCTATCTTGCCTCAGTTTGT | 120 |
| SEQ_ID_NO_231 | AGAAAGTTTTGGAGTGCAGATCTCATGACAATGATGTAAATCTATCTTGCCTCAGTTTGT | 120 |
| SEQ_ID_NO_229 | AGAAAGTTTTGGAGTGCAGATCTCATGACAATGATGTAAATCTATCTTGCCTCAGTTTGT | 120 |
| SEQ_ID_NO_230 | AGAAAGTTTTGGAGTGCAGATCTCATGACAATGATGTAAATCTATCTTGCCTCAGTTTGT | 120 |
| SEQ_ID_NO_232 | AGAAAGTTTTGGAGTGCAGATCTCATGACAATGATGTAAATCTATCTTGCCTCAGTTTGT | 120 |
| SEQ_ID_NO_234 | AGAAAGTTTTGGAGTGCAGATCTCATGACAATGATGTAAATCTATCTTGCCTCAGTTTGT | 120 |
| SEQ_ID_NO_218 | AGAAAGTTTTGGAGTGCAAATCTCATGACAATGATGTAAATCTATCTTGCCTCAGTTTGT | 120 |
| SEQ_ID_NO_219 | AGAAAGTTTTGGAGTGCAAATCTCATGACAATGATGTAAATCTATCTTGCCTCAGTTTGT | 120 |
| SEQ_ID_NO_217 | AGAAAGTTTTGGAGTGCAAATCTCATGACAATGATGTAAATCTATCTTGCCTCAGTTTGT | 120 |
| SEQ_ID_NO_221 | AGAAAGGTTTGGAGTGCAGATCTCATGACAATGATGTAAATCTATCTTGCCTCAGTTTGT | 120 |
| SEQ_ID_NO_224 | AGAAAGTTTTGGAGTGCAGATCTCATGACAATGATGTAAATCTATCTTGCCTCAGTTTGT | 120 |
| | ****** ********** ************************* **************** | |
| SEQ_ID_NO_213 | TCTTGTAGTTTCCTTTGGACTTGAATTTGATACCTTAGTGCATCGCTAAGTGCTATTTCT | 180 |
| SEQ_ID_NO_222 | TCTTGTAGTTTCCTTTGGACTTGAATTTGATACCTTAGTGCATCGCTAAGTGCTATTTCT | 180 |
| SEQ_ID_NO_220 | TCTTGTAGTTTCCTTTGGACTTGAATTTGATACCTTAGTGCATCGCTAAGTGCTATTTCT | 180 |
| SEQ_ID_NO_235 | TCTTGTAGTTTCCTTTGGACTTGAATTTGATACCTTAGTGCATCGCTAAGTGCTATTTCT | 180 |
| SEQ_ID_NO_225 | TCTTGTAGTTTCCTTTGGACTTGAATTTGATACCTTAGTGCATCGCTAAGTGCTATTTCT | 180 |
| SEQ_ID_NO_226 | TCTTGTAGTTTCCTTTGGACTTGAATTTGATACCTTAGTGCATCGCTAAGTGCTATTTCT | 180 |
| SEQ_ID_NO_228 | TCTTGTAGTTTCCTTTGGACTTGAATTTGATACCTTAGTGCATCGCTAAGTGCTATTTCT | 180 |
| SEQ_ID_NO_227 | TCTTGTAGTTTCCTTTGGACTTGAATTTGATACCTTAGTGCATCGCTAAGTGCTATTTCT | 180 |
| SEQ_ID_NO_223 | TCTTGTAGTTTCCTTTGGACTTGAATTTGATACCTTAGTGCATCGCTAAGTGCTATTTCT | 180 |
| SEQ_ID_NO_215 | TCTTGTAGTTTCCTTTGGACTTGAATTTGATACCTTAGTGCATCGCTAAGTGCTATTTCT | 180 |
| SEQ_ID_NO_216 | TCTTGTAGTTTCCTTTGGACTTGAATTTGATACCTTAGTGCATCGCTAAGTGCTATTTCT | 180 |
| SEQ_ID_NO_214 | TCTTGTAGTTTCCTTTGGACTTGAATTTGATACCTTAGTGCATCGCTAAGTGCTATTTCT | 180 |
| SEQ_ID_NO_233 | TCTTGTAGTTTCCTTTGGACTTGAATTTGATACCTTAGTGCATCGCTAAGTGCTATTTCT | 180 |
| SEQ_ID_NO_236 | TCTTGTAGTTTCCTTTGGACTTGAATTTGATACCTTAATGCATCGCTAAGTGCTATTTCT | 180 |

TABLE 27-continued

| | | |
|---|---|---|
| SEQ_ID_NO_231 | TCTTGTAGTTTCCTTTGGACTTGAATTTGATACCTTAGTGCATCGCTAAGTGCTATTTCT | 180 |
| SEQ_ID_NO_229 | TCTTGTAGTTTCCTTTGGACTTGAATTTGATACCTTAGTGCATCGCTAAGTGCTATTTCT | 180 |
| SEQ_ID_NO_230 | TCTTGTAGTTTCCTTTGGACTTGAATTTGATACCTTAGTGCATCGCTAAGTGCTATTTCT | 180 |
| SEQ_ID_NO_232 | TCTTGTAGTTTCCTTTGGACTTGAATTTGATACCTTAGTGCATCGCTAAGTGCTATTTCT | 180 |
| SEQ_ID_NO_234 | TCTTGTAGTTTCCTTTGGACTTGAATTTGATACCTTAATGCATCGCTAAGTGCTATTTCT | 180 |
| SEQ_ID_NO_218 | TCTTGTAGTTTCCTTTGGACTTGAATTTGATACCTTAGTGCATCGCTAAGTGCTATTTCT | 180 |
| SEQ_ID_NO_219 | TCTTGTAGTTTCCTTTGGACTTGAATTTGATACCTTAGTGCATCGCTAAGTGCTATTTCT | 180 |
| SEQ_ID_NO_217 | TCTTGTAGTTTCCTTTGGACTTGAATTTGATACCTTAGTGCATCGCTAAGTGCTATTTCT | 180 |
| SEQ_ID_NO_221 | TCTTGTAGTTTCCTTTGGACTTGAATTTGATACCTTAGTGCATCGCTAAGTGCTATTTCT | 180 |
| SEQ_ID_NO_224 | TCTTGTAGTTTCCTTTGGACTTGAATTTGATACCTTAGTGCATCGCTAAGTGCTGGTTCT | 180 |
| | ****************************************  ****************  **** | |
| SEQ_ID_NO_213 | CTGATTCACATAAGAAATGTGATACAAATGGTTAGTTCAATCAATGCAGAAAAGTTCAAT | 240 |
| SEQ_ID_NO_222 | CTGATTCACATAAGAAATGTGATACAAATGGTTAGCTCAATCAATGCAGAAAAGTTCAAC | 240 |
| SEQ_ID_NO_220 | CTGATTCACATAAGAAATGCGATACAAATGGTTAGTTCAGTCAATGCAGAAAAGTTCAAC | 240 |
| SEQ_ID_NO_235 | CTGATTCACATAAGAAATGTGATACAAATGGTTAGCTCAATCAATGCAGAAAAGTTCAAC | 240 |
| SEQ_ID_NO_225 | CTGATTCACATAAGAAATGTGATACAAATGGTTAGTTCAATCAATGCAGAAAAGTTCAAT | 240 |
| SEQ_ID_NO_226 | CTGATTCACATAAGAAATGTGATACAAATGGTTAGTTCAATCAATGCAGAAAAGTTCAAT | 240 |
| SEQ_ID_NO_228 | CTGATTCACATAAGAAATGTGATACAAATGGTTAGTTCAATCAATGCAGAAAAGTTCAAT | 240 |
| SEQ_ID_NO_227 | CTGATTCACATAAGAAATGTGATACAAATGGTTAGTTCAATCAATGCAGAAAAGTTCAAT | 240 |
| SEQ_ID_NO_223 | CTGATTCGCATAAGAAATGCGATACAAATGGTTAGTTCAATCAATGCAGAAAAGTTCAAC | 240 |
| SEQ_ID_NO_215 | CTGATTCACATAAGAAATGTGATACAAATGGTTAGTTCAATCAATGCAGAAAAGTTCAAC | 240 |
| SEQ_ID_NO_216 | CTGATTCACATAAGAAATGTGATACAAATGGTTAGTTCAATCAATGCAGAAAAGTTCAAC | 240 |
| SEQ_ID_NO_214 | CTGATTCACATAAGAAATGTGATACAAATGGTTAGTTCAATCAATGCAGAAAAGTTCAAC | 240 |
| SEQ_ID_NO_233 | CTGATTCACATAAGAAATGTGATACAAATGGTTAGTTCAATCAATGCAGAAAAGTTCAAT | 240 |
| SEQ_ID_NO_236 | CTGATTCACATAAGAAATGCGATACAAATGGTTAGTTCAATCAATGCAGAAAAGTTCAAC | 240 |
| SEQ_ID_NO_231 | CTGATTCACATAAGAAATGTGATACAAATGGTTAGTTCAATCAATGCAGAAAAGTTCAAT | 240 |
| SEQ_ID_NO_229 | CTGATTCACATAAGAAATGTGATACAAATGGTTAGTTCAATCAATGCAGAAAAGTTCAAT | 240 |
| SEQ_ID_NO_230 | CTGATTCACATAAGAAATGTGATACAAATGGTTAGTTCAATCAATGCAGAAAAGTTCAAT | 240 |
| SEQ_ID_NO_232 | CTGATTCACATAAGAAATGTGATACAAATGGTTAGTTCAATCAATGCAGAAAAGTTCAAT | 240 |
| SEQ_ID_NO_234 | CTGATTCACATAAGAAATGCGATACAAATGGTTAGTTCAATCAATGCAGAAAAGTTCAAC | 240 |
| SEQ_ID_NO_218 | CTGATTCACATAAGAAATGTGATACAAATGGTTAGTTCAATCAATGCAGAAAAGTTCAAC | 240 |
| SEQ_ID_NO_219 | CTGATTCACATAAGAAATGTGATACAAATGGTTAGTTCAATCAATGCAGAAAAGTTCAAC | 240 |
| SEQ_ID_NO_217 | CTGATTCACATAAGAAATGTGATACAAATGGTTAGTTCAATCAATGCAGAAAAGTTCAAC | 240 |
| SEQ_ID_NO_221 | CTGATTCACATAAGAAATGTGATACAAATGGTTAGCTCAATCAATGCAGAAAAGTTCAAC | 240 |
| SEQ_ID_NO_224 | CTGATTCACATAAGAAATGTGATACAAATGGTTAGTTCAATCAATGCAGAAAAGTTCAAT | 240 |
| | ******* ********** *************** *** ****************** | |
| SEQ_ID_NO_213 | CAAATAAAATGGGCCCACTGCAGTCAATTAACAGGCATTCAATAGGATTCACATTCCTGG | 300 |
| SEQ_ID_NO_222 | CAAATAAAATGGGCCCACTGCAGTCAATTAACAGGCATTCAATAGGATTCACATTCCTGG | 300 |
| SEQ_ID_NO_220 | AAAATAAAATGGGCCCACTGCAGTCAATTAACAGGCATTCAACAGCATTCACATTCCTGG | 300 |
| SEQ_ID_NO_235 | CAAATAAAATGGGCCCACTGCAGTCAATTAACAGGCATTCAATAGGATTCACATTCCTGG | 300 |
| SEQ_ID_NO_225 | CAAATAAAATGGGCCCACTGCAGTCAATTAACAGGCATTCAATAGGATTCACATTCCTGG | 300 |

TABLE 27-continued

| | | |
|---|---|---|
| SEQ_ID_NO_226 | CAAATAAAATGGGCCCACTGCAGTCAATTAACAGGCATTCAATAGGATTCACATTCCTGG | 300 |
| SEQ_ID_NO_228 | CAAATAAAATGGGCCCACTGCAGTCAATTAACAGGCATTCAATAGGATTCACATTCCTGG | 300 |
| SEQ_ID_NO_227 | CAAATAAAATGGGCCCACTGCAGTCAATTAACAGGCATTCAATAGGATTCACATTCCTGG | 300 |
| SEQ_ID_NO_223 | AAAATAAAATGGGCCCACTGCAGTCAATTAACAGGCATTCAACAGCATTCACATTCCTGG | 300 |
| SEQ_ID_NO_215 | CAAATAAAATGGGCCCACTGCAGTCAATTAACAGGCATTCAATAGGATTCACATTCCTGG | 300 |
| SEQ_ID_NO_216 | CAAATAAAATGGGCCCACTGCAGTCAATTAACAGGCATTCAATAGGATTCACATTCCTGG | 300 |
| SEQ_ID_NO_214 | CAAATAAAATGGGCCCACTGCAGTCAATTAACAGGCATTCAATAGGATTCACATTCCTGG | 300 |
| SEQ_ID_NO_233 | CAAATAAAATGGGCCCACTGCAGTCAATTAACAGGCATTCAATAGGATTCACATTCCTGG | 300 |
| SEQ_ID_NO_236 | CAAATAAAATGGGCCCACTGCAGTCAATTAACAGGCATTCAATAGGATTCACATTCCTGG | 300 |
| SEQ_ID_NO_231 | CAAATAAAATGGGCCCACTGCAGTCAATTAACAGGCATTCAATAGGATTCACATTCCTGG | 300 |
| SEQ_ID_NO_229 | CAAATAAAATGGGCCCACTGCAGTCAATTAACAGGCATTCAATAGGATTCACATTCCTGG | 300 |
| SEQ_ID_NO_230 | CAAATAAAATGGGCCCACTGCAGTCAATTAACAGGCATTCAATAGGATTCACATTCCTGG | 300 |
| SEQ_ID_NO_232 | CAAATAAAATGGGCCCACTGCAGTCAATTAACAGGCATTCAATAGGATTCACATTCCTGG | 300 |
| SEQ_ID_NO_234 | CAAATAAAATGGGCCCACTGCAGTCAATTAACAGGCATTCAATAGGATTCACATTCCTGG | 300 |
| SEQ_ID_NO_218 | CAAATAAAATGGGCCCACTGCAGTCAATTAACAGGCATTCAATAGGATTCACATTCCTGG | 300 |
| SEQ_ID_NO_219 | CAAATAAAATGGGCCCACTGCAGTCAATTAACAGGCATTCAATAGGATTCACATTCCTGG | 300 |
| SEQ_ID_NO_217 | CAAATAAAATGGGCCCACTGCAGTCAATTAACAGGCATTCAATAGGATTCACATTCCTGG | 300 |
| SEQ_ID_NO_221 | CAAATAAAATGGGCCCACTGCAGTCAATTAACAGGCATTCAATAGGATTCACATTCCTGG | 300 |
| SEQ_ID_NO_224 | CAAATAAAATGGGCCCACTGCAGTCAATTAACAGGCATTCAATAGGATTCACATTCCTGG | 300 |
| | ****************************************  ** ************* | |
| SEQ_ID_NO_213 | GCTTCTATATATGGAAGTTTGCATACAATGTTTTGGAAATAAAATGAAATATAAATTGCT | 360 |
| SEQ_ID_NO_222 | GCTTCTATATATGGAAGTTTGCATACAAAGTTTTGGAAATAAAATGGAATATAAATTGCT | 360 |
| SEQ_ID_NO_220 | GCCTCTATATATGGAAGTTTGCATACAAAGTTTTGGAAATAAAATGGAATAGAAATTGCT | 360 |
| SEQ_ID_NO_235 | GCTTCTATATATGGAAGTTTGCATACAAAGTTTTGGAAATAAAATGGAATAGAAATTGCT | 360 |
| SEQ_ID_NO_225 | GCTTCTATATATGGAAGTTTGCATACAATGTTTTGGAAATAAAATGAAATATAAATTGCT | 360 |
| SEQ_ID_NO_226 | GCTTCTATATATGGAAGTTTGCATACAATGTTTTGGAAATAAAATGAAATATAAATTGCT | 360 |
| SEQ_ID_NO_228 | GCTTCTATATATGGAAGTTTGCATACAATGTTTTGGAAATAAAATGAAATATAAATTGCT | 360 |
| SEQ_ID_NO_227 | GCTTCTATATATGGAAGTTTGCATACAATGTTTTGGAAATAAAATGAAATATAAATTGCT | 360 |
| SEQ_ID_NO_223 | GCCTCTATATATGGAAGTTTGCATACAAAGTTTTGGAAATAAAATGGAATAGAAATTGCT | 360 |
| SEQ_ID_NO_215 | GCTTCTATATATGGAAGTTTGCATACAAAGTTTTGGAAATAAAATGGAATAGAAATTGCT | 360 |
| SEQ_ID_NO_216 | GCTTCTATATATGGAAGTTTGCATACAAAGTTTTGGAAATAAAATGGAATAGAAATTGCT | 360 |
| SEQ_ID_NO_214 | GCTTCTATATATGGAAGTTTGCATACAAAGTTTTGGAAATAAAATGGAATAGAAATTGCT | 360 |
| SEQ_ID_NO_233 | GCTTCTATATATGGAAGTTTGCATACAATGTTTTGGAAATAAAATGAAATATAAATTGCT | 360 |
| SEQ_ID_NO_236 | GCTTCTATATATGGAAGTTTGCATACAAAGTTTTGGAAATAAAATGGAATAGAAATTGCT | 360 |
| SEQ_ID_NO_231 | GCTTCTATATATGGAAGTTTGCATACAATGTTTTGGAAATAAAATGAAATATAAATTGCT | 360 |
| SEQ_ID_NO_229 | GCTTCTATATATGGAAGTTTGCATACAATGTTTTGGAAATAAAATGAAATATAAATTGCT | 360 |
| SEQ_ID_NO_230 | GCTTCTATATATGGAAGTTTGCATACAATGTTTTGGAAATAAAATGAAATATAAATTGCT | 360 |
| SEQ_ID_NO_232 | GCTTCTATATATGGAAGTTTGCATACAATGTTTTGGAAATAAAATGAAATATAAATTGCT | 360 |
| SEQ_ID_NO_234 | GCTTCTATATATGGAAGTTTGCATACAAAGTTTTGGAAATAAAATGGAATAGAAATTGCT | 360 |
| SEQ_ID_NO_218 | GCTTCTATATATGGAAGTTTGCATACAAAGTTTTGGAAATAAAATGGAATAGAAATTGCT | 360 |
| SEQ_ID_NO_219 | GCTTCTATATATGGAAGTTTGCATACAAAGTTTTTGAAATAAAATGGAATAGAAATTGCT | 360 |

TABLE 27-continued

```
SEQ_ID_NO_217 GCTTCTATATATGGAAGTTTGCATACAAAGTTTTTGAAATAAAATGGAATAGAAATTGCT      360

SEQ_ID_NO_221 GCTTCTATATATGGAAGTTTGCATACAAAGTTTTGGAAATAAAATGGAATATAAATTGCT      360

SEQ_ID_NO_224 GCTTCTATATATGGAAGTTTGCATACAATGTTTTGGAAATAAAATGAAATATAAATTGCT      360
              ** ************************ ***** ********** **** ********

SEQ_ID_NO_213 TGCATTTAGTGTAAGTTAATACTCGCTCCCTTCTCGAATATTTGTCGTCCGCTAGTTCAT      420

SEQ_ID_NO_222 TGCATTTAGTGTAAGTTAATACCCGCTCTGTTCTCGAATATTTGTCACCCGCTAGTTCAT      420

SEQ_ID_NO_220 TGCATTTAGTGTAAGTTAATACCCGCTCCGTTCTCGAATATTTGTCGCCTGCTAGTTCAT      420

SEQ_ID_NO_235 TGCATTTAGTGTAAGTTAATACCCGCT-------------------------AGTTCAT      394

SEQ_ID_NO_225 TGCATTTAGTGTAAGTTAATACTCGCTCCCTTCTCGAATATTTGTCGTCCGCTAGTTCAT      420

SEQ_ID_NO_226 TGCATTTAGTGTAAGTTAATACTCGCTCCCTTCTCGAATATTTGTCGTCCGCTAGTTCAT      420

SEQ_ID_NO_228 TGCATTTAGTGTAAGTTAATACTCGCTCCCTTCTCGAATATTTGTCGTCCGCTAGTTCAT      420

SEQ_ID_NO_227 TGCATTTAGTGTAAGTTAATACTCGCTCCCTTCTCGAATATTTGTCGTCCGCTAGTTCAT      420

SEQ_ID_NO_223 TGCATTTAGTGTAAGTTAATACTCCATCGTTCTTAAATATTTGTCGGCCGCTAGTTTAT      420

SEQ_ID_NO_215 TGCATTTAGTGTAAGTTAATACTAGCTCCGTTCTCGAATATTTGTCGTCCGCTAGTTCAT      420

SEQ_ID_NO_216 TGCATTTAGTGTAAGTTAATACTAGCTCCGTTCTCGAATATTTGTCGTCCGCTAGTTCAT      420

SEQ_ID_NO_214 TGCATTTAGTGTAAGTTAATACTAGCTCCGTTCTCGAATATTTGTCGTCCGCTAGTTCAT      420

SEQ_ID_NO_233 TGCATTTAGTGTAAGTTAATACTCGCTCCCTTCTCGAATATTTGTCGTCCGCTAGTTCAT      420

SEQ_ID_NO_236 TGCATTTAGTGTAAGTTAATAC-------------------------CCGCTAGTTCAT      394

SEQ_ID_NO_231 TGCATTTAGTGTAAGTTAATACTCGCTCCCTTCTCGAATATTTGTCGTCCGCTAGTTCAT      420

SEQ_ID_NO_229 TGCATTTAGTGTAAGTTAATACTCGCTCCCTTCTCGAATATTTGTCGTCCGCTAGTTCAT      420

SEQ_ID_NO_230 TGCATTTAGTGTAAGTTAATACTCGCTCCCTTCTCGAATATTTGTCGTCCGCTAGTTCAT      420

SEQ_ID_NO_232 TGCATTTAGTGTAAGTTAATACTCGCTCCCTTCTCGAATATTTGTCGTCCGCTAGTTCAT      420

SEQ_ID_NO_234 TGCATTTAGTGTAAGTTAATAC-------------------------CCGCTAGTTCAT      394

SEQ_ID_NO_218 TGCATTTAGTGTAAGTTAATACTAGCTCCGTTCTCGAATATTTGTCGTCCGCTAGTTCAT      420

SEQ_ID_NO_219 TGCATTTAGTGTAAGTTAATACTAGCTCCGTTCTCGAATATTTGTCGTCCGCTAGTTCAT      420

SEQ_ID_NO_217 TGCATTTAGTGTAAGTTAATACTAGCTCCGTTCTCGAATATTTGTCGTCCGCTAGTTCAT      420

SEQ_ID_NO_221 TGCATTTAGTGTAAGTTAATACCCGCTCTGTTCTCGAATATTTGTCACCCGCTAGTTCAT      420

SEQ_ID_NO_224 TGCATTTAGTGTAAGTTAATACTCGCTCCCTTCTCGAATATTTGTCGTCCGCTAGTTCAT      420
              **********************                              **** **

SEQ_ID_NO_213 TTTTGAACTAAAACATGATAAATAAAAAAAC-GGAAGGAGTACATGTTTGTAACAGGAGA      479

SEQ_ID_NO_222 TTTTGAACTAAAACACGACAAATAAAAAAAC-GGAAGGAGTACATGTTTGTAACAGGAGA      479

SEQ_ID_NO_220 TTTTGAACTAAAACACGACAAATAAAAAAACGGAAGGAGTACATGTTTGTAACAGGAGA      480

SEQ_ID_NO_235 TTTTTAACTAAAACACGACAAATAAAAAAAT--GGAGGAGTACATCTTTGTAACAGGTGA      452

SEQ_ID_NO_225 TTTTGAACTAAAACATGATAAATAAAAAAAC-GGAAGGAGTACATGTTTGTAACAGGAGA      479

SEQ_ID_NO_226 TTTTGAACTAAAACATGATAAATAAAAAAAC-GGAAGGAGTACATGTTTGTAACAGGAGA      479

SEQ_ID_NO_228 TTTTGAACTAAAACATGATAAATAAAAAAAC-GGAAGGAGTACATGTTTGTAACAGGAGA      479

SEQ_ID_NO_227 TTTTGAACTAAAACATGATAAATAAAAAAAC-GGAAGGAGTACATGTTTGTAACAGGAGA      479

SEQ_ID_NO_223 TTTTGAACTAAAACACGACAAATAAAAAAAACGGAGGGAGTACATGTTTATAACAGGTGA      480

SEQ_ID_NO_215 TTTTGAACTAAAACACGACAAATAAAAAAAC-GGAAGGAGTACATGTTTGTAACAGGTGA      479

SEQ_ID_NO_216 TTTTGAACTAAAACACGACAAATAAAAAAAC-GGAAGGAGTACATGTTTGTAACAGGTGA      479

SEQ_ID_NO_214 TTTTGAACTAAAACACGACAAATAAAAAAAC-GGAAGGAGTACATGTTTGTAACAGGTGA      479
```

TABLE 27-continued

```
SEQ_ID_NO_233 TTTTGAACTAAAACATGATAAATAAAAAAAC-GGAAGGAGTACATGTTTGTAACAGGAGA    479
SEQ_ID_NO_236 TTTTTAACTAAAACACGACAAATAAAAAAAT-GGA-GGAGTACATCTTTGTAACAGGTGA    452
SEQ_ID_NO_231 TTTTGAACTAAAACATGATAAATAAAAAAAC-GGAAGGAGTACATGTTTGTAACAGGAGA    479
SEQ_ID_NO_229 TTTTGAACTAAAACATGATAAATAAAAAAAC-GGAAGGAGTACATGTTTGTAACAGGAGA    479
SEQ_ID_NO_230 TTTTGAACTAAAACATGATAAATAAAAAAAC-GGAAGGAGTACATGTTTGTAACAGGAGA    479
SEQ_ID_NO_232 TTTTGAACTAAAACATGATAAATAAAAAAAC-GGAAGGAGTACATGTTTGTAACAGGAGA    479
SEQ_ID_NO_234 TTTTTAACTAAAACACGACAAATAAAAAAAT--GGAGGAGTACATCTTTGTAACAGGTGA    452
SEQ_ID_NO_218 TTTTGAACTAAAACACGACAAATAAAAAAAC-GGAAGGAGTACATGTTTGTAACAGGTGA    479
SEQ_ID_NO_219 TTTTGAACTAAAACACGACAAATAAAAAAAC-GGAAGGAGTACATGTTTGTAACAGGTGA    479
SEQ_ID_NO_217 TTTTGAACTAAAACACGACAAATAAAAAAAC-GGAAGGAGTACATGTTTGTAACAGGTGA    479
SEQ_ID_NO_221 TTTTGAACTAAAACACGACAAATAAAAAAAC-GGAAGGAGTACATGTTTGTAACAGGAGA    479
SEQ_ID_NO_224 TTTTGAACTAAAACATGATAAATAAAAAAAC-GGAAGGAGTACATGTTTGTAACAGGAGA    479
              **** ********** ** ***********  * ********* *** ******* **

SEQ_ID_NO_213 GCCCATGAATACTTGCTTGTAACAGGTGGAGCGCTAAGTATGCTTAGGAGAACTTTAGGC    539
SEQ_ID_NO_222 GCCCCTGAATACTTGCTTGTAACAGGTGGAGCGCTAAGTATGCTTAGGAGAACTTTAGGC    539
SEQ_ID_NO_220 GCCCCTGAATACTTGCTTGTAACAGGTGGAGCGCTAAGTATGCTTAGGAGAACTTTAGGC    540
SEQ_ID_NO_235 GCC--TGAATACTTGTTTGTAGCAGGTGGGGCGCTAAGTATGCTTAGGAGAAGTTTAGGC    510
SEQ_ID_NO_225 GCCCATGAATACTTGCTTGTAACAGGTGGAGCGCTAAGTATGCTTAGGAGAACTTTAGGC    539
SEQ_ID_NO_226 GCCCATGAATACTTGCTTGTAACAGGTGGAGCGCTAAGTATGCTTAGGAGAACTTTAGGC    539
SEQ_ID_NO_228 GCCCATGAATACTTGCTTGTAACAGGTGGAGCGCTAAGTATGCTTAGGAGAACTTTAGGC    539
SEQ_ID_NO_227 GCCCATGAATACTTGCTTGTAACAGGTGGAGCGCTAAGTATGCTTAGGAGAACTTTAGGC    539
SEQ_ID_NO_223 GCC---GAATACTTGGTTGTAACAGGTGGGGCGCTAAGTATGCTTAGGAGAACTTTAGGC    537
SEQ_ID_NO_215 GCCCCTGAATACTTGCTTGTAACAGGTGGAGCACTAAGTATGCTTAG---AACTTTAGGC    536
SEQ_ID_NO_216 GCCCCTGAATACTTGCTTGTAACAGGTGGAGCACTAAGTATGCTTAG---AACTTTAGGC    536
SEQ_ID_NO_214 GCCCCTGAATACTTGCTTGTAACAGGTGGAGCACTAAGTATGCTTAG---AACTTTAGGC    536
SEQ_ID_NO_233 GCCCATGAATACTTGCTTGTAACAGGTGGAGCGCTAAGTATGCTTAGGAGAACTTTAGGC    539
SEQ_ID_NO_236 GCC--TGAATACTTGTTTGTAGCAGGTGGGGCGCTAAGTATGCTTAGGAGAAGTTTAGGC    510
SEQ_ID_NO_231 GCCCATGAATACTTGCTTGTAACAGGTGGAGCGCTAAGTATGCTTAGGAGAACTTTAGGC    539
SEQ_ID_NO_229 GCCCATGAATACTTGCTTGTAACAGGTGGAGCGCTAAGTATGCTTAGGAGAACTTTAGGC    539
SEQ_ID_NO_230 GCCCATGAATACTTGCTTGTAACAGGTGGAGCGCTAAGTATGCTTAGGAGAACTTTAGGC    539
SEQ_ID_NO_232 GCCCATGAATACTTGCTTGTAACAGGTGGAGCGCTAAGTATGCTTAGGAGAACTTTAGGC    539
SEQ_ID_NO_234 GCC--TGAATACTTGTTTGTAGCAGGTGGGGCGCTAAGTATGCTTAGGAGAAGTTTAGGC    510
SEQ_ID_NO_218 GCCCCTGAATACTTGCTTGTAACAGGTGGAGCACTAAGTATGCTTAG---AACTTTAGGC    536
SEQ_ID_NO_219 GCCCCTGAATACTTGCTTGTAACAGGTGGAGCACTAAGTATGCTTAG---AACTTTAGGC    536
SEQ_ID_NO_217 GCCCCTGAATACTTGCTTGTAACAGGTGGAGCACTAAGTATGCTTAG---AACTTTAGGC    536
SEQ_ID_NO_221 GCCCCTGAATACTTGCTTGTAACAGGTGGAGCGCTAAGTATGCTTAGGAGAACTTTAGGC    539
SEQ_ID_NO_224 GCCCATGAATACTTGCTTGTAACAGGTGGAGCGCTAAGTATGCTTAGGAGAACTTTAGGC    539
              ***   ******** ***** ** **  **************   ** *******

SEQ_ID_NO_213 AACTTGTATTCTTTAGCACTTCGACGCAGTTTGTATGGTAATATCTACTGATAGACAGAA    599
SEQ_ID_NO_222 AACTTGTATTCTTTAGCACTTCGACGCCGTTTGTATGGTAATATCTACTGATAGACAGAA    599
SEQ_ID_NO_220 AACTTGTATTCTTTAGCACTTCGACGCCGTTTGTATGGTAATATCTACTGATAGACAGAA    600
```

TABLE 27-continued

```
SEQ_ID_NO_235 AACTTGTATTCTGTAGCATTTCGACGCCGTTTGTATGGTAATATCTACTGATAGGCAGAA    570
SEQ_ID_NO_225 AACTTGTATTCTTTAGCACTTCGACGCAGTTTGTATGGTAATATCTACTGATAGACAGAA    599
SEQ_ID_NO_226 AACTTGTATTCTTTAGCACTTCGACGCAGTTTGTATGGTAATATCTACTGATAGACAGAA    599
SEQ_ID_NO_228 AACTTGTATTCTTTAGCACTTCGACGCAGTTTGTATGGTAATATCTACTGATAGACAGAA    599
SEQ_ID_NO_227 AACTTGTATTCTTTAGCACTTCGACGCAGTTTGTATGGTAATATCTACTGATAGACAGAA    599
SEQ_ID_NO_223 AACTTGTATTCTGTAGCACTTCGACGCCGTTTGTATGGTAATATCTACTGATAGACAGAA    597
SEQ_ID_NO_215 AACTTGTATTCTTTAGCACTTCGACGCCGTTTGTATGGTAATATCTACTGATAGACAGAA    596
SEQ_ID_NO_216 AACTTGTATTCTTTAGCACTTCGACGCCGTTTGTATGGTAATATCTACTGATAGACAGAA    596
SEQ_ID_NO_214 AACTTGTATTCTTTAGCACTTCGACGCCGTTTGTATGGTAATATCTACTGATAGACAGAA    596
SEQ_ID_NO_233 AACTTGTATTCTTTAGCACTTCGACGCAGTTTGTATGGTAATATCTACTGATAGACAGAA    599
SEQ_ID_NO_236 AACTTGTATTCTGTAGCATTTCGACGCCGTTTGTATGGTAATATCTACTGATAGGCAGAA    570
SEQ_ID_NO_231 AACTTGTATTCTTTAGCACTTCGACGCAGTTTGTATGGTAATATCTACTGATAGACAGAA    599
SEQ_ID_NO_229 AACTTGTATTCTTTAGCACTTCGACGCAGTTTGTATGGTAATATCTACTGATAGACAGAA    599
SEQ_ID_NO_230 AACTTGTATTCTTTAGCACTTCGACGCAGTTTGTATGGTAATATCTACTGATAGACAGAA    599
SEQ_ID_NO_232 AACTTGTATTCTTTAGCACTTCGACGCAGTTTGTATGGTAATATCTACTGATAGACAGAA    599
SEQ_ID_NO_234 AACTTGTATTCTGTAGCATTTCGACGCCGTTTGTATGGTAATATCTACTGATAGGCAGAA    570
SEQ_ID_NO_218 AACTTGTATTCTTTAGCACTTCGACGCCGTTTGTATGGTAATATCTACTGATAGACAGAA    596
SEQ_ID_NO_219 AACTTGTATTCTTTAGCACTTCGACGCCGTTTGTATGGTAATATCTACTGATAGACAGAA    596
SEQ_ID_NO_217 AACTTGTATTCTTTAGCACTTCGACGCCGTTTGTATGGTAATATCTACTGATAGACAGAA    596
SEQ_ID_NO_221 AACTTGTATTCTTTAGCACTTCGACGCCGTTTGTATGGTAATATCTACTGATAGACAGAA    599
SEQ_ID_NO_224 AACTTGTATTCTTTAGCACTTCGACGCAGTTTGTATGGTAATATCTACTGATAGACAGAA    599
              ************ ***** ******* ************************** *****

SEQ_ID_NO_213 TCCTGGTTTTGGA----TTTTTAATTTTTCCTGCTTTTGGTTACACCTCTACAGTCCCAT    655
SEQ_ID_NO_222 TCCTGGTTTTGGAATTTTTTTTATTTTTCCTGCTTTTGGTTACACCTCTACAGTCCCAT    659
SEQ_ID_NO_220 TCCTGGTTTTGGAATTTTTTT--ATTTTTCCTGCTTTTGGTTACACCTCTACAGTCCCAT    658
SEQ_ID_NO_235 TCCTGGTT---GGATTTTTTT-------TCCTGCTTTTGTTACACCTATACAGTCCCAT    620
SEQ_ID_NO_225 TCCTGGTTTTGGA--TTTTTA--ATTTTTCCTGCTTTTGGTTACACCTCTACAGTCCCAT    655
SEQ_ID_NO_226 TCCTGGTTTTGGA--TTTTTA--ATTTTTCCTGCTTTTGGTTACACCTCTACAGTCCCAT    655
SEQ_ID_NO_228 TCCTGGTTTTGGA--TTTTTA--ATTTTTCCTGCTTTTGGTTACACCTCTACAGTCCCAT    655
SEQ_ID_NO_227 TCCTGGTTTTGGA--TTTTTA--ATTTTTCCTGCTTTTGGTTACACCTCTACAGTCCCAT    655
SEQ_ID_NO_223 TCCTGGTTTTTGG--AAAAAA--AAAATTCCTGCTTTTGGTTACACCTCTACAGTCCCAT    653
SEQ_ID_NO_215 TCCTGGTTTTGGATTTTTTTTTATTTTTCCTGTTTTTGGTTACACCTCTACAGTCCCAT    656
SEQ_ID_NO_216 TCCTGGTTTTGGATTTTTTTTTATTTTTCCTGTTTTTGGTTACACCTCTACAGTCCCAT    656
SEQ_ID_NO_214 TCCTGGTTTTGGATTTTTTTTTATTTTTCCTGTTTTTGGTTACACCTCTACAGTCCCAT    656
SEQ_ID_NO_233 TCCTGGTTTTGGATTTTTA----ATTTTTCCTGCTTTTGGTTACACCTCTACAGTCCCAT    655
SEQ_ID_NO_236 TCCTGGTT--GGATTTTTT--------TTTCCTGCTTTTGTTACACCTATACAGTCCCAT    620
SEQ_ID_NO_231 TCCTGGTTTTGGATTTTTA----ATTTTTCCTGCTTTTGGTTACACCTCTACAGTCCCAT    655
SEQ_ID_NO_229 TCCTGGTTTTGGATTTTTA----ATTTTTCCTGCTTTTGGTTACACCTCTACAGTCCCAT    655
SEQ_ID_NO_230 TCCTGGTTTTGGATTTTTA----ATTTTTCCTGCTTTTGGTTACACCTCTACAGTCCCAT    655
SEQ_ID_NO_232 TCCTGGTTTTGGATTTTTA----ATTTTTCCTGCTTTTGGTTACACCTCTACAGTCCCAT    655
```

TABLE 27-continued

| | | |
|---|---|---|
| SEQ_ID_NO_234 | TCCTGGTT--GGATTTTT--------TTTCCTGCTTTTGTTTACACCTATACAGTCCCAT | 620 |
| SEQ_ID_NO_218 | TCCTGGTTTTGGATTTTTTTTTATTTTTCCTGTTTTTGGTTACACCTCTACAGTCCCAT | 656 |
| SEQ_ID_NO_219 | TCCTGGTTTTGGATTTTTTTTTATTTTTCCTGTTTTTGGTTACACCTCTACAGTCCCAT | 656 |
| SEQ_ID_NO_217 | TCCTGGTTTTGGATTTTTTTTTATTTTTCCTGTTTTTGGTTACACCTCTACAGTCCCAT | 656 |
| SEQ_ID_NO_221 | TCCTGGTTTTGGAATTTTTTTT-ATTTTTCCTGCTTTTGGTTACACCTCTACAGTCCCAT | 658 |
| SEQ_ID_NO_224 | TCCTGGTTTTGGA---TTTTTA-ATTTTTCCTGCTTTTGGTTACACCTCTACAGTCCCAT | 655 |
| | ********  *              ****  ***** ******** *********** | |
| SEQ_ID_NO_213 | ACTCGCAGTCCAATAGTACATGGTCTGATAATAAACCAATTAAGAAGGACTCATGTCTCA | 715 |
| SEQ_ID_NO_222 | ACTCGCAGTCGAATAATACATGGTCTGATAATAAACCAATTA---AGGACTCATGTCTCA | 716 |
| SEQ_ID_NO_220 | ACTCGCAGTCGAATAATACATGGTCTGATAATAAACCAATTAAG---GACTCATGTCTCA | 715 |
| SEQ_ID_NO_235 | ACTCGCAGTCGAATAATACATGGTCTGATGATAAACCAATTAAGAAGGACTCATGTCTCA | 680 |
| SEQ_ID_NO_225 | ACTCGCAGTCCAATAGTACATGGTCTGATAATAAACCAATTAAGAAGGACTCATGTCTCA | 715 |
| SEQ_ID_NO_226 | ACTCGCAGTCCAATAGTACATGGTCTGATAATAAACCAATTAAGAAGGACTCATGTCTCA | 715 |
| SEQ_ID_NO_228 | ACTCGCAGTCCAATAGTACATGGTCTGATAATAAACCAATTAAGAAGGACTCATGTCTCA | 715 |
| SEQ_ID_NO_227 | ACTCGCAGTCCAATAGTACATGGTCTGATAATAAACCAATTAAGAAGGACTCATGTCTCA | 715 |
| SEQ_ID_NO_223 | ACTCGCAGTCGAATAATACATGGTCTGATAATAAACCAATTAAG---GACTCATGTCTCA | 710 |
| SEQ_ID_NO_215 | ACTCGCAGTCCAATAATACATGGTCTGATAATAAACCAATTAAGAAGGACTCATGTCTCA | 716 |
| SEQ_ID_NO_216 | ACTCGCAGTCCAATAATACATGGTCTGATAATAAACCAATTAAGAAGGACTCATGTCTCA | 716 |
| SEQ_ID_NO_214 | ACTCGCAGTCCAATAATACATGGTCTGATAATAAACCAATTAAGAAGGACTCATGTCTCA | 716 |
| SEQ_ID_NO_233 | ACTCGCAGTCCAATAGTACATGGTCTGATAATAAACCAATTAAGAAGGACTCATGTCTCA | 715 |
| SEQ_ID_NO_236 | ACTCGCAGTCGAATAATACATGGTCTGATGATAAACCAATTAAGAAGGACTCATGTCTCA | 680 |
| SEQ_ID_NO_231 | ACTCGCAGTCCAATAGTACATGGTCTGATAATAAACCAATTAAGAAGGACTCATGTCTCA | 715 |
| SEQ_ID_NO_229 | ACTCGCAGTCCAATAGTACATGGTCTGATAATAAACCAATTAAGAAGGACTCATGTCTCA | 715 |
| SEQ_ID_NO_230 | ACTCGCAGTCCAATAGTACATGGTCTGATAATAAACCAATTAAGAAGGACTCATGTCTCA | 715 |
| SEQ_ID_NO_232 | ACTCGCAGTCCAATAGTACATGGTCTGATAATAAACCAATTAAGAAGGACTCATGTCTCA | 715 |
| SEQ_ID_NO_234 | ACTCGCAGTCGAATAATACATGGTCTGATGATAAACCAATTAAGAAGGACTCATGTCTCA | 680 |
| SEQ_ID_NO_218 | ACTCGCAGTCCAATAATACATGGTCTGATAATAAACCAATTAAGAAGGACTCATGTCTCA | 716 |
| SEQ_ID_NO_219 | ACTCGCAGTCCAATAATACATGGTCTGATAATAAACCAATTAAGAAGGACTCATGTCTCA | 716 |
| SEQ_ID_NO_217 | ACTCGCAGTCCAATAATACATGGTCTGATAATAAACCAATTAAGAAGGACTCATGTCTCA | 716 |
| SEQ_ID_NO_221 | ACTCGCAGTCGAATAATACATGGTCTGATAATAAACCAATTAAG---GACTCATGTCTCA | 715 |
| SEQ_ID_NO_224 | ACTCGCAGTCCAATAGTACATGGTCTGATAATAAACCAATTAAGAAGGACTCATGTCTCA | 715 |
| | ********* **** ************* ************      ************ | |
| SEQ_ID_NO_213 | GTCATTA----------------------------------------------------- | 722 |
| SEQ_ID_NO_222 | GTCATTA----------------------------------------------------- | 723 |
| SEQ_ID_NO_220 | GTCATTA----------------------------------------------------- | 722 |
| SEQ_ID_NO_235 | GTCATTA----------------------------------------------------- | 687 |
| SEQ_ID_NO_225 | GTCATTA----------------------------------------------------- | 722 |
| SEQ_ID_NO_226 | GTCATTA----------------------------------------------------- | 722 |
| SEQ_ID_NO_228 | GTCATTA----------------------------------------------------- | 722 |
| SEQ_ID_NO_227 | GTCATTA----------------------------------------------------- | 722 |
| SEQ_ID_NO_223 | GTCATTA----------------------------------------------------- | 717 |

TABLE 27-continued

| | | |
|---|---|---|
| SEQ_ID_NO_215 | GTCATTAGGCTGTCTCCAACAACGTCCTCTATATTCATCCTCTATATCTGTCCTTTACAG | 776 |
| SEQ_ID_NO_216 | GTCATTAGGCTGTCTCCAACAACGTCCTCTATATTCATCCTCTATATCTGTCCTTTACAG | 776 |
| SEQ_ID_NO_214 | GTCATTAGGCTGTCTCCAACAACGTCCTCTATATTCATCCTCTATATCTGTCCTTTACAG | 776 |
| SEQ_ID_NO_233 | GTCATTA----------------------------------------------------- | 722 |
| SEQ_ID_NO_236 | GTCATTA----------------------------------------------------- | 687 |
| SEQ_ID_NO_231 | GTCATTA----------------------------------------------------- | 722 |
| SEQ_ID_NO_229 | GTCATTA----------------------------------------------------- | 722 |
| SEQ_ID_NO_230 | GTCATTA----------------------------------------------------- | 722 |
| SEQ_ID_NO_232 | GTCATTA----------------------------------------------------- | 722 |
| SEQ_ID_NO_234 | GTCATTA----------------------------------------------------- | 687 |
| SEQ_ID_NO_218 | GTCATTAGGCTGTCTCCAACAACGTCCTCTATATTCATCCTCTATATCTGTCCTTTACAG | 776 |
| SEQ_ID_NO_219 | GTCATTAGGCTGTCTCCAACAACGTCCTCTATATTCATCCTCTATATCTGTCCTTTACAG | 776 |
| SEQ_ID_NO_217 | GTCATTAGGCTGTCTCCAACAACGTCCTCTATATTCATCCTCTATATCTGTCCTTTACAG | 776 |
| SEQ_ID_NO_221 | GTCATTA----------------------------------------------------- | 722 |
| SEQ_ID_NO_224 | GTCATTA----------------------------------------------------- | 722 |
| | ******* | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | TCTCCTCTAAAAAATTTCATCCTATATATCTCATTTCTCTCCAACAACGTCCTCTAAATC | 836 |
| SEQ_ID_NO_216 | TCTCCTCTAAAAAATTTCATCCTATATATCTCATTTCTCTCCAACAACGTCCTCTAAATC | 836 |
| SEQ_ID_NO_214 | TCTCCTCTAAAAAATTTCATCCTATATATCTCATTTCTCTCCAACAACGTCCTCTAAATC | 836 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | TCTCCTCTAAAAAATTTCATCCTATATATCTCATTTCTCTCCAACAACGTCCTCTAAATC | 836 |
| SEQ_ID_NO_219 | TCTCCTCTAAAAAATTTCATCCTATATATCTCATTTCTCTCCAACAACGTCCTCTAAATC | 836 |
| SEQ_ID_NO_217 | TCTCCTCTAAAAAATTTCATCCTATATATCTCATTTCTCTCCAACAACGTCCTCTAAATC | 836 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |

TABLE 27-continued

| | | |
|---|---|---|
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | ACGTCCTCTATACTCAAATACTCATATTAAAGACATTTTTTAATTTTATTTTTTATACAT | 896 |
| SEQ_ID_NO_216 | ACGTCCTCTATACTCAAATACTCATATTAAAGACATTTTTTAATTTTATTTTTTATACAT | 896 |
| SEQ_ID_NO_214 | ACGTCCTCTATACTCAAATACTCATATTAAAGACATTTTTTAATTTTATTTTTTATACAT | 896 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | ACGTCCTCTATACTCAAATACTCATATTAAAGACATTTTTTAATTTTATTTTTTATACAT | 896 |
| SEQ_ID_NO_219 | ACGTCCTCTATACTCAAATACTCATATTAAAGACATTTTTTAATTTTATTTTTTATACAT | 896 |
| SEQ_ID_NO_217 | ACGTCCTCTATACTCAAATACTCATATTAAAGACATTTTTTAATTTTATTTTTTATACAT | 896 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | ACGTAATTATCATACTCTCAAATGTATTGTGCATATTTTAGTTTTGCTAAACCGGTTATT | 956 |
| SEQ_ID_NO_216 | ACGTAATTATCATACTCTCAAATGTATTGTGCATATTTTAGTTTTGCTAAACCGGTTATT | 956 |
| SEQ_ID_NO_214 | ACGTAATTATCATACTCTCAAATGTATTGTGCATATTTTAGTTTTGCTAAACCGGTTATT | 956 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |

TABLE 27-continued

| | | |
|---|---|---|
| SEQ_ID_NO_232 | ------------------------------------------------------------ | |
| SEQ_ID_NO_234 | ------------------------------------------------------------ | |
| SEQ_ID_NO_218 | ACGTAATTATCATACTCTCAAATGTATTGTGCATATTTTAGTTTTGCTAAACCGGTTATT | 956 |
| SEQ_ID_NO_219 | ACGTAATTATCATACTCTCAAATGTATTGTGCATATTTTAGTTTTGCTAAACCGGTTATT | 956 |
| SEQ_ID_NO_217 | ACGTAATTATCATACTCTCAAATGTATTGTGCATATTTTAGTTTTGCTAAACCGGTTATT | 956 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | TAAAGTAGTCAAATGGATAGAGGACCGTTTAGAGAAACTCTATATATAGAGAATTCAGCA | 1016 |
| SEQ_ID_NO_216 | TAAAGTAGTCAAATGGATAGAGGACCGTTTAGAGAAACTCTATATATAGAGAATTCAGCA | 1016 |
| SEQ_ID_NO_214 | TAAAGTAGTCAAATGGATAGAGGACCGTTTAGAGAAACTCTATATATAGAGAATTCAGCA | 1016 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | TAAAGTAGTCAAATGGATAGAGGACCGTTTAGAGAAACTCTATATATAGAGAATTCAGCA | 1016 |
| SEQ_ID_NO_219 | TAAAGTAGTCAAATGGATAGAGGACCGTTTAGAGAAACTCTATATATAGAGAATTCAGCA | 1016 |
| SEQ_ID_NO_217 | TAAAGTAGTCAAATGGATAGAGGACCGTTTAGAGAAACTCTATATATAGAGAATTCAGCA | 1016 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |

TABLE 27-continued

| | | |
|---|---|---|
| SEQ_ID_NO_215 | GCGTCCTCTAAATTTAAAGGACCGTTTAGAGGACGTTGCTGGAGAGCGTAGAGGACCGTT | 1076 |
| SEQ_ID_NO_216 | GCGTCCTCTAAATTTAAAGGACCGTTTAGAGGACGTTGCTGGAGAGCGTAGAGGACCGTT | 1076 |
| SEQ_ID_NO_214 | GCGTCCTCTAAATTTAAAGGACCGTTTAGAGGACGTTGCTGGAGAGCGTAGAGGACCGTT | 1076 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | GCGTCCTCTAAATTTAAAGGACCGTTTAGAGGACGTTGCTGGAGAGCGTAGAGGACCGTT | 1076 |
| SEQ_ID_NO_219 | GCGTCCTCTAAATTTAAAGGACCGTTTAGAGGACGTTGCTGGAGAGCGTAGAGGACCGTT | 1076 |
| SEQ_ID_NO_217 | GCGTCCTCTAAATTTAAAGGACCGTTTAGAGGACGTTGCTGGAGAGCGTAGAGGACCGTT | 1076 |
| SEQ_ID_NO_221 | ------------------------------------------------------------ | |
| SEQ_ID_NO_224 | ------------------------------------------------------------ | |
| SEQ_ID_NO_213 | ----------------------------------------------------------TG | 724 |
| SEQ_ID_NO_222 | ----------------------------------------------------------TG | 725 |
| SEQ_ID_NO_220 | ----------------------------------------------------------TG | 724 |
| SEQ_ID_NO_235 | ----------------------------------------------------------TG | 689 |
| SEQ_ID_NO_225 | ----------------------------------------------------------TG | 724 |
| SEQ_ID_NO_226 | ----------------------------------------------------------TG | 724 |
| SEQ_ID_NO_228 | ----------------------------------------------------------TG | 724 |
| SEQ_ID_NO_227 | ----------------------------------------------------------TG | 724 |
| SEQ_ID_NO_223 | ----------------------------------------------------------TG | 719 |
| SEQ_ID_NO_215 | TGGTCCTCTATATTTAGGGTAGAGAACCCTTTAGGGGGCCTTGTTGGAGCCAGCCTTATG | 1136 |
| SEQ_ID_NO_216 | TGGTCCTCTATATTTAGGGTAGAGAACCCTTTAGGGGGCCTTGTTGGAGCCAGCCTTATG | 1136 |
| SEQ_ID_NO_214 | TGGTCCTCTATATTTAGGGTAGAGAACCCTTTAGGGGGCCTTGTTGGAGCCAGCCTTATG | 1136 |
| SEQ_ID_NO_233 | ----------------------------------------------------------TG | 724 |
| SEQ_ID_NO_236 | ----------------------------------------------------------TG | 689 |
| SEQ_ID_NO_231 | ----------------------------------------------------------TG | 724 |
| SEQ_ID_NO_229 | ----------------------------------------------------------TG | 724 |
| SEQ_ID_NO_230 | ----------------------------------------------------------TG | 724 |
| SEQ_ID_NO_232 | ----------------------------------------------------------TG | 724 |
| SEQ_ID_NO_234 | ----------------------------------------------------------TG | 689 |
| SEQ_ID_NO_218 | TGGTCCTCTATATTTAGGGTAGAGAACCCTTTAGGGGGCCTTGTTGGAGCCAGCCTTATG | 1136 |
| SEQ_ID_NO_219 | TGGTCCTCTATATTTAGGGTAGAGAACCCTTTAGGGGGCCTTGTTGGAGCCAGCCTTATG | 1136 |
| SEQ_ID_NO_217 | TGGTCCTCTATATTTAGGGTAGAGAACCCTTTAGGGGGCCTTGTTGGAGCCAGCCTTATG | 1136 |
| SEQ_ID_NO_221 | ----------------------------------------------------------TG | 724 |

TABLE 27-continued

```
SEQ_ID_NO_224 ----------------------------------------------------------TG        724
                                                                         **

SEQ_ID_NO_213 ACTTGAGCATAGGAGTTGAGATCAAGAAATATTTGAGTTGCAGCTTAAGGTCCAGA----        780
SEQ_ID_NO_222 ACTTGAGCATAGGAGTTGAGATCAAGAAATATTTGAGTTGCAGCTTAAGGTTCAGA----        781
SEQ_ID_NO_220 ACTTGAGCATAGGAGTTCAGATCGAGAAATATTTGAGTTGCAGCTTAAGGTTCAGA----        780
SEQ_ID_NO_235 ACTTGAGCATAGGAGTTCAGATCGAGAAATATTTGAGTTGCAGCTTAAGGTTCAGA----        745
SEQ_ID_NO_225 ACTTGAGCATAGGAGTTGAGATCAAGAAATATTTGAGTTGCAGCTTAAGGTCCAGA----        780
SEQ_ID_NO_226 ACTTGAGCATAGGAGTTGAGATCAAGAAATATTTGAGTTGCAGCTTAAGGTCCAGA----        780
SEQ_ID_NO_228 ACTTGAGCATAGGAGTTGAGATCAAGAAATATTTGAGTTGCAGCTTAAGGTCCAGA----        780
SEQ_ID_NO_227 ACTTGAGCATAGGAGTTGAGATCAAGAAATATTTGAGTTGCAGCTTAAGGTCCAGA----        780
SEQ_ID_NO_223 ACTTGAGCATAGGAGTTGAGATCGAGAAATATTTGAGTTACAGCTTAAGGTTCAGACTTC        779
SEQ_ID_NO_215 ACTTGAGCATAGGAGTTGAGATCAAGAAATATGTGAGTTGCAGCTTAAGGTTCAGA----       1192
SEQ_ID_NO_216 ACTTGAGCATAGGAGTTGAGATCAAGAAATATGTGAGTTGCAGCTTAAGGTTCAGA----       1192
SEQ_ID_NO_214 ACTTGAGCATAGGAGTTGAGATCAAGAAATATGTGAGTTGCAGCTTAAGGTTCAGA----       1192
SEQ_ID_NO_233 ACTTGAGCATAGGAGTTGAGATCAAGAAATATTTGAGTTGCAGCTTAAGGTCCAGA----        780
SEQ_ID_NO_236 ACTTGAGCATAGGAGTTCAGATCGAGAAATATTTGAGTTGCAGCTTAAGGTTCAGA----        745
SEQ_ID_NO_231 ACTTGAGCATAGGAGTTGAGATCAAGAAATATTTGAGTTGCAGCTTAAGGTCCAGA----        780
SEQ_ID_NO_229 ACTTGAGCATAGGAGTTGAGATCAAGAAATATTTGAGTTGCAGCTTAAGGTCCAGA----        780
SEQ_ID_NO_230 ACTTGAGCATAGGAGTTGAGATCAAGAAATATTTGAGTTGCAGCTTAAGGTCCAGA----        780
SEQ_ID_NO_232 ACTTGAGCATAGGAGTTGAGATCAAGAAATATTTGAGTTGCAGCTTAAGGTCCAGA----        780
SEQ_ID_NO_234 ACTTGAGCATAGGAGTTGAGATCAAGAAATATTTGAGTTGCAGCTTAAGGTCCAGA----        745
SEQ_ID_NO_218 ACTTGAGCATAGGAGTTGAGATCAAGAAATATGTGAGTTGCAGCTTAAGGTTCAGA----       1192
SEQ_ID_NO_219 ACTTGAGCATAGGAGTTGAGATCAAGAAATATGTGAGTTGCAGCTTAAGGTTCAGA----       1192
SEQ_ID_NO_217 ACTTGAGCATAGGAGTTGAGATCAAGAAATATGTGAGTTGCAGCTTAAGGTTCAGA----       1192
SEQ_ID_NO_221 ACTTGAGCATAGGAGTTGAGATCAAGAAATATTTGAGTTGCAGCTTAAGGTTCAGA----        780
SEQ_ID_NO_224 ACTTGAGCATAGGAGTTGAGATCAAGAAATATTTGAGTTGCAGCTTAAGGTCCAGA----        780
              ****************  **** *******  ****** *********** ****

SEQ_ID_NO_213 ---GAGGAAATCCCCATACACTTGCTTGTAACGGTATGAATGTATGATCATTTTTTTTTC        837
SEQ_ID_NO_222 ---GAGGAAATCCCCATACACGTGCTTGTAACGGTATGGTCAT-------TTTTTTTTTC        831
SEQ_ID_NO_220 ---GAGGAAACCCCCATACACTTGCTTGTAACGGT--------ATGATCATTTTTTTT-G        828
SEQ_ID_NO_235 ---GAGGAAATCCC-ATACACTTGCTTGTAACGAT--------ATGATCATTTTTTTT-C        792
SEQ_ID_NO_225 ---GAGGAAATCCCCATACACTTGCTTGTAACGGTATGAATGTATGATCATTTTTTTTTC        837
SEQ_ID_NO_226 ---GAGGAAATCCCCATACACTTGCTTGTAACGGTATGAATGTATGATCATTTTTTTTTC        837
SEQ_ID_NO_228 ---GAGGAAATCCCCATACACTTGCTTGTAACGGTATGAATGTATGATCATTTTTTTTTC        837
SEQ_ID_NO_227 ---GAGGAAATCCCCATACACTTGCTTGTAACGGTATGAATGTATGATCATTTTTTTTTC        837
SEQ_ID_NO_223 AGAGAGGAAATCCCCATACACTTGCTTGTAACGGT--------ATGATCATTTTTTTT-C        830
SEQ_ID_NO_215 ---GAGGAAATCCCCATACACTTGCTTGTAACGGT--------ATGATCATATCTTTT-C       1240
SEQ_ID_NO_216 ---GAGGAAATCCCCATACACTTGCTTGTAACGGT--------ATGATCATATCTTTT-C       1240
SEQ_ID_NO_214 ---GAGGAAATCCCCATACACTTGCTTGTAACGGT--------ATGATCATATCTTTT-C       1240
SEQ_ID_NO_233 ---GAGGAAATCCCCATACACTTGCTTGTAACGGTATGAATGTATGATCATTTTTTTTTC        837
SEQ_ID_NO_236 ---GAGGAAATCCC-ATACACTTGCTTGTAACGAT--------ATGATCATTTTTTTT-C        792
```

TABLE 27-continued

```
SEQ_ID_NO_231 ---GAGGAAATCCCCATACACTTGCTTGTAACGGTATGAATGTATGATCATTTTTTTTTC      837
SEQ_ID_NO_229 ---GAGGAAATCCCCATACACTTGCTTGTAACGGTATGAATGTATGATCATTTTTTTTTC      837
SEQ_ID_NO_230 ---GAGGAAATCCCCATACACTTGCTTGTAACGGTATGAATGTATGATCATTTTTTTTTC      837
SEQ_ID_NO_232 ---GAGGAAATCCCCATACACTTGCTTGTAACGGTATGAATGTATGATCATTTTTTTTTC      837
SEQ_ID_NO_234 ---GAGGAAATCCCCATACACTTGCTTGTAACGGTATGAATGTATGATCATTTTTTTTTC      802
SEQ_ID_NO_218 ---GAGGAAATCCCCATACACTTGCTTGTAACGGT--------ATGATCATATCTTTT-C     1240
SEQ_ID_NO_219 ---GAGGAAATCCCCATACACTTGCTTGTAACGGT--------ATGATCATATCTTTT-C     1240
SEQ_ID_NO_217 ---GAGGAAATCCCCATACACTTGCTTGTAACGGT--------ATGATCATATCTTTT-C     1240
SEQ_ID_NO_221 ---GAGGAAATCCCCATACACGTGCTTGTAACGGTATGG---------TCATTTTTTTTC     829
SEQ_ID_NO_224 ---GAGGAAATCCCCATACACTTGCTTGTAACGGTATGAATGTATGATCATTTTTTTTTC      837
                ******* *** ****** *********** *              * * ****

SEQ_ID_NO_213 AAGGTAACATTTTCTAGCATCTTCACCTGTCTACTTGACTGAATGCAGTATATATTAGTT      897
SEQ_ID_NO_222 AAGGTAACATTTTCTAGCATCTTCAGCTGTCTACTTGACTGAATGCAGTATATATTAGTT      891
SEQ_ID_NO_220 AAGGTAACATTTTCTAGCATCTTCAGCTGTCTACTTGACTGAATGCAGTATATATTAGTT      888
SEQ_ID_NO_235 AAGGTAACATTTTCTAGCATCTTCAGCTGTCTACTTGACTGAATGCAGTATATATTAGTT      852
SEQ_ID_NO_225 AAGGTAACATTTTCTAGCATCTTCACCTGTCTACTTGACTGAATGCAGTATATATTAGTT      897
SEQ_ID_NO_226 AAGGTAACATTTTCTAGCATCTTCACCTGTCTACTTGACTGAATGCAGTATATATTAGTT      897
SEQ_ID_NO_228 AAGGTAACATTTTCTAGCATCTTCACCTGTCTACTTGACTGAATGCAGTATATATTAGTT      897
SEQ_ID_NO_227 AAGGTAACATTTTCTAGCATCTTCACCTGTCTACTTGACTGAATGCAGTATATATTAGTT      897
SEQ_ID_NO_223 AAGGTAACATTTTCTAGCATCTTCACCTGTCTACTTGACTGAATGCAGTATATATTAGTT      890
SEQ_ID_NO_215 AAGGTAACATTTTCTAGCATCTTCAGCTGTCTACTTGACTGAATGCAGTATATATTAGTT     1300
SEQ_ID_NO_216 AAGGTAACATTTTCTAGCATCTTCAGCTGTCTACTTGACTGAATGCAGTATATATTAGTT     1300
SEQ_ID_NO_214 AAGGTAACATTTTCTAGCATCTTCAGCTGTCTACTTGACTGAATGCAGTATATATTAGTT     1300
SEQ_ID_NO_233 AAGGTAACATTTTCTAGCATCTTCACCTGTCTACTTGACTGAATGCAGTATATATTAGTT      897
SEQ_ID_NO_236 AAGGTAACATTTTCTAGCATCTTCAGCTGTCTACTTGACTGAATGCAGTATATATTAGTT      852
SEQ_ID_NO_231 AAGGTAACATTTTCTAGCATCTTCACCTGTCTACTTGACTGAATGCAGTATATATTAGTT      897
SEQ_ID_NO_229 AAGGTAACATTTTCTAGCATCTTCACCTGTCTACTTGACTGAATGCAGTATATATTAGTT      897
SEQ_ID_NO_230 AAGGTAACATTTTCTAGCATCTTCACCTGTCTACTTGACTGAATGCAGTATATATTAGTT      897
SEQ_ID_NO_232 AAGGTAACATTTTCTAGCATCTTCACCTGTCTACTTGACTGAATGCAGTATATATTAGTT      897
SEQ_ID_NO_234 AAGGTAACATTTTCTAGCATCTTCACCTGTCTACTTGACTGAATGCAGTATATATTAGTT      862
SEQ_ID_NO_218 AAGGTAACATTTTCTAGCATCTTCAGCTGTCTACTTGACTGAATGCAGTATATATTAGTT     1300
SEQ_ID_NO_219 AAGGTAACATTTTCTAGCATCTTCAGCTGTCTACTTGACTGAATGCAGTATATATTAGTT     1300
SEQ_ID_NO_217 AAGGTAACATTTTCTAGCATCTTCAGCTGTCTACTTGACTGAATGCAGTATATATTAGTT     1300
SEQ_ID_NO_221 AAGGTAACATTTTCTAGCATCTTCAGCTGTCTACTTGACTGAATGCAGTATATATTAGTT      889
SEQ_ID_NO_224 AAGGTAACATTTTCTAGCATCTTCACCTGTCTACTTGACTGAATGCAGTATATATTAGTT      897
                ********************** ** ********************************

SEQ_ID_NO_213 GTAATAACTACTGGCCTTCTGCTGTGCACAAAAGGCGGGTATTACCACTTGCAGAAATTT      957
SEQ_ID_NO_222 GTAATAAATACTGGCCTTCTGCTGTGCACAAAAGGCGGGTATTACCACTTGCAGAAATTT      951
SEQ_ID_NO_220 GTAATAAATACTGCCCTTCTGCTGTGCACAAAAGGCGGGTATTACCACTTGCAGAAATTT      948
SEQ_ID_NO_235 GTAATAAATACTGCCCTTCTGCTGTGCACAAAAGGCGGGTATTACCACTTGCAGAAATTT      912
SEQ_ID_NO_225 GTAATAACTACTGGCCTTCTGCTGTGCACAAAAGGCGGGTATTACCACTTGCAGAAATTT      957
```

TABLE 27-continued

```
SEQ_ID_NO_226 GTAATAACTACTGGCCTTCTGCTGTGCACAAAAGGCGGGTATTACCACTTGCAGAAATTT     957
SEQ_ID_NO_228 GTAATAACTACTGGCCTTCTGCTGTGCACAAAAGGCGGGTATTACCACTTGCAGAAATTT     957
SEQ_ID_NO_227 GTAATAACTACTGGCCTTCTGCTGTGCACAAAAGGCGGGTATTACCACTTGCAGAAATTT     957
SEQ_ID_NO_223 GTAATAAATACTGCTCTTCTGCTGTGCAGAAAAGGCGGGTATTACCACTTGCAGAAATTT     950
SEQ_ID_NO_215 GTAATAAATACTGCCCTTCTGCTGTGCACAAAAGGCGGGTATTACCACTTGCAGAAATTT    1360
SEQ_ID_NO_216 GTAATAAATACTGCCCTTCTGCTGTGCACAAAAGGCGGGTATTACCACTTGCAGAAATTT    1360
SEQ_ID_NO_214 GTAATAAATACTGCCCTTCTGCTGTGCACAAAAGGCGGGTATTACCACTTGCAGAAATTT    1360
SEQ_ID_NO_233 GTAATAACTACTGGCCTTCTGCTGTGCACAAAAGGCGGGTATTACCACTTGCAGAAATTT     957
SEQ_ID_NO_236 GTAATAAATACTGCCCTTCTGCTGTGCACAAAAGGCGGGTATTACCACTTGCAGAAATTT     912
SEQ_ID_NO_231 GTAATAACTACTGGCCTTCTGCTGTGCACAAAAGGCGGGTATTACCACTTGCAGAAATTT     957
SEQ_ID_NO_229 GTAATAACTACTGGCCTTCTGCTGTGCACAAAAGGCGGGTATTACCACTTGCAGAAATTT     957
SEQ_ID_NO_230 GTAATAACTACTGGCCTTCTGCTGTGCACAAAAGGCGGGTATTACCACTTGCAGAAATTT     957
SEQ_ID_NO_232 GTAATAACTACTGGCCTTCTGCTGTGCACAAAAGGCGGGTATTACCACTTGCAGAAATTT     957
SEQ_ID_NO_234 GTAATAACTACTGGCCTTCTGCTGTGCACAAAAGGCGGGTATTACCACTTGCAGAAATTT     922
SEQ_ID_NO_218 GTAATAAATACTGCCCTTCTGCTGTGCACAAAAGGCGGGTATTACCACTTGCAGAAATTT    1360
SEQ_ID_NO_219 GTAATAAATACTGCCCTTCTGCTGTGCACAAAAGGCGGGTATTACCACTTGCAGAAATTT    1360
SEQ_ID_NO_217 GTAATAAATACTGCCCTTCTGCTGTGCACAAAAGGCGGGTATTACCACTTGCAGAAATTT    1360
SEQ_ID_NO_221 GTAATAAATACTGGCCTTCTGCTGTGCACAAAAGGCGGGTATTACCACTTGCAGAAATTT     949
SEQ_ID_NO_224 GTAATAACTACTGGCCTTCTGCTGTGCACAAAAGGCGGGTATTACCACTTGCAGAAATTT     957
              ****** ****  ************ *******************************

SEQ_ID_NO_213 GTCGGGTAAAGGTAATTGCCAGTTACCTTGTGTTCTTCCCTTGATCAGGAACACCTGGAG    1017
SEQ_ID_NO_222 GTCGGGTCAAGGTAATTGCCAGTTACCTTGTGTTCTTCCCTTCATCAGGAACACCTGGAG    1011
SEQ_ID_NO_220 GTCGGGTAAAGGTAATTGCCAGTTACCTTGTGTTCTTCCCTTCATCAGGAACACCTGGAG    1008
SEQ_ID_NO_235 GTCGGGTAAAGGTAATTGCCAGTTACCTTGTGTTCTTCCCTTCATCAGGAACACCTGGAG     972
SEQ_ID_NO_225 GTCGGGTAAAGGTAATTGCCAGTTACCTTGTGTTCTTCCCTTGATCAGGAACACCTGGAG    1017
SEQ_ID_NO_226 GTCGGGTAAAGGTAATTGCCAGTTACCTTGTGTTCTTCCCTTGATCAGGAACACCTGGAG    1017
SEQ_ID_NO_228 GTCGGGTAAAGGTAATTGCCAGTTACCTTGTGTTCTTCCCTTGATCAGGAACACCTGGAG    1017
SEQ_ID_NO_227 GTCGGGTAAAGGTAATTGCCAGTTACCTTGTGTTCTTCCCTTGATCAGGAACACCTGGAG    1017
SEQ_ID_NO_223 GTCGGGTAAAGGTAATTGCCAGTTACCTTGTGTTCTTCCCTTCATCAGGAACACCTGGAG    1010
SEQ_ID_NO_215 GTCGGGTAAAGGTAATTGCCAGTTACCTTGTGTTCTTCCCTTGATCAGGAACACCTGGAG    1420
SEQ_ID_NO_216 GTCGGGTAAAGGTAATTGCCAGTTACCTTGTGTTCTTCCCTTGATCAGGAACACCTGGAG    1420
SEQ_ID_NO_214 GTCGGGTAAAGGTAATTGCCAGTTACCTTGTGTTCTTCCCTTGATCAGGAACACCTGGAG    1420
SEQ_ID_NO_233 GTCGGGTAAAGGTAATTGCCAGTTACCTTGTGTTCTTCCCTTGATCAGGAACACCTGGAG    1017
SEQ_ID_NO_236 GTCGGGTAAAGGTAATTGCCAGTTACCTTGTGTTCTTCCCTTCATCAGGAACACCTGGAG     972
SEQ_ID_NO_231 GTCGGGTAAAGGTAATTGCCAGTTACCTTGTGTTCTTCCCTTGATCAGGAACACCTGGAG    1017
SEQ_ID_NO_229 GTCGGGTAAAGGTAATTGCCAGTTACCTTGTGTTCTTCCCTTGATCAGGAACACCTGGAG    1017
SEQ_ID_NO_230 GTCGGGTAAAGGTAATTGCCAGTTACCTTGTGTTCTTCCCTTGATCAGGAACACCTGGAG    1017
SEQ_ID_NO_232 GTCGGGTAAAGGTAATTGCCAGTTACCTTGTGTTCTTCCCTTGATCAGGAACACCTGGAG    1017
SEQ_ID_NO_234 GTCGGGTAAAGGTAATTGCCAGTTACCTTGTGTTCTTCCCTTGATCAGGAACACCTGGAG     982
SEQ_ID_NO_218 GTCGGGTAAAGGTAATTGCCAGTTACCTTGTGTTCTTCCCTTGATCAGGAACACCTGGAG    1420
```

TABLE 27-continued

| | | |
|---|---|---|
| SEQ_ID_NO_219 | GTCGGGTAAAGGTAATTGCCAGTTACCTTGTGTTCTTCCCTTGATCAGGAACACCTGGAG | 1420 |
| SEQ_ID_NO_217 | GTCGGGTAAAGGTAATTGCCAGTTACCTTGTGTTCTTCCCTTGATCAGGAACACCTGGAG | 1420 |
| SEQ_ID_NO_221 | GTCGGGTCAAGGTAATTGCCAGTTACCTTGTGTTCTTCCCTTGATCAGGAACACCTGGAG | 1009 |
| SEQ_ID_NO_224 | GTCGGGTAAAGGTAATTGCCAGTTACCTTGTGTTCTTCCCTTGATCAGGAACACCTGGAG | 1017 |
| | ****** ***************************** ***************** | |
| SEQ_ID_NO_213 | GAGGATGCGCTGTGGTTGAACCGAAGCC---CTGTGAGCGAAGTACTGATGACAGAAAGA | 1074 |
| SEQ_ID_NO_222 | GAGGATGCGCTGTGGTTGAACTGAAGCCGCCCTGTGAGCGAAGTACTGATGACAGAAAGA | 1071 |
| SEQ_ID_NO_220 | GAGGATGCGCTGTGGTTGAACTGAAGCC---CTGCGAGAGAAGTACTGATGACAGAAAGA | 1065 |
| SEQ_ID_NO_235 | GAGGATGCGCTGTGGTTGAACTGAAGCC---CTGCGAGAGAAGTACTGATGACAGAAAGA | 1029 |
| SEQ_ID_NO_225 | GAGGATGCGCTGTGGTTGAACCGAAGCC---CTGTGAGCGAAGTACTGATGACAGAAAGA | 1074 |
| SEQ_ID_NO_226 | GAGGATGCGCTGTGGTTGAACCGAAGCC---CTGTGAGCGAAGTACTGATGACAGAAAGA | 1074 |
| SEQ_ID_NO_228 | GAGGATGCGCTGTGGTTGAACCGAAGCC---CTGTGAGCGAAGTACTGATGACAGAAAGA | 1074 |
| SEQ_ID_NO_227 | GAGGATGCGCTGTGGTTGAACCGAAGCC---CTGTGAGCGAAGTACTGATGACAGAAAGA | 1074 |
| SEQ_ID_NO_223 | GAGGATGCGCTGTGGTTGAACCGAAGCC---CTGTGAGCGAAGTACTGATGACAGAAAGA | 1067 |
| SEQ_ID_NO_215 | GAGGATGCGCTGTGGTTGAACCGAAGCC---CTGTGAGCGAAGTACTGATGACAGAAAGA | 1477 |
| SEQ_ID_NO_216 | GAGGATGCGCTGTGGTTGAACCGAAGCC---CTGTGAGCGAAGTACTGATGACAGAAAGA | 1477 |
| SEQ_ID_NO_214 | GAGGATGCGCTGTGGTTGAACCGAAGCC---CTGTGAGCGAAGTACTGATGACAGAAAGA | 1477 |
| SEQ_ID_NO_233 | GAGGATGCGCTGTGGTTGAACCGAAGCC---CTGTGAGCGAAGTACTGATGACAGAAAGA | 1074 |
| SEQ_ID_NO_236 | GAGGATGCGCTGTGGTTGAACTGAAGCC---CTGCGAGAGAAGTACTGATGACAGAAAGA | 1029 |
| SEQ_ID_NO_231 | GAGGATGCGCTGTGGTTGAACCGAAGCC---CTGTGAGCGAAGTACTGATGACAGAAAGA | 1074 |
| SEQ_ID_NO_229 | GAGGATGCGCTGTGGTTGAACCGAAGCC---CTGTGAGCGAAGTACTGATGACAGAAAGA | 1074 |
| SEQ_ID_NO_230 | GAGGATGCGCTGTGGTTGAACCGAAGCC---CTGTGAGCGAAGTACTGATGACAGAAAGA | 1074 |
| SEQ_ID_NO_232 | GAGGATGCGCTGTGGTTGAACCGAAGCC---CTGTGAGCGAAGTACTGATGACAGAAAGA | 1074 |
| SEQ_ID_NO_234 | GAGGATGCGCTGTGGTTGAACCGAAGCC---CTGTGAGCGAAGTACTGATGACAGAAAGA | 1039 |
| SEQ_ID_NO_218 | GAGGATGCGCTGTGGTTGAACCGAAGCC---CTGTGAGCGAAGTACTGATGACAGAAAGA | 1477 |
| SEQ_ID_NO_219 | GAGGATGCGCTGTGGTTGAACCGAAGCC---CTGTGAGCGAAGTACTGATGACAGAAAGA | 1477 |
| SEQ_ID_NO_217 | GAGGATGCGCTGTGGTTGAACCGAAGCC---CTGTGAGCGAAGTACTGATGACAGAAAGA | 1477 |
| SEQ_ID_NO_221 | GAGGATGCGCTGTGGTTGAACTGAAGCCGCCCTGTGAGCGAAGTACTGATGACAGAAAGA | 1069 |
| SEQ_ID_NO_224 | GAGGATGCGCTGTGGTTGAACCGAAG---CCCTGTGAGCGAAGTACTGATGACAGAAAGA | 1074 |
| | ******************** ****    *** *** ******************** | |
| SEQ_ID_NO_213 | GCGGAAGATAAGATAAGAAAGGAA-CCCTTGCGCGGCAAGGCCTGGTGACATAGAGGTAG | 1133 |
| SEQ_ID_NO_222 | GCGGAAGATAAGATAAGAAAGGAA-CGCTTGCGCGGCAAGGCCTGGTGACATAGAGGTAG | 1130 |
| SEQ_ID_NO_220 | GCGGAAGATAAGATAAGAAAGGAAACCCTTGCGCGGCAGGGCCTGGTGACATAGAGGTAG | 1125 |
| SEQ_ID_NO_235 | GCGGAAGATAAGATAAGAAAGGAAACCCTTGCGCGGCAAGGCCTGGTGACATAGAGGTAG | 1089 |
| SEQ_ID_NO_225 | GCGGAAGATAAGATAAGAAAGGAA-CCCTTGCGCGGCAAGGCCTGGTGACATAGAGGTAG | 1133 |
| SEQ_ID_NO_226 | GCGGAAGATAAGATAAGAAAGGAA-CCCTTGCGCGGCAAGGCCTGGTGACATAGAGGTAG | 1133 |
| SEQ_ID_NO_228 | GCGGAAGATAAGATAAGAAAGGAA-CCCTTGCGCGGCAAGGCCTGGTGACATAGAGGTAG | 1133 |
| SEQ_ID_NO_227 | GCGGAAGATAAGATAAGAAAGGAA-CCCTTGCGCGGCAAGGCCTGGTGACATAGAGGTAG | 1133 |
| SEQ_ID_NO_223 | GCGGAAGATAAGATAAGAAAGGAA-CCCTTGCGCGGCAAGGCCTGGTGACATAGAGGTAG | 1126 |
| SEQ_ID_NO_215 | GCGGAAGATAAGATAAGAAAGGAA-CCCTTGCGCGGCAAGGCCTGGTGACATAGAGGTAG | 1536 |
| SEQ_ID_NO_216 | GCGGAAGATAAGATAAGAAAGGAA-CCCTTGCGCGGCAAGGCCTGGTGACATAGAGGTAG | 1536 |

TABLE 27-continued

| | | |
|---|---|---|
| SEQ_ID_NO_214 | GCGGAAGATAAGATAAGAAAGGAA-CCCTTGCGCGGCAAGGCCTGGTGACATAGAGGTAG | 1536 |
| SEQ_ID_NO_233 | GCGGAAGATAAGATAAGAAAGGAA-CCCTTGCGCGGCAAGGCCTGGTGACATAGAGGTAG | 1133 |
| SEQ_ID_NO_236 | GCGGAAGATAAGATAAGAAAGGAAACCCTTGCGCGGCAAGGCCTGGTGACATAGAGGTAG | 1089 |
| SEQ_ID_NO_231 | GCGGAAGATAAGATAAGAAAGGAA-CCCTTGCGCGGCAAGGCCTGGTGACATAGAGGTAG | 1133 |
| SEQ_ID_NO_229 | GCGGAAGATAAGATAAGAAAGGAA-CCCTTGCGCGGCAAGGCCTGGTGACATAGAGGTAG | 1133 |
| SEQ_ID_NO_230 | GCGGAAGATAAGATAAGAAAGGAA-CCCTTGCGCGGCAAGGCCTGGTGACATAGAGGTAG | 1133 |
| SEQ_ID_NO_232 | GCGGAAGATAAGATAAGAAAGGAA-CCCTTGCGCGGCAAGGCCTGGTGACATAGAGGTAG | 1133 |
| SEQ_ID_NO_234 | GCGGAAGATAAGATAAGAAAGGAA-CCCTTGCGCGGCAAGGCCTGGTGACATAGAGGTAG | 1098 |
| SEQ_ID_NO_218 | GCGGAAGATAAGATAAGAAAGGAA-CCCTTGCGCGGCAAGGCCTGGTGACATAGAGGTAG | 1536 |
| SEQ_ID_NO_219 | GCGGAAGATAAGATAAGAAAGGAA-CCCTTGCGCGGCAAGGCCTGGTGACATAGAGGTAG | 1536 |
| SEQ_ID_NO_217 | GCGGAAGATAAGATAAGAAAGGAA-CCCTTGCGCGGCAAGGCCTGGTGACATAGAGGTAG | 1536 |
| SEQ_ID_NO_221 | GCGGAAGATAAGATAAGAAAGGAA-CGCTTGCGCGGCAAGGCCTGGTGACATAGAGGTAG | 1128 |
| SEQ_ID_NO_224 | GCGGAAGATAAGATAAGAAAGGAA-CCCTTGCGCGGCAAGGCCTGGTGACATAGAGGTAG | 1133 |
| | ********************* * ********** ********************* | |
| SEQ_ID_NO_213 | TG-CGAGGCTCATACCGCCGCCGCTGGCAGGTTCCAGGCCTGTGCTTTTCTTGCCCTGTA | 1192 |
| SEQ_ID_NO_222 | TG-CGAGGCTCATACCGCCGCCGCTGGCAGGTTCGAGGCCTGTGCTTTTCTTGCCCTGTT | 1189 |
| SEQ_ID_NO_220 | TG-CGAGGCTCATACCGCCGCCGCTGGCAGGTTCCAGGCCTGTGCTTTTCTTGCCCTGTA | 1184 |
| SEQ_ID_NO_235 | TG-CGAGGCTCATACCGCCG---CTGGCAGGTTCCAGGCCTGTGCTTTTCTTGCCCTGTA | 1145 |
| SEQ_ID_NO_225 | TG-CGAGGCTCATACCGCCGCCGCTGGCAGGTTCCAGGCCTGTGCTTTTCTTGCCCTGTA | 1192 |
| SEQ_ID_NO_226 | TG-CGAGGCTCATACCGCCGCCGCTGGCAGGTTCCAGGCCTGTGCTTTTCTTGCCCTGTA | 1192 |
| SEQ_ID_NO_228 | TGGCGAGGCTCATACCGCCGCCGCTGGCAGGTTCCAGGCCTGTGCTTTTCTTGCCCTGTA | 1193 |
| SEQ_ID_NO_227 | TG-CGAGGCTCATACCGCCGCCGCTGGCAGGTTCCAGGCCTGTGCTTTTCTTGCCCTGTA | 1192 |
| SEQ_ID_NO_223 | TG-CGAGGCTCATACCGCCGCCGCTGGCAGGTTCCAGGCCTGTGCTTTTCTTGCCCTGTA | 1185 |
| SEQ_ID_NO_215 | TG-CGAGGCTCATACCGCCGCCGCTGGCAGGTTCCAGGCCTGTGCTTTTCTTGCCCTGTA | 1595 |
| SEQ_ID_NO_216 | TG-CGAGGCTCATACCGCCGCCGCTGGCAGGTTCCAGGCCTGTGCTTTTCTTGCCCTGTA | 1595 |
| SEQ_ID_NO_214 | TG-CGAGGCTCATACCGCCGCCGCTGGCAGGTTCCAGGCCTGTGCTTTTCTTGCCCTGTA | 1595 |
| SEQ_ID_NO_233 | TG-CGAGGCTCATACCGCCGCCGCTGGCAGGTTCSAGGCCTGTGCTTTTCTTGCCCTGTA | 1192 |
| SEQ_ID_NO_236 | TG-CGAGGCTCATACCGCC---GCTGGCAGGTTCCAGGCCTGTGCTTTTCTTGCCCTGTA | 1145 |
| SEQ_ID_NO_231 | TG-CGAGGCTCATACCGCCGCCGCTGGCAGGTTCCAGGCCTGTGCTTTTCTTGCCCTGTA | 1192 |
| SEQ_ID_NO_229 | TG-CGAGGCTCATACCGCCGCCGCTGGCAGGTTCCAGGCCTGTGCTTTTCTTGCCCTGTA | 1192 |
| SEQ_ID_NO_230 | TG-CGAGGCTCATACCGCCGCCGCTGGCAGGTTCCAGGCCTGTGCTTTTCTTGCCCTGTA | 1192 |
| SEQ_ID_NO_232 | TG-CGAGGCTCATACCGCCGCCGCTGGCAGGTTCCAGGCCTGTGCTTTTCTTGCCCTGTA | 1192 |
| SEQ_ID_NO_234 | TG-CGAGGCTCATACCGCCGCCGCTGGCAGGTTCCAGGCCTGTGCTTTTCTTGCCCTGTA | 1157 |
| SEQ_ID_NO_218 | TG-CGAGGCTCATACCGCCGCCGCTGGCAGGTTCCAGGCCTGTGCTTTTCTTGCCCTGTA | 1595 |
| SEQ_ID_NO_219 | TG-CGAGGCTCATACCGCCGCCGCTGGCAGGTTCCAGGCCTGTGCTTTTCTTGCCCTGTA | 1595 |
| SEQ_ID_NO_217 | TG-CGAGGCTCATACCGCCGCCGCTGGCAGGTTCCAGGCCTGTGCTTTTCTTGCCCTGTA | 1595 |
| SEQ_ID_NO_221 | TG-CGAGGCTCATACCGCCGCCGCTGGCAGGTTCGAGGCCTGTGCTTTTCTTGCCCTGTA | 1187 |
| SEQ_ID_NO_224 | TG-CGAGGCTCATACCGCCGCCGCTGGCAGGTTCCAGGCCTGTGCTTTTCTTGCCCTGTA | 1192 |
| | ** ***************    ********** ************************ | |
| SEQ_ID_NO_213 | TCCCCAGTCTATACTTCTGCGCACATCAGACGAGCCTCAGTGTTTCGGCACAGTGGTGCA | 1252 |
| SEQ_ID_NO_222 | TCCCCATTCTATACTTCTGCGCACATCAGACGAGCCTCAGTGTTTCGGCACAGTGGTGCA | 1249 |

TABLE 27-continued

| | | |
|---|---|---|
| SEQ_ID_NO_220 | TCCCCAGTCTATACTTCTGCGCACATCAGACGAGCGTCAGTGTTTCGGCACAGTGGTGCA | 1244 |
| SEQ_ID_NO_235 | TCCCCAGTCTATACTTCTGCGCACATCAGACGAGCCTCAGTGTTTCGGCACAGTGGTGCA | 1205 |
| SEQ_ID_NO_225 | TCCCCAGTCTATACTTCTGCGCACATCAGACGAGCCTCAGTGTTTCGGCACAGTGGTGCA | 1252 |
| SEQ_ID_NO_226 | TCCCCAGTCTATACTTCTGCGCACATCAGACGAGCCTCAGTGTTTCGGCACAGTGGTGCA | 1252 |
| SEQ_ID_NO_228 | TCCCCAGTCTATACTTCTGCGCACATCAGACGAGCCTCAGTGTTTCGGCACAGTGGTGCA | 1253 |
| SEQ_ID_NO_227 | TCCCCAGTCTATACTTCTGCGCACATCAGACGAGCCTCAGTGTTTCGGCACAGTGGTGCA | 1252 |
| SEQ_ID_NO_223 | TCCCCAGTCTATACTTCTGCGCACATCAGACGAGCCTCAGTGTTTCGGCACAGTGGTGCA | 1245 |
| SEQ_ID_NO_215 | TCCCCAGTCTATACTTCTGCGCACATCAGACGAGCCTCAGTGTTTCGGCACAGTGGTGCA | 1655 |
| SEQ_ID_NO_216 | TCCCCAGTCTATACTTCTGCGCACATCAGACGAGCCTCAGTGTTTCGGCACAGTGGTGCA | 1655 |
| SEQ_ID_NO_214 | TCCCCAGTCTATACTTCTGCGCACATCAGACGAGCCTCAGTGTTTCGGCACAGTGGTGCA | 1655 |
| SEQ_ID_NO_233 | TCCCCAGTCTATACTTCTGCGCACATCAGACGAGCGTCAGTGTTTCGGCACAGTGGTGCA | 1252 |
| SEQ_ID_NO_236 | TCCCCAGTCTATACTTCTGCGCACATCAGACGAGCCTCAGTGTTTCGGCACAGTGGTGCA | 1205 |
| SEQ_ID_NO_231 | TCCCCAGTCTATACTTCTGCGCACATCAGACGAGCCTCAGTGTTTCGGCACAGTGGTGCA | 1252 |
| SEQ_ID_NO_229 | TCCCCAGTCTATACTTCTGCGCACATCAGACGAGCCTCAGTGTTTCGGCACAGTGGTGCA | 1252 |
| SEQ_ID_NO_230 | TCCCCAGTCTATACTTCTGCGCACATCAGACGAGCCTCAGTGTTTCGGCACAGTGGTGCA | 1252 |
| SEQ_ID_NO_232 | TCCCCAGTCTATACTTCTGCGCACATCAGACGAGCCTCAGTGTTTCGGCACAGTGGTGCA | 1252 |
| SEQ_ID_NO_234 | TCCCCAGTCTATACTTCTGCGCACATCAGACGAGCCTCAGTGTTTCGGCACAGTGGTGCA | 1217 |
| SEQ_ID_NO_218 | TCCCCAGTCTATACTTCTGCGCACATCAGACGAGCCTCAGTGTTTCGGCACAGTGGTGCA | 1655 |
| SEQ_ID_NO_219 | TCCCCAGTCTATACTTCTGCGCACATCAGACGAGCCTCAGTGTTTCGGCACAGTGGTGCA | 1655 |
| SEQ_ID_NO_217 | TCCCCAGTCTATACTTCTGCGCACATCAGACGAGCCTCAGTGTTTCGGCACAGTGGTGCA | 1655 |
| SEQ_ID_NO_221 | TCCCCAGTCTATACTTCTGCGCACATCAGACGAGCCTCAGTGTTTCGGCACAGTGGTGCA | 1247 |
| SEQ_ID_NO_224 | TCCCCAGTCTATACTTCTGCGCACATCAGACGAGCCTCAGTGTTTCGGCACAGTGGTGCA | 1252 |
| | ****** *************************** *********************** | |
| SEQ_ID_NO_213 | ACAGAAAA-GGAGAGTGCTGG----TAGGTAACGCTGAGGCGGTGAAGAAAGAGAGGTCA | 1307 |
| SEQ_ID_NO_222 | ACAAAAAA-AGAGAGTGCTGG----TAGGTAACCCTNNNNNNNNNNNNNNNNNNNNNNNN | 1304 |
| SEQ_ID_NO_220 | ACAGAAAA-GGAGAGTGCTGG----TAGGTAACGCTGAGGCGGTGAAGAAAGAGAGGTCA | 1299 |
| SEQ_ID_NO_235 | ACAGAAAA-GGAGAGTGCTGG----TAGGTAACGCTGAGGCGGTGAAGAAAGAGAGGTCA | 1260 |
| SEQ_ID_NO_225 | ACAGAAAA-GGAGAGTGCTGG----TAGGTAACGCTGAGGCGGTGAAGAAAGAGAGGTCA | 1307 |
| SEQ_ID_NO_226 | ACAGAAAA-GGAGAGTGCTGG----TAGGTAACGCTGAGGCGGTGAAGAAAGAGAGGTCA | 1307 |
| SEQ_ID_NO_228 | ACAGAAAA-GGAGAGTGCTGG----TAGGTAACGCTGAGGCGGTGAAGAAAGAGAGGTCA | 1308 |
| SEQ_ID_NO_227 | ACAGAAAA-GGAGAGTGCTGG----TAGGTAACGCTGAGGCGGTGAAGAAAGAGAGGTCA | 1307 |
| SEQ_ID_NO_223 | ACAGAAAA-GGAGAGTGCTGC----TA----ACGCTGAGGCGGTGAAGAAAGAGAGGTCG | 1296 |
| SEQ_ID_NO_215 | ACAGAAAA-GGAGAGTGCTGG----TAGGTAACGCTGAGGCGGTGAAGAAAGAGAGGTCA | 1710 |
| SEQ_ID_NO_216 | ACAGAAAA-GGAGAGTGCTGG----TAGGTAACGCTGAGGCGGTGAAGAAAGAGAGGTCA | 1710 |
| SEQ_ID_NO_214 | ACAGAAAA-GGAGAGTGCTGG----TAGGTAACGCTGAGGCGGTGAAGAAAGAGAGGTCA | 1710 |
| SEQ_ID_NO_233 | ACAGAAAA-GGAGAGTGCTGG----TAGGTAACGCTGAGGCGGTGAAGAAAGAGAGGTCA | 1307 |
| SEQ_ID_NO_236 | ACAGAAAAAGGAGAGTGCTGGACTGCTGGTAACGCTGAGGCGGTGAAGAAAGAGAGGTCA | 1265 |
| SEQ_ID_NO_231 | ACAGAAAA-GGAGAGTGCTGG----TAGGTAACGCTGAGGCGGTGAAGAAAGAGAGGTCA | 1307 |
| SEQ_ID_NO_229 | ACAGAAAA-GGAGAGTGCTGG----TAGGTAACGCTGAGGCGGTGAAGAAAGAGAGGTCA | 1307 |
| SEQ_ID_NO_230 | ACAGAAAA-GGAGAGTGCTGG----TAGGTAACGCTGAGGCGGTGAAGAAAGAGAGGTCA | 1307 |
| SEQ_ID_NO_232 | ACAGAAAA-GGAGAGTGCTGG----TAGGTAACGCTGAGGCGGTGAAGAAAGAGAGGTCA | 1307 |

TABLE 27-continued

| | | |
|---|---|---|
| SEQ_ID_NO_234 | ACAGAAAA-GGAGAGTGCTGG----TAGGTAACGCTGAGGCGGTGAAGAAAGAGAGGTCA | 1272 |
| SEQ_ID_NO_218 | ACAGAAAA-GGAGAGTGCTGG----TAGGTAACGCTGAGGCGGTGAAGAAAGAGAGGTCA | 1710 |
| SEQ_ID_NO_219 | ACAGAAAA-GGAGAGTGCTGG----TAGGTAACGCTGAGGCGGTGAAGAAAGAGAGGTCA | 1710 |
| SEQ_ID_NO_217 | ACAGAAAA-GGAGAGTGCTGG----TAGGTAACGCTGAGGCGGTGAAGAAAGAGAGGTCA | 1710 |
| SEQ_ID_NO_221 | ACAGAAAA-GGAGAGTGCTGG----TAGGTAACGCTGAGGCGGTGAAGAAAGAGAGGTCA | 1302 |
| SEQ_ID_NO_224 | ACAGAAAA-GGAGAGTGCTGG----TAGGTAACGCTGAGGCGGTGAAGAAAGAGAGGTCA | 1307 |
| | *** **** **********          ** ** | |
| SEQ_ID_NO_213 | GACGGACCTGGAGGTGGCTTTTTAACTGGTAAAGAGTGAGGTCTTTCATGCCCATCAATC | 1367 |
| SEQ_ID_NO_222 | NNNNNNNNNNNNNNNNNNNNNNNNNNNNNNNNNNNNNNNNNNNNNNNNNNNNNNNNNNNN | 1364 |
| SEQ_ID_NO_220 | GACGGACCTGGAGGTGGCTTTTTAACTGGTAAAGAGTGAGGTCTTTCATGCCCATCAATC | 1359 |
| SEQ_ID_NO_235 | GACGGACCTGGAGGTGGCTTTTTAACTGGTAAAGAGTGAGGTCTTTCATGCCCATCAATC | 1320 |
| SEQ_ID_NO_225 | GACGGACCTGGAGGTGGCTTTTTAACTGGTAAAGAGTGAGGTCTTTCATGCCCATCAATC | 1367 |
| SEQ_ID_NO_226 | GACGGACCTGGAGGTGGCTTTTTAACTGGTAAAGAGTGAGGTCTTTCATGCCCATCAATC | 1367 |
| SEQ_ID_NO_228 | GACGGACCTGGAGGTGGCTTTTTAACTGGTAAAGAGTGAGGTCTTTCATGCCCATCAATC | 1368 |
| SEQ_ID_NO_227 | GACGGACCTGGAGGTGGCTTTTTAACTGGTAAAGAGTGAGGTCTTTCATGCCCATCAATC | 1367 |
| SEQ_ID_NO_223 | GACGGACCTGGAGGTGGCTTTTTAACTGGTAAAGAGTGAGGTCTTTCATGCCCATCAATC | 1356 |
| SEQ_ID_NO_215 | GACGGACCTGGAGGTGGCTTTTTAACTGGTAAAGAGTGAGGTCTTTCATGCCCATCAATC | 1770 |
| SEQ_ID_NO_216 | GACGGACCTGGAGGTGGCTTTTTAACTGGTAAAGAGTGAGGTCTTTCATGCCCATCAATC | 1770 |
| SEQ_ID_NO_214 | GACGGACCTGGAGGTGGCTTTTTAACTGGTAAAGAGTGAGGTCTTTCATGCCCATCAATC | 1770 |
| SEQ_ID_NO_233 | GACGGACCTGGAGGTGGCTTTTTAACTGGTAAAGAGTGAGGTCTTTCATGCCCATCAATC | 1367 |
| SEQ_ID_NO_236 | GACGGACCTGGAGGTGGCTTTTTAACTGGTAAAGAGTGAGGTCTTTCATGCCCATCAATC | 1325 |
| SEQ_ID_NO_231 | GACGGACCTGGAGGTGGCTTTTTAACTGGTAAAGAGTGAGGTCTTTCATGCCCATCAATC | 1367 |
| SEQ_ID_NO_229 | GACGGACCTGGAGGTGGCTTTTTAACTGGTAAAGAGTGAGGTCTTTCATGCCCATCAATC | 1367 |
| SEQ_ID_NO_230 | GACGGACCTGGAGGTGGCTTTTTAACTGGTAAAGAGTGAGGTCTTTCATGCCCATCAATC | 1367 |
| SEQ_ID_NO_232 | GACGGACCTGGAGGTGGCTTTTTAACTGGTAAAGAGTGAGGTCTTTCATGCCCATCAATC | 1367 |
| SEQ_ID_NO_234 | GACGGACCTGGAGGTGGCTTTTTAACTGGTAAAGAGTGAGGTCTTTCATGCCCATCAATC | 1332 |
| SEQ_ID_NO_218 | GACGGACCTGGAGGTGGCTTTTTAACTGGTAAAGAGTGAGGTCTTTCATGCCCATCAATC | 1770 |
| SEQ_ID_NO_219 | GACGGACCTGGAGGTGGCTTTTTAACTGGTAAAGAGTGAGGTCTTTCATGCCCATCAATC | 1770 |
| SEQ_ID_NO_217 | GACGGACCTGGAGGTGGCTTTTTAACTGGTAAAGAGTGAGGTCTTTCATGCCCATCAATC | 1770 |
| SEQ_ID_NO_221 | GACGGACCTGGAGGTGGCTTTTTAACTGGTAAAGAGTGAGGTCTTTCATGCCCATCAATC | 1362 |
| SEQ_ID_NO_224 | GACGGACCTGGAGGTGGCTTTTTAACTGGTAAAGAGTGAGGTCTTTCATGCCCATCAATC | 1367 |
| SEQ_ID_NO_213 | TGAGCACCGACTTGGGTGTTGCTCCTGTTCGCAGGAAGCACAAGAAATGGTCAGTACTCC | 1427 |
| SEQ_ID_NO_222 | NNNNNNNNNNNNNNNNNNNNNNNNNNNNNNNNNNNNNNNNNNNNNNNNNNNNNNNNNNNN | 1424 |
| SEQ_ID_NO_220 | TGAGCACCGACTTGGGTGTTGCTCCTGTTCGCAGGAAGCACAAGAAATGGTCAGTACTCC | 1419 |
| SEQ_ID_NO_235 | TGAGCACCGACTTGGGTGTTGCTCCTGTTCGCAGGAAGCACAAGAAATGGTCAGTACTCC | 1380 |
| SEQ_ID_NO_225 | TGAGCACCGACTTGGGTGTTGCTCCTGTTCGCAGGAAGCACAAGAAATGGTCAGTACTCC | 1427 |
| SEQ_ID_NO_226 | TGAGCACCGACTTGGGTGTTGCTCCTGTTCGCAGGAAGCACAAGAAATGGTCAGTACTCC | 1427 |
| SEQ_ID_NO_228 | TGAGCACCGACTTGGGTGTTGCTCCTGTTCGCAGGAAGCACAAGAAATGGTCAGTACTCC | 1428 |
| SEQ_ID_NO_227 | TGAGCACCGACTTGGGTGTTGCTCCTGTTCGCAGGAAGCACAAGAAATGGTCAGTACTCC | 1427 |
| SEQ_ID_NO_223 | TGAGCACCGACTTGGGTGTTGCTCCTGTTCGCAGGAAGCACAAGAAATGGTCAGTACTCC | 1416 |

TABLE 27-continued

| | | |
|---|---|---|
| SEQ_ID_NO_215 | TGAGCACCGACTTGGGTGTTGCTCCTGTTCGCAGGAAGCACAAGAAATGGTCAGTACTCC | 1830 |
| SEQ_ID_NO_216 | TGAGCACCGACTTGGGTGTTGCTCCTGTTCGCAGGAAGCACAAGAAATGGTCAGTACTCC | 1830 |
| SEQ_ID_NO_214 | TGAGCACCGACTTGGGTGTTGCTCCTGTTCGCAGGAAGCACAAGAAATGGTCAGTACTCC | 1830 |
| SEQ_ID_NO_233 | TGAGCACCGACTTGGGTGTTGCTTCTGTTCGCAGGAAGCACAAGAAATGGTCAGTACTCC | 1427 |
| SEQ_ID_NO_236 | TGAGCACCGACTTGGGTGTTGCTTCTGTTCGCAGGAAGCACAAGAAATGGTCAGTACTCC | 1385 |
| SEQ_ID_NO_231 | TGAGCACCGACTTGGGTGTTGCTCCTGTTCGCAGGAAGCACAAGAAATGGTCAGTACTCC | 1427 |
| SEQ_ID_NO_229 | TGAGCACCGACTTGGGTGTTGCTCCTGTTCGCAGGAAGCACAAGAAATGGTCAGTACTCC | 1427 |
| SEQ_ID_NO_230 | TGAGCACCGACTTGGGTGTTGCTCCTGTTCGCAGGAAGCACAAGAAATGGTCAGTACTCC | 1427 |
| SEQ_ID_NO_232 | TGAGCACCGACTTGGGTGTTGCTCCTGTTCGCAGGAAGCACAAGAAATGGTCAGTACTCC | 1427 |
| SEQ_ID_NO_234 | TGAGCACCGACTTGGGTGTTGCTCCTGTTCGCAGGAAGCACAAGAAATGGTCAGTACTCC | 1392 |
| SEQ_ID_NO_218 | TGAGCACCGACTTGGGTGTTGCTCCTGTTCGCAGGAAGCACAAGAAATGGTCAGTACTCC | 1830 |
| SEQ_ID_NO_219 | TGAGCACCGACTTGGGTGTTGCTCCTGTTCGCAGGAAGCACAAGAAATGGTCAGTACTCC | 1830 |
| SEQ_ID_NO_217 | TGAGCACCGACTTGGGTGTTGCTCCTGTTCGCAGGAAGCACAAGAAATGGTCAGTACTCC | 1830 |
| SEQ_ID_NO_221 | TGAGCACCGACTTGGGTGTTGCTCCTGTTCGCAGGAAGCACAAGAAATGGTCAGTACTCC | 1422 |
| SEQ_ID_NO_224 | TGAGCACCGACTTGGGTGTTGCTCCTGTTCGCAGGAAGCACAAGAAATGGTCAGTACTCC | 1427 |
| SEQ_ID_NO_213 | ACACCATAAGCATGTCGGTGGTGTGTTGGANNNNNNNNNNNNNNNNNNNNNNNNNNNNNN | 1487 |
| SEQ_ID_NO_222 | NNNNNNNNNNNNNNNNNNNNNNNNNNNNNNNNNNNNNNNNNNNNNNNNNNNNNNNNNNNN | 1484 |
| SEQ_ID_NO_220 | ACAGCGTAGGCATGTCGGTGGTGTGTTGGAGGAGGCAAGATTCAGATGATTATTATATGA | 1479 |
| SEQ_ID_NO_235 | ACAGCGTAGGCATGTCGGTGGTGTGTTGGAGGAGGCAAGATTCAGATGATTATTATATGA | 1440 |
| SEQ_ID_NO_225 | ACAGCGTAGGCATGTCGGTGGTGTGTTGGAGGAGGCAAGATTCAGATGATTATTATATGA | 1487 |
| SEQ_ID_NO_226 | ACAGCGTAGGCATGTCGGTGGTGTGTTGGAGGAGGCAAGATTCAGATGATTATTATATGA | 1487 |
| SEQ_ID_NO_228 | ACAGCGTAGGCATGTCGGTGGTGTGTTGGAGGAGGCAAGATTCAGATGATTATTATATGA | 1488 |
| SEQ_ID_NO_227 | ACAGCGTAGGCATGTCGGTGGTGTGTTGGAGGAGGCAAGATTCAGATGATTATTATATGA | 1487 |
| SEQ_ID_NO_223 | ACAGCGTAGGCATGTCGGTG---TGTTCGAGGAGGCAAGATTCAGATGATTATTATATGA | 1473 |
| SEQ_ID_NO_215 | ACAGCGTAGGCATGTCGGTGGTGTGTTGGAGGAGGCAAGATTCAGATGATTATTATATGA | 1890 |
| SEQ_ID_NO_216 | ACAGCGTAGGCATGTCGGTGGTGTGTTGGAGGAGGCAAGATTCAGATGATTATTATATGA | 1890 |
| SEQ_ID_NO_214 | ACAGCGTAGGCATGTCGGTGGTGTGTTGGAGGAGGCAAGATTCAGATGATTATTATATGA | 1890 |
| SEQ_ID_NO_233 | ACAGCGTAGGCATGTCGGTG---TGTTCGAGGAGGCAAGATTCAGATGATTATTATATGA | 1484 |
| SEQ_ID_NO_236 | ACAGCGTAGGCATGTCGGTG---TGTTCGAGGAGGCAAGATTCAGATGATTATTATATGA | 1442 |
| SEQ_ID_NO_231 | ACAGCGTAGGCATGTCGGTGGTGTGTTGGAGGAGGCAAGATTCAGATGATTATTATATGA | 1487 |
| SEQ_ID_NO_229 | ACAGCGTAGGCATGTCGGTGGTGTGTTGGAGGAGGCAAGATTCAGATGATTATTATATGA | 1487 |
| SEQ_ID_NO_230 | ACAGCGTAGGCATGTCGGTGGTGTGTTGGAGGAGGCAAGATTCAGATGATTATTATATGA | 1487 |
| SEQ_ID_NO_232 | ACAGCGTAGGCATGTCGGTGGTGTGTTGGAGGAGGCAAGATTCAGATGATTATTATATGA | 1487 |
| SEQ_ID_NO_234 | ACAGCGTAGGCATGTCGGTGGTGTGTTGGAGGAGGCAAGATTCAGATGATTATTATATGA | 1452 |
| SEQ_ID_NO_218 | ACAGCGTAGGCATGTCGGTGGTGTGTTGGAGGAGGCAAGATTCAGATGATTATTATATGA | 1890 |
| SEQ_ID_NO_219 | ACAGCGTAGGCATGTCGGTGGTGTGTTGGAGGAGGCAAGATTCAGATGATTATTATATGA | 1890 |
| SEQ_ID_NO_217 | ACAGCGTAGGCATGTCGGTGGTGTGTTGGAGGAGGNNNNNNNNNNNNNNNNNNNNNNNNN | 1890 |
| SEQ_ID_NO_221 | ACAGCGTAGGCATGTCGGTGGTGTGTTGGAGGAGGCAAGATNNNNNNNNNNNNNNNNNNN | 1482 |
| SEQ_ID_NO_224 | ACAGCGTAGGCATGTCGGTGGTGTGTTGGAGGAGGCAAGATTCAGATGATTATTATATGA | 1487 |
| SEQ_ID_NO_213 | NNNNNNNNNNNNNNNNNNNNNNNNNNNNNNNNNNNNNNNNNNNNNNNNNNNNNNNNNNNN | 1547 |

TABLE 27-continued

| | | |
|---|---|---|
| SEQ_ID_NO_222 | NNNNNNNNNNNNNNNNNNNNNNNNNNNNNNNNNNNNNNNNNNNNNNNNNN | 1544 |
| SEQ_ID_NO_220 | GCTCGAAAAGCTAGAGAATGGATGTTCAGACTTGAGAGCTCTGATTTGAGAGAAATTGCA | 1539 |
| SEQ_ID_NO_235 | GCTCGAAAAGCTAGAGAATGGATGTTCAGACTTGAGAGCTCTGATTTGAGAGGAATTGCA | 1500 |
| SEQ_ID_NO_225 | GCTCGAAAAGCTAGAGAATGGATGTTCAGACTTGAGAGCTCTGATTTGAGAGRAATTGCA | 1547 |
| SEQ_ID_NO_226 | GCTCGAAAAGCTAGAGAATGGATGTTCAGACTTGAGAGCTCTGATTTGAGAGRAATTGCA | 1547 |
| SEQ_ID_NO_228 | GCTCGAAAAGCTAGAGAATGGATGTTCAGACTTGAGAGCTCTGATTTGAGAGGAATTGCA | 1548 |
| SEQ_ID_NO_227 | GCTCGAAAAGCTAGAGAATGGATGTTCAGACTTGAGAGCTCTGATTTGAGAGGAATTGCA | 1547 |
| SEQ_ID_NO_223 | GCTCGAAAAGCTAGAGAATGGATGTTCAGACTTGAGAGGTCTGATTTGAGAGGAATTGCA | 1533 |
| SEQ_ID_NO_215 | GCTCGAAAAGCTAGAGAATGGATGTTCAGACTTGAGAGCTCTGATTTGAGAGGAATTGCA | 1950 |
| SEQ_ID_NO_216 | GCTCGAAAAGCTAGAGAATGGATGTTCAGACTTGAGAGCTCTGATTTGAGAGGAATTGCA | 1950 |
| SEQ_ID_NO_214 | GCTCGAAAAGCTAGAGAATGGATGTTCAGACTTGAGAGCTCTGATTTGAGAGGAATTGCA | 1950 |
| SEQ_ID_NO_233 | GCTCGAAAAGCTAGAGAATGGATGTTCAGACTTGAGATCTCTGATTTGAGAGGAATTGCA | 1544 |
| SEQ_ID_NO_236 | GCTCGAAAAGCTAGAGAATGGATGTTCAGACTTGAGATCTCTGATTTGAGAGGAATTGCA | 1502 |
| SEQ_ID_NO_231 | GCTCGAAAAGCTAGAGAATGGATGTTCAGACTTGAGAGCTCTGATTTGAGAGGAATTGCA | 1547 |
| SEQ_ID_NO_229 | GCTCGAAAAGCTAGAGAATGGATGTTCAGACTTGAGAGCTCTGATTTGATATGAATTGCA | 1547 |
| SEQ_ID_NO_230 | GCTCGAAAAGCTAGAGAATGGATGTTCAGACTTGAGAGCTCTGATTTGAGAGGAATTGCA | 1547 |
| SEQ_ID_NO_232 | GCTCGAAAAGCTAGAGAATGGATGTTCAGACTTGAGAGCTCTGATTTGAGAGGAATTGCA | 1547 |
| SEQ_ID_NO_234 | GCTCGAAAAGCTAGAGAATGGATGTTCAGACTTGAGAGCTCTGATTTGAGAGGAATTGCA | 1512 |
| SEQ_ID_NO_218 | GCTCGAAAAGCTAGAGAATGGATGTTCAGACTTGAGAGCTCTGATTTGAGAGGAATTGCA | 1950 |
| SEQ_ID_NO_219 | GCTCGAAAAGCTAGAGAATGGATGTTCAGACTTGAGAGCTCTGATTTGAGAGGAATTGCA | 1950 |
| SEQ_ID_NO_217 | NNNNNNNNNNNNNNNNNNNNNNNNNNNNNNNNNNNNNNNNNNNNNNNNNN | 1950 |
| SEQ_ID_NO_221 | NNNNNNNNNNNNNNNNNNNNNNNNNNNNNNNNNNNNNNNNNNNNNNNNNN | 1542 |
| SEQ_ID_NO_224 | GCTCGAAAAGCTAGAGAATGGATGTTCAGACTTGAGAGCTCTGATTTGAGAGRAATTGCA | 1547 |
| SEQ_ID_NO_213 | NNNNNNNNNNNNNNNNNNNNNNNNNNNNNNNNNNNNNNNNN-NNNNNNNNNNNNNNNNNN | 1606 |
| SEQ_ID_NO_222 | NNNNNNNNNNNNNNNNNNNNNNNNNNNNNNNNNNNNNNNNN-NNNNNNNNNNNNNNNNNN | 1603 |
| SEQ_ID_NO_220 | CTTGTCGTTTTCCCAAGGCGACGCGGCCTTTT-CCAGAGGTTTTTTTTTTTNNNNNNNN | 1598 |
| SEQ_ID_NO_235 | CTTGTCGTTTTCCCAAGGCGACGCGGCCTTTT-CCAGAGGTTTTTTTTTTTNNNNNNNN | 1559 |
| SEQ_ID_NO_225 | CTTGTCGTTTTCCCAAGGCGACGCGGCCTTTT-CCAGAGGTTTTTTTTTTTNNNNNNNN | 1606 |
| SEQ_ID_NO_226 | CTTGTCGTTTTCCCAAGGCGACGCGGCCTTTTTCCAGAGGTTTTTTTTTTTNNNNNNNN | 1607 |
| SEQ_ID_NO_228 | CTTGTCGTTTTCCCAAGGCGACGCGGCCTTTT-CCAGAGGTTTTTTTTTTTTTNNN | 1607 |
| SEQ_ID_NO_227 | CTTGTCGTTTTCCCAAGGCGACGCGGCCTTTT-CCAGAGGTTTTTTTTTTTNNNNNNNN | 1606 |
| SEQ_ID_NO_223 | CTTGTCGTTTTCCCAGGGCGACGCGGCCTTTTTCCAGAGGCTTTTTTTTNNNNNNNNNN | 1593 |
| SEQ_ID_NO_215 | CTTGTCGTTTTCCCAAGGCGACGCGGCCTTTTTCCAGAGTT-TTTTTTTTNNNNNNNNN | 2009 |
| SEQ_ID_NO_216 | CTTGTCGTTTTCCCAAGGCGACGCGGCCTTTTTCCAGAGTT-TTTTTTTTNNNNNNNNN | 2009 |
| SEQ_ID_NO_214 | CTTGTCGTTTTCCCAAGGCGACGCGGCCTTTTTCCAGAGTT-TTTTTTTTNNNNNNNNN | 2009 |
| SEQ_ID_NO_233 | CTTGTCGTTTTCCCAGGGCGACGCGGCCTTTTTCCAGAGGCATTTTTTTCAACTGCCTT | 1604 |
| SEQ_ID_NO_236 | CTTGTCGTTTTCCCARGGCGACGCGGCCTTTTTCCAGAGGCATTTTTTTCANNNNNNNN | 1562 |
| SEQ_ID_NO_231 | CTTGTCGTTTTCCCAAGGCGACGCGGCCTTTTTCCAGAGTTTTTTTTTTNNNNNNNNN | 1607 |
| SEQ_ID_NO_229 | CTTGTCGTTTTCCCAAGGCGACACGGCCTTTTTCCAGAGTTTTTTTTTTTNNNNNNNNN | 1607 |
| SEQ_ID_NO_230 | CTTGTCGTTTTCCCAAGGCGACGCGGCCTTTTTCCAGAGGCTTTTTTTTTNNNNNNNNN | 1607 |

TABLE 27-continued

| | | |
|---|---|---|
| SEQ_ID_NO_232 | CTTGTCGTTTTCCCAAGGCGACGCGGCCTTTTTCCAGAGGCTTTTTTTTTTNNNNNNNN | 1607 |
| SEQ_ID_NO_234 | CTTGTCGTTTTCCCAAGGCGACGCGGCCTTTTTCCAGAGTT-TTTTTTTTTNNNNNNNN | 1571 |
| SEQ_ID_NO_218 | CTTGTCGTTTTCCCAAGGCGACGCGGCCTTTTTCCAGAGTT-TTTTTTTTTTNNNNNNN | 2009 |
| SEQ_ID_NO_219 | CTTGTCGTTTTCCCAAGGCGACGCGGCCTTTTTCCAGAGTT-TTTTTTTTTTNNNNNNN | 2009 |
| SEQ_ID_NO_217 | NNNNNNNNNNNNNNNNNNNNNNNNNNNNNNNNNNNNNNNNN-NNNNNNNNNNNNNNNNN | 2009 |
| SEQ_ID_NO_221 | NNNNNNNNNNNNNNNNNNNNNNNNNNNNNNNNNNNNNNNNNNNNNNNNNNNNNNNNNNN | 1602 |
| SEQ_ID_NO_224 | CTTGTCGTTTTCCCAAGGCGACGCGGCCTTTTTCCAGAGGTTTTTTTTTTTNNNNNNNN | 1607 |
| SEQ_ID_NO_213 | NNNNNNNNNNNNNNNNNNNNNNNNNNNNNNNNNNNNNNNNNNNNNNNNNNNNNNNNNNN | 1666 |
| SEQ_ID_NO_222 | NNNNNNNNNNNNNNNNNNNNNNNNNNNNNNNNNNNNNNNNNNNNNNNNNNNNNNNNNNN | 1663 |
| SEQ_ID_NO_220 | NNNNNNNNNNNNNNNNNNNNNNNNNNNNNNNNNNNNNNNNNNNNNNNNNNNNNNNNNNN | 1658 |
| SEQ_ID_NO_235 | NNNNNNNNNNNNNNNNNNNNNNNNNNNNNNNNNNNNNNNNNNNNNNNNNNNNNNNNNNN | 1619 |
| SEQ_ID_NO_225 | NNNNNNNNNNNNNNNNNNNNNNNNNNNNNNNNNNNNNNNNNNNNNNNNNNNNNNNNNNN | 1666 |
| SEQ_ID_NO_226 | NNNNNNNNNNNNNNNNNNNNNNNNNNNNNNNNNNNNNNNNNNNNNNNNNNNNNNNNNNN | 1667 |
| SEQ_ID_NO_228 | NNNNNNNNNNNNNNNNNNNNNNNNNNNNNNNNNNNNNNNNNNNNNNNNNNNNNNNNNNN | 1667 |
| SEQ_ID_NO_227 | NNNNNNNNNNNNNNNNNNNNNNNNNNNNNNNNNNNNNNNNNNNNNNNNNNNNNNNNNNN | 1666 |
| SEQ_ID_NO_223 | NNNNNNNNNNNNNNNNNNNNNNNNNNNNNNNNNNNNNNNNNNNNNNNNNNNNNNNNNNN | 1653 |
| SEQ_ID_NO_215 | NNNNNNNNNNNNNNNNNNNNNNNNNNNNNNNNNNNNNNNNNNNNNNNNNNNNNNNNNNN | 2069 |
| SEQ_ID_NO_216 | NNNNNNNNNNNNNNNNNNNNNNNNNNNNNNNNNNNNNNNNNNNNNNNNNNNNNNNNNNN | 2069 |
| SEQ_ID_NO_214 | NNNNNNNNNNNNNNNNNNNNNNNNNNNNNNNNNNNNNNNNNNNNNNNNNNNNNNNNNNN | 2069 |
| SEQ_ID_NO_233 | TTGGTCATGTCAACGGAACTGCCTTTTCCTCTGACTGCATGCTATAGACTTGGCAATGGC | 1664 |
| SEQ_ID_NO_236 | NNNNNNNNNNNNNNNNNNNNNNNNNNNNNNNNNNNNNNNNNNNNNNNNNNNNNNNNNNN | 1622 |
| SEQ_ID_NO_231 | NNNNNNNNNNNNNNNNNNNNNNNNNNNNNNNNNNNNNNNNNNNNNNNNNNNNNNNNNNN | 1667 |
| SEQ_ID_NO_229 | NNNNNNNNNNNNNNNNNNNNNNNNNNNNNNNNNNNNNNNNNNNNNNNNNNNNNNNNNNN | 1667 |
| SEQ_ID_NO_230 | NNNNNNNNNNNNNNNNNNNNNNNNNNNNNNNNNNNNNNNNNNNNNNNNNNNNNNNNNNN | 1667 |
| SEQ_ID_NO_232 | NNNNNNNNNNNNNNNNNNNNNNNNNNNNNNNNNNNNNNNNNNNNNNNNNNNNNNNNNNN | 1667 |
| SEQ_ID_NO_234 | NNNNNNNNNNNNNNNNNNNNNNNNNNNNNNNNNNNNNNNNNNNNNNNNNNNNNNNNNNN | 1631 |
| SEQ_ID_NO_218 | NNNNNNNNNNNNNNNNNNNNNNNNNNNNNNNNNNNNNNNNNNNNNNNNNNNNNNNNNNN | 2069 |
| SEQ_ID_NO_219 | NNNNNNNNNNNNNNNNNNNNNNNNNNNNNNNNNNNNNNNNNNNNNNNNNNNNNNNNNNN | 2069 |
| SEQ_ID_NO_217 | NNNNNNNNNNNNNNNNNNNNNNNNNNNNNNNNNNNNNNNNNNNNNNNNNNNNNNNNNNN | 2069 |
| SEQ_ID_NO_221 | NNNNNNNNNNNNNNNNNNNNNNNNNNNNNNNNNNNNNNNNNNNNNNNNNNNNNNNNNNN | 1662 |
| SEQ_ID_NO_224 | NNNNNNNNNNNNNNNNNNNNNNNNNNNNNNNNNNNNNNNNNNNNNNNNNNNNNNNNNNN | 1667 |
| SEQ_ID_NO_213 | NNNNNNNNNNNNNNNNNNNNNNNNNNNNNNNNNNNNNNNNNNNNNNNNNNNNNNNNNNN | 1726 |
| SEQ_ID_NO_222 | NNNNNNNNNNNNNNNNNNNNNNNNNNNNNNNNNNNNNNNNNNNNNNNNNNNNNNNNNNN | 1723 |
| SEQ_ID_NO_220 | NNNNNNNNNNNNNNNNNNNNNNNNNNNNNNNNNNNNNNNNNNNNNNNNNNNNNNNNNNN | 1718 |
| SEQ_ID_NO_235 | NNNNNNNNNNNNNNNNNNNNNNNNNNNNNNNNNNNNNNNNNNNNNNNNNNNNNNNNNNN | 1679 |
| SEQ_ID_NO_225 | NNNNNNNNNNNNNNNNNNNNNNNNNNNNNNNNNNNNNNNNNNNNNNNNNNNNNNNNNNN | 1726 |
| SEQ_ID_NO_226 | NNNNNNNNNNNNNNNNNNNNNNNNNNNNNNNNNNNNNNNNNNNNNNNNNNNNNNNNNNN | 1727 |
| SEQ_ID_NO_228 | NNNNNNNNNNNNNNNNNNNNNNNNNNNNNNNNNNNNNNNNNNNNNNNNNNNNNNNNNNN | 1727 |
| SEQ_ID_NO_227 | NNNNNNNNNNNNNNNNNNNNNNNNNNNNNNNNNNNNNNNNNNNNNNNNNNNNNNNNNNN | 1726 |
| SEQ_ID_NO_223 | NNNNNNNNNNNNNNNNNNNNNNNNNNNNNNNNNNNNNNNNNNNNNNNNNNNNNNNNNNN | 1713 |

TABLE 27-continued

| | |
|---|---|
| SEQ_ID_NO_215 NNNNNNNNNNNNNNNNNNNNNNNNNNNNNNNNNNNNNNNNNNNNNNNNNNNN | 2129 |
| SEQ_ID_NO_216 NNNNNNNNNNNNNNNNNNNNNNNNNNNNNNNNNNNNNNNNNNNNNNNNNNNN | 2129 |
| SEQ_ID_NO_214 NNNNNNNNNNNNNNNNNNNNNNNNNNNNNNNNNNNNNNNNNNNNNNNNNNNN | 2129 |
| SEQ_ID_NO_233 AGAAGCGCAAAGCCAGGCAGCGAAGGATTCGGACTGCAACTGGCCGTCGTTTTACAANNN | 1724 |
| SEQ_ID_NO_236 NNNNNNNNNNNNNNNNNNNNNNNNNNNNNNNNNNNNNNNNNNNNNNNNNNNN | 1682 |
| SEQ_ID_NO_231 NNNNNNNNNNNNNNNNNNNNNNNNNNNNNNNNNNNNNNNNNNNNNNNNNNNN | 1727 |
| SEQ_ID_NO_229 NNNNNNNNNNNNNNNNNNNNNNNNNNNNNNNNNNNNNNNNNNNNNNNNNNNN | 1727 |
| SEQ_ID_NO_230 NNNNNNNNNNNNNNNNNNNNNNNNNNNNNNNNNNNNNNNNNNNNNNNNNNNN | 1727 |
| SEQ_ID_NO_232 NNNNNNNNNNNNNNNNNNNNNNNNNNNNNNNNNNNNNNNNNNNNNNNNNNNN | 1727 |
| SEQ_ID_NO_234 NNNNNNNNNNNNNNNNNNNNNNNNNNNNNNNNNNNNNNNNNNNNNNNNNNNN | 1691 |
| SEQ_ID_NO_218 NNNNNNNNNNNNNNNNNNNNNNNNNNNNNNNNNNNNNNNNNNNNNNNNNNNN | 2129 |
| SEQ_ID_NO_219 NNNNNNNNNNNNNNNNNNNNNNNNNNNNNNNNNNNNNNNNNNNNNNNNNNNN | 2129 |
| SEQ_ID_NO_217 NNNNNNNNNNNNNNNNNNNNNNNNNNNNNNNNNNNNNNNNNNNNNNNNNNNN | 2129 |
| SEQ_ID_NO_221 NNNNNNNNNNNNNNNNNNNNNNNNNNNNNNNNNNNNNNNNNNNNNNNNNNNN | 1722 |
| SEQ_ID_NO_224 NNNNNNNNNNNNNNNNNNNNNNNNNNNNNNNNNNNNNNNNNNNNNNNNNNNNN | 1727 |

\*\*\*

| | |
|---|---|
| SEQ_ID_NO_213 NNNNNNNNNNNNAAAAAAAAAAAAAAAAAAAGAATGCACACCGACATGCTCTGTAGCACAA | 1786 |
| SEQ_ID_NO_222 NNNNNNNNNNNNAAAAAAAAAAAAAAAAAAAGAATGCAGACCGACATGCTCTGTAGCACAA | 1783 |
| SEQ_ID_NO_220 NNNNNNNNNNNNNNNNNNNNNCTGAAAAAAAATGCACACCGACATGCTCTGTAGCACAA | 1778 |
| SEQ_ID_NO_235 NNNNNNNNNNNNNNNNNNNNNNNTGAAAAAAAATGCACACCGACATGCTCTGTAGCACAA | 1739 |
| SEQ_ID_NO_225 NNNNNNNNNNNNNNNNNNNNNNNTGAAAAAAAATGCACACCGACATGCTCTGTAGCACAA | 1786 |
| SEQ_ID_NO_226 NNNNNNNNNNNNNNNNNNNNNNNNNNNNNNNNNNNNNNNNNNNNNNNNNNNNN | 1787 |
| SEQ_ID_NO_228 NNNNNNNNNNNNNNNNNNNNNNNNNAAAAAAAATGCACACCGACATGCTCTGTAGCACAA | 1787 |
| SEQ_ID_NO_227 NNNNNNNNNNNNNNNNNNNNNNNNNTGAAAAAAAATGCACACCGACATGCTCTGTAGCACAA | 1786 |
| SEQ_ID_NO_223 NNNNNNNNNNNNNNNNNAAAAAAA-AAAAAAGAATGCAGACCGACATGCTCTGTAGCACAA | 1772 |
| SEQ_ID_NO_215 NNNNNNNNNNNAAAAAAAAAAAAAAAAAAAGAATGCACACCGACATGCTCTGTAGCACAA | 2189 |
| SEQ_ID_NO_216 NNNNNNNNNNNNAAAAAAAAAAAAAAAAAAAGAATGCACACCGACATGCTCTGTAGCACAA | 2189 |
| SEQ_ID_NO_214 NNNNNNNNNNNNAAAAAAAAAAAAAAAAAAAGAATGCACACCGACATGCTCTGTAGCACAA | 2189 |
| SEQ_ID_NO_233 NNNNNNNNNNNNNNNNNNNAAAAAAAAAAGAATGCAGACCGACATGCTCTGTAGCACAA | 1784 |
| SEQ_ID_NO_236 NNNNNNNNNNNNNTNNNNNNGAAAAAAAAAAGAATGCAGACCGACATGCTCTGTAGCACAA | 1742 |
| SEQ_ID_NO_231 NNNNNNNNNNNNNNAAAAAAAAAAAAAAGAATGCACACCGACATGCTCTGTAGCACAA | 1787 |
| SEQ_ID_NO_229 NNNNNNNNNNNNNNNAAAAAAAAAAAAAAGAATGCACACCGACATGCTCTGTAGCACAA | 1787 |
| SEQ_ID_NO_230 NNNNNNNNNNNNNNNAAAAAAAAAAAAAAGAATGCAGACCGACATGCTCTGTAGCACAA | 1787 |
| SEQ_ID_NO_232 NNNNNNNNNNNNNNNAAAAAAAAAAAAAAGAATGCAGACCGACATGCTCTGTAGCACAA | 1787 |
| SEQ_ID_NO_234 NNNNNNNNNNNNNNNAAAAAAAAAAAAAAGAATGCAGACCGACATGCTCTGTAGCACAA | 1751 |
| SEQ_ID_NO_218 NNNNNNNNNNNNAAAAAAAAAAAAAAAAAAAGAATGCAGACCGACATGCTCTGTAGCACAA | 2189 |
| SEQ_ID_NO_219 NNNNNNNNNNNNAAAAAAAAAAAAAAAAAAAGAATGCAGACCGACATGCTCTGTAGCACAA | 2189 |
| SEQ_ID_NO_217 NNNNNNNNNNNNAAAAAAAAAAAAAAAAAAAGAATGCAGACCGACATGCTCTGTAGCACAA | 2189 |
| SEQ_ID_NO_221 NNNNNNNNNNNNNNNNNNNNNNNNNNNNNNNNNNNNNNNNNNNNNNNNNNNNN | 1782 |

TABLE 27-continued

| | | |
|---|---|---|
| SEQ_ID_NO_224 | NNNNNNNNNNNNNNNNNNNNNNNNNNNNNNNNNNNNNNNNNNNNNNNNNNNNNN<br>********** | 1787 |
| SEQ_ID_NO_213 | GCACCATACTGGCGAACTGGAGAGGTCTCGGCTCATCAAGCAATCGCC-TTGGTGTCGGA | 1845 |
| SEQ_ID_NO_222 | GCACCATACTGGCGAACTGGAGAGGTCTCGGCTCATCAAGCAATCGCC-TTGGTGTCGGA | 1842 |
| SEQ_ID_NO_220 | GCACCATACCGGCGAACTGGAGAGGTCTCGGCTCATCAAGCAATCGCC-TTGGTGTCGGA | 1837 |
| SEQ_ID_NO_235 | GCACCATACCGGCGAACTGGAGAGGTCTCGGCTCATCAAGCAATCGCCCTTGGTGTCGGA | 1799 |
| SEQ_ID_NO_225 | GCACCATACCGGCGAACTGGAGAGGTCTCGGCTCATCAAGCAATCGCC-TTGGTGTCGGA | 1845 |
| SEQ_ID_NO_226 | NNNNNNNNNNNNNNNNNNNNNGGAGAGGTCTCGGCTCATCAAGCAATCGCC-TTGGTGTCGGA | 1846 |
| SEQ_ID_NO_228 | GCACCATACCGGCGAACTGGAGAGGTCTCGGCTCATCAAGCAATCGCC-TTGGTGTCGGA | 1846 |
| SEQ_ID_NO_227 | GCACCATACCGGCGAACTGGAGAGGTCTCGGCTCATCAAGCAATCGCC-TTGGTGTCGGA | 1845 |
| SEQ_ID_NO_223 | GCACCATACTGGCGAACTGGAGAGGTCTCGGCTCATCAAGCAATCGCC-TTGGTGTCGGA | 1831 |
| SEQ_ID_NO_215 | GCACCATACTGGCGAACTGGAGAGGTCTCGGCTCATCAAGCAATCGCC-TTGGTGTCGGA | 2248 |
| SEQ_ID_NO_216 | GCACCATACTGGCGAACTGGAGAGGTCTCGGCTCATCAAGCAATCGCC-TTGGTGTCGGA | 2248 |
| SEQ_ID_NO_214 | GCACCATACTGGCGAACTGGAGAGGTCTCGGCTCATCAAGCAATCGCC-TTGGTGTCGGA | 2248 |
| SEQ_ID_NO_233 | GCACCATACTTGCGAACTGCAGAGGTGTCGGGTCATCAAGCAATCGCC-TTGGTGTCGGA | 1843 |
| SEQ_ID_NO_236 | GCACCATACTTGCGAACTGCAGAGGTGTCGGGTCATCAAGCAATCGCC-TTGGTGTCGGA | 1801 |
| SEQ_ID_NO_231 | GCACCATACTGGCGAACTGGAGAGGTCTCGGCTCATCAAGCAATCGCC-TTGGTGTCGGA | 1846 |
| SEQ_ID_NO_229 | GCACCATACTGGCGAACTGGAGAGGTCTCGGCTCATCAAGCAATCGCC-TTGGTGTCGGA | 1846 |
| SEQ_ID_NO_230 | GCACCATACTGGCGAACTGGAGAGGTCTCGGCTCATCAAGCAATCGCC-TTGGTGTCGGA | 1846 |
| SEQ_ID_NO_232 | GCACCATACTGGCGAACTGGAGAGGTCTCGGCTCATCAAGCAATCGCC-TTGGTGTCGGA | 1846 |
| SEQ_ID_NO_234 | GCACCATACTGGCGAACTGGAGAGGTCTCGGCTCATCAAGCAATCGCC-TTGGTGTCGGA | 1810 |
| SEQ_ID_NO_218 | GCACCATACTGGCGAACTGGAGAGGTCTCGGCTCATCAAGCAATCGCC-TTGGTGTCGGA | 2248 |
| SEQ_ID_NO_219 | GCACCATACTGGCGAACTGGAGAGGTCTCGGCTCATCAAGCAATCGCC-TTGGTGTCGGA | 2248 |
| SEQ_ID_NO_217 | GCACCATACTGGCGAACTGGAGAGGTCTCGGCTCATCAAGCAATCGCC-TTGGTGTCGGA | 2248 |
| SEQ_ID_NO_221 | NNNNNNNNNNNNNNNNNNNNNNNNNNNNNNNNNNNNNNNNNNNNNNNNNNNNNNNN | 1842 |
| SEQ_ID_NO_224 | NNNNNNNNNNNNNNNNNNNNNNNNNNNNNNNNNNNNNNNNNNNNNNNNNNNNNNNN | 1847 |
| SEQ_ID_NO_213 | CGGGGT-----CATCAAGACAAGACGACTAGACGAGCACTACATATAGACGGG------- | 1893 |
| SEQ_ID_NO_222 | CGGGGT-----CATCAAGACAAGACGACTAGACGAGCACTACATATAGACGGG------- | 1890 |
| SEQ_ID_NO_220 | CGGGGT-----CATCAAGACAAGGCGACTAGAGGAGCACTACATCTACACGGGGTGAACG | 1892 |
| SEQ_ID_NO_235 | CGGGGT-----CATCAAGACAAGGCGACTAGAGGAGCACTACATCTACACGGGGTGAACG | 1854 |
| SEQ_ID_NO_225 | CGGGGT-----CATCAAGACAAGGCGACTAGAGGAGCACTACATCTACACGGGGTGAACG | 1900 |
| SEQ_ID_NO_226 | CGGGGT-----CATCAAGACAAGRCGACTAGAGGAGCACTACATCTACACGGGGTGAACG | 1901 |
| SEQ_ID_NO_228 | CGGGGT-----CATCAAGACAAGGCGACTAGAGGAGCACTACATCTACACGGGGTGAACG | 1901 |
| SEQ_ID_NO_227 | CGGGGT-----CATCAAGACAAGGCGACTAGAGGAGCACTACATCTACACGGGGTGAACG | 1900 |
| SEQ_ID_NO_223 | CGGGGT-----CATCAAGACAAGACGACTAGACGAGCACTACATATAGACGGGA------ | 1880 |
| SEQ_ID_NO_215 | CGGGGT-----CATCAAGACAAGACGACTAGACGAGCACTACATATAGACGGG------- | 2296 |
| SEQ_ID_NO_216 | CGGGGT-----CATCAAGACAAGACGACTAGACGAGCACTACATATAGACGGG------- | 2296 |
| SEQ_ID_NO_214 | CGGGGT-----CATCAAGACAAGACGACTAGACGAGCACTACATATAGACGGG------- | 2296 |
| SEQ_ID_NO_233 | CGGGGTGGGGTCATCAAGACAAGACGACTAGAGGAGCACTACATCTACACGGGG------ | 1897 |
| SEQ_ID_NO_236 | CGGGGTGGGGTCATCAAGACAAGACGACTAGAGGAGCACTACATCTACACGGGG------ | 1855 |

TABLE 27-continued

| | | |
|---|---|---|
| SEQ_ID_NO_231 | CGGGGT-----CATCAAGACAAGACGACTAGACGAGCACTACATATAGACGGG------- | 1894 |
| SEQ_ID_NO_229 | CGGGGT-----CATCAAGACAAGACGACTAGACGAGCACTACATATAGACGGG------- | 1894 |
| SEQ_ID_NO_230 | CGGGGT-----CATCAAGACAAGACGACTAGACGAGCACTACATATAGACGGG------- | 1894 |
| SEQ_ID_NO_232 | CGGGGT-----CATCAAGACAAGACGACTAGACGAGCACTACATATAGACGGG------- | 1894 |
| SEQ_ID_NO_234 | CGGGGT-----CATCAAGACAAGACGACTAGACGAGCACTACATATAGACGGG------- | 1858 |
| SEQ_ID_NO_218 | CGGGGT-----CATCAAGACAAGACGACTAGACGAGCACTACATATAGACGGG------- | 2296 |
| SEQ_ID_NO_219 | CGGGGT-----CATCAAGACAAGACGACTAGACGAGCACTACATATAGACGGG------- | 2296 |
| SEQ_ID_NO_217 | CGGGGT-----CATCAAGACAAGACGACTAGACGAGCACTACATATAGACGGG------- | 2296 |
| SEQ_ID_NO_221 | NNNNNN-----NNNNNNNNNNNNNNNNNNNNNNNNNNNNNNNNNNNNNNNNN------ | 1891 |
| SEQ_ID_NO_224 | NNNNNN-----NNNNNNNNNNNNNNNNNNNNNNNNNNNNNNNNNNNNNNNNNN------ | 1896 |
| SEQ_ID_NO_213 | ----------------------AAC--------------------------------- | 1896 |
| SEQ_ID_NO_222 | ----------------------AAC--------------------------------- | 1893 |
| SEQ_ID_NO_220 | GACGGGAGCAGTGGCGGACCCAGGAACTGATGACAGCCTTGGCGAGAATACGGTGTGATC | 1952 |
| SEQ_ID_NO_235 | GACGGGAGCAGTGGCGGACCCAGGAACTGATGACAGCCTTGGCGAGAATACGGTGTGATC | 1914 |
| SEQ_ID_NO_225 | GACGGGAGCAGTGGCGGACCCAGGAACTGATGACAGCCTTGGCGAGAATACGGTGTGATC | 1960 |
| SEQ_ID_NO_226 | GACGGGAGCAGTGGCGGACCCAGGAACTGATGACAGCCTTGGCGAGAATACGGTGTGATC | 1961 |
| SEQ_ID_NO_228 | GACGGGAGCAGTGGCGGACCCAGGAACTGATGACAGCCTTGGCGAGAATACGGTGTGATC | 1961 |
| SEQ_ID_NO_227 | GACGGGAGCAGTGGCGGACCCAGGAACTGATGACAGCCTTGGCGAGAATACGGTGTGATC | 1960 |
| SEQ_ID_NO_223 | ------------------------------------------------------------ | |
| SEQ_ID_NO_215 | ----------------------AAC--------------------------------- | 2299 |
| SEQ_ID_NO_216 | ----------------------AAC--------------------------------- | 2299 |
| SEQ_ID_NO_214 | ----------------------AAC--------------------------------- | 2299 |
| SEQ_ID_NO_233 | -------------------GGGAAC--------------------------------- | 1903 |
| SEQ_ID_NO_236 | -------------------GGGAAC--------------------------------- | 1861 |
| SEQ_ID_NO_231 | ----------------------AAC--------------------------------- | 1897 |
| SEQ_ID_NO_229 | ----------------------AAC--------------------------------- | 1897 |
| SEQ_ID_NO_230 | ----------------------AAC--------------------------------- | 1897 |
| SEQ_ID_NO_232 | ----------------------AAC--------------------------------- | 1897 |
| SEQ_ID_NO_234 | ----------------------AAC--------------------------------- | 1861 |
| SEQ_ID_NO_218 | ----------------------AAC--------------------------------- | 2299 |
| SEQ_ID_NO_219 | ----------------------AAC--------------------------------- | 2299 |
| SEQ_ID_NO_217 | ----------------------AAC--------------------------------- | 2299 |
| SEQ_ID_NO_221 | ----------------------GGAC-------------------------------- | 1895 |
| SEQ_ID_NO_224 | ----------------------NNNN-------------------------------- | 1900 |
| SEQ_ID_NO_213 | ------------------------------------------------------------ | |
| SEQ_ID_NO_222 | ------------------------------------------------------------ | |
| SEQ_ID_NO_220 | CCCACGCCTGTGCTCGTGCCACGTGCTGCTTGCTTCCGTGCACTGTGCTCGCGCCTTGCC | 2012 |
| SEQ_ID_NO_235 | CCCACGCCTGTGCTCGTGCCACGTGCTGCTTGCTTCCGTGCACTGTGCTCGCGCCTTGCC | 1974 |
| SEQ_ID_NO_225 | CCCACGCCTGTGCTCGTGCCACGTGCTGCTTGCTTCCGTGCACTGTGCTCGTGCCTTGCC | 2020 |
| SEQ_ID_NO_226 | CCCACGCCTGTGCTCGTGCCACGTGCTGCTTGCTTCCGTGCACTGTGCTCGTGCCTTGCC | 2021 |

TABLE 27-continued

| | | |
|---|---|---|
| SEQ_ID_NO_228 | CCCACGCCTGTGCTCGTGCCACGTGCTGCTTGCTTCCGTGCACTGTGCTCGCGCCTTGCC | 2021 |
| SEQ_ID_NO_227 | CCCACGCCTGTGCTCGTGCCACGTGCTGCTTGCTTCCGTGCACTGTGCTCGCGCCTTGCC | 2020 |
| SEQ_ID_NO_223 | --------------------ACGT------------------------------------ | 1884 |
| SEQ_ID_NO_215 | ------------------------------------------------------------ | |
| SEQ_ID_NO_216 | ------------------------------------------------------------ | |
| SEQ_ID_NO_214 | ------------------------------------------------------------ | |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | ------------------------------------------------------------ | |
| SEQ_ID_NO_219 | ------------------------------------------------------------ | |
| SEQ_ID_NO_217 | ------------------------------------------------------------ | |
| SEQ_ID_NO_221 | ------------------------------------------------------------ | |
| SEQ_ID_NO_224 | ------------------------------------------------------------ | |
| SEQ_ID_NO_213 | -----------------------------------------------------------G | 1897 |
| SEQ_ID_NO_222 | -----------------------------------------------------------G | 1894 |
| SEQ_ID_NO_220 | CATTGCAGCCGGCGAGCCAGCTCAGGCCACCGCCTGCGGTGCCTGGTGAGTCCGCCCCTG | 2072 |
| SEQ_ID_NO_235 | CATTGCAGCCGGCGAGCCAGCTCAGGCCACCGCCTGCGGTGCCTGGTGAGTCCGCCCCTG | 2034 |
| SEQ_ID_NO_225 | CATTGCAGCCGGCGAGCCAGCTCAGGCCACCGCCTGCGGTGCCTGGTGAGTCCGCCCCTG | 2080 |
| SEQ_ID_NO_226 | CATTGCAGCCGGCGAGCCAGCTCAGGCCACCGCCTGCGGTGCCTGGTGAGTCCGCCCCTG | 2081 |
| SEQ_ID_NO_228 | CATTGCAGCCGGCGAGCCAGCTCAGGCCACCGCCTGCGGTGCCTGGTGAGTCCGCCCCTG | 2081 |
| SEQ_ID_NO_227 | CATTGCAGCCGGCGAGCCAGCTCAGGCCACCGCCTGCGGTGCCTGGTGAGTCCGCCCCTG | 2080 |
| SEQ_ID_NO_223 | ------------------------------------------------------------ | |
| SEQ_ID_NO_215 | -----------------------------------------------------------G | 2300 |
| SEQ_ID_NO_216 | -----------------------------------------------------------G | 2300 |
| SEQ_ID_NO_214 | -----------------------------------------------------------G | 2300 |
| SEQ_ID_NO_233 | -----------------------------------------------------------G | 1904 |
| SEQ_ID_NO_236 | -----------------------------------------------------------G | 1862 |
| SEQ_ID_NO_231 | -----------------------------------------------------------G | 1898 |
| SEQ_ID_NO_229 | -----------------------------------------------------------G | 1898 |
| SEQ_ID_NO_230 | -----------------------------------------------------------G | 1898 |
| SEQ_ID_NO_232 | -----------------------------------------------------------G | 1898 |
| SEQ_ID_NO_234 | -----------------------------------------------------------G | 1862 |
| SEQ_ID_NO_218 | -----------------------------------------------------------G | 2300 |
| SEQ_ID_NO_219 | -----------------------------------------------------------G | 2300 |
| SEQ_ID_NO_217 | -----------------------------------------------------------G | 2300 |

TABLE 27-continued

| | | |
|---|---|---|
| SEQ_ID_NO_221 | ------------------------------------------------------------G | 1896 |
| SEQ_ID_NO_224 | ------------------------------------------------------------N | 1901 |
| SEQ_ID_NO_213 | TACGGGAGGAAGGAAGGAAAACGAGAGCGAGGACTCACTGTCCGGTCCGCCCAGCTTGGT | 1957 |
| SEQ_ID_NO_222 | TACGGGAGGAAGGAAGGAAAACGAGAGCGAGGACTCACTGTCCGGTCCGCCCAGCTTGGT | 1954 |
| SEQ_ID_NO_220 | GACGGGAGGAAGGAAGGAAAACGAGAGCGAGGACTCACTGTCCGGTCCGCCCAGCTTGGT | 2132 |
| SEQ_ID_NO_235 | GACGGGAGGAAGGAAGGAAAACGAGAGCGAGGACTCACTGTCCGGTCCGCCCAGCTTGGT | 2094 |
| SEQ_ID_NO_225 | GACGGGAGGAAGGAAGGAAAACGAGAGCGAGGACTCACTGTCCGGTCCGCCCAGCTTGGT | 2140 |
| SEQ_ID_NO_226 | GACGGGAGGAAGGAAGGAAAACGAGAGCGAGGACTCACTGTCCGGTCCGCCCAGCTTGGT | 2141 |
| SEQ_ID_NO_228 | GACGGGAGGAAGGAAGGAAAACGAGAGCGAGGACTCACTGTCCGGTCCGCCCAGCTTGGT | 2141 |
| SEQ_ID_NO_227 | GACGGGAGGAAGGAAGGAAAACGAGAGCGAGGACTCACTGTCCGGTCCGCCCAGCTTGGT | 2140 |
| SEQ_ID_NO_223 | -ACGGGAGGAAGGAAGGAAAACGAGAGCGAGGACTCACTGTCCGGTCCGCCCAGCTTGGT | 1943 |
| SEQ_ID_NO_215 | TACGGGAGGAAGGAAGGAAAACGAGAGCGAGGACTCACTGTCCGGTCCGCCCAGCTTGGT | 2360 |
| SEQ_ID_NO_216 | TACGGGAGGAAGGAAGGAAAACGAGAGCGAGGACTCACTGTCCGGTCCGCCCAGCTTGGT | 2360 |
| SEQ_ID_NO_214 | TACGGGAGGAAGGAAGGAAAACGAGAGCGAGGACTCACTGTCCGGTCCGCCCAGCTTGGT | 2360 |
| SEQ_ID_NO_233 | GACGGGAGGAAGGAAGGAAAACGAGAGCGAGGACTCACTGTCCGGTCCGCCCAGCTTGGT | 1964 |
| SEQ_ID_NO_236 | GACGGGAGGAAGGAAGGAAAACGAGAGCGAGGACTCACTGTCCGGTCCGCCCAGCTTGGT | 1922 |
| SEQ_ID_NO_231 | TACGGGAGGAAGGAAGGAAAACGAGAGCGAGGACTCACTGTCCGGTCCGCCCAGCTTGGT | 1958 |
| SEQ_ID_NO_229 | TACGGGAGGAAGGAAGGAAAACGAGAGCGAGGACTCACTGTCCGGTCCGCCCAGCTTGGT | 1958 |
| SEQ_ID_NO_230 | TACGGGAGGAAGGAAGGAAAACGAGAGCGAGGACTCACTGTCCGGTCCGCCCAGCTTGGT | 1958 |
| SEQ_ID_NO_232 | TACGGGAGGAAGGAAGGAAAACGAGAGCGAGGACTCACTGTCCGGTCCGCCCAGCTTGGT | 1958 |
| SEQ_ID_NO_234 | TACGGGAGGAAGGAAGGAAAACGAGAGCGAGGACTCACTGTCCGGTCCGCCCAGCTTGGT | 1922 |
| SEQ_ID_NO_218 | TACGGGAGGAAGGAAGGAAAACGAGAGCGAGGACTCACTGTCCGGTCCGCCCAGCTTGGT | 2360 |
| SEQ_ID_NO_219 | TACGGGAGGAAGGAAGGAAAACGAGAGCGAGGACTCACTGTCCGGTCCGCCCAGCTTGGT | 2360 |
| SEQ_ID_NO_217 | TACGGGAGGAAGGAAGGAAAACGAGAGCGAGGACTCACTGTCCGGTCCGCCCAGCTTGGT | 2360 |
| SEQ_ID_NO_221 | G----GAGGAAGGAAGGAAAACGAGAGCGAGGACTCACTGTCCGGTCCGCCCAGCTTGGT | 1952 |
| SEQ_ID_NO_224 | NACGGGAGGAAGGAAGGAAAACGAGAGCGAGGACTCACTGTCCGGTCCGCCCAGCTTGGT | 1961 |
| | ************************************************************ | |
| SEQ_ID_NO_213 | GACGGCGTCGACGAAGCGCTGGTGGAGGTCCGGCGTCCAGCGCAGCCGCGGCTTGGGGTC | 2017 |
| SEQ_ID_NO_222 | GACGGCGTCGACGAAGCGCTGGTGGAGGTCCGGCGTCCAGCGCAGCCGCGGCTTGGGGTC | 2014 |
| SEQ_ID_NO_220 | GACGGCGTCGACGAAGCGCTGGTGGAGGTCCGGCGTCCAGCGCAGCCGCGGCTTGGGGTC | 2192 |
| SEQ_ID_NO_235 | GACGGCGTCGACGAAGCGCTGGTGGAGGTCCGGCGTCCAGCGCAGCCGCGGCTTGGGGTC | 2154 |
| SEQ_ID_NO_225 | GACGGCGTCGACGAAGCGCTGGTGGAGGTCCGGCGTCCAGCGCAGCCGCGGCTTGGGGTC | 2200 |
| SEQ_ID_NO_226 | GACGGCGTCGACGAAGCGCTGGTGGAGGTCCGGCGTCCAGCGCAGCCGCGGCTTGGGGTC | 2201 |
| SEQ_ID_NO_228 | GACGGCGTCGACGAAGCGCTGGTGGAGGTCCGGCGTCCAGCGCAGCCGCGGCTTGGGGTC | 2201 |
| SEQ_ID_NO_227 | GACGGCGTCGACGAAGCGCTGGTGGAGGTCCGGCGTCCAGCGCAGCCGCGGCTTGGGGTC | 2200 |
| SEQ_ID_NO_223 | GACGGCGTCGACGAAGCGCTGGTGGAGGTCCGGCGTCCAGCGCAGCCGCGGCTTGGGGTC | 2003 |
| SEQ_ID_NO_215 | GACGGCGTCGACGAAGCGCTGGTGGAGGTCCGGCGTCCAGCGCAGCCGCGGCTTGGGGTC | 2420 |
| SEQ_ID_NO_216 | GACGGCGTCGACGAAGCGCTGGTGGAGGTCCGGCGTCCAGCGCAGCCGCGGCTTGGGGTC | 2420 |
| SEQ_ID_NO_214 | GACGGCGTCGACGAAGCGCTGGTGGAGGTCCGGCGTCCAGCGCAGCCGCGGCTTGGGGTC | 2420 |
| SEQ_ID_NO_233 | GACGGCGTCGACGAAGCGCTGGTGGAGGACCGGCGTCCAGCGCAGCCGCGGCTTGGGGTC | 2024 |
| SEQ_ID_NO_236 | GACGGCGTCGACGAAGCGCTGGTGGAGGACCGGCGTCCAGCGCAGCCGCGGCTTGGGGTC | 1982 |

TABLE 27-continued

| | | |
|---|---|---|
| SEQ_ID_NO_231 | GACGGCGTCGACGAAGCGCTGGTGGAGGTCCGGCGTCCAGCGCAGCCGCGGCTTGGGGTC | 2018 |
| SEQ_ID_NO_229 | GACGGCGTCGACGAAGCGCTGGTGGAGGTCCGGCGTCCAGCGCAGCCGCGGCTTGGGGTC | 2018 |
| SEQ_ID_NO_230 | GACGGCGTCGACGAAGCGCTGGTGGAGGTCCGGCGTCCAGCGCAGCCGCGGCTTGGGGTC | 2018 |
| SEQ_ID_NO_232 | GACGGCGTCGACGAAGCGCTGGTGGAGGTCCGGCGTCCAGCGCAGCCGCGGCTTGGGGTC | 2018 |
| SEQ_ID_NO_234 | GACGGCGTCGACGAAGCGCTGGTGGAGGTCCGGCGTCCAGCGCAGCCGCGGCTTGGGGTC | 1982 |
| SEQ_ID_NO_218 | GACGGCGTCGACGAAGCGCTGGTGGAGGTCCGGCGTCCAGCGCAGCCGCGGCTTGGGGTC | 2420 |
| SEQ_ID_NO_219 | GACGGCGTCGACGAAGCGCTGGTGGAGGTCCGGCGTCCAGCGCAGCCGCGGCTTGGGGTC | 2420 |
| SEQ_ID_NO_217 | GACGGCGTCGACGAAGCGCTGGTGGAGGTCCGGCGTCCAGCGCAGCCGCGGCTTGGGGTC | 2420 |
| SEQ_ID_NO_221 | GACGGCGTCGACGAAGCGCTGGTGGAGGTCCGGCGTCCAGCGCAGCCGCGGCTTGGGGTC | 2012 |
| SEQ_ID_NO_224 | GACGGCGTCGACGAAGCGCTGGTGGAGGTCCGGCGTCCAGCGCAGCCGCGGCTTGGGGTC | 2021 |
| | ****************************** ****************************** | |
| SEQ_ID_NO_213 | CCGTGACGCCGCCC--CGTCGTAGCCGTAGCTCCCCTGCATCGTCGTTCCTTCCTGGCGA | 2075 |
| SEQ_ID_NO_222 | CCGTGACGCCGCCC--CGTCGTAGCCGTAGCTCCCCTGCATCGCCGTTCCTTCCTGGCGA | 2072 |
| SEQ_ID_NO_220 | CCGTGACGCCGCCC--CGTCGTAGCCGTAGCTCCCCTGCATCGCCGTTCCTTCCTGGCGA | 2250 |
| SEQ_ID_NO_235 | CCGTGACGCCGCCC--CGTCGTAGCCGTAGCTCCCCTGCATCGCCGTTCCTTCCTGGCGA | 2212 |
| SEQ_ID_NO_225 | CCGTGACGCCGCCC--CGTCGTAGCCGTAGCTCCCCTGCATCGCCGTTCCTTCCTGGCGA | 2258 |
| SEQ_ID_NO_226 | CCGTGACGCCGCCC--CGTCGTAGCCGTAGCTCCCCTGCATCGCCGTTCCTTCCTGGCGA | 2259 |
| SEQ_ID_NO_228 | CCGTGACGCCGCCC--CGTCGTAGCCGTAGCTCCCCTGCATCGCCGTTCCTTCCTGGCGA | 2259 |
| SEQ_ID_NO_227 | CCGTGACGCCGCCC--CGTCGTAGCCGTAGCTCCCCTGCATCGCCGTTCCTTCCTGGCGA | 2258 |
| SEQ_ID_NO_223 | CCGTGACGCAAACCAACGTCGTAGCCGTAGCTCCCCTGCATCGCCGTTCCTTCCTGGCGA | 2063 |
| SEQ_ID_NO_215 | CCGTGACGCCGCCC--CGTCGTAGCCGTAGCTCCCCTGCATCGTCGTTCCTTCCTGGCGA | 2478 |
| SEQ_ID_NO_216 | CCGTGACGCCGCCC--CGTCGTAGCCGTAGCTCCCCTGCATCGTCGTTCCTTCCTGGCGA | 2478 |
| SEQ_ID_NO_214 | CCGTGACGCCGCCC--CGTCGTAGCCGTAGCTCCCCTGCATCGTCGTTCCTTCCTGGCGA | 2478 |
| SEQ_ID_NO_233 | CCGTGACGCCGCCC--CGTCGTAGCCGTAGCTCCCCTGCATCGTCGTTCCTTCCTGGCGA | 2082 |
| SEQ_ID_NO_236 | CCGTGACGCCGCCC--CGTCGTAGCCGTAGCTCCCCTGCATCGTCGTTCCTTCCTGGCGA | 2040 |
| SEQ_ID_NO_231 | CCGTGACGCCGCCC--CGTCGTAGCCGTAGCTCCCCTGCATCGTCGTTCCTTCCTGGCGA | 2076 |
| SEQ_ID_NO_229 | CCGTGACGCCGCCC--CGTCGTAGCCGTAGCTCCCCTGCATCGTCGTTCCTTCCTGGCGA | 2076 |
| SEQ_ID_NO_230 | CCGTGACGCCGCCC--CGTCGTAGCCGTAGCTCCCCTGCATCGTCGTTCCTTCCTGGCGA | 2076 |
| SEQ_ID_NO_232 | CCGTGACGCCGCCC--CGTCGTAGCCGTAGCTCCCCTGCATCGTCGTTCCTTCCTGGCGA | 2076 |
| SEQ_ID_NO_234 | CCGTGACGCCGCCC--CGTCGTAGCCGTAGCTCCCCTGCATCGCCGTTCCTTCCTGGCGA | 2040 |
| SEQ_ID_NO_218 | CCGTGACGCCGCCC--CGTCGTAGCCGTAGCTCCCCTGCATCGCCGTTCCTTCCTGGCGA | 2478 |
| SEQ_ID_NO_219 | CCGTGACGCCGCCC--CGTCGTAGCCGTAGCTCCCCTGCATCGCCGTTCCTTCCTGGCGA | 2478 |
| SEQ_ID_NO_217 | CCGTGACGCCGCCC--CGTCGTAGCCGTAGCTCCCCTGCATCGCCGTTCCTTCCTGGCGA | 2478 |
| SEQ_ID_NO_221 | CCGTGACGCCGCCC--CGTCGTAGCCGTAGCTCCCCTGCATCGCCGTTCCTTCCTGGCGA | 2070 |
| SEQ_ID_NO_224 | CCGTGACGCCGCCC--CGTCGTAGCCGTAGCTCCCCTGCATCGCCGTTCCTTCCTGGCGA | 2079 |
| | ********  **  ****************************** **************** | |
| SEQ_ID_NO_213 | TCGCCGCTTCCTAGCTATCCGGTGGCCAAAGACACGGCTAGTGGTAGGCTCGAGTGAGAC | 2135 |
| SEQ_ID_NO_222 | TCGCCGCTCCCTAGCTATCCGGTGGCCAAAGACACGGCTAGTGGTAGGCTCGAGCGAGAC | 2132 |
| SEQ_ID_NO_220 | TCGCCGCTCCCTAGCTATCCGGTGGCCAAAGACACGGCTAGTGGTAGGCTCGAGCGAGAC | 2310 |
| SEQ_ID_NO_235 | TCGCCGCTCCCTAGCTATCCGGTGGCCAAAGACACGGCTAGTGGTAGGCTCGAGCGAGAC | 2272 |
| SEQ_ID_NO_225 | TCGCCGCTCCCTAGCTATCCGGTGGCCAAAGACACGGCTAGTGGTAGGCTCGAGCGAGAC | 2318 |

TABLE 27-continued

```
SEQ_ID_NO_226 TCGCCGCTCCCTAGCTATCCGGTGGCCAAAGACACGGCTAGTGGTAGGCTCGAGCGAGAC    2319
SEQ_ID_NO_228 TCGCCGCTCCCTAGCTATCCGGTGGCCAAAGACACGGCTAGTGGTAGGCTCGAGCGAGAC    2319
SEQ_ID_NO_227 TCGCCGCTCCCTAGCTATCCGGTGGCCAAAGACACGGCTAGTGGTAGGCTCGAGCGAGAC    2318
SEQ_ID_NO_223 TCGCCGCTCCCTAGCTATCCGGTGGCCAAAGACACGGCTAGTGGTAGGCTCGAGCGAGAC    2123
SEQ_ID_NO_215 TCGCCGCTTCCTAGCTATCCGGTGGCCAAAGACACGGCTAGTGGTAGGCTCGAGTGAGAC    2538
SEQ_ID_NO_216 TCGCCGCTTCCTAGCTATCCGGTGGCCAAAGACACGGCTAGTGGTAGGCTCGAGTGAGAC    2538
SEQ_ID_NO_214 TCGCCGCTTCCTAGCTATCCGGTGGCCAAAGACACGGCTAGTGGTAGGCTCGAGTGAGAC    2538
SEQ_ID_NO_233 TCGCCGCTCCCTAGCTATCCGGTGGCCAAAGACACGGCTAGTG-----------------   2125
SEQ_ID_NO_236 TCGCCGCTCCCTAGCTATCCGGTGGCCAAAGACACGGCTAGTG-----------------   2083
SEQ_ID_NO_231 TCGCCGCTTCCTAGCTATCCGGTGGCCAAAGACACGGCTAGTGGTAGGCTCGAGTGAGAC    2136
SEQ_ID_NO_229 TCGCCGCTTCCTAGCTATCCGGTGGCCAAAGACACGGCTAGTGGTAGGCTCGAGTGAGAC    2136
SEQ_ID_NO_230 TCGCCGCTTCCTAGCTATCCGGTGGCCAAAGACACGGCTAGTGGTAGGCTCGAGTGAGAC    2136
SEQ_ID_NO_232 TCGCCGCTTCCTAGCTATCCGGTGGCCAAAGACACGGCTAGTGGTAGGCTCGAGTGAGAC    2136
SEQ_ID_NO_234 TCGCCGCTCCCTAGCTATCCGGTGGCCAAAGACACGGCTAGTGGTAGGCTCGAGCGAGAC    2100
SEQ_ID_NO_218 TCGCCGCTCCCTAGCTATCCGGTGGCCAAAGACACGGCTAGTGGTAGGCTCGAGCGAGAC    2538
SEQ_ID_NO_219 TCGCCGCTCCCTAGCTATCCGGTGGCCAAAGACACGGCTAGTGGTAGGCTCGAGCGAGAC    2538
SEQ_ID_NO_217 TCGCCGCTCCCTAGCTATCCGGTGGCCAAAGACACGGCTAGTGGTAGGCTCGAGCGAGAC    2538
SEQ_ID_NO_221 TCGCCGCTCCCTAGCTATCCGGTGGCCAAAGACACGGCTAGTGGTAGGCTCGAGCGAGAC    2130
SEQ_ID_NO_224 TCGCCGCTCCCTAGCTATCCGGTGGCCAAAGACACGGCTAGTGGTAGGCTCGAGCGAGAC    2139
              ******* ************************************

SEQ_ID_NO_213 GAGCTCTTGCTGAAGAGAGAATGAATGTAACGTTACCGCCTCCTGGTCGTAGGTGTAATA    2195
SEQ_ID_NO_222 GAGCTCTTGCTGAAGAGAGAATGAATGTAGCGTTACCGCCTCCTGGTCGTAGG-------   2185
SEQ_ID_NO_220 GAGCTCTTGCTGAAGAGAGAATGAATGTAGCGTTACCGCCTCCTGGTCGTAGG-------   2363
SEQ_ID_NO_235 GAGCTCTTGCTGAAGAGAGAATGAATGTAGCGTTACCGCCTCCTGGTCGTAGG-------   2325
SEQ_ID_NO_225 GAGCTCTTGCTGAAGAGAGAATGAATGTAGCGTTACCGCCTCCTGGTCGTAGG-------   2371
SEQ_ID_NO_226 GAGCTCTTGCTGAAGAGAGAATGAATGTAGCGTTACCGCCTCCTGGTCGTAGG-------   2372
SEQ_ID_NO_228 GAGCTCTTGCTGAAGAGAGAATGAATGTAGCGTTACCGCCTCCTGGTCGTAGG-------   2372
SEQ_ID_NO_227 GAGCTCTTGCTGAAGAGAGAATGAATGTAGCGTTACCGCCTCCTGGTCGTAGG-------   2371
SEQ_ID_NO_223 GAGCTCTTGGTGAAGAGAGAATGAATGTAACGTTACCGCCTCCTGGTCGTAGG-------   2176
SEQ_ID_NO_215 GAGCTCTTGCTGAAGAGAGAATGAATGTAACGTTACCGCCTCCTGGTCGTAGGTGTAATA    2598
SEQ_ID_NO_216 GAGCTCTTGCTGAAGAGAGAATGAATGTAACGTTACCGCCTCCTGGTCGTAGGTGTAATA    2598
SEQ_ID_NO_214 GAGCTCTTGCTGAAGAGAGAATGAATGTAACGTTACCGCCTCCTGGTCGTAGGTGTAATA    2598
SEQ_ID_NO_233 ---------CTGAAGAGAGAATGAATGTAACGTTACCGCCTCCTGGTCGTAGGTGTAATA    2176
SEQ_ID_NO_236 ---------CTGAAGAGAGAATGAATGTAACGTTACCGCCTCCTGGTCGTAGGTGTAATA    2134
SEQ_ID_NO_231 GAGCTCTTGCTGAAGAGAGAATGAATGTAACGTTACCGCCTCCTGGTCGTAGGTGTAATA    2196
SEQ_ID_NO_229 GAGCTCTTGCTGAAGAGAGAATGAATGTAACGTTACCGCCTCCTGGTCGTAGGTGTAATA    2196
SEQ_ID_NO_230 GAGCTCTTGCTGAAGAGAGAATGAATGTAACGTTACCGCCTCCTGGTCGTAGGTGTAATA    2196
SEQ_ID_NO_232 GAGCTCTTGCTGAAGAGAGAATGAATGTAACGTTACCGCCTCCTGGTCGTAGGTGTAATA    2196
SEQ_ID_NO_234 GAGCTCTTGGTGAAGAGAGAATGAATGTAACGTTACCGCCTCCTGGTCGTAGG-------   2153
SEQ_ID_NO_218 GAGCTCTTGGTGAAGAGAGAATGAATGTAACGTTACCGCCTCCTGGTCGTAGG-------   2591
```

TABLE 27-continued

```
SEQ_ID_NO_219 GAGCTCTTGGTGAAGAGAGAATGAATGTAACGTTACCGCCTCCTGGTCGTAGG-------  2591
SEQ_ID_NO_217 GAGCTCTTGGTGAAGAGAGAATGAATGTAACGTTACCGCCTCCTGGTCGTAGG-------  2591
SEQ_ID_NO_221 GAGCTCTTGCTGAAGAGAGAATGAATGTAGCGTTACCGCCTCCTGGTCGTAGG-------  2183
SEQ_ID_NO_224 GAGCTCTTGCTGAAGAGAGAATGAATGTAGCGTTACCGCCTCCTGGTCGTAGG-------  2192
                ******************  **********************

SEQ_ID_NO_213 AGTTGTAACGCGAGCGTCGTTAGCAAGCACAGGGGTTTGTGTATGTGAGGACAAGAGGAG  2255
SEQ_ID_NO_222 --------------------------------GGTGTGGGTATGTGAGGACAAGAGGAG  2212
SEQ_ID_NO_220 --------------------------------GGTGTGGGTATGTGAGGACAAGAGGAG  2390
SEQ_ID_NO_235 --------------------------------GGTGTGGGTATGTGAGGACAAGAGGAG  2352
SEQ_ID_NO_225 --------------------------------GGTGTGGGTATGTGAGGACAAGAGGAG  2398
SEQ_ID_NO_226 --------------------------------GGTGTGGGTATGTGAGGACAAGAGGAG  2399
SEQ_ID_NO_228 --------------------------------GGTGTGGGTATGTGAGGACAAGAGGAG  2399
SEQ_ID_NO_227 --------------------------------GGTGTGGGTATGTGAGGACAAGAGGAG  2398
SEQ_ID_NO_223 --------------------------------GGTGTGTGTATGTGAGGACAAGAGGAG  2203
SEQ_ID_NO_215 AGTTGTAACGCGAGCGTCGTTAGCAAGCACAGGGGTTTGTGTATGTGAGGACAAGAGGAG  2658
SEQ_ID_NO_216 AGTTGTAACGCGAGCGTCGTTAGCAAGCACAGGGGTTTGTGTATGTGAGGACAAGAGGAG  2658
SEQ_ID_NO_214 AGTTGTAACGCGAGCGTCGTTAGCAAGCACAGGGGTTTGTGTATGTGAGGACAAGAGGAG  2658
SEQ_ID_NO_233 AGTTGTAACGCGAGTGTCGTTAG-AAGCACAGGGGTGTGTGTATGTGAGGACAAGAGGAG  2235
SEQ_ID_NO_236 AGTTGTAACGCGAGTGTCGTTAG-AAGCACAGGGGTGTGTGTATGTGAGGACAAGAGGAG  2193
SEQ_ID_NO_231 AGTTGTAACGCGAGCGTCGTTAGCAAGCACAGGGGTTTGTGTATGTGAGGACAAGAGGAG  2256
SEQ_ID_NO_229 AGTTGTAACGCGAGCGTCGTTAGCAAGCACAGGGGTTTGTGTATGTGAGGACAAGAGGAG  2256
SEQ_ID_NO_230 AGTTGTAACGCGAGCGTCGTTAGCAAGCACAGGGGTTTGTGTATGTGAGGACAAGAGGAG  2256
SEQ_ID_NO_232 AGTTGTAACGCGAGCGTCGTTAGCAAGCACAGGGGTTTGTGTATGTGAGGACAAGAGGAG  2256
SEQ_ID_NO_234 --------------------------------GGTGTGTGTATGTGAGGACAAGAGGAG  2180
SEQ_ID_NO_218 --------------------------------GGTGTGTGTATGTGAGGACAAGAGGAG  2618
SEQ_ID_NO_219 --------------------------------GGTGTGTGTATGTGAGGACAAGAGGAG  2618
SEQ_ID_NO_217 --------------------------------GGTGTGTGTATGTGAGGACAAGAGGAG  2618
SEQ_ID_NO_221 --------------------------------GGTGTGGGTATGTGAGGACAAGAGGAG  2210
SEQ_ID_NO_224 --------------------------------GGTGTGGGTATGTGAGGACAAGAGGAG  2219
                                                *** ** *******************

SEQ_ID_NO_213 GAGCGAGAGGAGGAGCGCAGAGCGTGGCGGGGAAGGAGGGCGTCATGTGTGCGAGGAATC  2315
SEQ_ID_NO_222 GAGCGAGAGGAGGAGCGCAGAGCGTGGCGGGGAAGGAGGGCGTCATGTGTGTGAGGAATC  2272
SEQ_ID_NO_220 GAGCGAGAGGAGGAGCGCAGAGCGTGGCGGGGAAGGAGGGCGTCATGTGTGTGAGGAATC  2450
SEQ_ID_NO_235 GAGCGAGAGGAGGAGCGCAGAGCGTGGCGGGGAAGGAGGGCGTCATGTGTGTGAGGAATC  2412
SEQ_ID_NO_225 GAGCGAGAGGAGGAGCGCAGAGCGTGGCGGGGAAGGAGGGCGTCATGTGTGCGAGGAATC  2458
SEQ_ID_NO_226 GAGCGAGAGGAGGAGCGCAGAGCGTGGCGGGGAAGGAGGGCGTCATGTGTGCGAGGAATC  2459
SEQ_ID_NO_228 GAGCGAGAGGAGGAGCGCAGAGCGTGGCGGGGAAGGAGGGCGTCATGTGTGTGAGGAATC  2459
SEQ_ID_NO_227 GAGCGAGAGGAGGAGCGCAGAGCGTGGCGGGGAAGGAGGGCGTCATGTGTGTGAGGAATC  2458
SEQ_ID_NO_223 GAGCGAGAGGAGGAGCGCAGAGCGTGGCGGGGAAGGAGGGCGTCATGTGTGCGAGGAATC  2263
SEQ_ID_NO_215 GAGCGAGAGGAGGAGCGCAGAGCGTGGCGGGGAAGGAGGGCGTCATGTGTGCGAGGAATC  2718
SEQ_ID_NO_216 GAGCGAGAGGAGGAGCGCAGAGCGTGGCGGGGAAGGAGGGCGTCATGTGTGCGAGGAATC  2718
```

TABLE 27-continued

| | | |
|---|---|---|
| SEQ_ID_NO_214 | GAGCGAGAGGAGGAGCGCAGAGCGTGGCGGGGAAGGAGGGCGTCATGTGTGCGAGGAATC | 2718 |
| SEQ_ID_NO_233 | GAGCGAGAGGAGGAGCGCAGAGCGTGGCGGGGAAGGAGGGCGTCATGTGTGTGAGGAATC | 2295 |
| SEQ_ID_NO_236 | GAGCGAGAGGAGGAGCGCAGAGCGTGGCGGGGAAGGAGGGCGTCATGTGTGTGAGGAATC | 2253 |
| SEQ_ID_NO_231 | GAGCGAGAGGAGGAGCGCAGAGCGTGGCGGGGAAGGAGGGCGTCATGTGTGCGAGGAATC | 2316 |
| SEQ_ID_NO_229 | GAGCGAGAGGAGGAGCGCAGAGCGTGGCGGGGAAGGAGGGCGTCATGTGTGCGAGGAATC | 2316 |
| SEQ_ID_NO_230 | GAGCGAGAGGAGGAGCGCAGAGCGTGGCGGGGAAGGAGGGCGTCATGTGTGCGAGGAATC | 2316 |
| SEQ_ID_NO_232 | GAGCGAGAGGAGGAGCGCAGAGCGTGGCGGGGAAGGAGGGCGTCATGTGTGCGAGGAATC | 2316 |
| SEQ_ID_NO_234 | GAGCGAGAGGAGGAGCGCAGAGCGTGGCGGGGAAGGAGGGCGTCATGTGTGTGAGGAATC | 2240 |
| SEQ_ID_NO_218 | GAGCGAGAGGAGGAGCGCAGAGCGTGGCGGGGAAGGAGGGCGTCATGTGTGCGAGGAATC | 2678 |
| SEQ_ID_NO_219 | GAGCGAGAGGAGGAGCGCAGAGCGTGGCGGGGAAGGAGGGCGTCATGTGTGCGAGGAATC | 2678 |
| SEQ_ID_NO_217 | GAGCGAGAGGAGGAGCGCAGAGCGTGGCGGGGAAGGAGGGCGTCATGTGTGCGAGGAATC | 2678 |
| SEQ_ID_NO_221 | GAGCGAGAGGAGGAGCGCAGAGCGTGGCGGGGAAGGAGGGCGTCATGTGTGTGAGGAATC | 2270 |
| SEQ_ID_NO_224 | GAGCGAGAGGAGGAGCGCAGAGCGTGGCGGGGAAGGAGGGCGTCATGTGTGCGAGGAATC | 2279 |
| | ****************************************************  ******** | |
| SEQ_ID_NO_213 | TAGGACGACTTGTTGGCACTTGGCAGCTGGGCCGGGGTGCGTGCGAGATGCAATGCAAGA | 2375 |
| SEQ_ID_NO_222 | TAGGACGACTTGT-------TGGCAGCTGGGCCGGGGTGCGTGCGAGATGCAATGCAAGA | 2325 |
| SEQ_ID_NO_220 | TAGGACGACTTGTT-------GGCAGCTGGGCCGGGGTGCGTGCGAGATGCAATGCAAGA | 2503 |
| SEQ_ID_NO_235 | TAGGACGACTTGTT-------GGCAGCTGGGCCGGGGTGCGTGCGAGATGCAATGCAAGA | 2465 |
| SEQ_ID_NO_225 | TAGGACGACTTGTT-------GGCAGCTGGGCCGGGGTGCGTGCGAGATGCAATGCAAGA | 2511 |
| SEQ_ID_NO_226 | TAGGACGACTTGTT-------GGCAGCTGGGCCGGGGTGCGTGCGAGATGCAATGCAAGA | 2512 |
| SEQ_ID_NO_228 | TAGGACGACTTGTT-------GGCAGCTGGGCCGGGGTGCGTGCGAGATGCAATGCAAGA | 2512 |
| SEQ_ID_NO_227 | TAGGACGACTTGTT-------GGCAGCTGGGCCGGGGTGCGTGCGAGATGCAATGCAAGA | 2511 |
| SEQ_ID_NO_223 | TCGGACGACTTGTT-------GGCAGCTGGGCCGGGGTGCGTGCGAGATGCAATGCAAGA | 2316 |
| SEQ_ID_NO_215 | TAGGACGACTTGTTGGCACTTGGCAGCTGGGCCGGGGTGCGTGCGAGATGCAATGCAAGA | 2778 |
| SEQ_ID_NO_216 | TAGGACGACTTGTTGGCACTTGGCAGCTGGGCCGGGGTGCGTGCGAGATGCAATGCAAGA | 2778 |
| SEQ_ID_NO_214 | TAGGACGACTTGTTGGCACTTGGCAGCTGGGCCGGGGTGCGTGCGAGATGCAATGCAAGA | 2778 |
| SEQ_ID_NO_233 | TAGGACGACTTGTT-------GGCAGCTGGGCCGGGGTGCGTGCGAGATGCAATGCAAGA | 2348 |
| SEQ_ID_NO_236 | TAGGACGACTTGTT-------GGCAGCTGGGCCGGGGTGCGTGCGAGATGCAATGCAAGA | 2306 |
| SEQ_ID_NO_231 | TAGGACGACTTGTTGGCACTTGGCAGCTGGGCCGGGGTGCGTGCGAGATGCAATGCAAGA | 2376 |
| SEQ_ID_NO_229 | TAGGACGACTTGTTGGCACTTGGCAGCTGGGCCGGGGTGCGTGCGAGATGCAATGCAAGA | 2376 |
| SEQ_ID_NO_230 | TAGGACGACTTGTTGGCACTTGGCAGCTGGGCCGGGGTGCGTGCGAGATGCAATGCAAGA | 2376 |
| SEQ_ID_NO_232 | TAGGACGACTTGTTGGCACTTGGCAGCTGGGCCGGGGTGCGTGCGAGATGCAATGCAAGA | 2376 |
| SEQ_ID_NO_234 | TAGGACGACTTGTT-------GGCAGCTGGGCCGGGGTGCGTGCGAGATGCAATGCAAGA | 2293 |
| SEQ_ID_NO_218 | TAGGACGACTTGTT-------GGCAGCTGGGCCGGGGTGCGTGCGAGATGCAATGCAAGA | 2731 |
| SEQ_ID_NO_219 | TAGGACGACTTGTT-------GGCAGCTGGGCCGGGGTGCGTGCGAGATGCAATGCAAGA | 2731 |
| SEQ_ID_NO_217 | TAGGACGACTTGTT-------GGCAGCTGGGCCGGGGTGCGTGCGAGATGCAATGCAAGA | 2731 |
| SEQ_ID_NO_221 | TAGGACGACTTGTT-------GGCAGCTGGGCCGGGGTGCGTGCGAGATGCAATGCAAGA | 2323 |
| SEQ_ID_NO_224 | TAGGACGACTTGTT-------GGCAGCTGGGCCGGGGTGCGTGCGAGATGCAATGCAAGA | 2332 |
| | * ***********        **************************************** | |
| SEQ_ID_NO_213 | ACAAAGCGGACGGGCATC----------ACGCCTCCAGGTCCAACCCGGGGCGCCACTC | 2425 |
| SEQ_ID_NO_222 | ACAAAGCGGACGGGCATC----------ACGCCTCCAGGTCCAACCCGGGGCGCCACTC | 2375 |

TABLE 27-continued

| | | |
|---|---|---|
| SEQ_ID_NO_220 | ACAAAGCGGACGGGCATC----------ACGCCTCCAAGTCCAACCCGGGGCGCCACTC | 2553 |
| SEQ_ID_NO_235 | ACAAAGCGGACGGGCATC----------ACGCCTCCAGGTCCAACCCGGGGCGCCACTC | 2515 |
| SEQ_ID_NO_225 | ACAAAGCGGACGGGCATCTCGCTCGGCCACGCTTCCAAGTCCATCCGGGGGCGCCACTC | 2571 |
| SEQ_ID_NO_226 | ACAAAGCGGACGGGCATCTCGCTCGGCCACGCTTCCAAGTCCATCCGGGGGCGCCACTC | 2572 |
| SEQ_ID_NO_228 | ACAAAGCGGACGGGCATC----------ACGCCTCCAGGTCCAACCCGGGGCGCCACTC | 2562 |
| SEQ_ID_NO_227 | ACAAAGCGGACGGGCATC----------ACGCCTCCAGGTCCAACCCGGGGCGCCACTC | 2561 |
| SEQ_ID_NO_223 | ACAAAGCGGACGGGCATCTCGCTCGGCCACGCTTCCAAGTCCAACCGGGGGCGCCACTC | 2376 |
| SEQ_ID_NO_215 | ACAAAGCGGACGGGCATC----------ACGCCTCCAGGTCCAACCCGGGGCGCCACTC | 2828 |
| SEQ_ID_NO_216 | ACAAAGCGGACGGGCATC----------ACGCCTCCAGGTCCAACCCGGGGCGCCACTC | 2828 |
| SEQ_ID_NO_214 | ACAAAGCGGACGGGCATC----------ACGCCTCCAGGTCCAACCCGGGGCGCCACTC | 2828 |
| SEQ_ID_NO_233 | ACAAAGC---------ATC----------ACGCCTCCAAGTCCAACCGGGGGCGCCACTC | 2390 |
| SEQ_ID_NO_236 | ACAAAGC---------ATC----------ACGCCTCCAAGTCCAACCGGGGGCGCCACTC | 2348 |
| SEQ_ID_NO_231 | ACAAAGCGGACGGGCATC----------ACGCCTCCAGGTCCAACCCGGGGCGCCACTC | 2426 |
| SEQ_ID_NO_229 | ACAAAGCGGACGGGCATC----------ACGCCTCCAGGTCCAACCCGGGGCGCCACTC | 2426 |
| SEQ_ID_NO_230 | ACAAAGCGGACGGGCATC----------ACGCCTCCAGGTCCAACCCGGGGCGCCACTC | 2426 |
| SEQ_ID_NO_232 | ACAAAGCGGACGGGCATC----------ACGCCTCCAGGTCCAACCCGGGGCGCCACTC | 2426 |
| SEQ_ID_NO_234 | ACAAAGCGGACGGGCATC----------ACGCCTCCAGGTCCAACCCGGGGCGCCACTC | 2343 |
| SEQ_ID_NO_218 | ACAAAGCGGACGGGCATCTCGCTCGGCCACGCTTCCAAGTCCATCCGGGGGCGCCACTC | 2791 |
| SEQ_ID_NO_219 | ACAAAGCGGACGGGCATCTCGCTCGGCCACGCTTCCAAGTCCATCCGGGGGCGCCACTC | 2791 |
| SEQ_ID_NO_217 | ACAAAGCGGACGGGCATCTCGCTCGGCCACGCTTCCAAGTCCATCCGGGGGCGCCACTC | 2791 |
| SEQ_ID_NO_221 | ACAAAGCGGACGGGCATC----------ACGCCTCCAGGTCCAACCCGGGGCGCCACTC | 2373 |
| SEQ_ID_NO_224 | ACAAAGCGGACGGGCATCTCGCTCGGCCACGCTTCCAAGTCCATCCGGGGGCGCCAC-- | 2390 |
| | ******* *** **** **** ***** ** *********** | |
| SEQ_ID_NO_213 | G----GCCGCCGCTCATTGAGGCCCAGGCGCCAAGACGGCGGCTCCACCCACATCACAAT | 2481 |
| SEQ_ID_NO_222 | GATCGGCCGCCGCTCATTGAGGCCCAGGCGCCAAGACGGCGGCTCCACCCACGTCACAAT | 2435 |
| SEQ_ID_NO_220 | G----GCCGCCGCTCATTGAGGCCCAGGCGCCAAGACGGCGGCTCCACCCACGTCACAAT | 2609 |
| SEQ_ID_NO_235 | GATCGGCCGCCGCTCATTGAGGCCCAGGCGCCAAGACGGCGGCTCCACCCACGTCACAAT | 2575 |
| SEQ_ID_NO_225 | G----GCCGCCGCTCATTGAGGCCCAGGCGCCAAGACGGCGGCTCCACCCACGTCACAAT | 2627 |
| SEQ_ID_NO_226 | G----GCCGCCGCTCATTGAGGCCCAGGCGCCAAGACGGCGGCTCCACCCACGTCACAAT | 2628 |
| SEQ_ID_NO_228 | G----GCCGCCGCTCATTGAGGCCCAGGCGCCAAGACGGCGGCTCCACCCACGTCACAAT | 2618 |
| SEQ_ID_NO_227 | G----GCCGCCGCTCATTGAGGCCCAGGCGCCAAGACGGCGGCTCCACCCACGTCACAAT | 2617 |
| SEQ_ID_NO_223 | G----GCCGCCGCTCATTGAGGCCCAGGCGCCAAGACGGCGGCTCCACCCACATCACAAT | 2432 |
| SEQ_ID_NO_215 | G----GCCGCCGCTCATTGAGGCCCAGGCGCCAAGACGGCGGCTCCACCCACATCACAAT | 2884 |
| SEQ_ID_NO_216 | G----GCCGCCGCTCATTGAGGCCCAGGCGCCAAGACGGCGGCTCCACCCACATCACAAT | 2884 |
| SEQ_ID_NO_214 | G----GCCGCCGCTCATTGAGGCCCAGGCGCCAAGACGGCGGCTCCACCCACATCACAAT | 2884 |
| SEQ_ID_NO_233 | G----GCCGCCGCTCATTGAGGCCCAGGCGCCAAGACGGCGGCTCCACCCACATCACAAT | 2446 |
| SEQ_ID_NO_236 | G----GCCGCCGCTCATTGAGGCCCAGGCGCCAAGACGGCGGCTCCACCCACATCACAAT | 2404 |
| SEQ_ID_NO_231 | G----GCCGCCGCTCATTGAGGCCCAGGCGCCAAGACGGCGGCTCCACCCACATCACAAT | 2482 |
| SEQ_ID_NO_229 | G----GCCGCCGCTCATTGAGGCCCAGGCGCCAAGACGGCGGCTCCACCCACATCACAAT | 2482 |
| SEQ_ID_NO_230 | G----GCCGCCGCTCATTGAGGCCCAGGCGCCAAGACGGCGGCTCCACCCACATCACAAT | 2482 |
| SEQ_ID_NO_232 | G----GCCGCCGCTCATTGAGGCCCAGGCGCCAAGACGGCGGCTCCACCCACATCACAAT | 2482 |

TABLE 27-continued

```
SEQ_ID_NO_234 G----GCCGCCGCTCATTGAGGCCCAGGCGCCAAGACGGCGGCTCCACCCACGTCACAAT     2399

SEQ_ID_NO_218 G----GCCGCCGCTCATTGAGGCCCAGGCGCCAAGACGGCGGCTCCACCCACGTCACAAT     2847

SEQ_ID_NO_219 G----GCCGCCGCTCATTGAGGCCCAGGCGCCAAGACGGCGGCTCCACCCACGTCACAAT     2847

SEQ_ID_NO_217 G----GCCGCCGCTCATTGAGGCCCAGGCGCCAAGACGGCGGCTCCACCCACGTCACAAT     2847

SEQ_ID_NO_221 GATCGGCCGCCGCTCATTGAGGCCCAGGCGCCAAGACGGCGGCTCCACCCACGTCACAAT     2433

SEQ_ID_NO_224 --TCGGCCGCCGCTCATTGAGGCCCAGGCGCCAAGACGGCGGCTCCACCCACGTCACAAT     2448
                ************************************************ *******

SEQ_ID_NO_213 TGGCAACAAGAAGCACACGGCTGGGGTTGGGACGCGTCGAATTTTTCACCAGAAAATACC     2541

SEQ_ID_NO_222 TGGCAATAAGAAGCACACGGCTGGGGCTGGGACGCGTCGAATTTTTCACCAGAAAATACC     2495

SEQ_ID_NO_220 TGGCAACAAGAAGCACACGGCTGGGGCTGGGACGCGTCGAATTTTTCACCAGAAAATACC     2669

SEQ_ID_NO_235 TGGCAATAAGAAGCACACGGCTGGGGCTGGGACGCGTCGAATTTTTCACCAGAAAATACC     2635

SEQ_ID_NO_225 TGGCAACAAGAAGCACACGGCTGGGGCTGGGACGCGTCGAATTTTTCACCAGAAAATACC     2687

SEQ_ID_NO_226 TGGCAACAAGAAGCACACGGCTGGGGCTGGGACGCGTCGAATTTTTCACCAGAAAATACC     2688

SEQ_ID_NO_228 TGGCAATAAGAAGCACACGGCTGGGGCTGGGACGCGTCGAATTTTTCACCAGAAAATACC     2678

SEQ_ID_NO_227 TGGCAATAAGAAGCACACGGCTGGGGCTGGGACGCGTCGAATTTTTCACCAGAAAATACC     2677

SEQ_ID_NO_223 TGGCAACAAGAAGCACACGGCTGGGGCTGGGACGCGTCGAATTTTTCACCAGAAAATACC     2492

SEQ_ID_NO_215 TGGCAACAAGAAGCACACGGCTGGGGTTGGGACGCGTCGAATTTTTCACCAGAAAATACC     2944

SEQ_ID_NO_216 TGGCAACAAGAAGCACACGGCTGGGGTTGGGACGCGTCGAATTTTTCACCAGAAAATACC     2944

SEQ_ID_NO_214 TGGCAACAAGAAGCACACGGCTGGGGTTGGGACGCGTCGAATTTTTCACCAGAAAATACC     2944

SEQ_ID_NO_233 TGGCAACAAGAAGCACACGGCTGGGGCTGGGACGCGTCGAATTTTTCACCAGAAAATACC     2506

SEQ_ID_NO_236 TGGCAACAAGAAGCACACGGCTGGGGCTGGGACGCGTCGAATTTTTCACCAGAAAATACC     2464

SEQ_ID_NO_231 TGGCAACAAGAAGCACACGGCTGGGGTTGGGACGCGTCGAATTTTTCACCAGAAAATACC     2542

SEQ_ID_NO_229 TGGCAACAAGAAGCACACGGCTGGGGTTGGGACGCGTCGAATTTTTCACCAGAAAATACC     2542

SEQ_ID_NO_230 TGGCAACAAGAAGCACACGGCTGGGGTTGGGACGCGTCGAATTTTTCACCAGAAAATACC     2542

SEQ_ID_NO_232 TGGCAACAAGAAGCACACGGCTGGGGTTGGGACGCGTCGAATTTTTCACCAGAAAATACC     2542

SEQ_ID_NO_234 TGGCAATAAGAAGCACACGGCTGGGGCTGGGACGCGTCGAATTTTTCACCAGAAAATACC     2459

SEQ_ID_NO_218 TGGCAACAAGAAGCACACGGCTGGGGCTGGGACGCGTCGAATTTTTCACCAGAAAATACC     2907

SEQ_ID_NO_219 TGGCAACAAGAAGCACACGGCTGGGGCTGGGACGCGTCGAATTTTTCACCAGAAAATACC     2907

SEQ_ID_NO_217 TGGCAACAAGAAGCACACGGCTGGGGCTGGGACGCGTCGAATTTTTCACCAGAAAATACC     2907

SEQ_ID_NO_221 TGGCAATAAGAAGCACACGGCTGGGGCTGGGACGCGTCGAATTTTTCACCAGAAAATACC     2493

SEQ_ID_NO_224 TGGCAACAAGAAGCACACGGCTGGGGCTGGGACGCGTCGAATTTTTCACCAGAAAATACC     2508
              ***** ******************  *********************************

SEQ_ID_NO_213 GTCTGATCCTGGCGTTTCGTCAGATGCTATGCTACGTGAACGGCAAAACCTAGCAGCAGC     2601

SEQ_ID_NO_222 GTCTGATCCTGGCGTTTCGTCAGATGCTATGCTACGTGAACGGCAAAACCTAGCAGCAGC     2555

SEQ_ID_NO_220 GTC-------GGCGTTTCGTCAGATGCTATGCTACGTGAACGGCAAAACCTAGCAGCAGC     2722

SEQ_ID_NO_235 GTCTGATCCTGGCGTTTCGTCAGATGCTATGCTACGTGAACGGCAAAACCTAGCAGCAGC     2695

SEQ_ID_NO_225 GTCTGATCCTGGCGTTTCGT----------------GAACGGCAAAACCTAGCAGCAGC     2730

SEQ_ID_NO_226 GTCTGATCCTGGCGTTTCGT----------------GAACGGCAAAACCTAGCAGCAGC     2731

SEQ_ID_NO_228 GTCTGATCCTGGCGTTTCGTCAGATGCTATGCTACGTGAACGGCAAAACCTAGCAGCAGC     2738

SEQ_ID_NO_227 GTCTGATCCTGGCGTTTCGTCAGATGCTATGCTACGTGAACGGCAAAACCTAGCAGCAGC     2737

SEQ_ID_NO_223 GTC-------GGCGTTTCGTCAGATGCTATGCTACGTGAACGGCAAAACCTAGCAGCAGC     2545
```

TABLE 27-continued

| | | |
|---|---|---|
| SEQ_ID_NO_215 | GTCTGATCCTGGCGTTTCGTCAGATGCTATGCTACGTGAACGGCAAAACCTAGCAGCAGC | 3004 |
| SEQ_ID_NO_216 | GTCTGATCCTGGCGTTTCGTCAGATGCTATGCTACGTGAACGGCAAAACCTAGCAGCAGC | 3004 |
| SEQ_ID_NO_214 | GTCTGATCCTGGCGTTTCGTCAGATGCTATGCTACGTGAACGGCAAAACCTAGCAGCAGC | 3004 |
| SEQ_ID_NO_233 | GTC-------GGCGTTTCGTCAGATGCTATGCTACGTGAACGGCAAAACCTAGCAGCAGC | 2559 |
| SEQ_ID_NO_236 | GTC-------GGCGTTTCGTCAGATGCTATGCTACGTGAACGGCAAAACCTAGCAGCAGC | 2517 |
| SEQ_ID_NO_231 | GTCTGATCCTGGCGTTTCGTCAGATGCTATGCTACGTGAACGGCAAAACCTAGCAGCAGC | 2602 |
| SEQ_ID_NO_229 | GTCTGATCCTGGCGTTTCGTCAGATGCTATGCTACGTGAACGGCAAAACCTAGCAGCAGC | 2602 |
| SEQ_ID_NO_230 | GTC-------GGCGTTTCGTCAGATGCTATGCTACGTGAACGGCAAAACCTAGCAGCAGC | 2595 |
| SEQ_ID_NO_232 | GTC-------GGCGTTTCGTCAGATGCTATGCTACGTGAACGGCAAAACCTAGCAGCAGC | 2595 |
| SEQ_ID_NO_234 | GTCTGATCCTGGCGTTTCGTCAGATGCTATGCTACGTGAACGGCAAAACCTAGCAGCAGC | 2519 |
| SEQ_ID_NO_218 | GTCTGATCCTGGCGTTTCGT----------------GAACGGCAAAACCTAGCAGCAGC | 2950 |
| SEQ_ID_NO_219 | GTCTGATCCTGGCGTTTCGT----------------GAACGGCAAAACCTAGCAGCAGC | 2950 |
| SEQ_ID_NO_217 | GTCTGATCCTGGCGTTTCGT----------------GAACGGCAAAACCTAGCAGCAGC | 2950 |
| SEQ_ID_NO_221 | GTCTGATCCTGGCGTTTCGTCAGATGCTATGCTACGTGAACGGCAAAACCTAGCAGCAGC | 2553 |
| SEQ_ID_NO_224 | GTCTGATCCTGGCGTTTCGT----------------GAACGGCAAAACCTAGCAGCAGC | 2551 |
| | ***       *********              *********************** | |
| SEQ_ID_NO_213 | AGCAGC---ACTCAGACTGGACAAGAGGAGGGAAATCTTTGCGTGGGAACCAAACTGAAC | 2658 |
| SEQ_ID_NO_222 | AGC------ACTCAGACTGGACAAGAGGAGGGAAATCTTTGCGTGGGAACCAAACTGAAC | 2609 |
| SEQ_ID_NO_220 | AGCAGC---ATTCAGACTGGACAAGAGGAGGGAAATCTTTGCGTGGGAACCAAACTGAAC | 2779 |
| SEQ_ID_NO_235 | AGC------ACTCAGACTGGACAAGAGGAGGGAAATCTTTGCGTGGGAACCAAACTGAAC | 2749 |
| SEQ_ID_NO_225 | AGC------A------------------------------------------------- | 2734 |
| SEQ_ID_NO_226 | AGC------A------------------------------------------------- | 2735 |
| SEQ_ID_NO_228 | AGC------ACTCAGACTGGACAAGAGGAGGGAAATCTTTGCGTGGGAACCAAACTGAAC | 2792 |
| SEQ_ID_NO_227 | AGCAGC---ACTCAGACTGGACAAGAGGAGGGAAATCTTTGCGTGGGAACCAAACTGAAC | 2794 |
| SEQ_ID_NO_223 | AGC------ACTCAGACTGGACAAGAGGAGGGAAATCTTTGCGTGGGAACCAAACTGAAC | 2599 |
| SEQ_ID_NO_215 | AGCAGC---ACTCAGACTGGACAAGAGGAGGGAAATCTTTGCGTGGGAACCAAACTGAAC | 3061 |
| SEQ_ID_NO_216 | AGCAGC---ACTCAGACTGGACAAGAGGAGGGAAATCTTTGCGTGGGAACCAAACTGAAC | 3061 |
| SEQ_ID_NO_214 | AGCAGC---ACTCAGACTGGACAAGAGGAGGGAAATCTTTGCGTGGGAACCAAACTGAAC | 3061 |
| SEQ_ID_NO_233 | AGCAGCAGCACTCAGACTGGACAAGAGGAGGGAAATCTTTGCGTGGGAACCAAACTGAAC | 2619 |
| SEQ_ID_NO_236 | AGCAGC---ACTCAGACTGGACAAGAGGAGGGAAATCTTTGCGTGGGAACCAAACTGAAC | 2574 |
| SEQ_ID_NO_231 | AGCAGC---ACTCAGACTGGACAAGAGGAGGGAAATCTTTGCGTGGGAACCAAACTGAAC | 2659 |
| SEQ_ID_NO_229 | AGCAGC---ACTCAGACTGGACAAGAGGAGGGAAATCTTTGCGTGGGAACCAAACTGAAC | 2659 |
| SEQ_ID_NO_230 | AGCA------CTCAGACTGGACGAGAGGAGGGAAATCTTTGCGTGGGAACCAAACTGAAC | 2649 |
| SEQ_ID_NO_232 | AGCA------CTCAGACTGGACGAGAGGAGGGAAATCTTTGCGTGGGAACCAAACTGAAC | 2649 |
| SEQ_ID_NO_234 | AGC------ACTCAGACTGGACAAGAGGAGGGAAATCTTTGCGTGGGAACCAAACTGAAC | 2573 |
| SEQ_ID_NO_218 | AGCA-------------------------------------------------------- | 2954 |
| SEQ_ID_NO_219 | AGCA-------------------------------------------------------- | 2954 |
| SEQ_ID_NO_217 | AGCA-------------------------------------------------------- | 2954 |
| SEQ_ID_NO_221 | AGCACT------CAGACTGGACAAGAGGAGGGAAATCTTTGCGTGGGAACCAAACTGAAC | 2607 |
| SEQ_ID_NO_224 | AGCA-------------------------------------------------------- | 2555 |
| | *** | |

TABLE 27-continued

```
SEQ_ID_NO_213 GCGAATCGCACGAGTCGGATGACATATC-----CTCGTCCGGAGCGGACTCGACCGCGAG   2713
SEQ_ID_NO_222 GCGAATCGCACGGGTCGGATGACATATCATATCCTCGTGCGGAGCGGACTCAACGGCGAG   2669
SEQ_ID_NO_220 GCGAATCGCACGAGTCGGATGACATATC-----CTCGTGCGGAGCGGACTCGACCGCGAG   2834
SEQ_ID_NO_235 GCGAATCGCACGGGTCGGATGACATATCATATCCTCGTGCGGAGCGGACTCAACGGCGAG   2809
SEQ_ID_NO_225 --GCATTCCACGGGTCGGATGACATATCATATCCTCGTGCGGAGCGGACTCAACGGCGAG   2792
SEQ_ID_NO_226 --GCATTCCACGGGTCGGATGACATATCATATCCTCGTGCGGAGCGGACTCAACGGCGAG   2793
SEQ_ID_NO_228 GCGAATCGCACGGGTCGGATGACATATCATATCCTCGTGCGGAGCGGACTCAACGGCGAG   2852
SEQ_ID_NO_227 GCGAATCGCACGAGTCGGATGACATATC-----CTCGTCCGGAGCGGACTCGACCGCGAG   2849
SEQ_ID_NO_223 GCGAATCGCACGAGTCGGATGACATATC-----CTCGTCCGGAGCGGACTCGGCCGCGAG   2654
SEQ_ID_NO_215 GCGAATCGCACGAGTCGGATGACATATC-----CTCGTCCGGAGCGGACTCGACCGCGAG   3116
SEQ_ID_NO_216 GCGAATCGCACGAGTCGGATGACATATC-----CTCGTCCGGAGCGGACTCGACCGCGAG   3116
SEQ_ID_NO_214 GCGAATCGCACGAGTCGGATGACATATC-----CTCGTCCGGAGCGGACTCGACCGCGAG   3116
SEQ_ID_NO_233 GCGAATCGCACGAGTCGGATGACATATC-----CTCGTCCGGAGCGGACTCGGCCGCGAG   2674
SEQ_ID_NO_236 GCGAATCGCACGAGTCGGATGACATATC-----CTCGTCCGGAGCGGACTCGGCCGCGAG   2629
SEQ_ID_NO_231 GCGAATCGCACGAGTCGGATGACATATC-----CTCGTCCGGAGCGGACTCGACCGCGAG   2714
SEQ_ID_NO_229 GCGAATCGCACGAGTCGGATGACATATC-----CTCGTCCGGAGCGGACTCGACCGCGAG   2714
SEQ_ID_NO_230 GCGAATCGCACGAGTCGGATGACATATC-----CTCGTCCGGAGCGGACTCGACCGCGAG   2704
SEQ_ID_NO_232 GCGAATCGCACGAGTCGGATGACATATC-----CTCGTCCGGAGCGGACTCGACCGCGAG   2704
SEQ_ID_NO_234 GCGAATCGCACGGGTCGGATGACATATCATATCCTCGTGCGGAGCGGACTCAACGGCGAG   2633
SEQ_ID_NO_218 --GCATTCCACGGGTCGGATGACATATCATATCCTCGTGCGGAGCGGACTCTACGGCGAG   3012
SEQ_ID_NO_219 --GCATTCCACGGGTCGGATGACATATCATATCCTCGTGCGGAGCGGACTCTACGGCGAG   3012
SEQ_ID_NO_217 --GCATTCCACGGGTCGGATGACATATCATATCCTCGTGCGGAGCGGACTCTACGGCGAG   3012
SEQ_ID_NO_221 GCGAATCGCACGGGTCGGATGACATATCATATCCTCGTGCGGAGCGGACTCAACGGCGAG   2667
SEQ_ID_NO_224 --GCATTCCACGGGTCGGATGACATATCATATCCTCGTGCGGAGCGGACTCAACGGCGAG   2613
              * **  **** **************     ***** ************ *  *****
SEQ_ID_NO_213 TCCAGCTGTGGCTGCGGAATATTCCGGCGGAAGCGCGGGGAGAACGACGGCGGCCTCCGG   2773
SEQ_ID_NO_222 TCCAGCTGTGGCTGCGGAATATTCCGGCGGAAGCGCGGGGAGAGCGACGGCGGCCTCCGG   2729
SEQ_ID_NO_220 TCCAGCTGTGGNTGCGGAATATTCCGGCGGAAGCGCGGGGAGAACGACGGCGGCCTCCGG   2894
SEQ_ID_NO_235 TCCAGCTGTGGCTGCGGAATATTCCGGCGGAAGCGCGGGGAGAGCGACGGCGGCCTCCGG   2869
SEQ_ID_NO_225 TCCAGCTGTGGNNNCGGAATATTCCGGCGGAAGCGCGGGGAGAGCGACGGCGGCCTCCGG   2852
SEQ_ID_NO_226 TCCAGCTGTGGCTGCGGAATATTCCGGCGGAAGCGCGGGGAGAGCGACGGCGGCCTCCGG   2853
SEQ_ID_NO_228 TCCAGCTGTGGCTGCGGAATATTCCGGCGGAAGCGCGGGGAGAGCGACGGCGGCCTCCGG   2912
SEQ_ID_NO_227 TCCAGCTGTGGCTGCGGAATATTCCGGCGGAAGCGCGGGGAGAACGACGGCGGCCTCCGG   2909
SEQ_ID_NO_223 TCCAGCTGTGGCTGCGGAATATTCCGGCGGAATCGCGGGGAGAACGACGGCGGCCTCCGG   2714
SEQ_ID_NO_215 TCCAGCTGTGGCTGCGGAATATTCCGGCGGAAGCGCGGGGAGAACGACGGCGGCCTCCGG   3176
SEQ_ID_NO_216 TCCAGCTGTGGCTGCGGAATATTCCGGCGGAAGCGCGGGGAGAACGACGGCGGCCTCCGG   3176
SEQ_ID_NO_214 TCCAGCTGTGGCTGCGGAATATTCCGGCGGAAGCGCGGGGAGAACGACGGCGGCCTCCGG   3176
SEQ_ID_NO_233 TCCAGCTGTGGCTGCGGAATATTCCGGCGGAAGCGCGGGGAGAACGACGGCGGCCTCCGG   2734
SEQ_ID_NO_236 TCCAGCTGTGGCTGCGGAATATTCCGGCGGAAGCGCGGGGAGAACGACGGCGGCCTCCGG   2689
SEQ_ID_NO_231 TCCAGCTGTGGCTGCGGAATATTCCGGCGGAAGCGCGGGGAGAACGACGGCGGCCTCCGG   2774
```

TABLE 27-continued

| | | |
|---|---|---|
| SEQ_ID_NO_229 | TCCAGCTGTGGCTGCGGAATATTCCGGCGGAAGCGCGGGGAGAACGACGGCGGCCTCCGG | 2774 |
| SEQ_ID_NO_230 | TCCAGCTGTGGCTGCGGAATATTCCGGCGGAAGCGCGGGGAGAACGACGGCGGCCTCCGG | 2764 |
| SEQ_ID_NO_232 | TCCAGCTGTGGCTGCGGAATATTCCGGCGGAAGCGCGGGGAGAACGACGGCGGCCTCCGG | 2764 |
| SEQ_ID_NO_234 | TCCAGCTGTGGCTGCGGAATATTCCGGCGGAAGCGCGGGGAGAGCGACGGCGGCCTCCGG | 2693 |
| SEQ_ID_NO_218 | TCCAGCTGTGGCTGCGGAATATTCCGGCGGAAGCGCGGGGAGAGCGACGGCGGCCTCCGG | 3072 |
| SEQ_ID_NO_219 | TCCAGCTGTGGCTGCGGAATATTCCGGCGGAAGCGCGGGGAGAGCGACGGCGGCCTCCGG | 3072 |
| SEQ_ID_NO_217 | TCCAGCTGTGGCTGCGGAATATTCCGGCGGAAGCGCGGGGAGAGCGACGGCGGCCTCCGG | 3072 |
| SEQ_ID_NO_221 | TCCAGCTGTGGCTGCGGAATATTCCGGCGGAAGCGCGGGGAGAGCGACGGCGGCCTCCGG | 2727 |
| SEQ_ID_NO_224 | TCCAGCTGTGGCTGCGGAATATTCCGGCGGAAGCGCGGGGAGAGCGACGGCGGCCTCCGG | 2673 |
| | ********** ****************** ********** **************** | |
| SEQ_ID_NO_213 | TGGGACCCGGGGCGAGCGGGAGATGCGGCGAAGATGTTCGGCGCTGATGTCGCTGGAATA | 2833 |
| SEQ_ID_NO_222 | TGGGACCCGGGGCGAGCGGGAGATGCGGCGAAGATGTTCGGCGCTGATGTCGCTGGAATA | 2789 |
| SEQ_ID_NO_220 | TGGGACCCGGGGCGAGCGGGAGATGCGGCGAAGATGTTCGGCGCTGATGTCGCTGGAATA | 2954 |
| SEQ_ID_NO_235 | TGGGACCCGGGGCGAGCGGGAGATGCGGCGAAGATGTTCGGCGCTGATGTCGCTGGAATA | 2929 |
| SEQ_ID_NO_225 | TGG--------------------------------------------------------- | 2855 |
| SEQ_ID_NO_226 | TGGGACCCGGGGCGAGCGGGAGATGCGGCGAAGATGTTCGGCGCTGATGTCGCTGGAATA | 2913 |
| SEQ_ID_NO_228 | TGGGACCCGGGGCGAGCGGGAGATGCGGCGAAGATGTTCGGCGCTGATGTCGCTGGAATA | 2972 |
| SEQ_ID_NO_227 | TGGGACCCGGGGCGAGCGGGAGATGCGGCGAAGATGTTCGGCGCTGATGTCGCTGGAATA | 2969 |
| SEQ_ID_NO_223 | TGGGACCCGGGGCGAGCGGGAGATGCGGCGAAGATGTTCGGCGCTGATGTCGCTGGAATA | 2774 |
| SEQ_ID_NO_215 | TGGGACCCGGGGCGAGCGGGAGATGCGGCGAAGATGTTCGGCGCTGATGTCGCTGGAATA | 3236 |
| SEQ_ID_NO_216 | TGGGACCCGGGGCGAGCGGGAGATGCGGCGAAGATGTTCGGCGCTGATGTCGCTGGAATA | 3236 |
| SEQ_ID_NO_214 | TGGGACCCGGGGCGAGCGGGAGATGCGGCGAAGATGTTCGGCGCTGATGTCGCTGGAATA | 3236 |
| SEQ_ID_NO_233 | TGGGACCCGGGGCGAGCGGGAGATGCGGCGAAGATGTTCGGCGCTGATGTCGCTGGAATA | 2794 |
| SEQ_ID_NO_236 | TGGGACCCGGGGCGAGCGGGAGATGCGGCGAAGATGTTCGGCGCTGATGTCGCTGGAATA | 2749 |
| SEQ_ID_NO_231 | TGGGACCCGGGGCGAGCGGGAGATGCGGCGAAGATGTTCGGCGCTGATGTCGCTGGAATA | 2834 |
| SEQ_ID_NO_229 | TGGGACCCGGGGCGAGCGGGAGATGCGGCGAAGATGTTCGGCGCTGATGTCGCTGGAATA | 2834 |
| SEQ_ID_NO_230 | TGGGAACCGGGGCGAGCGGGAGATGCGGCGAAGATGTTCGGCGCTGATGTCGCTGGAATA | 2824 |
| SEQ_ID_NO_232 | TGGGAACCGGGGCGAGCGGGAGATGCGGCGAAGATGTTCGGCGCTGATGTCGCTGGAATA | 2824 |
| SEQ_ID_NO_234 | TGGGACCCGGGGCGAGCGGGAGATGCGGCGAAGATGTTCGGCGCTGATGTCGCTGGAATA | 2753 |
| SEQ_ID_NO_218 | TGGGACCCGGGGCGAGCGGGAGATGCGGCGAAGATGTTCGGCGCTGATGTCGCTGGAATA | 3132 |
| SEQ_ID_NO_219 | TGGGACCCGGGGCGAGCGGGAGATGCGGCGAAGATGTTCGGCGCTGATGTCGCTGGAATA | 3132 |
| SEQ_ID_NO_217 | TGGGACCCGGGGCGAGCGGGAGATGCGGCGAAGATGTTCGGCGCTGATGTCGCTGGAATA | 3132 |
| SEQ_ID_NO_221 | TGGGACCCGGGGCGAGCGGGAGATGCGGCGAAGATGTTCGGCGCTGATGTCGCTGGAATA | 2787 |
| SEQ_ID_NO_224 | TGGGACCCGGGGCGAGCGGGAGATGCGGCGAAGATGTTCGGCGCTGATGTCGCTGGAATA | 2733 |
| | *** | |
| SEQ_ID_NO_213 | TTCGCGCCAGCTGTGGCTGCCGGTGTGACCTGCTGACCAGACGACCAGTGGCAGTGGCCA | 2893 |
| SEQ_ID_NO_222 | TTCGCGCCAGCTGTGGCTGCCGGTGCGACCTGCTGACCAGACGACCAGTGGCAATGGCCA | 2849 |
| SEQ_ID_NO_220 | TTCGCGCCAGCTGTGGCTGCCGG------------------------------------- | 2977 |
| SEQ_ID_NO_235 | TTCGCGCCAGCTGTGGCTGCCGGTGCGACCTGCTGACCAG--------TGGCAATGGCCA | 2981 |
| SEQ_ID_NO_225 | ------------------------------------------------------------ | |
| SEQ_ID_NO_226 | TTCGCGCCAGCTGTGGCTGCCGGTGCGACCTGCTGACCAGACGACCAGTGGCAATGGCCA | 2973 |

TABLE 27-continued

| | | |
|---|---|---|
| SEQ_ID_NO_228 | TTCGCGCCAGCTGTGGCTGCCGGTGCGACCTGCTGACCAGACGACCAGTGGCAATGGCCA | 3032 |
| SEQ_ID_NO_227 | TTCGCGCCAGCTGTGGCTGCCGGTGTGACCTGCTGACCAGACGACCAGTGGCAGTGGCCA | 3029 |
| SEQ_ID_NO_223 | TTCGCGCCAGCTGTGGCTGCCGGTGTGACCTGCTGACCAGACGACCAGTGGCAGTGGCCA | 2834 |
| SEQ_ID_NO_215 | TTCGCGCCAGCTGTGGCTGCCGGTGTGACCTGCTGACCAGACGACCAGTGGCAGTGGCCA | 3296 |
| SEQ_ID_NO_216 | TTCGCGCCAGCTGTGGCTGCCGGTGTGACCTGCTGACCAGACGACCAGTGGCAGTGGCCA | 3296 |
| SEQ_ID_NO_214 | TTCGCGCCAGCTGTGGCTGCCGGTGTGACCTGCTGACCAGACGACCAGTGGCAGTGGCCA | 3296 |
| SEQ_ID_NO_233 | TTCGCGCCAGCTGTGGCTGCCGGTGTGACCTGCTGACCAGACGACCAGTGGCAGTGGCCA | 2854 |
| SEQ_ID_NO_236 | TTCGCGCCAGCTGTGGCTGCCGGTGTGACCTGCTGACCAGACGACCAGTGGCAGTGGCCA | 2809 |
| SEQ_ID_NO_231 | TTCGCGCCAGCTGTGGCTGCCGGTGTGACCTGCTGACCAGACGACCAGTGGCAGTGGCCA | 2894 |
| SEQ_ID_NO_229 | TTCGCGCCAGCTGTGGCTGCCGGTGTGACCTGCTGACCAGACGACCAGTGGCAGTGGCCA | 2894 |
| SEQ_ID_NO_230 | TTCGCGCCAGCTGTGGCTGCCGGTGTGACCTGCT--------GACCAGTGGCAGTGGCCA | 2876 |
| SEQ_ID_NO_232 | TTCGCGCCAGCTGTGGCTGCCGGTGTGACCTGCT--------GACCAGTGGCAGTGGCCA | 2876 |
| SEQ_ID_NO_234 | TTCGCGCCAGCTGTGGCTGCCGGTGCGACCTGCTGACCAGACGACCAGTGGCAATGGCCA | 2813 |
| SEQ_ID_NO_218 | TTCGCGCCAGCTGTGGCTGCCGGTGCGACCTGCTGACCAGACGACCAATGGCAGTGGCCA | 3192 |
| SEQ_ID_NO_219 | TTCGCGCCAGCTGTGGCTGCCGGTGCGACCTGCTGACCAGACGACCAATGGCAGTGGCCA | 3192 |
| SEQ_ID_NO_217 | TTCGCGCCAGCTGTGGCTGCCGGTGCGACCTGCTGACCAGACGACCAATGGCAGTGGCCA | 3192 |
| SEQ_ID_NO_221 | TTCGCGCCAGCTGTGGCTGCCGGTGCGACCTGCTGACCAGACGACCAGTGGCAATGGCCA | 2847 |
| SEQ_ID_NO_224 | TTCGCGCCAGCTGTGGCTGCCGGTGCGACCTGCTGACCAGACGACCAGTGGCAATGGCCA | 2793 |
| SEQ_ID_NO_213 | CCGCCTCTCC-----------------------------------ATC---------- | 2906 |
| SEQ_ID_NO_222 | CCGCCTCTCC-----------------------------------ATCCAACCTCCAT | 2872 |
| SEQ_ID_NO_220 | ------------------------------------------------------------ | |
| SEQ_ID_NO_235 | CCGCCTCTCC-----------------------------------ATCCAACCTCCAT | 3004 |
| SEQ_ID_NO_225 | ------------------------------------------------------------ | |
| SEQ_ID_NO_226 | CCGCCTCTCC-----------------------------------ATCCAACCTCCAT | 2996 |
| SEQ_ID_NO_228 | CCGCCTCTCC-----------------------------------ATCCAACCTCCAT | 3055 |
| SEQ_ID_NO_227 | CCGCCTCTC-----------------------------------------------CAT | 3041 |
| SEQ_ID_NO_223 | CCGCCTCTG-----------------------------------------------CAT | 2846 |
| SEQ_ID_NO_215 | CCGCCTCTC-----------------------------------------------CAT | 3308 |
| SEQ_ID_NO_216 | CCGCCTCTC-----------------------------------------------CAT | 3308 |
| SEQ_ID_NO_214 | CCGCCTCTC-----------------------------------------------CAT | 3308 |
| SEQ_ID_NO_233 | CCGCCTCTC-----------------------------------------------CAT | 2866 |
| SEQ_ID_NO_236 | CCGCCTCTC-----------------------------------------------CAT | 2821 |
| SEQ_ID_NO_231 | CCGCCTCTC-----------------------------------------------CAT | 2906 |
| SEQ_ID_NO_229 | CCGCCTCTC-----------------------------------------------CAT | 2906 |
| SEQ_ID_NO_230 | CCGCCTCTC-----------------------------------------------CAT | 2888 |
| SEQ_ID_NO_232 | CCGCCTCTC-----------------------------------------------CAT | 2888 |
| SEQ_ID_NO_234 | CCGCCTCTCC-----------------------------------ATCCAACCTCCAT | 2836 |
| SEQ_ID_NO_218 | CCGCCTCTCCCTCTTGCTGTTGGAGTTGGATCCACGGACCACTCTCCATCCAACATCCAT | 3252 |
| SEQ_ID_NO_219 | CCGCCTCTCCCTCTTGCTGTTGGAGTTGGATCCACGGACCACTCTCCATCCAACATCCAT | 3252 |
| SEQ_ID_NO_217 | CCGCCTCTCCCTCTTGCTGTTGGAGTTGGATCCACGGACCACTCTCCATCCAACATCCAT | 3252 |

TABLE 27-continued

| | | |
|---|---|---|
| SEQ_ID_NO_221 | CCGCCTCTCC---------------------------------------ATCCAACCTCCAT | 2870 |
| SEQ_ID_NO_224 | CCGCCTCTCC---------------------------------------ATCCAACCTCCAT | 2816 |
| SEQ_ID_NO_213 | -ACAGATTCGCGGACGATTAGCCGAGACTAATCGCTATTCTCAACACTTTTAAAACCGTG | 2965 |
| SEQ_ID_NO_222 | CACAGATTGGCGGACGATTAGCCGAGACTAATCGCTATTCTCAACACTTTTAAAACCGTG | 2932 |
| SEQ_ID_NO_220 | ------------------------------------------------------------ | |
| SEQ_ID_NO_235 | CACAGATTGGCGGACGATTAGCCGAGACTAATCGCTATTCTCAACACTTTTAAAACCGTG | 3064 |
| SEQ_ID_NO_225 | ------------------------------------------------------------ | |
| SEQ_ID_NO_226 | CACAGATTGGCGGACGATTAGCCGAGACTAATCGCTATTCTCAACACTTTTAAAACCGTG | 3056 |
| SEQ_ID_NO_228 | CACAGATTGGCGGACGATTAGCCGAGACTAATCGCTATTCTCAACACTTTTAAAACCGTG | 3115 |
| SEQ_ID_NO_227 | CACAGATTCGCGGACGATTAGCCGAGACTAATCGCTATTCTCAACACTTTTAAAACCGTG | 3101 |
| SEQ_ID_NO_223 | CACAGATTGGCGGACGATTAGCCGAGACTAATTGCCATTCTCAACACTTTTAAAACCGTG | 2906 |
| SEQ_ID_NO_215 | CACAGATTCGCGGACGATTAGCCGAGACTAATCGCTATTCTCAACACTTTTAAAACCGTG | 3368 |
| SEQ_ID_NO_216 | CACAGATTCGCGGACGATTAGCCGAGACTAATCGCTATTCTCAACACTTTTAAAACCGTG | 3368 |
| SEQ_ID_NO_214 | CACAGATTCGCGGACGATTAGCCGAGACTAATCGCTATTCTCAACACTTTTAAAACCGTG | 3368 |
| SEQ_ID_NO_233 | CACAGATTCGCGGACGATTAGCCGAGACTAATCGCTATTCTCAACACTTTTAAAACCGTG | 2926 |
| SEQ_ID_NO_236 | CACAGATTCGCGGACGATTAGCCGAGACTAATCGCTATTCTCAACACTTTTAAAACCGTG | 2881 |
| SEQ_ID_NO_231 | CACAGATTCGCGGACGATTAGCCGAGACTAATCGCTATTCTCAACACTTTTAAAACCGTG | 2966 |
| SEQ_ID_NO_229 | CACAGATTCGCGGACGATTAGCCGAGACTAATCGCTATTCTCAACACTTTTAAAACCGTG | 2966 |
| SEQ_ID_NO_230 | CACAGATTGGCGGACGATTAGCCGAGACTAATCGCTATTCTCAACACTTTTAAAACCGTG | 2948 |
| SEQ_ID_NO_232 | CACAGATTGGCGGACGATTAGCCGAGACTAATCGCTATTCTCAACACTTTTAAAACCGTG | 2948 |
| SEQ_ID_NO_234 | CACAGATTGGCGGACGATTAGCCGAGACTAATCGCTATTCTCAACACTTTTAAAACCGTG | 2896 |
| SEQ_ID_NO_218 | CACAGATTGGCGGACGATTAGCCGAGACTAATCGCTATTCTCAACACTTTTAAAACCGTA | 3312 |
| SEQ_ID_NO_219 | CACAGATTGGCGGACGATTAGCCGAGACTAATCGCTATTCTCAACACTTTTAAAACCGTA | 3312 |
| SEQ_ID_NO_217 | CACAGATTGGCGGACGATTAGCCGAGACTAATCGCTATTCTCAACACTTTTAAAACCGTA | 3312 |
| SEQ_ID_NO_221 | CACAGATTGGCGGACGATTAGCCGAGACTAATCGCTATTCTCAACACTTTTAAAACCGTG | 2930 |
| SEQ_ID_NO_224 | CACAGATTGGCGGACGATTAGCCGAGACTAATCGCTATTCTCAACACTTTTAAAACCGTG | 2876 |
| SEQ_ID_NO_213 | CGTGCAGAATGCTAAGGGCGCGTTCGTTTGCACAGCAATAGACATGGATTTATTTCAGCT | 3025 |
| SEQ_ID_NO_222 | CGTGCAGAATGCTAAG-------------------------------------------- | 2948 |
| SEQ_ID_NO_220 | ------------------------------------------------------------ | |
| SEQ_ID_NO_235 | CGTGCAGAATGCTAAGCCTGC-----TAGATTCGAGCATCTGCGTGACTCTACTTTGGCT | 3119 |
| SEQ_ID_NO_225 | ------------------------------------------------------------ | |
| SEQ_ID_NO_226 | CGTGCAGAATGCTAAGCCTGC-----TAGATTCGAGCATCTGCGTGACTCTACTTTGGCT | 3111 |
| SEQ_ID_NO_228 | CGTGCAGAATGCTAAGCCTGC-----TAGATTCGAGCATCTGCGTGACTCTACTTTGGCT | 3170 |
| SEQ_ID_NO_227 | CGTGCAGAATGCTAAGGGCGCGTTCGTTTGCACAGCAATAGACATGGATTTATTTCAGCT | 3161 |
| SEQ_ID_NO_223 | CGTGCAGAATGCTAAGCCTGC-----TAGATTCGAGCATCTGCGTGACTCTACTT----- | 2956 |
| SEQ_ID_NO_215 | CGTGCAGAATGCTAAGGGCGCGTTCGTTTGCACAGCAATAGACATGGATTTATTTCAGCT | 3428 |
| SEQ_ID_NO_216 | CGTGCAGAATGCTAAGGGCGCGTTCGTTTGCACAGCAATAGACATGGATTTATTTCAGCT | 3428 |
| SEQ_ID_NO_214 | CGTGCAGAATGCTAAGGGCGCGTTCGTTTGCACAGCAATAGACATGGATTTATTTCAGCT | 3428 |
| SEQ_ID_NO_233 | CGTGCAGAATGCTAAGGGCGCGTTCGTTTGCACAGCAATAGACATTGATTTATTTCAGCT | 2986 |
| SEQ_ID_NO_236 | CGTGCAGAATGCTAAGGGCGCGTTCGTTTGCACAGCAATAGACATGGATTTATTTCAGCT | 2941 |

TABLE 27-continued

| | | |
|---|---|---|
| SEQ_ID_NO_231 | CGTGCAGAATGCTAAGGGCGCGTTCGTTTGCACAGCAATAGACATGGATTTATTTCAGCT | 3026 |
| SEQ_ID_NO_229 | CGTGCAGAATGCTAAGGGCGCGTTCGTTTGCACAGCAATAGACATGGATTTATTTCAGCT | 3026 |
| SEQ_ID_NO_230 | CGTGCAGAATGATAA--CCCTGCTAGATT---CGAGCATCTGCGTGACTCTACTCTGGCT | 3003 |
| SEQ_ID_NO_232 | CGTGCAGAATGATAA--CCCTGCTAGATT---CGAGCATCTGCGTGACTCTACTCTGGCT | 3003 |
| SEQ_ID_NO_234 | CGTGCAGAATGCTAAGCCTGC-----TAGATTCGAGCATCTGCGTGACTCTACTTTGGCT | 2951 |
| SEQ_ID_NO_218 | CGTGCAAAATGCTAAGGGGCCGTTCGTTT-------CTTAGCCGGAATGGCGGTTTGTTT | 3365 |
| SEQ_ID_NO_219 | CGTGCAAAATGCTAAGGGGCCGTTCGTTT-------CTTAGCCGGAATGGCGGTTTGTTT | 3365 |
| SEQ_ID_NO_217 | CGTGCAAAATGCTAAGGGGCCGTTCGTTT-------CTTAGCCGGAATGGCGGTTTGTTT | 3365 |
| SEQ_ID_NO_221 | CGTGCAGAATGCTAAGCCTGC-----TAGATTCGAGCATCTGCGTGACTCTACTTTGGCT | 2985 |
| SEQ_ID_NO_224 | CGTGCAGAATGCTAAGCCTGC-----TAGATTCGAGCATCTGCGTGACTCTACTTTGGCT | 2931 |
| SEQ_ID_NO_213 | CATCAAAATCTATATAAATTAAAGAAGTAATCCGGCTAGAAATTAATCCGGAGCTTCAAT | 3085 |
| SEQ_ID_NO_222 | ------------------------------------------------------------ | |
| SEQ_ID_NO_220 | ------------------------------------------------------------ | |
| SEQ_ID_NO_235 | CTTCTCGTACGATGCGACCTGACGATGCATTTGGGNNN------CCTNTAGCGTCACTTT | 3173 |
| SEQ_ID_NO_225 | ------------------------------------------------------------ | |
| SEQ_ID_NO_226 | CTTCTCGTACGATGCGACCTGACGATGCATTTGGGCNNN-----CCTNTAGCGTCACTTT | 3166 |
| SEQ_ID_NO_228 | CTTCTCGTACGATGCGACCTGACGATGCATTTGGGCGTT-----CCTNTAGCGTCACTTT | 3225 |
| SEQ_ID_NO_227 | CATCAAAATTTATATAAATTAAAGAAGTAATCCGGCTAGAAATTAATCCGGAGCTTCAAT | 3221 |
| SEQ_ID_NO_223 | ------------------------------------------------------------ | |
| SEQ_ID_NO_215 | CATCAAAATCTATATAAATTAAAGAAGTAATCCGGCTAGAAATTAATCCGGAGCTTCAAT | 3488 |
| SEQ_ID_NO_216 | CATCAAAATCTATATAAATTAAAGAAGTAATCCGGCTAGAAATTAATCCGGAGCTTCAAT | 3488 |
| SEQ_ID_NO_214 | CATCAAAATCTATATAAATTAAAGAAGTAATCCGGCTAGAAATTAATCCGGAGCTTCAAT | 3488 |
| SEQ_ID_NO_233 | CATCAAAATCTATATAAATTAAAGAAGTAATCCGGCTAGAAATTAATCCGGAGCTTCAAT | 3046 |
| SEQ_ID_NO_236 | CATCAAAATCTATATAAATTAAAGAAGTAATCCGGCTAGAAATTAATCCGGAGCTTCAAT | 3001 |
| SEQ_ID_NO_231 | CATCAAAATCTATATAAATTAAAGAAGTAATCCGGCTAGAAATTAATCCGGAGCTTCAAT | 3086 |
| SEQ_ID_NO_229 | CATCAAAATCTATATAAATTAAAGAAGTAATCCGGCTAGAAATTAATCCGGAGCTTCAAT | 3086 |
| SEQ_ID_NO_230 | CTTCTCGTACGATGCGACTTGACGATGCATTTGCGCGCCTTTAGCGTCACTTTCCTGATT | 3063 |
| SEQ_ID_NO_232 | CTTCTCGTACGATGCGACTTGACGATGCATT----------------------------- | 3034 |
| SEQ_ID_NO_234 | CTTCTCGTACGATGCGACCTGACGATGCATTTGGGNNNN-----CCTNTAGCGTCACTTT | 3006 |
| SEQ_ID_NO_218 | CTCTAATTTATATAAGTTTTGATTAGCTGTATTGATTCC------------TGATCCAAT | 3413 |
| SEQ_ID_NO_219 | CTCTAATTTATATAAGTTTTGATTAGCTGTATTGATTCC------------TGATCCAAT | 3413 |
| SEQ_ID_NO_217 | CTCTAATTTATATAAGTTTTGATTAGCTGTATTGATTCC------------TGATCCAAT | 3413 |
| SEQ_ID_NO_221 | CTTCTCGTACGATGCGACCTGACGATGCATTTGGGCGNC-------CTNTAGCGTCACTT | 3038 |
| SEQ_ID_NO_224 | CTTCTCGTACGATGCGACCTGACGATGCATTTGG-------------------------- | 2965 |
| SEQ_ID_NO_213 | CCCTAACAACCGAACAGGGTCTAAGCCTGCTAGATTCGAGCATCTGCGTGACTCTACTTT | 3145 |
| SEQ_ID_NO_222 | -------------------------CCTGCTAGATTCGAGCATCTGCGTGACTCTACTTT | 2983 |
| SEQ_ID_NO_220 | ------------------------------------------------------------ | |
| SEQ_ID_NO_235 | CCTGATTAGTCCCCCGGAAACGCAACTCTACCACTATCAGCCGCCG-------------- | 3219 |
| SEQ_ID_NO_225 | ------------------------------------------------------------ | |
| SEQ_ID_NO_226 | CCTGATTAGTCCCCCGGAAACGCAACTCTACCACTATCAGCCGCCG-------------- | 3212 |

TABLE 27-continued

| | | |
|---|---|---|
| SEQ_ID_NO_228 | CCTGATTAGTCCCCCGGAAACGCAACTCTACCACTATCAGCCGCCG-------------- | 3271 |
| SEQ_ID_NO_227 | CCCTAACAACCGAACAGGGTCTAAGCCTGCTAGATTCGAGCATCTGCGTGACTCTACTTT | 3281 |
| SEQ_ID_NO_223 | ------------------------------------------------------------ | |
| SEQ_ID_NO_215 | CCCTAACAACCGAACAGGGTCTAAGCCTGCTAGATTCGAGCATCTGCGTGACTCTACTTT | 3548 |
| SEQ_ID_NO_216 | CCCTAACAACCGAACAGGGTCTAAGCCTGCTAGATTCGAGCATCTGCGTGACTCTACTTT | 3548 |
| SEQ_ID_NO_214 | CCCTAACAACCGAACAGGGTCTAAGCCTGCTAGATTCGAGCATCTGCGTGACTCTACTTT | 3548 |
| SEQ_ID_NO_233 | CCCTAACAACCGAACAGGGTCTAAGCCTGCTAGATTCGAGCATCTGCGTGACTCTACTTT | 3106 |
| SEQ_ID_NO_236 | CCCTAACAACCGAACAGGGTCTAAGCCTGCTAGATTCGAGCATCTGCGTGACTCTACTTT | 3061 |
| SEQ_ID_NO_231 | CCCTAACAACCGAACAGGGTCTAAGCCTGCTAGATTCGAGCATCTGCGTGACTCTACTTT | 3146 |
| SEQ_ID_NO_229 | CCCTAACAACCGAACAGGGTCTAAGCCTGCTAGATTCGAGCATCTGCGTGACTCTACTTT | 3146 |
| SEQ_ID_NO_230 | AGTCCCACGGAAACGCAACTCTACCACTATCAGCCGCCA--------------------- | 3102 |
| SEQ_ID_NO_232 | ------------------------------------------------------------ | |
| SEQ_ID_NO_234 | CCTGATTAGTCCCCCGGAAACGCAACTCTACCACTATCAGCCGCCG-------------- | 3052 |
| SEQ_ID_NO_218 | TCTGAACAAACGAACA------AAACCTGCTAGATTCGNGCATCTGCGTGACTCTACTTT | 3467 |
| SEQ_ID_NO_219 | TCTGAACAAACGAACA------AAACCTGCTAGATTCGAGCATCTGCGTGACTCTACTTT | 3467 |
| SEQ_ID_NO_217 | TCTGAACAAACGAACA------AAACCTGCTAGATTCGAGCATCTGCGTGACTCTACTTT | 3467 |
| SEQ_ID_NO_221 | CCTGATTAGTCCCCCGGAAACGCAAC---------------------------------- | 3064 |
| SEQ_ID_NO_224 | ------------------------------------------------------------ | |
| SEQ_ID_NO_213 | GGCTCTTCTCGTACGATGCGACTTGACGATGCATTTGGGNNNNNCCNTTAGCGACACTCTC | 3205 |
| SEQ_ID_NO_222 | GGCTCTTCTCGTACGATGCGACCTGACGATGCATT-GGGCGNNCCTNTAGCGTCACTTTC | 3042 |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | GGCTCTTCTCGTACGATGCGACTTGACGATGCAT-------------------------- | 3315 |
| SEQ_ID_NO_223 | ------------------------------------------------------------ | |
| SEQ_ID_NO_215 | GGCTCTTCTCGTACGATGCGACTTGACGATGCATTTGG---------------------- | 3586 |
| SEQ_ID_NO_216 | GGCTCTTCTCGTACGATGCGACTTGACGATGCATTTGGGC-------------------- | 3588 |
| SEQ_ID_NO_214 | GGCTCTTCTCGTACGATGCGACTTGACGATGCATTTGGGNNNNNNNNTAGCGACACTCTC | 3608 |
| SEQ_ID_NO_233 | GGCTCTTCTCGTACGATGCGACTTGACGATGCA--------------------------- | 3139 |
| SEQ_ID_NO_236 | GGCTCTTCTCGTACGATGCGACTTGACGATGCATTTGG---------------------- | 3099 |
| SEQ_ID_NO_231 | GGCTCTTCTCGTACGATGCGACTTGACGATGCATTTGGGNNNNNNNGTAGCGACACTCTC | 3206 |
| SEQ_ID_NO_229 | GGCTCTTCTCGTACGATGCGACTTGACGATGCATTNGGGNCNNCCNNTAGCGACACTCTC | 3206 |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | GGCCCTTCTCGTACGAGCTTTTNGGCGTTCCTCTAGCGTCACTTTCCCCCGGAAACGCAA | 3527 |
| SEQ_ID_NO_219 | GGCCCTTCTCGTACG--------------------------------------------- | 3482 |
| SEQ_ID_NO_217 | GGCCCTTCTCGTACGNNNNNNNTGGCGTTCCTCTAGCGTCACTTTCCCCCGGAAACGCAA | 3527 |

TABLE 27-continued

| | | |
|---|---|---|
| SEQ_ID_NO_221 | ------------------------------------------------------------- | |
| SEQ_ID_NO_224 | ------------------------------------------------------------- | |
| SEQ_ID_NO_213 | CTGATTAGTCCCACGGAAACGCAACTCTACCACTATCAGCCGCCG | 3250 |
| SEQ_ID_NO_222 | CTGATTAGTCCCCCGGAAACGCAACTCTACCACTATCAGCCGCCG | 3087 |
| SEQ_ID_NO_220 | --------------------------------------------- | |
| SEQ_ID_NO_235 | --------------------------------------------- | |
| SEQ_ID_NO_225 | --------------------------------------------- | |
| SEQ_ID_NO_226 | --------------------------------------------- | |
| SEQ_ID_NO_228 | --------------------------------------------- | |
| SEQ_ID_NO_227 | --------------------------------------------- | |
| SEQ_ID_NO_223 | --------------------------------------------- | |
| SEQ_ID_NO_215 | --------------------------------------------- | |
| SEQ_ID_NO_216 | --------------------------------------------- | |
| SEQ_ID_NO_214 | CTGATTAGTCCCACGGAAACGCAACTCTACCACTATCAGCCGCCG | 3653 |
| SEQ_ID_NO_233 | --------------------------------------------- | |
| SEQ_ID_NO_236 | --------------------------------------------- | |
| SEQ_ID_NO_231 | CTGATTAGTCCCACGGAAACGCAACTCTACCACTATCAGCCGCCG | 3251 |
| SEQ_ID_NO_229 | CTGATTAGTCCCACGGAAACGCAACTCTACCACTATCAGCCGCCG | 3251 |
| SEQ_ID_NO_230 | --------------------------------------------- | |
| SEQ_ID_NO_232 | --------------------------------------------- | |
| SEQ_ID_NO_234 | --------------------------------------------- | |
| SEQ_ID_NO_218 | CTCTACCACTATCAGCCGCCG------------------------ | 3548 |
| SEQ_ID_NO_219 | --------------------------------------------- | |
| SEQ_ID_NO_217 | CTCTACCACTATCAGCCGCCG------------------------ | 3548 |
| SEQ_ID_NO_221 | --------------------------------------------- | |
| SEQ_ID_NO_224 | --------------------------------------------- | |

Sequence data was used to identify a putative homologue by descent segments between independent sources of resistance or susceptibility. The region from MRQV_00005-1 to MRQV_08351-1 was shared for most of the independent sources of susceptibility. The data for a key recombinant (from the high resolution mapping population; susceptible to the disease) showed that the recombinant point for this genetic material is located inside a putative Myb transcription factor (PCO644442) and that the sequence variation generating the resistance should be located from the position of this candidate gene towards MZA2038. There was also an expected IBD (identity-by-descent) relationship between independent sources of resistance at the region of or close to PCO644442 as:

a) PHR33 and PH467.

b) PHR33, PH9TJ, PHJ40 and PHDG9.

c) PHK09 showed a specific haplotype.

d) 630 showed a specific haplotype.

There was a group of target SNPs at MRQV_08351-1 very specific for most of resistant sources. However, recombinant data indicates that the target sequence should be located from MRQV_08351-1 (located at PCO644442) towards MZA2038.

Considering the specificity of target SNPs at MRQV_08351-1, this specific fragment was sequenced in a total of 625 inbreds from Pioneer germplasm. A genetic description was developed in relationship to MRCV resistance of part of Pioneer germplasm by using the combined information from: a) flanking markers of this interval (MZA15490 and MZA2038), b) the sequence data for the 625 inbreds and the tester's lines, c) the pedigree relationship between inbreds, and d) the phenotypic data for these inbreds.

A specific group of haplotypes at MRQV_08351-1 or combined with haplotypic information for MRQV_10673-1 and MZA2038 was used to increase the characterization and identity by descent information for the major resistance sources in Pioneer germplasm and to consider putative variants of the target region. Table 28 shows a description of specific haplotypes and the observed and expected response to the disease across materials by haplotype. The representative sources are included as reference.

TABLE 28

| MRQV_08351 | MRQV_10673 | MZA2038 link | Expected phenotype | MRCVSC | n | Source | Segregation data |
|---|---|---|---|---|---|---|---|
| 1 | 1, 2, 8, 9 | 4, 5, 9, 11 | Susceptible | 3.02 | 247 | PHFV5, 274, PHAN0, 165, OH7, other | |
| 1 | 3 | 5 | Resistant | 4.60 | 5 | PHJ40 | No |
| 2 | 1 | 12 | Resistant | 4.59 | 22 | PH7WT, 173, 630, PHB04, PH14J, PHAA4, PHG64 | Yes |
| 3 | 6 | 1, 14 | Susceptible | 3.21 | 19 | C103, 157, other | |
| 4 | | 4 | Susceptible | 3.31 | 13 | 216, other | |
| 5 | 4 | 4, 11 | Resistant | 5.00 | 3 | PHR33, PH467, 501 LACAUNEOP | No |
| 7 | 3 | 10, 15 | Resistant | 5.90 | 10 | PHP51, PHDG9, 546, LACAUNEOP | Yes |
| 9 | 7 | 6 | Resistant | 5.00 | 2 | PHK09, PH884, PHBD6, PHFCF | Yes |

Using the information for MRQV_08351-1 or combined with flanking sequences (MRQV_10673-1 and MZA2038), Applicants inferred the following:
  a) Resistance source 1. The sources PHR33 and PH467 may share a common ancestor at MRQV_08351-1. Shared regions with European materials derived from LACAUNE open pollinated variety support a probable common origin from a single haplotype region.
  b) Resistance source 2. The sources PHR33, PH9TJ, PHJ40 and PHDG9 may share a common ancestor at the flanking region of MRQV_08351-1. In addition, PHP51 may be inferred as part of this group. Shared regions with European materials derived from LACAUNE open pollinated variety support a probable common origin from a single haplotype region.
  c) Resistance source 3. PHK09 showed a shared haplotype with PHBD6 at MRQV_08351-1, and they should share a common origin from Tuxpen germplasm.
  d) Resistance source 4. 630 showed a specific haplotype, and there is not a confirmed IBD relationship with other sources.

From mapping population results, Applicants thus demonstrate a QTL at the region of preferred markers in these independent sources:
  630.
  PH9TJ. Allelic to 630.
  PHP51. Allelic to 630.
  PHBD6. Allelic to 630.

The integration of recombination, sequence, and pedigree analysis and the inference of an expected IBD relationship between independent sources permitted Applicants to consider that four major haplotypes at the region of two of the preferred markers (MZA15490 and MZA2038) can be used to characterize most of the sources of resistance in Pioneer germplasm. These four major haplotypes maybe grouped as these germplasm sources:
  (a) Resistance source 1 and 2. Flint SWAN germplasm sharing homologue region with materials from the European flint LACAUNE open pollinated population.
  (b) Resistance source 3. Materials from TUXPEN origin.
  (c) Resistance source 4. Specific source, 630 is the representative inbred. The development of this inbred included a broad genetic base including TUXPEN and MEXICAN JUNE germplasm.

PCO644442 (FIG. 6, a putative Myb transcription factor) appears to be the likeliest candidate gene for the resistance to MRCV disease. Sequences closely linked to PCO644442 should be also considered as targets for gene cloning, including the putative EPSIN1 and flanking sequences of the interval MZA11826 to MZA9105.

A single recombinant at MZA15490 to MZA2038 from the cross PH3DT and PH7WT was characterized and the recombination point was located inside the PCO644442. The region from intron 3 of PCO644442 to the PCO644442's promoter sequences are considered key targets for the validation of effects on variations on resistance/susceptibility responses across genotypes. FIG. 8 shows the characterization of the recombinant at MZA15490 to MZA2038; a quimeric PCO644442 was originated from PH3DT and PH7WT genotypes. The sequences at promoter region of PCO644442 of PH3DT (SEQ ID NO:212) and PH7WT (SEQ ID NO:211) are included herein, showing polymorphic sites (see FIGS. 13A-13C for sequence alignment).

Example 9

MRDV—Main Hybrids Characterization—Europe

A set of key European genetic materials was phenotypically and genetically characterized to confirm maize genetic marker loci associated with resistance to MRDV. By identifying such genetic markers, marker assisted selection (MAS) can be used to improve the efficiency of breeding for improved resistance of maize to MRDV.

Maize Hybrids and Resistance Scoring

The plant varieties used in the analysis were from diverse sources, including elite germplasm, commercially released cultivars and pre-commercial hybrids representing a broad range of germplasm related to a European breeding program.

The groups of maize hybrids were planted in a field experiment in Spain. The classifications of resistance and susceptible were based solely on observations of fortuitous, naturally occurring disease incidence in field tests. The degree of plant resistance to MRDV infection varied widely, as measured using a scale of incidence of MRDV symptoms.

Data collection was typically done in one scoring time. Scoring time is placed after flowering time.

In assessing association of markers to resistance, a comparison by using the IBD information of parent lines was used. Allele origin was checked by the identity by descent approach. Using this approach, those maize lines that were considered to be representative of either the genotypic classes were used for assessing association and predict performance at hybrid level.

Maize Genotyping

Each parent line of these hybrids has been genotyped and IBD calculations have been estimated for each line.

The underlying logic is that markers with significantly different allele distributions between the resistant and susceptible groups (i.e., non-random distributions) might be associated with the trait and can be used to separate them for purposes of marker assisted selection of maize lines with previously uncharacterized or characterized resistance or susceptibility to MRDV. The present analysis examined the IBD information at the genetic position of the region of preferred markers and determined if the allele distribution within the resistant group is significantly different from the allele distribution within the susceptible group. This analysis compares the plants' phenotypic score with the genotypes at the target loci; the genotypes were predicted by IBD.

Results

In order to evaluate the effect of the allelic variation at this QTL at the hybrid level, a set of 212 hybrids (heterogenous genetic backgrounds) was characterized according to the presence of one (heterozygous for the QTL) or two resistant alleles (homozygous for the QTL) from the parent lines. A positive and additive effect of the resistant allele at the major QTL was observed on the hybrid combinations. Table 29 shows the field performance of hybrids with different genotypes at the major QTL. The field performance was characterized as MRDV_score, similar protocol to MRCV score.

TABLE 29

| Hybrid genotype at major QTL | # hybrids | Average of MRDV_score | STD Dev |
|---|---|---|---|
| AA, homozygous susceptible allele | 163 | 4.25 | 0.92 |
| BA, heterozygous, female resistant allele | 37 | 5.45 | 1.01 |
| BB, homozygous resistant allele | 3 | 6.00 | 0.88 |

FIG. 9 shows the performance of maize hybrids under MRDV infection. The field performance expressed as MRDV_score.

Discussion/Conclusions

This example has identified chromosome intervals that correlate with MRDV resistance. Markers that lie within these intervals are useful for MAS, as well as other purposes. The prediction of MRDV increased resistance by using the preferred markers for MRCV resistance indicates that these markers may be used for MAS for different *Fijivirus*. A positive effect of the preferred markers for resistance to other *Fijivirus*, such as rice black-streaked dwarf *fijivirus*, is thus expected.

Example 10

MRCV Resistance Phenotypic Assay

What: A 1-9 score of Mal de Rio Cuarto Virus with 1 meaning no resistance (stunted, internodes shortening, no ear), and 9 meaning that the genetic material is resistance to the disease (no symptoms).

When: From flowering through harvest

Check scores of known susceptible lines to see if their present ratings agree with historical ratings.

How:

1. Compare ratings that you would give a few known susceptible lines today with their historical ratings to see if they agree.
2. If the ratings are too high, then there is not enough disease pressure to score this location. However, note any plot that has more disease than the susceptible checks.
3. Score on a plot basis. Plants within a plot may vary in symptoms due to timing of infection or some plants may escape to the disease (natural infection depends on population of vectors).
4. Consider severity of symptoms and frequency of plants with symptoms. Scores of 1-3 are in susceptible category; 4-6 are in resistant category; 7-9 are in highly resistant category.

Description of Field Scores:

a) Scores 1-3. Susceptible category. Symptoms include severe dwarfism, severe internodes shortening, no ears or very poor ear development, premature dead of plants.

b) Scores 4-6. Resistant category. Plants with symptoms as enations and soft internodes shortening. Low frequency of plants with severe symptoms.

c) Scores 7-9. Highly resistant category. Healthy plant. Presence of enations or no symptoms.

What is claimed is:

1. A method of identifying and selecting a maize plant or germplasm that displays newly conferred resistance or enhanced resistance to a member of Serogroup 2 of *Fijivirus*, said method comprising:
   a. isolating nucleic acids from a maize plant or germplasm;
   b. analyzing the isolated nucleic acids for the presence of a QTL allele associated with the newly conferred resistance or enhanced resistance to a member of Serogroup 2 of *Fijivirus*, wherein the presence of said QTL allele is determined by detecting in the maize plant or germplasm a haplotype within a chromosomal interval flanked by and including MZA8381 and MZA18180, wherein said haplotype comprises:
      i. a "C" at MZA-625-29-A,
      ii. a "T" at MZA625-30-A, and
      iii. a "T" at MZA16656-8-A, and
   c. selecting said maize plant or germplasm if said QTL allele is detected.

2. The method of claim 1, wherein the member of Serogroup 2 of *Fijivirus* is Mal de Río Cuarto Virus (MRCV).

3. The method of claim 1, wherein the member of Serogroup 2 of *Fijivirus* is Maize Rough Dwarf Virus (MRDV).

4. A method of identifying and selecting a maize plant that displays newly conferred resistance or enhanced resistance to a member of Serogroup 2 of *Fijivirus*, said method comprising:
   a. isolating nucleic acids from a maize plant or germplasm;
   b. analyzing the isolated nucleic acids for the presence of the following marker alleles:
      i. a "C" at MZA-625-29-A,
      ii. a "T" at MZA625-30-A, and
      iii. a "T" at MZA16656-8-A, and
   c. selecting a maize plant that has the marker alleles set forth in i-iii of step (b).

5. The method of claim 4, wherein the member of Serogroup 2 of *Fijivirus* is Mal de Río Cuarto Virus (MRCV).

6. The method of claim 4, wherein the member of Serogroup 2 of *Fijivirus* is Maize Rough Dwarf Virus (MRDV).

* * * * *

SEQUENCE LISTING

<160> NUMBER OF SEQ ID NOS: 236

<210> SEQ ID NO 1
<211> LENGTH: 510
<212> TYPE: DNA
<213> ORGANISM: Zea mays

<400> SEQUENCE: 1

| | | | | | | |
|---|---|---|---|---|---|---|
| ggtttccccc | aggtccagtt | agttgttcat | ggtggagtga | taaatatatc | agagcatctt | 60 |
| ttgcctcttc | ccccagtttt | tgtcgcacat | ccctgacagt | tctgtttgtg | cagcccctga | 120 |
| tgacgcaacc | tctaatgata | aggaagacaa | caagcccgag | ccttgagatg | tcagcaagat | 180 |
| tgatggttgc | taacaatgac | cttgtgctgt | tcttaccgg | gttttgacgt | gttggatttg | 240 |
| tgattaccac | tgattgctat | tgtacttcaa | acaggaaggc | tggaaatgca | actcggcttc | 300 |
| tcttgagacc | ttgtcatttg | ctgtagttcg | ttcgcaactg | tatattgtag | cttggaagac | 360 |
| tctgtgccgt | ggtgcgtgta | tttgagaaat | ttctatgcaa | agtgagctgg | cgataacatt | 420 |
| ggatggcgca | gcaaagcatc | gcgcgcagtg | tttcctaggc | atcatccagt | gcggctcgtg | 480 |
| gatcctttat | ggtcatagct | ggtccctccc | | | | 510 |

<210> SEQ ID NO 2
<211> LENGTH: 694
<212> TYPE: DNA
<213> ORGANISM: Zea mays

<400> SEQUENCE: 2

| | | | | | | |
|---|---|---|---|---|---|---|
| ttgggttaaa | tctggggttt | aaatttgtaa | gcttaatcaa | ggataagggg | ttcaacatcc | 60 |
| agtcatccag | tattgattat | ggtgatagta | tttgcttttg | atgagtagaa | gatgcacgtt | 120 |
| gatgcatgta | tattcaatta | gtttctgtta | aaacattgct | acaataggag | agtctggagg | 180 |
| tagttactgc | atctttgctt | ggtgactcca | gcttctcatg | accttgctaa | actgatatat | 240 |
| cttgtttagg | tacccgaact | tgaagagtgt | cagggagttg | atctacaaga | ggggctacgg | 300 |
| aaaactgaac | aagcagagga | tccctctgtc | taacaaccaa | gtcatcgagg | aggtttgcaa | 360 |
| tcttgaactc | tgcacctgga | tcctttgtga | tctgtttgta | tttgacaatt | tacatgatga | 420 |
| tctccaccat | ttggtgttct | atcagggctt | gggcaagcac | aacatcatct | gtattgagga | 480 |
| tcttgttcac | gagatcatga | ctgttggccc | acacttcaag | gaggcgaaca | acttcctttg | 540 |
| gccatttaag | ctgaaggcac | cgctgggagg | tctgaagaag | aagaggaacc | actatgtgga | 600 |
| gggtggtgat | gccggtaacc | gtgagaatta | catcaacgag | ctcatcaaaa | ggatgaatta | 660 |
| gttcacgatc | aagctctatg | actttccgta | aata | | | 694 |

<210> SEQ ID NO 3
<211> LENGTH: 532
<212> TYPE: DNA
<213> ORGANISM: Zea mays

<400> SEQUENCE: 3

| | | | | | | |
|---|---|---|---|---|---|---|
| tatatttytt | tttttctaag | gttgattgga | taaaaggggg | atgcaggtct | tgacagcaat | 60 |
| gggttgcact | cactaaggag | aacagtggca | gggcatcacc | aactaaacag | caccagcagt | 120 |
| ataagaagaa | gcctttgctg | aagagattcg | gtggtctgct | aaaaaagaaa | agcgaaaatt | 180 |
| agcataaaac | cgtctgatga | tattctttgt | tctatcattt | gacatttctt | tgattagata | 240 |
| tctagttccc | gagtcttccc | ccatattatg | gtaaactaag | tgatggatgc | ttcaaagaat | 300 |
| acaaaatgtc | gactttattt | acataattgc | ctctcttgag | ttagggagtg | ttcgcagttc | 360 |

```
agttcagctg tctggtgtga gctgtcggaa acagttgtg agctgcctgc tgtgaaaaac      420
tgttgtgagt aaactaaaag aaagtctttg gttggagctt cggtaaaaca ttagattttt      480
tatgatttat ctgtattgct tctgagattg ttatggtcaa cctgtccctt cc              532
```

```
<210> SEQ ID NO 4
<211> LENGTH: 522
<212> TYPE: DNA
<213> ORGANISM: Zea mays

<400> SEQUENCE: 4
aaagacccat agaacgttgt gctgtgggag ctcataactg gcatgctccc ttttgctaat       60
atgacagcag tgcaggctgc tttcgctgtg gtgaacaagg gtgtccgccc agctataccc      120
caggactgcc tgcccaccct tgctgagatc atgaccaggt gctgggatcc aaatcctgat      180
gtccgtccgc cattcactga agttgtgagg atgctggagc atgctgagat ggagatcctg      240
agcactgtcc gcaaggcccg atttcggtgt tgcatgtccc aaccgatgac taccgactga      300
atcaaacaag agagttgaaa tgaactccat ggaagcgtaa ttgagtgtat ttatcatgtg      360
tccaaacttc gctcagctga agtagaaagc acacctgagt ttatggctgt atgtgtgtat      420
actcaggtgt aagccttgtt gtctttgaaa tattcctgca cttagaatat acctagttcg      480
cgttttcaga ctcttgagat gttttaggct atctattcct ga                         522
```

```
<210> SEQ ID NO 5
<211> LENGTH: 652
<212> TYPE: DNA
<213> ORGANISM: Zea mays

<400> SEQUENCE: 5 ttttttacc cctgcccttt ataccccgaa tcgagcagat agctgatctg attggggatg         60
ctggcaacac agtatgctcc ggaacttggt ccaccatagc tgagcttttc tttaatcgtt      120
gattattatg accgtaactt ccgttatctc aatttttctat ctgaagtttg agctcctgaa     180
aaattttagg aacgacaaga tgtctataag ccggcaataa ttttcgtat cctgtaggga       240 tcatcaaggc tcacattctg tatcggtgga ccatacggtc tcgggttaca agtgcgagag      300
cgtgcagatg caacgattag gctgtcctca ctagttttga accatcaagt tgccttgata     360
gtcctcatgg agcagctcta caggtaagca attagcctat ctgatgctgt ttctgcactt      420
accacagttt ctgtggagca taccccttta tggctgtatg gcctatggta tgagaaaggc     480
acaatgtaac actaccattt aaataccttc tttcaactat gaccggtcac tagtgacaat     540
tgcattaatt ttgcagggca tggactataa taaagggaca gaagtatcac cattaggcct     600
aagtgctatc atcattcgct gctgtttagg acttggaaaa tggaaaactg cc              652
```

```
<210> SEQ ID NO 6
<211> LENGTH: 159
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (84)..(84)
<223> OTHER INFORMATION: n is either agtcaccgtcgtc or cgtcaccgtcgtg

<400> SEQUENCE: 6
```

```
gccggcaaga tcgagaaygt cccgccccg gccatcgcca tcgactastg gcgcctcccc      60
gntaacgcca cgctcaagga cgtncgcgcc gacgaggctc accaccgcga cgtcaaccac     120
tttgcatcgg tacggrtact tccraattcc aataccagc                            159

<210> SEQ ID NO 7
<211> LENGTH: 280
<212> TYPE: DNA
<213> ORGANISM: Zea mays

<400> SEQUENCE: 7
ccgatgcaca acagaaagag gaaagctgat gacaagaaac agcaacatca aagaatgtct      60
gagaagtcaa gaacrggaat tcgagcatc catgaactgc tgcaggattt cctggtgcag     120
caacagcaca ttgatgtccg gtggcgggag atgatcgaga gacgygccca ggagcgggtg    180
gttttygaac aacaatggyg gctgacaatg cagaggctgg agcaggagcg gttgttgctg    240
gaacactcst ggatggaacg ggaggagcga agaaggatga                          280

<210> SEQ ID NO 8
<211> LENGTH: 480
<212> TYPE: DNA
<213> ORGANISM: Zea mays

<400> SEQUENCE: 8
ggaaaatccc agtcagaacg ctgaatctgg agtttctgtc aaaacgaaac tgaagcgacc      60
tggtggtgac tggtcatctc gggagtctga cgacaaggac gatgatggtg aagaaagtga    120
tgatgagaag ccgatgcaca acagaaagag gaaagctgat gacaagaaac agcaacatca    180
aagaatgtct gagaagtcaa gaacaggaat tcgagcatc catgaactgc tgcaggattt    240
cctggtgcag caacagcaca ttgatgtccg gtggcgggag atgatcgaga gacgtgccca    300
ggagcgggtg gttttcgaac aacaatggcg gctgacaatg cagaggctgg agcaggagcg    360
gttgttgctg gaacactcgt ggatggaacg ggaggagcga agaaggatga gagaagaagc    420
acgagctgaa aaaggatgc actcctgacc actctgtgaa caaactcctg cagaatatta    480

<210> SEQ ID NO 9
<211> LENGTH: 643
<212> TYPE: DNA
<213> ORGANISM: Zea mays

<400> SEQUENCE: 9
cacatactca catttcaggc acgtcttcgc tacatctaac cctgtaccaa caaaccaaag      60
gtattgccac ctaagaccct gttttgtttac accaatccag ctctggatta gaatggattg   120
gaattaaatc catgtcccaa ataaaccaag cctactcaat tttttttatt tggctaaacc    180
catcatgaat tataacccaa gggtttatga ttttttaaaa ctatggaagg tatggattct    240
atccataact cattaggtat ggaacaaatc catgaagata ttgcacaagt ttatattaga    300
actgaaactg aaaggcaata taggcatata gcactatagc agaactgaaa ctgaaatatt    360
gaatacaagg ctacaatcag taatgcagta cctactacct agagcatatc atcatccaag    420
caaaaagcag cagcagcttc tccaacatat tcagattcat cagaattcag acaataggaa    480
agataggaaa gggggagaag gggggaacct tgagatgagg agctcatctc gtcgctagtg    540
ttctggagcc gccgccggtg ttctggagct actgctggtg ttctaaagcc gcagcctgtg    600
ttctggactc ggcaaggggg aaaaatttca agggttaaaa ggg                      643
```

<210> SEQ ID NO 10
<211> LENGTH: 694
<212> TYPE: DNA
<213> ORGANISM: Zea mays

<400> SEQUENCE: 10

| | | | | | |
|---|---|---|---|---|---|
| gaccccctaat | tttctcgtga | ctttgaattt | gtgggaccta | tgaatttgtg | caggaactgg | 60 |
| gggaggaggg | tgacttcgtt | tctatttggg | gaacactgct | cgcgtcctgc | aaagcacagg | 120 |
| acaagcagga | attggtgaat | ttggtgacag | agagattgat | ctgcattgag | aagaagtatg | 180 |
| gccatgctgg | ttacagcgtt | ttgttgtcac | atattttgc | tgctgagggc | aactggagta | 240 |
| gtgctgatag | cctgaggaag | gagatgaggt | tgagaggatt | gagcaagatg | gcaggttcta | 300 |
| gttggattaa | agtccagcat | gcagcattgc | aaagctaccc | taaaaatggc | catgaacact | 360 |
| cattactgca | tgtagttgat | tacggtagag | atgaaatcat | ctgacatgaa | tcagtactgc | 420 |
| agcagtggaa | agcttgctga | tctggtgttt | gttcatgtcc | catgacgtga | tcagctcagg | 480 |
| ctatgacaga | ttggccttt | ggttatctgc | agcattgaca | ccttgtcacc | ttgacgaaat | 540 |
| tggggcattt | cggaacattt | acatatatat | gaacaacaaa | ctgaactccc | gcactactcg | 600 |
| taagcggtga | ataaccctg | caggttaaaa | ccctgatggc | ctggacctgg | atgcagtcat | 660 |
| gcaggaagga | tatcgcatta | gttgaatact | taaa | | | 694 |

<210> SEQ ID NO 11
<211> LENGTH: 710
<212> TYPE: DNA
<213> ORGANISM: Zea mays

<400> SEQUENCE: 11

| | | | | | |
|---|---|---|---|---|---|
| ttaagggccg | gaaggcaagc | caaggggttg | ttgttcgaaa | cggtggcggc | cgtgccgggc | 60 |
| atggtgggcg | gcatgttctt | caacctgggt | tcgttccgcc | gtttcgagca | cagcggcggc | 120 |
| tggatccgcg | cgctgctcga | ggaggccgag | aacgagcgca | tgcacctcat | gacgttcctc | 180 |
| gaggtcacgc | agccgcgctg | gtgggagcgc | gcgctcgtgc | tcaccgcgca | gggcgtcttc | 240 |
| ttcaacgcct | acttcgtcgg | ctacctcctc | tcccccaagt | tcgcgcaccg | cgtcgtcggc | 300 |
| tacctcgagg | aggaggcagt | gcactcgtac | accgagtacc | tcaaggacct | cgaggccggc | 360 |
| atcatcgaca | caccccggc | gccggccatc | gccatcgact | actggcgcct | ccccgccgac | 420 |
| gccaagctca | aggacgtcgt | caccgtcgtg | cgcgccgacg | aggcgcacca | ccgcgacgtc | 480 |
| aaccacttcg | cgtcggtacg | cactctgcac | cttgcaacag | gattcattgc | tgtgagcaat | 540 |
| ctccagcagt | tctagctaat | tcattggttt | atgtttgctt | aatggagtac | attattttgc | 600 |
| aggacatcca | ttaccagggg | atgaagctca | aggacacgcc | cgcaccgctc | agttatcact | 660 |
| gacaagtagg | cgttgcctgc | ctgctgctca | attcggaagt | tggttaaaaa | | 710 |

<210> SEQ ID NO 12
<211> LENGTH: 423
<212> TYPE: DNA
<213> ORGANISM: Zea mays

<400> SEQUENCE: 12

| | | | | | |
|---|---|---|---|---|---|
| tagggtacat | ggaccctgrg | tacttccaga | caagccaact | gactgagaag | agtgatgtst | 60 |
| acagctttgg | cgtcgtactc | atcgagctac | tgacaagraa | gaagcctatc | atggatgata | 120 |
| tcrcggaaga | cattagaagc | ctagcgctgc | aatttagtat | gctattccat | ggaartaagc | 180 |
| tgttggaaat | cgttgatcct | gtagtagctg | aagaagctgg | agtcagacat | gttgaaacgg | 240 |

```
tttcgaagtt ggcgttacga tgcttaaggt tgaaagggga agaacgccca aggatgatag     300
atgttgcgat tgaacttgaa gcactgagaa ggctgatgaa acaacacttc atcttgaaga     360
acgagtcttt gcttcaggag tyatgttgca atgaagaaat gagcatcgac gcaccatcaa     420
gtt                                                                   423
```

<210> SEQ ID NO 13
<211> LENGTH: 423
<212> TYPE: DNA
<213> ORGANISM: Zea mays

<400> SEQUENCE: 13

```
tagggtacat ggaccctgrg tacttccaga caagccaact gactgagaag agtgatgtst     60
acagctttgg cgtcgtactc atcgagctac tgacaagraa gaagcctatc atggatgata    120
tcrcggaaga cattagaagc ctagcgctgc aatttagtat gctattccat ggaartaagc    180
tgttggaaat cgttgatcct gtagtagctg aagaagctgg agtcagacat gttgaaacgg    240
tttcgaagtt ggcgttacga tgcttaaggt tgaaagggga agaacgccca aggatgatag    300
atgttgcgat tgaacttgaa gcactgagaa ggctgatgaa acaacacttc atcttgaaga    360
acgagtcttt gcttcaggag tyatgttgca atgaagaaat gagcatcgac gcaccatcaa    420
gtt                                                                  423
```

<210> SEQ ID NO 14
<211> LENGTH: 503
<212> TYPE: DNA
<213> ORGANISM: Zea mays

<400> SEQUENCE: 14

```
aaaggggaag gtcccagtca caacgtacat tagtgcaagg gacactaggg tacatggacc     60
ctgagtactt ccagacaagc caactgactg agaagagtga tgtgtacagc tttggcgtcg    120
tactcatcga gctactgaca aggaagaagc ctatcatgga tgatatcacg aagacatta    180 gaagcctagc gctgcaattt agtatgctat tccatggaaa taagctgttg gaaatcgttg    240
atcctgtagt agctgaagaa gctggagtca gacatgttga aacggtttcg aagttggcgt    300
tacgatgctt aaggttgaaa ggggaagaac gcccaaggat gatagatgtt gcgattgaac    360
ttgaagcact gagaaggctg atgaaacaac acttcatctt gaagaacgag tctttgcttc    420
aggagtcatg ttgcaatgaa gaaatgagca tcgacgcacc atcaagtttg ttccttgcgt    480
taatgcattt acttttcggt ata                                            503
```

<210> SEQ ID NO 15
<211> LENGTH: 613
<212> TYPE: DNA
<213> ORGANISM: Zea mays
<220> FEATURE:
<221> NAME/KEY: misc_feature
<222> LOCATION: (2)..(4)
<223> OTHER INFORMATION: n is unknown
<220> FEATURE:
<221> NAME/KEY: misc_feature
<222> LOCATION: (10)..(10)
<223> OTHER INFORMATION: n is unknown

<400> SEQUENCE: 15

```
annnggcttn acgacttacc catacctcgt tacaccgccg ccgccgtcac cgtaccaacc     60
tactcgtacc cgccgccgcc gcagccgcag ccgcggccac accagcaagc agaactagca    120
gccatgccgc ccaaattgga cccctctcag gtggtggagg tcttcgtccg cgtgacggga    180
```

```
ggcgaggtcg gcgcggcgtc gtcgctggcc cccaagatcg gcccgctcgg tctctccccg    240
aagaagatcg gcgaggacat cgccaaggag accgccaagg actggaaggg cctccgcgtc    300
accgtcaagc tcaccgtgca gaaccggcag gccaaggtct ccgtcgtccc ctccgccgcg    360
gcgctcgtca tcaaggcgct caaggaaccc gagagggaca ggaagaaggt caagaacatc    420
aagcacagcg gcaacatcag cctcgacgac gtcatcgaga tcgccaagac catgcggaac    480
aggtccatgg ccaaggagtt ggccgggact gtcaaggaga tcctggggac ctgcgtcagc    540
gtcgggtgca ctgtcgatgg gaaggacccc aaggacttgc agcaggagat cgatatggtc    600
atagcttgct ctt                                                       613
```

```
<210> SEQ ID NO 16
<211> LENGTH: 469
<212> TYPE: DNA
<213> ORGANISM: Zea mays
<220> FEATURE:
<221> NAME/KEY: misc_feature
<222> LOCATION: (306)..(306)
<223> OTHER INFORMATION: n is unknown
<220> FEATURE:
<221> NAME/KEY: misc_feature
<222> LOCATION: (311)..(311)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (322)..(323)
<223> OTHER INFORMATION: n is unknown
<220> FEATURE:
<221> NAME/KEY: misc_feature
<222> LOCATION: (326)..(327)
<223> OTHER INFORMATION: n is unknown
<220> FEATURE:
<221> NAME/KEY: misc_feature
<222> LOCATION: (404)..(404)
<223> OTHER INFORMATION: n is unknown
<220> FEATURE:
<221> NAME/KEY: misc_feature
<222> LOCATION: (421)..(424)
<223> OTHER INFORMATION: n is unknown
<220> FEATURE:
<221> NAME/KEY: misc_feature
<222> LOCATION: (437)..(438)
<223> OTHER INFORMATION: n is unknown

<400> SEQUENCE: 16
```

```
tgacaagctg cagcgaagaa ggtgaaccta gctgatattg gcatcgtcgg tggccttggc     60
gatgggtccg atgagaagrc mctgccctct tggaccatgg gcgccgkatc cggcctagga   120
atgtctggta ttccaccgtc aacacaacaa gctggtggca tcgagagctt ggccaactac   180
aacaagcatc atttcggctt caaataggcc tcgatctttc atactggaaa atacccgtca   240
tctgcggttt cctcctcwgt cggcctgctt cttacaygtg ctgccctatt gatttaatca   300
cttttntttg ntttntggt tnnttnnggt gatyacatta catggtrtcg accaatcttg    360
gccccgtctt gtcacrcgtg tatgttattt gtcgggtttg tggntaagca tgcaactaca   420
nnnncatcac accccnnkt gttccagytc gatrataggt ggyatgttg                 469
```

```
<210> SEQ ID NO 17
<211> LENGTH: 469
<212> TYPE: DNA
<213> ORGANISM: Zea mays
<220> FEATURE:
```

```
<221> NAME/KEY: misc_feature
<222> LOCATION: (306)..(306)
<223> OTHER INFORMATION: n is unknown
<220> FEATURE:
<221> NAME/KEY: misc_feature
<222> LOCATION: (311)..(311)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (322)..(323)
<223> OTHER INFORMATION: n is unknown
<220> FEATURE:
<221> NAME/KEY: misc_feature
<222> LOCATION: (326)..(327)
<223> OTHER INFORMATION: n is unknown
<220> FEATURE:
<221> NAME/KEY: misc_feature
<222> LOCATION: (404)..(404)
<223> OTHER INFORMATION: n is unknown
<220> FEATURE:
<221> NAME/KEY: misc_feature
<222> LOCATION: (421)..(424)
<223> OTHER INFORMATION: n is unknown
<220> FEATURE:
<221> NAME/KEY: misc_feature
<222> LOCATION: (437)..(438)
<223> OTHER INFORMATION: n is unknown

<400> SEQUENCE: 17
tgacaagctg cagcgaagaa ggtgaaccta gctgatattg gcatcgtcgg tggccttggc      60
gatgggtccg atgagaagrc mctgccctct tggaccatgg gcgccgkatc cggcctagga     120
atgtctggta ttccaccgtc aacacaacaa gctggtggca tcgagagctt ggccaactac     180
aacaagcatc atttcggctt caaataggcc tcgatctttc atactggaaa atacccgtca     240
tctgcggttt cctcctcwgt cggcctgctt cttacaygtg ctgccctatt gatttaatca     300
cttttntttg nttttntggt tnnttnnggt gatyacatta catggtrtcg accaatcttg     360
gccccgtctt gtcacrcgtg tatgttattt gtcgggtttg tggntaagca tgcaactaca     420
nnnncatcac accccennkt gttccagytc gatrataggt ggyatgttg                469

<210> SEQ ID NO 18
<211> LENGTH: 704
<212> TYPE: DNA
<213> ORGANISM: Zea mays

<400> SEQUENCE: 18
ccaatcagag agcctagggc aaagaaagac aattttcagg tcaagtccgg catatgggca      60
aactcgctga gccggggatt gattgatctg aacataactg cacgtatgtt cctcgttcct     120
gtttcccctg ttgccatggc atctatcagc ttggtgtaaa tttgtttatg gttcagacat     180
gttcatggtt ctccttgttt ctgacaagct gcagcgaaga aggtgaacct agctgatatt     240
ggcatcgtcg gtggccttgg cgatgggtcc gatgagaagg ccctgccctc ttggaccatg     300
ggcgccggat ccggcctagg aatgtctggt attccaccgt caacacaaca agctggtggc     360
atcgagagct tggccaacta caacaagcat catttcggct tcaaataggc ctcgatcttt     420
catactggaa atacccgtca tctgcggtt tcctcctctg tcggcctgct tcttacatgt     480
gctgccctat tgatttaatc actttttttg ttttggttt tggtgattac attacatggt     540
gtcgaccaat cttggccccg tcttgtcacg cgtgtatgtt atttgtcggg tttgtgggta     600
agcatgcaac tacatacaca tcacaccccc tgtgttccag ctcgatgata ggtggtatgt     660
```

```
tggccatgca gtttgtgaaa ttccggccga acttggttat ttaa              704
```

<210> SEQ ID NO 19
<211> LENGTH: 406
<212> TYPE: DNA
<213> ORGANISM: Zea mays
<220> FEATURE:
<221> NAME/KEY: misc_feature
<222> LOCATION: (123)..(126)
<223> OTHER INFORMATION: n is unknown
<220> FEATURE:
<221> NAME/KEY: misc_feature
<222> LOCATION: (174)..(176)
<223> OTHER INFORMATION: n is unknown

<400> SEQUENCE: 19

```
cagcaacgtt agcgacctgg aagccacgga gtggatcgag gargacgagc cgggcgtgtg    60
cctcaccatc cgcgagctcg gcgayggcac ycgcgarctc cgccgcatcc ggttcaggta   120
tgnnnngcac tgaycagtca tggacatgcg gaagcataca tcactggytc agtnnnaacc   180
aaaatccttc ttgatcactc ggttcattca tgtgatcatg tctgttccat gtttctgtgr   240
tgctgcagcc gggagatatt cggcgaggat agggccaagg tgtggtggga gcagaacagg   300
gagagaatac aggcggaata tctgtagcaa gcgatcagac actgagctga tgcaattttc   360
aggcctgatg ggataatcaa atatgtttgt gagaggatag attagg                 406
```

<210> SEQ ID NO 20
<211> LENGTH: 372
<212> TYPE: DNA
<213> ORGANISM: Zea mays
<220> FEATURE:
<221> NAME/KEY: misc_feature
<222> LOCATION: (153)..(155)
<223> OTHER INFORMATION: n is unknown

<400> SEQUENCE: 20

```
gccacggagt ggatcgagga rgacgagccg ggcgtgtgcc tcaccatccg cgagctcggc    60
gayggcacyc gcgarctccg ccgcatccgg ttcaggtatg catggcactg atcagtcatg   120
gacatgcgga agcatacatc actggctcag tannnaccaa aatccttctt gatcactcgg   180
ttcattcatg tgatcatgtc tgttccatgt ttctgtgrtg ctgcagccgg gagatattcg   240
gcgaggatag ggccaaggtg tggtgggagc agaacaggga gagaatacag gcggaatatc   300
tgtagcaagc gatcagacac tgagctgatg caattttcag gcctgatggg ataatcaaat   360
atgtttgtga ga                                                      372
```

<210> SEQ ID NO 21
<211> LENGTH: 582
<212> TYPE: DNA
<213> ORGANISM: Zea mays

<400> SEQUENCE: 21

```
ccaagtcaaa aagctcaact ccgctgctgc ggcggccggc acgtcagctg cgatgggcgg    60
cggggccccg tcgtcctacg acccgtcgcg cgccaccacg tcgtccaggg acgaggcctc   120
cgtgtccctc agcaacgtta gcgacctgga agccacggag tggatcgagg aggacgagcc   180
gggcgtgtgc ctcaccatcc gcgagctcgg cgacggcact cgcgagctcc gccgcatccg   240
gttcaggtat gcatggcact gatcagtcat ggacatgcgg aagcatacat cactggctca   300
gtagtaacca aaatccttct tgatcactcg gttcattcat gtgatcatgt ctgttccatg   360
```

```
tttctgtgat gctgcagccg ggagatattc ggcgaggata gggccaaggt gtggtgggag    420
cagaacaggg agagaataca ggcggaatat ctgtagcaag cgatcagaca ctgagctgat    480
gcaattttca ggcctgatgg gataatcaaa tatgtttgtg agaggataga ttagggagat    540
gataccgcta tatacatgta aaaccactaa tttggtaaaa aa                       582
```

```
<210> SEQ ID NO 22
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 22
gccggcaaga tcgagaaygt ccccgccccg gccatcgcca tcgactastg gcgcctcccc    60
gntaacgcca cgctcaagga cgtmgtcacc gtcgtscgcg ccgacgaggc tcaccaccgc   120
gacgtcaacc actttgcatc ggtacggrta cttccraatt ccaataccag c            171
```

```
<210> SEQ ID NO 23
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 23
gccggcaaga tcgagaaygt ccccgccccg gccatcgcca tcgactastg gcgcctcccc    60
gntaacgcca cgctcaagga cgtmgtcacc gtcgtscgcg ccgacgaggc tcaccaccgc   120
gacgtcaacc actttgcatc ggtacggrta cttccraatt ccaataccag c            171
```

```
<210> SEQ ID NO 24
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 24
gccggcaaga tcgagaaygt ccccgccccg gccatcgcca tcgactastg gcgcctcccc    60
gntaacgcca cgctcaagga cgtmgtcacc gtcgtscgcg ccgacgaggc tcaccaccgc   120
gacgtcaacc actttgcatc ggtacggrta cttccraatt ccaataccag c            171
```

```
<210> SEQ ID NO 25
<211> LENGTH: 557
<212> TYPE: DNA
<213> ORGANISM: Zea mays

<400> SEQUENCE: 25
ggatwagggg agggtcccag tcacgacgat ccactcgtac accgagtacc tcaaggatct    60
ggaggccggc aagatcgaga acgtccccgc cccggccatc gccatcgact actggcgcct   120
ccccgctaac gccacgctca aggacgtagt caccgtcgtc cgcgccgacg aggctcacca   180
ccgcgacgtc aaccactttg catcggtacg gatacttccg aattccaata ccagcagcaa   240
ctctgcttga tctcgctcgc cgggcacgcg tatctcgtta tgggattggt tctgaaatct   300
```

```
gaattggtat gagcttgtgc cgtgcaggac atccattgcc agggaatgca gctgaagcag    360 tccctgcgc cgatcggata ccactgagga agtgatgctg tttgtgctct tcttaatttt    420
gcatcgctaa taagcaaatg agtgtcttgt cttaaggga aggaaaggat gcttattgag    480
ttacgagtac tgctacggcg attaggagga tattttccaa acccagtttt tggggaaatt    540
tgtaagtaat aaggtta                                                  557
```

<210> SEQ ID NO 26
<211> LENGTH: 794
<212> TYPE: DNA
<213> ORGANISM: Zea mays
<220> FEATURE:
<221> NAME/KEY: misc_feature
<222> LOCATION: (307)..(699)
<223> OTHER INFORMATION: n is unknown
<220> FEATURE:
<221> NAME/KEY: misc_feature
<222> LOCATION: (714)..(714)
<223> OTHER INFORMATION: n is either tgtactggtattataatgcacctactctct or
      cgttctggtattatagtgcacgtactct

<400> SEQUENCE: 26

```
attgaaaygc atttgagtga tgagagtatt acctttggg agaagtttga gtcgtttcaa    60
gtctttatgc atgaccaggt gagttagtrg ttttactttt twcctcaatg ccgtgtgaat   120
gtgaggttca tatwttttt tmtgctaatc tttgtagaag gactcaaggg ttattattct    180
attccttgaa agtcttcttt cttggcttga gcgtcgagac cytccagaaa atatggatgt    240
tcaattattc gtagagatca ggcacatatg cagtcaattt caagagaagt atcttaggta    300
tgtttcnnnn nnnnnnnnn nnnnnnnnn nnnnnnnnn nnnnnnnnn nnnnnnnnn        360 nnnnnnnnn nnnnnnnnn nnnnnnnnn nnnnnnnnn nnnnnnnnn nnnnnnnnn        420 nnnnnnnnn nnnnnnnnn nnnnnnnnn nnnnnnnnn nnnnnnnnn nnnnnnnnn        480 nnnnnnnnn nnnnnnnnn nnnnnnnnn nnnnnnnnn nnnnnnnnn nnnnnnnnn        540 nnnnnnnnn nnnnnnnnn nnnnnnnnn nnnnnnnnn nnnnnnnnn nnnnnnnnn        600 nnnnnnnnn nnnnnnnnn nnnnnnnnn nnnnnnnnn nnnnnnnnn nnnnnnnnn        660 nnnnnnnnn nnnnnnnnn nnnnnnnnn nnnnnnnna gcatttatga wacnaattag      720
tagttgggta ttagagtgtg atgtttaact atcagcatcc ttctgttgat gcatgaagta   780
ttcttgtaaa agtt                                                   794
```

<210> SEQ ID NO 27
<211> LENGTH: 810
<212> TYPE: DNA
<213> ORGANISM: Zea mays
<220> FEATURE:
<221> NAME/KEY: misc_feature
<222> LOCATION: (89)..(89)
<223> OTHER INFORMATION: n is either ggttttactttttt or agttttacttttta
<220> FEATURE:
<221> NAME/KEY: misc_feature
<222> LOCATION: (294)..(686)
<223> OTHER INFORMATION: n is unknown
<220> FEATURE:
<221> NAME/KEY: misc_feature
<222> LOCATION: (729)..(730)
<223> OTHER INFORMATION: n is unknown

<400> SEQUENCE: 27

```
attgaaaygc atttgagtga tgagagtatt acctttggg agaagtttga gtcgtttcaa    60
gtctttatgc atgaccaggt gagttagtnc ctcaatgccg tgtgaatgtg aggttcatat  120
```

```
awttttttmt gctaatctttt gtagaaggac tcaagggtta ttattctatt ccttgaaagt    180
cttctttctt ggcttgagcg tcgagaccyt ccagaaaata tggatgttca attattcgta    240
gagatcaggc acatatgcag tcaatttcaa gagaagtatc ttaggtatgt ttcnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnagca tttatgawac ygtwctggta ttatartgca    720
cstactctnn aattagtagt tgggtattag agtgtgatgt ttaactatca gcatccttct    780
gttgatgcat gaagtattct tgtaaaagtt                                     810

<210> SEQ ID NO 28
<211> LENGTH: 823
<212> TYPE: DNA
<213> ORGANISM: Zea mays
<220> FEATURE:
<221> NAME/KEY: misc_feature
<222> LOCATION: (307)..(699)
<223> OTHER INFORMATION: n is unknown
<220> FEATURE:
<221> NAME/KEY: misc_feature
<222> LOCATION: (742)..(743)
<223> OTHER INFORMATION: n is unknown

<400> SEQUENCE: 28
attgaaaygc atttgagtga tgagagtatt acctttrggg agaagtttga gtcgtttcaa     60
gtctttatgc atgaccaggt gagttagtrg ttttactttt twcctcaatg ccgtgtgaat    120
gtgaggttca tatawttttt tmtgctaatc tttgtagaag gactcaaggg ttattattct    180
attccttgaa agtcttcttt cttggcttga gcgtcgagac cytccagaaa atatggatgt    240
tcaattattc gtagagatca ggcacatatg cagtcaattt caagagaagt atcttaggta    300
tgtttcnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnna gcatttatga wacygtwctg    720 gtattataart gcacstactc tnnaattagt agtgggtat tagagtgtga tgtttaacta    780
tcagcatcct tctgttgatg catgaagtat tcttgtaaaa gtt                      823

<210> SEQ ID NO 29
<211> LENGTH: 583
<212> TYPE: DNA
<213> ORGANISM: Zea mays

<400> SEQUENCE: 29
gagatcaggc acatatgcag tcaatttcaa gagaagtatc ttaggtatgt ttctgtcaag     60
```

```
ggcgttaaac ccttggctgg ctggaccgcg gctacggagc tcgtagccgt cggccgtctt      120
ctccggtgag gttattcccc tctaccgtag gctttagaaa ataagagaga gagatgaggc      180
taataatctg cttgctttaa tggtcctggt tacaagaata tatagggcca tagcccaact      240
aactggagta acaaactcct gaaattatgg aactgataac tcctaaatcc atctgcctta      300
tctactcgat cagctcgagc cagctgtgcg cgcgtccccc ctggccgcac gttcctctgc      360
tcggcgtacg tccctggccc tgcgcctcct agtgtagact tgtccccaca tgacagtttc      420
agcatttatg aaaccgttct ggtattatag tgcacgtact ctctaattag tagttgggta      480
ttagagtgtg atgtttaact atcagcatcc ttctgttgat gcatgaagta ttcttgtaaa      540
agttttcctg caaaatcagt aattagtatc aatttagggt taa                       583

<210> SEQ ID NO 30
<211> LENGTH: 669
<212> TYPE: DNA
<213> ORGANISM: Zea mays

<400> SEQUENCE: 30
gtggaacgtc tcaaaggtaa cagctactat gttcaaaatg gaactgagga ctagtggatg       60
aatccagctg tgtatcttca catgaagaga ctaacgcccc gtttggatcc ttggaattga      120
atttcattct aaaaatcata atttagtcac aaatcaattt aagttaatat ggttttatac      180
ggaatctatt tgtgtaccct attagccata tggggtacat atttatatgc tagaattcta      240
ttatagagta gcgagtcaaa gagtgtgtta taaattgtag agtagaaaca tagcctggag      300
atacataaaa tcaatttcca tccctccact ctatgaattt gagatagact tatatttgaa      360
ctttggaaag tggtaggatg ttaaattcca agctaaatag actactctat taagtaaatt      420
tcgattcctc caaaatgaag ggatccaaac tgccoctaat agaattttgt ttctggctat      480 ttacatttt aaagttgtgg ttccgttcag gacttcgccc atatacgttt tggtttgtgc       540
tttgaccttt tagttgtgaa cttgtgatta tttcatttat gggattagaa ttattattat      600
taaataacga gattgaataa caagagccat gacttgattg aatttcataa gcgctagcaa      660
attatttgg                                                              669

<210> SEQ ID NO 31
<211> LENGTH: 359
<212> TYPE: DNA
<213> ORGANISM: Zea mays
<220> FEATURE:
<221> NAME/KEY: misc_feature
<222> LOCATION: (30)..(30)
<223> OTHER INFORMATION: n is unknown
<220> FEATURE:
<221> NAME/KEY: misc_feature
<222> LOCATION: (48)..(48)
<223> OTHER INFORMATION: n is unknown
<220> FEATURE:
<221> NAME/KEY: misc_feature
<222> LOCATION: (50)..(50)
<223> OTHER INFORMATION: n is unknown

<400> SEQUENCE: 31
tagttttycc ctcttcctaa cgtgtttaan ctcttataag agtgtgtntn catggtccga       60
caaacttttg cttcycctca tgagatsatt tgtgcyctta tctctgcaga taaagggcat      120
cagtgagctc ctygagggcc ttattccgta ttcgcagagg catttcagca gagtggacag      180
actagtccga agcacgtttc tgttggacta tacgctgayg cgaatgtccg tggtagaycc      240
agatgtggat gcggggtcaa tcaaagacga aatgaatggt tcgtctgtgg agaacggtga      300
```

```
acttgcagag cctcggcctg cttcacctgt gccagagaag tcaagcaaga agagaaaat    359
```

<210> SEQ ID NO 32
<211> LENGTH: 591
<212> TYPE: DNA
<213> ORGANISM: Zea mays

<400> SEQUENCE: 32

```
tcatgtttca gttgtgcttt tcgggtattg aggagtttct ctcccactga tatcctggag    60
gtagtagttt ttccctcttc ctaacgtgtt taaactctta taagagtgtg ttcatggtcc   120
gacaaacttt tgcttctcct catgagatga tttgtgctct tatctctgca gataaagggc   180
atcagtgagc tccttgaggg ccttattccg tattcgcaga ggcatttcag cagagtggac   240
agactagtcc gaagcacgtt tctgttggac tatacgctga cgcgaatgtc cgtggtagac   300
ccagatgtgg atgcggggtc aatcaaagac gaaatgaatg gttcgtctgt ggagaacggt   360
gaacttgcag agcctcggcc tgcttcacct gtgccagaga agtcaagcaa gagagaaaa    420
tctggcaaat caagtaaaaa gggaaaggag aaggtgatga agcttgcctc gagtggactt   480
ggcaagggtg tttctgttga agcctgaaaa tctagctgag aatctggttt tgcttatgca   540
tgcatgcatc caattttgta gcagctgttg aaactgactt tctaacatgg t            591
```

<210> SEQ ID NO 33
<211> LENGTH: 298
<212> TYPE: DNA
<213> ORGANISM: Zea mays
<220> FEATURE:
<221> NAME/KEY: misc_feature
<222> LOCATION: (188)..(188)
<223> OTHER INFORMATION: n is either gtacgaagtcgatcg or atacgaagtcgatca

<400> SEQUENCE: 33

```
tgttgccagg aactcctgga tcagaaactt tcagagagaa gttcatcaag gtcgatgacg    60
aaaactacat caaggagacg gtggtcactg aaggaggcct tctggatcac ggctttcgga   120
agtacatggt tcgaatcgag atcgtgggwa gagaagagaa grcatccatc gtaaggtcra   180
caattcantg agcatgcagg ttcacacgca ccccctgtgt tcagtaccga tgggytrgct   240
accattgccg aggccatcac caagyatatc aaggagmaga gaggctctga gtccgtaa     298
```

<210> SEQ ID NO 34
<211> LENGTH: 669
<212> TYPE: DNA
<213> ORGANISM: Zea mays

<400> SEQUENCE: 34

```
tcaggaaaat tgccatgag ttggaaaccg ggctcccagc tgccgccgtg tgggaggtca     60
taatggaagc ctcctcttcg ggaaactgat gccccagctg ctccctgaag tggtctcgaa   120
ggttgagctt gtggagggag acggtggcgc tggaacggtc ctgcttgtta ccttccctcc   180
aggttagaag aacaacctga aaacacatac gagcttcttt tgaggtgtgg tacgatgatg   240
cggtctcggt ctcggctcca aacagttttt gctttcttgt ggttcatggc ttcatgcatg   300
ttgccaggaa ctcctggatc agaaactttc agagagaagt tcatcaaggt cgatgacgaa   360
aactacatca aggagacggt ggtcactgaa ggaggccttc tggatcacgg ctttcggaag   420
tacatggttc gaatcgagat cgtgggaaga gaagagaaga catccatcgt aaggtcaaca   480
attcagtacg aagtcgatcg tgagcatgca ggttcacacg cacccctgt gttcagtacc   540
```

```
gatgggttgg ctaccattgc cgaggccatc accaagtata tcaaggagaa gagaggctct    600
gagtccgtaa gctctcccaa gtaattaact caagtaattg aactctggaa ttaaaatttg    660
gggtaaaaa                                                             669
```

```
<210> SEQ ID NO 35
<211> LENGTH: 517
<212> TYPE: DNA
<213> ORGANISM: Zea mays

<400> SEQUENCE: 35
ccccaaaaac cccagtcaca acgtgtgccc tctcgtaatc ctcctcgcct gctccacgtc     60
caacgcttcc gtcctacaag acgcgtgcaa gtccttcgcc gctaagatcc cggacaccgg    120
ctacgcctac tgcatcaagt tcttccaggc cgacagggga agcgccggcg cggacaagcg    180
tggcctcgcc gccatcgccg tgaggatcat ggggcagcg gccaagagca ccgccagtca    240
catcgccgcc ctgcgggcct ccgagaagga caaggagcgg ctggcgtgcc tcagcgattg    300
ctccgaggtg tacgcgcagg ccgtggacca gaccggcgtg gcggcgaagg gcatcgcctc    360
gggcacgccc cggggccgcg cggacgcggt gatggcgctc agcacggtgg aggatgcccc    420
cggcacctgt gagcaggggt tccaggacct gggcgtgcgt tcgccgctgg cctcggagac    480
gccggttccg aagatctcag aattttttga aaaagaa                             517
```

```
<210> SEQ ID NO 36
<211> LENGTH: 647
<212> TYPE: DNA
<213> ORGANISM: Zea mays

<400> SEQUENCE: 36
ccagtcagaa cggaggtttt acttgagaac aagagtaatc tctttctctc tcgcacagtg     60
tgtgtatata tgaaccacct aattaccgct gtagtctctt aatcccatca atcaatcaat    120
ggcgcactgc atgttgacac acgctaatac atacaggtat ctacgaggcc aagacagatc    180
tcggcaagaa cacgtgcacc atcgagggtg tcattgagga ggacaagctc gtcaagtaca    240
tctacgagag gatgcgcaag aagggcgtcg tcgacaaggt cgagaagaag gtgatcatca    300
aggaggagaa ggtcttagtg aagaaggcgg ataaggagaa ggagaagaag gagaaggaga    360
aggagaaaga aaaggagaag gccaaggaga aggtgaagga ggctgtcgac aaggtcaagg    420
aggtcatcgc cccctacttc atccctgca cgcacccgaa cttcgtcgac tactcgcacc    480
cctggcaccg cggcggcggc ggctactgct cgtcgtacgg tgacggttac ggctacggct    540
acggcggggg ctgcggaggg tacccaccgt acggtttcag ctacacacac tctgagctca    600
aaggctacca tgacacgtcg ttctgcactc acacaacttg ggggtaa                  647
```

```
<210> SEQ ID NO 37
<211> LENGTH: 589
<212> TYPE: DNA
<213> ORGANISM: Zea mays

<400> SEQUENCE: 37
aggatcccag tcaggacgat ggcaggcgga ttcgttaac cactaaagct ggacgtgtcc      60
atgtgctaga ttcattccat ggcaatagcg taagcataca acctactgta ccttgtatct    120
tgcatatacc aacactagta agacatggtt cttatgattc ctttttttctt tcagattgcg    180 tcgtgcaatg tgaagccagt ggtaaccaac tcaacactgg aggcgtcgtt cagccctgat    240
ggaaaccata tcatatctgg ttagagacca tccctatcgt gctttacaaa gagttgccat    300
```

```
cttctctcct gcttagcaat gcgttatggt cttctcttgc aggctccggt gacggtagtg    360
tttatgcttg gaatgttagg agtggaaagg tgcagaaaga tatatcatgt cgatattgaa    420
atcacttcgt atgttatatc tatttgactt gtatatggta aaacactttg acatgcaggt    480
cgcgcgctgg ggaagcacag acgacgaacc gccgctggta aggtgggctc caggatcctt    540
gatgttcgtg acagatcatc agaactgtca tgctgtactg ggcttatta               589
```

<210> SEQ ID NO 38
<211> LENGTH: 1180
<212> TYPE: DNA
<213> ORGANISM: Zea mays
<220> FEATURE:
<221> NAME/KEY: misc_feature
<222> LOCATION: (1164)..(1164)
<223> OTHER INFORMATION: n is unknown

<400> SEQUENCE: 38

```
tttgattctt gtcaatagca agttcactgc agcaactttt gcaaggacct tttctggttt     60
acatgctaga ggaatcgagc ctggtgttct ttatccagct gtctctgttg agcagtttca    120
cgaaccccat gcttataagt aacttcatgc ttgcatatct ccttacattt aggtctaact    180
tattcagttt atagactaaa cagatctttt taccattatc atattaatat ttagctaaag    240
tagacaacaa tcttttgtac aggttgaatt tcctatcaat caaccggttt gagaggaaaa    300
agaatcttga tcttgccatt tcagcatttg ctttgctccg ttctgctgct tggactctac    360
ctggtgatgc tctacaagaa gcaacattaa cagtggcagg tgtttatatt ttattttcc     420 ttctagttgc atgttcaatg ttacaacacc accggtttta aaccatatga atattgact     480 gctgatttcc taccatgcct attatttagg tggctatgat aagcgtctca aggaaaatgt    540
tgaatacctt gaggaactca aaagactcgc attgacggaa ggggtttctg acaggttaa     600 wtttgttaca tcttgctcaa catctgaaag aaacgagctt ctctccaact gcctctgcgt    660
tttatacact ccaaaggtaa gtgcctaggg cttacatcca gctaagcagt ttgtttacct    720
ttaatttaac aagcctgcgt ctcttatcca ggatgaacat ttcggtattg tacctcttga    780
agccatggcc gcccataagc cggtaattgc ctgcaatagt ggtggcccag tggaaacagt    840
tgtgaatgaa gtaacagggt ttctgtgtga tccctctccc gcagaattct ccaaagccat    900
gctgaaactt gtgaatgatc atgatcttgc tgtcagattg ggtgaacaag cacgtgacca    960
tgtggtgcaa aaattctcga ccaagacatt tggtgatctc ctcaacagct acgtcttgaa   1020
catctaccat gagaggatgg aatgatctat aatattgggt cagccatgcc atatgaaaac   1080
aatttgttca atacaaggtt ttttttgcac ctttacgtct aatctgattt tgatggacac   1140
acataatgac aatgacattc catngaatcc ctttggcata                          1180
```

<210> SEQ ID NO 39
<211> LENGTH: 601
<212> TYPE: DNA
<213> ORGANISM: Zea mays
<220> FEATURE:
<221> NAME/KEY: misc_feature
<222> LOCATION: (10)..(10)
<223> OTHER INFORMATION: n is unknown

<400> SEQUENCE: 39

```
cccccaaaan ccccaaaatt ctwraaaaat tccagaacac cttcttttaa gaagcaacat     60
taacagtggc aggtgtttat atttattttt tccttctagt tgcatgttca atgttacaac    120
```

| | |
|---|---:|
| accaccggtt ttaaaccata tgaaatattg actgctgatt tcctaccatg cccattattt | 180 |
| aggtggctat gataagcgtc tcaaggaaaa tgttgaatac cttgaggaac tcaaaagact | 240 |
| cgcattgacg aaggggtttt ctggacaggt taattttgtt acatcttgct caacatctga | 300 |
| aagaaacgag cttctctcca actgcctctg cgttttatac actccaaagg taagtgccta | 360 |
| gtggcttaca tccagctaag cagtttgttt accttaattt aacaagcctg cgtctcttac | 420 |
| ttatccagga tgaacatttc ggtattgtac ctcttgaagc catggccgcc cataagccgg | 480 |
| taattgcctg caatagtggt ggcccagtgg aaacagttgt gaatgaagta acagggtttc | 540 |
| tgtgtgatcc ctctcccgca gaattctcca aagccatgct gaaatggtca tagctgccct | 600 |
| t | 601 |

```
<210> SEQ ID NO 40
<211> LENGTH: 369
<212> TYPE: DNA
<213> ORGANISM: Zea mays
<220> FEATURE:
<221> NAME/KEY: misc_feature
<222> LOCATION: (54)..(56)
<223> OTHER INFORMATION: n is unknown
<220> FEATURE:
<221> NAME/KEY: misc_feature
<222> LOCATION: (119)..(121)
<223> OTHER INFORMATION: n is unknown
<220> FEATURE:
<221> NAME/KEY: misc_feature
<222> LOCATION: (305)..(305)
<223> OTHER INFORMATION: n is unknown

<400> SEQUENCE: 40
```

| | |
|---|---:|
| gcggcggaca tggaactgga ygatgcttca gccgagacac caaccagtgg aacnnntggg | 60 |
| aagctgtctt cccatgccgc agaagaagcr gagacatggt gcccgtggct ggtcggtann | 120 |
| ncacagcagt ttctgtacta tctccctcrg ggagaggtgt tctctatgca tcctggttgc | 180 |
| cagttcctaa actacggtaa cggaagcata tcctacwcag cgttggacgc acrgacagtt | 240 |
| acctcaaaca agcagcggag ccrrccatgg acggagtcga tcgaracctc cagcagcgtg | 300 |
| cctgnaacag ctcagaattc aratcctgya gaatctacga aagtaaacag aggtgaagac | 360 |
| aaagtggct | 369 |

```
<210> SEQ ID NO 41
<211> LENGTH: 462
<212> TYPE: DNA
<213> ORGANISM: Zea mays
<220> FEATURE:
<221> NAME/KEY: misc_feature
<222> LOCATION: (54)..(56)
<223> OTHER INFORMATION: n is unknown
<220> FEATURE:
<221> NAME/KEY: misc_feature
<222> LOCATION: (119)..(121)
<223> OTHER INFORMATION: n is unknown
<220> FEATURE:
<221> NAME/KEY: misc_feature
<222> LOCATION: (305)..(305)
<223> OTHER INFORMATION: n is unknown

<400> SEQUENCE: 41
```

| | |
|---|---:|
| gcggcggaca tggaactgga ygatgcttca gccgagacac caaccagtgg aacnnntggg | 60 |
| aagctgtctt cccatgccgc agaagaagcr gagacatggt gcccgtggct ggtcggtann | 120 |
| ncacagcagt ttctgtacta tctccctcrg ggagaggtgt tctctatgca tcctggttgc | 180 |
| cagttcctaa actacggtaa cggaagcata tcctacwcag cgttggacgc acrgacagtt | 240 |

```
acctcaaaca agcagcggag ccrrccatgg acggagtcga tcgaraccte cagcagcgtg      300 cctgnaacag ctcagaattc aratcctgya gaatctacga aagtaaacag aggtgaagac      360
aaagtggctg tacccgttcc aggttcaagg aaatgcgcgr gcgcaattcc agcctgccgt      420
cgaggttttg taccgtacaa gaagtgcaca gctcggagca ag                        462

<210> SEQ ID NO 42
<211> LENGTH: 669
<212> TYPE: DNA
<213> ORGANISM: Zea mays

<400> SEQUENCE: 42
gagaaaaacc cctggtttga atttgacagc agcaagctca atactgggag cctacaacac      60
gcggcggaca tggaactgga tgatgcttca gccgagacac caaccagtgg aactgggaag     120
ctgtcttccc atgccgcaga agaagcagag acatggtgcc cgtggctggt cggtagtaca     180
cagcagtttc tgtactatct ccctcgggga gaggtgttct ctatgcatcc tggttgccag     240
ttcctaaact acggtaacgg aagcatatcc tacacagcgt tggacgcacg gacagttacc     300
tcaaacaagc agcggagcca accatggacg gagtcgatcg aaacctccag cagcgtgcct     360
gaaacagctc agaattcaga tcctgcagaa tctacgaaag taaacagagg tgaagacaaa     420
gtggctgtac ccgttccagg ttcaaggaaa tgcgcgagcg caattccagc ctgccgtcga     480
ggttttgtac cgtacaagaa gtgcacagct cggagcaagg tgctggcgct gcagcctgtg     540
gcacctggcg aggaggcaga tagagagctg acaaggctgt gcctgtagaa ttctgggccc     600
ttgccaccca cctctactct gtggataatt tttgctgcta ctcgaacact taatggtcat     660
agctgtttt                                                             669

<210> SEQ ID NO 43
<211> LENGTH: 498
<212> TYPE: DNA
<213> ORGANISM: Zea mays

<400> SEQUENCE: 43
aagtcccagt cacaacgaaa gaacattacg aatgccattg tgatcgaggt ccagtattta      60
gcgtaggatt gcgtacccgg tggacgtagg agtccggcat gagcgaacgg agcgcggcga     120
ggtactcgtt cacctggcgg cggcggttgc gctcgacggc gatgtgggtc atccgctggc     180
tctcggcgtt cttggtgctc ctctgccggc gccgccgccg ccgcttcatc cgcccctgct     240
gcacgctgtt cgcctgggac gccccccgcg gcggtgccac ctccgccgat ggtgcattgc     300
cggaaaagct cccccgtccc cccgcagaag cggcagacgc gtcggcggcg ttgaaggtgt     360
cgtagatgag atgagtacgt cgcggcacaa agcttccagc gtcatgtcga tcggcgattt     420
ggcggcctgt ggacttgtgg tatggcacgg aggccagcaa gaacctacgc gcggaccgcc     480
gcccgatttt ttgaattt                                                   498

<210> SEQ ID NO 44
<211> LENGTH: 608
<212> TYPE: DNA
<213> ORGANISM: Zea mays

<400> SEQUENCE: 44
agtcagaacg caacagagaa aaattcatgt acaggtaaaa aaaaccacca ccgatttaga      60
gactagagta tccggggggg tcccttcccc tagaagaaga gatctccgtc cgtggcatgg     120
```

| | |
|---|---|
| aggaacggac gaatggttcg ctgacggcgg tgtggctgtt tcttttttt gctatcgcag | 180 |
| aggtgacctg ccgttctgca gcgaggagtg ccggcaggag cagatcgaga tcgacgaggc | 240 |
| gcgagagcag cggctgaagc agacggggcg ggccgagcag cagcggcagc ggcagcagaa | 300 |
| gcagagcccc cagaggatcc ccatctgggc gtggtaggag gagaaaaatt ttgggcgccg | 360 |
| ggaaaacgaa cgaacgtagt aggatttagc tgcacctcaa gaagaacccc ccaagcaagg | 420 |
| gcgacttgct gcgtgtggaa acaaacggcc gtggatcacc gccggctcga cgcaggaaga | 480 |
| aggccacgcg ccacggcaca ggccgggcag ggcagggcat ccaaccggct gcgtcttttt | 540 |
| accttcgttg gttgacgaaa ccgaatgacc tctctcctcc tatctccgta gtaactttgg | 600 |
| taaaataa | 608 |

<210> SEQ ID NO 45
<211> LENGTH: 637
<212> TYPE: DNA
<213> ORGANISM: Zea mays

<400> SEQUENCE: 45

| | |
|---|---|
| aaggtctata ggggaggcaa acttgaaaaa gcgagaattc gctgttgatc catccacagc | 60 |
| tcgtttccac ctttcggaac ctttccgccg gcctgttctg acgtcagaac catctatatc | 120 |
| ttcaagaatt cttggttcgc aagaccgttt tttgatcttt gcatcggatg gactatggga | 180 |
| gcacctctca aaccagcaag ctgttgaaat tgtccacaat agtccacgag aagtatggtt | 240 |
| ttcttctttc tcgctgcatt ttgtcttgaa ctggcaactc ttctcatatc gctcttgctg | 300 |
| atgatagcat tcctgttgcg gcaacgctga aatgggtttt ccttgttttt gtagggtgtt | 360 |
| gcaaggagat tggtacaaac agctctaaaa gaagctgcga ggaagaggga aatgaggtat | 420 |
| ggcgatatta agaagctcga aaaggagtc cggcgctact tccacgacga cataacagtt | 480 |
| gtcgtcgtct tcatagacca tgaactgcgg gcggagcatt cttcctcgac ctctgttcct | 540 |
| gaactctcgg tccgtgggtt cgttgatgcg ggggcacgct ccagcttttc agggatgaac | 600 |
| gacattactt atacagtaac cttgttaatt tttaaaa | 637 |

<210> SEQ ID NO 46
<211> LENGTH: 631
<212> TYPE: DNA
<213> ORGANISM: Zea mays

<400> SEQUENCE: 46

| | |
|---|---|
| tccgcccccc ccagtcaggt ttttgaagct ctttgaaaac tcacttttat tgtccgcccc | 60 |
| attacatcct ggaaaagatt attctcaatg ttactatcta atttggagaa atctttaggt | 120 |
| gtcaacattt taatgactag ctcaatgata atgatacaag actgataaac tggtcccatg | 180 |
| ttgtagaaaa ctgaatcatt aagtgatatt aggtcattct cagtgatcag ttttaatgta | 240 |
| ctgtttccaa aactgccaca tcagatttaa actagataac cgtgtatgca gagttctccc | 300 |
| ccatgaaact ctaccatctt ccatgaaatg gtgaaactct ccctatatct ctcttattaa | 360 |
| ttgcactgcc atgtcactaa gtgtgatgat gtgtcaccgc atttaatgag tatgaaaatc | 420 |
| ccattgagaa tggtcttaca agaaaattcca tgtccactaa gttgtgaaag cctcattgga | 480 |
| ggagaacgca agtgacgtca atagatggac catggatgcg ctaggacgta atttagataa | 540 |
| catcttctac ttcacacccm ctcaatctat ctgatgctga atcgtgaaac tacaccatgg | 600 |
| tgcaaaccaa acgcatcaat gcaacyatgg t | 631 |

```
<210> SEQ ID NO 47
<211> LENGTH: 672
<212> TYPE: DNA
<213> ORGANISM: Zea mays

<400> SEQUENCE: 47
gggcattcat ggaaaaggcc caaccgggtt tttcagggaa ggggattcct tacctccaga      60
tgttgatcca gatacagtta gatggattcc agcaaaccat cctttgctg ctgcgtcaag     120
tgaagtagac gaggagaccg ccaaacaaaa tgtctatcaa aaggatggcg tcccatcccg    180
tgttaaggct gagcatgaag ctttgcaggc aaggctagag cttcaaacg atgtgagtgc     240
cttgccgatg aacatgatct ccttgacatt taaaataaca acaatatatc tattattagt    300
tcctctcttc tgcaaaattg attatattga ttgataaaac tccaagctta gtttgacaaa    360
agagccaatc acattgtgta ttttgttaa tcaccagcct tccagaataa cgattcctga     420
atcccaacac tgctttgcag gttaccagac tccctccgga tccaaggagt atgcagcgta    480
atgagagaca aatggaattg tcaggcaagc catctgaaaa tcttcagggc tccaagtttg    540
agaaccaaga tagacaactg gttatcgagt ctggtaaaca tagctccgat ggaagtttac    600
aatcaaatga gccggaaggg caataaaatt tggtactcaa gcgcttgata cattgtaatt    660
ggttgtatta tt                                                         672

<210> SEQ ID NO 48
<211> LENGTH: 450
<212> TYPE: DNA
<213> ORGANISM: Zea mays

<400> SEQUENCE: 48
taaaattaaa ggggaagtcc cagtcaaaac ggcatgtgct agattatctt ctttaagatg     60
gggtaagcaa cttcatgctc aggtgattcg gaacctaccg cacattgatc catatgttgc    120
aagtgctctt gttgaactgt atgcaaaatg tggctgtttc aaggaagcta aggggggtctt  180
caactctttta catgaccgta acaatgtggc ttggacagtt ctcatctcag gattcttgca   240
gtatgggtgt ttcactgaat ctgttgaatt gttcaaccag atgagagctg agttgatgac   300
acttgatcag ttcgctttgg ctactcttat aagtggctgc tgcagcagga tggatttgtg    360
ccttgggagg caactacatt cactttgtct gaaaagtggg cagattcaag ctgtagtcgt   420
ctccaatttt tatttcactt tctggtaata                                     450

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
tctctctcgc gtgtgtgc                                                   18

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tgggtctcct tctccgtcta                                                 20
```

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gaaaggctcg ctagtcgcta                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aattcctatc gatcctggcc                                                   20

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
agaagtgcgt atgctacagt ggtg                                              24

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
cctagtggtg gagttctagg caaa                                              24

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gtgaagctct gcaccacgct                                                   20

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
atcgtccaaa gaagaagagg gaga                                              24

<210> SEQ ID NO 57
<211> LENGTH: 20
<212> TYPE: DNA
<213> ORGANISM: Artificial Sequence
<220> FEATURE:
<223> OTHER INFORMATION: Primer

```
<400> SEQUENCE: 57
aaggggagca aacaaggtag                                                     20

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
atttaagtag tgcatggtgg ag                                                  22

<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59
aaagcatcca cgagccgca                                                      19

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
atgcatggca cgaacacag                                                      19

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tctatgtcag tcctgaggca                                                     20

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
aggctaccat taacatgctt c                                                   21

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
acacaataga gcttgatcgt ga                                                  22

<210> SEQ ID NO 64
```

```
<211> LENGTH: 22
<212> TYPE: DNA
<213> ORGANISM: Artificial Sequence
<220> FEATURE:
<223> OTHER INFORMATION: Primer

<400> SEQUENCE: 64
aaattgggag agcacagaaa gt                                              22

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
aaatgtggga gaacagcaag tt                                              22

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
acaggttgat ttggaatcaa ac                                              22

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
aacaatctca gaagcaatac ag                                              22

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
cgttctatta cggtcatttg c                                               21

<210> SEQ ID NO 69
<211> LENGTH: 18
<212> TYPE: DNA
<213> ORGANISM: Artificial Sequence
<220> FEATURE:
<223> OTHER INFORMATION: Primer

<400> SEQUENCE: 69
ctatcgttgg atggcacc                                                   18

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
```
ttgtgctgtg ggagctcata 20

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
atgtttcgac aggacataga c 21

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
aggcacattc cagtagcag 19

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
agcaactcaa gtctgacgat t 21

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gggaaggatg tcatatccga 20

<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75
acaccaatcc agaagggga 19

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
gaatggaaag tacaatgagt cc 22

<210> SEQ ID NO 77
<211> LENGTH: 22
<212> TYPE: DNA

```
<213> ORGANISM: Artificial Sequence
<220> FEATURE:
<223> OTHER INFORMATION: Primer

<400> SEQUENCE: 77
ttcacagagc gtgctagaaa ta                                              22

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
ctgaatctgg agtttctgtc a                                               21

<210> SEQ ID NO 79
<211> LENGTH: 22
<212> TYPE: DNA
<213> ORGANISM: Artificial Sequence
<220> FEATURE:
<223> OTHER INFORMATION: Primer

<400> SEQUENCE: 79
tatagatctt cctgcaggag tt                                              22

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ctgcagctaa accctgatga                                                 20

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
tcagggagtg gtatttcctt g                                               21

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
tatcaggtca gcaaatttcc aa                                              22

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
cattcctcct gtccacaaca                                                 20
```

```
<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
tttacgactg caatgaatca ac                                              22

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
tggcagcaat ttcagcatgt aa                                              22

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
gaggaagctt atgaatttgt gc                                              22

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
ctggtcttgt aaacactcac t                                               21

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
tgcaccgagc aaatacctttt g                                              21

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
tacctgatcg tcaagtcgct                                                 20

<210> SEQ ID NO 90
<211> LENGTH: 19
<212> TYPE: DNA
<213> ORGANISM: Artificial Sequence
<220> FEATURE:
```

```
<223> OTHER INFORMATION: Primer

<400> SEQUENCE: 90
tgcccatgga cctcttctt                                                  19

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
actctgaatt gagcagcagg                                                 20

<210> SEQ ID NO 92
<211> LENGTH: 21
<212> TYPE: DNA
<213> ORGANISM: Artificial Sequence
<220> FEATURE:
<223> OTHER INFORMATION: Primer

<400> SEQUENCE: 92
actttggcta gcacaacaac a                                               21

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
acttagctgc aaagatgc                                                   18

<210> SEQ ID NO 94
<211> LENGTH: 21
<212> TYPE: DNA
<213> ORGANISM: Artificial Sequence
<220> FEATURE:
<223> OTHER INFORMATION: Primer

<400> SEQUENCE: 94
aacattggtg caagggacac t                                               21

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
cagaaatgcc atcaacgcca                                                 20

<210> SEQ ID NO 96
<211> LENGTH: 22
<212> TYPE: DNA
<213> ORGANISM: Artificial Sequence
<220> FEATURE:
<223> OTHER INFORMATION: Primer

<400> SEQUENCE: 96
ggaatgatct ccatgctttc at                                              22
```

```
<210> SEQ ID NO 97
<211> LENGTH: 19
<212> TYPE: DNA
<213> ORGANISM: Artificial Sequence
<220> FEATURE:
<223> OTHER INFORMATION: Primer

<400> SEQUENCE: 97
ccagtccaaa ccctacggc                                              19

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
cgaccaaacc ctactcgta                                              19

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
atcgatctcc tgctgcaagt                                             20

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
aataataggc gattgaggtg c                                           21

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
aataataggc gattgaggtg c                                           21

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
agcctagcgc aaagaaagac                                             20

<210> SEQ ID NO 103
<211> LENGTH: 21
<212> TYPE: DNA
<213> ORGANISM: Artificial Sequence
<220> FEATURE:
<223> OTHER INFORMATION: Primer
```

<400> SEQUENCE: 103
caggccacgg aatttacaca a    21

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
tcgctgcgta gagtactgta    20

<210> SEQ ID NO 105
<211> LENGTH: 18
<212> TYPE: DNA
<213> ORGANISM: Artificial Sequence
<220> FEATURE:
<223> OTHER INFORMATION: Primer

<400> SEQUENCE: 105
acccgtcgga ccacgtct    18

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
gctcaactcc gctgctgc    18

<210> SEQ ID NO 107
<211> LENGTH: 22
<212> TYPE: DNA
<213> ORGANISM: Artificial Sequence
<220> FEATURE:
<223> OTHER INFORMATION: Primer

<400> SEQUENCE: 107
tcacgttgtt ttcaccatgt at    22

<210> SEQ ID NO 108
<211> LENGTH: 22
<212> TYPE: DNA
<213> ORGANISM: Artificial Sequence
<220> FEATURE:
<223> OTHER INFORMATION: Primer

<400> SEQUENCE: 108
tattagttta ggcaactaag ga    22

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
aacgcatact tcctcggcta    20

<210> SEQ ID NO 110
<211> LENGTH: 20

```
<212> TYPE: DNA
<213> ORGANISM: Artificial Sequence
<220> FEATURE:
<223> OTHER INFORMATION: Primer

<400> SEQUENCE: 110
atccactcgt acaccgagta                                              20

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
tcactctcaa acaactggtt g                                            21

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
gaagaagtga taaacgccag a                                            21

<210> SEQ ID NO 113
<211> LENGTH: 22
<212> TYPE: DNA
<213> ORGANISM: Artificial Sequence
<220> FEATURE:
<223> OTHER INFORMATION: Primer

<400> SEQUENCE: 113
tactttgtcc agaagagcag aa                                           22

<210> SEQ ID NO 114
<211> LENGTH: 22
<212> TYPE: DNA
<213> ORGANISM: Artificial Sequence
<220> FEATURE:
<223> OTHER INFORMATION: Primer

<400> SEQUENCE: 114
tgtggaaatt tgtctattgc ta                                           22

<210> SEQ ID NO 115
<211> LENGTH: 21
<212> TYPE: DNA
<213> ORGANISM: Artificial Sequence
<220> FEATURE:
<223> OTHER INFORMATION: Primer

<400> SEQUENCE: 115
aggatgcttt cattactgat t                                            21

<210> SEQ ID NO 116
<211> LENGTH: 22
<212> TYPE: DNA
<213> ORGANISM: Artificial Sequence
<220> FEATURE:
<223> OTHER INFORMATION: Primer

<400> SEQUENCE: 116
```
aataggcaga taccaaggca at                                        22

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
aaatgaatca aagggtcgga                                           20

<210> SEQ ID NO 118
<211> LENGTH: 19
<212> TYPE: DNA
<213> ORGANISM: Artificial Sequence
<220> FEATURE:
<223> OTHER INFORMATION: Primer

<400> SEQUENCE: 118
ccctacatgt cggcaaccg                                            19

<210> SEQ ID NO 119
<211> LENGTH: 21
<212> TYPE: DNA
<213> ORGANISM: Artificial Sequence
<220> FEATURE:
<223> OTHER INFORMATION: Primer

<400> SEQUENCE: 119
gttcctgttc atgttcccga a                                         21

<210> SEQ ID NO 120
<211> LENGTH: 22
<212> TYPE: DNA
<213> ORGANISM: Artificial Sequence
<220> FEATURE:
<223> OTHER INFORMATION: Primer

<400> SEQUENCE: 120
aatttacaag gttctatcgg tt                                        22

<210> SEQ ID NO 121
<211> LENGTH: 19
<212> TYPE: DNA
<213> ORGANISM: Artificial Sequence
<220> FEATURE:
<223> OTHER INFORMATION: Primer

<400> SEQUENCE: 121
gcttctagag tacgcccgt                                            19

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
catgttgcgc agtttgtgct t                                         21

<210> SEQ ID NO 123
<211> LENGTH: 20
<212> TYPE: DNA
<213> ORGANISM: Artificial Sequence

```
<220> FEATURE:
<223> OTHER INFORMATION: Primer

<400> SEQUENCE: 123
gttgggcaac gtcagtttca                                              20

<210> SEQ ID NO 124
<211> LENGTH: 21
<212> TYPE: DNA
<213> ORGANISM: Artificial Sequence
<220> FEATURE:
<223> OTHER INFORMATION: Primer

<400> SEQUENCE: 124
gccttctaat aaacgcagca a                                            21

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
ctacggagct caaagctatg                                              20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
atctgccatg agttcgagac                                              20

<210> SEQ ID NO 127
<211> LENGTH: 22
<212> TYPE: DNA
<213> ORGANISM: Artificial Sequence
<220> FEATURE:
<223> OTHER INFORMATION: Primer

<400> SEQUENCE: 127
tcttcaattc ccagagttca at                                           22

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
ttcacgctat ggccctttct                                              20

<210> SEQ ID NO 129
<211> LENGTH: 22
<212> TYPE: DNA
<213> ORGANISM: Artificial Sequence
<220> FEATURE:
<223> OTHER INFORMATION: Primer

<400> SEQUENCE: 129
atttggattt gcattgtcag tc                                           22
```

```
<210> SEQ ID NO 130
<211> LENGTH: 19
<212> TYPE: DNA
<213> ORGANISM: Artificial Sequence
<220> FEATURE:
<223> OTHER INFORMATION: Primer

<400> SEQUENCE: 130
tgtgccctct cgtcatcct                                                      19

<210> SEQ ID NO 131
<211> LENGTH: 18
<212> TYPE: DNA
<213> ORGANISM: Artificial Sequence
<220> FEATURE:
<223> OTHER INFORMATION: Primer

<400> SEQUENCE: 131
cgatggacgc atccttcc                                                       18

<210> SEQ ID NO 132
<211> LENGTH: 19
<212> TYPE: DNA
<213> ORGANISM: Artificial Sequence
<220> FEATURE:
<223> OTHER INFORMATION: Primer

<400> SEQUENCE: 132
ttacaacgcg gccgttaca                                                      19

<210> SEQ ID NO 133
<211> LENGTH: 21
<212> TYPE: DNA
<213> ORGANISM: Artificial Sequence
<220> FEATURE:
<223> OTHER INFORMATION: Primer

<400> SEQUENCE: 133
cataactgta aagctgccgt t                                                   21

<210> SEQ ID NO 134
<211> LENGTH: 22
<212> TYPE: DNA
<213> ORGANISM: Artificial Sequence
<220> FEATURE:
<223> OTHER INFORMATION: Primer

<400> SEQUENCE: 134
gaggttttac ttgagaacaa ga                                                  22

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
tgtgtgcagt gcaagaacga                                                     20

<210> SEQ ID NO 136
<211> LENGTH: 20
<212> TYPE: DNA
<213> ORGANISM: Artificial Sequence
<220> FEATURE:
<223> OTHER INFORMATION: Primer
```

```
<400> SEQUENCE: 136
gttctcctcg ctgatgaact                                               20

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
tctgttggta ataacgattc ag                                            22

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
atggcaggcg gattctgtta                                               20

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
gaacccagca tgacagttct                                               20

<210> SEQ ID NO 140
<211> LENGTH: 22
<212> TYPE: DNA
<213> ORGANISM: Artificial Sequence
<220> FEATURE:
<223> OTHER INFORMATION: Primer

<400> SEQUENCE: 140
ttcacctact tgctaatggt aa                                            22

<210> SEQ ID NO 141
<211> LENGTH: 21
<212> TYPE: DNA
<213> ORGANISM: Artificial Sequence
<220> FEATURE:
<223> OTHER INFORMATION: Primer

<400> SEQUENCE: 141
tttgctttgc tccgttctgc t                                             21

<210> SEQ ID NO 142
<211> LENGTH: 22
<212> TYPE: DNA
<213> ORGANISM: Artificial Sequence
<220> FEATURE:
<223> OTHER INFORMATION: Primer

<400> SEQUENCE: 142
gctctacaag aagcaacatt aa                                            22

<210> SEQ ID NO 143
```

```
<211> LENGTH: 21
<212> TYPE: DNA
<213> ORGANISM: Artificial Sequence
<220> FEATURE:
<223> OTHER INFORMATION: Primer

<400> SEQUENCE: 143
ttcagcatgg ctttggagaa t                                              21

<210> SEQ ID NO 144
<211> LENGTH: 21
<212> TYPE: DNA
<213> ORGANISM: Artificial Sequence
<220> FEATURE:
<223> OTHER INFORMATION: Primer

<400> SEQUENCE: 144
cacccaatct gacagcaaga t                                              21

<210> SEQ ID NO 145
<211> LENGTH: 21
<212> TYPE: DNA
<213> ORGANISM: Artificial Sequence
<220> FEATURE:
<223> OTHER INFORMATION: Primer

<400> SEQUENCE: 145
gctatttggc aagagggttg t                                              21

<210> SEQ ID NO 146
<211> LENGTH: 22
<212> TYPE: DNA
<213> ORGANISM: Artificial Sequence
<220> FEATURE:
<223> OTHER INFORMATION: Primer

<400> SEQUENCE: 146
gttagtaatt tagaccagca gc                                             22

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
tatgtgttcg agtagcagca a                                              21

<210> SEQ ID NO 148
<211> LENGTH: 21
<212> TYPE: DNA
<213> ORGANISM: Artificial Sequence
<220> FEATURE:
<223> OTHER INFORMATION: Primer

<400> SEQUENCE: 148
aaatggaaac actagtcccg a                                              21

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
```

```
ccagtgtgcc actatctgaa                                              20

<210> SEQ ID NO 150
<211> LENGTH: 22
<212> TYPE: DNA
<213> ORGANISM: Artificial Sequence
<220> FEATURE:
<223> OTHER INFORMATION: Primer

<400> SEQUENCE: 150
aaagaacact acgaatgcca tt                                           22

<210> SEQ ID NO 151
<211> LENGTH: 18
<212> TYPE: DNA
<213> ORGANISM: Artificial Sequence
<220> FEATURE:
<223> OTHER INFORMATION: Primer

<400> SEQUENCE: 151
accgggcggc ggtcgcgc                                                18

<210> SEQ ID NO 152
<211> LENGTH: 19
<212> TYPE: DNA
<213> ORGANISM: Artificial Sequence
<220> FEATURE:
<223> OTHER INFORMATION: Primer

<400> SEQUENCE: 152
tagcacccgt agtggcata                                               19

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
cactacctcg acatctgctt                                              20

<210> SEQ ID NO 154
<211> LENGTH: 22
<212> TYPE: DNA
<213> ORGANISM: Artificial Sequence
<220> FEATURE:
<223> OTHER INFORMATION: Primer

<400> SEQUENCE: 154
caacagagac atcttcatgt ac                                           22

<210> SEQ ID NO 155
<211> LENGTH: 21
<212> TYPE: DNA
<213> ORGANISM: Artificial Sequence
<220> FEATURE:
<223> OTHER INFORMATION: Primer

<400> SEQUENCE: 155
tccatctttc ggagatcagg a                                            21

<210> SEQ ID NO 156
<211> LENGTH: 21
<212> TYPE: DNA
```

```
<213> ORGANISM: Artificial Sequence
<220> FEATURE:
<223> OTHER INFORMATION: Primer

<400> SEQUENCE: 156
aaactcacgc acaaaccaac c                                              21

<210> SEQ ID NO 157
<211> LENGTH: 21
<212> TYPE: DNA
<213> ORGANISM: Artificial Sequence
<220> FEATURE:
<223> OTHER INFORMATION: Primer

<400> SEQUENCE: 157
cgcatcaaag gcatcataca g                                              21

<210> SEQ ID NO 158
<211> LENGTH: 21
<212> TYPE: DNA
<213> ORGANISM: Artificial Sequence
<220> FEATURE:
<223> OTHER INFORMATION: Primer

<400> SEQUENCE: 158
ttcaaggtct ataggtgatg c                                              21

<210> SEQ ID NO 159
<211> LENGTH: 21
<212> TYPE: DNA
<213> ORGANISM: Artificial Sequence
<220> FEATURE:
<223> OTHER INFORMATION: Primer

<400> SEQUENCE: 159
gcaacacaag gttactgtat c                                              21

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
actacgcgct agtaacacca a                                              21

<210> SEQ ID NO 161
<211> LENGTH: 21
<212> TYPE: DNA
<213> ORGANISM: Artificial Sequence
<220> FEATURE:
<223> OTHER INFORMATION: Primer

<400> SEQUENCE: 161
gtgcctctct ataatagtgc c                                              21

<210> SEQ ID NO 162
<211> LENGTH: 21
<212> TYPE: DNA
<213> ORGANISM: Artificial Sequence
<220> FEATURE:
<223> OTHER INFORMATION: Primer

<400> SEQUENCE: 162
agctggtctt ctgaagctct t                                              21
```

<210> SEQ ID NO 163
<211> LENGTH: 21
<212> TYPE: DNA
<213> ORGANISM: Artificial Sequence
<220> FEATURE:
<223> OTHER INFORMATION: Primer

<400> SEQUENCE: 163
ggttgcattg atgcgtttgg t                                              21

<210> SEQ ID NO 164
<211> LENGTH: 19
<212> TYPE: DNA
<213> ORGANISM: Artificial Sequence
<220> FEATURE:
<223> OTHER INFORMATION: Primer

<400> SEQUENCE: 164
tcccatgtga gcgtgtcga                                                 19

<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
ggaacaagaa atgcatcaga ag                                             22

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
ggagatcacg tgcatatcag                                                20

<210> SEQ ID NO 167
<211> LENGTH: 22
<212> TYPE: DNA
<213> ORGANISM: Artificial Sequence
<220> FEATURE:
<223> OTHER INFORMATION: Primer

<400> SEQUENCE: 167
caaagcaaat gtcatcaaag cg                                             22

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
ctatgtaaac cggtaagccc a                                              21

<210> SEQ ID NO 169
<211> LENGTH: 21
<212> TYPE: DNA
<213> ORGANISM: Artificial Sequence
<220> FEATURE:

<223> OTHER INFORMATION: Primer

<400> SEQUENCE: 169
gggtgcgtct tgattcaaca a            21

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
gcatgtgcta gattatcttc tt            22

<210> SEQ ID NO 171
<211> LENGTH: 21
<212> TYPE: DNA
<213> ORGANISM: Artificial Sequence
<220> FEATURE:
<223> OTHER INFORMATION: Primer

<400> SEQUENCE: 171
ggagatgaga gaattggaga c            21

<210> SEQ ID NO 172
<211> LENGTH: 22
<212> TYPE: DNA
<213> ORGANISM: Artificial Sequence
<220> FEATURE:
<223> OTHER INFORMATION: Primer

<400> SEQUENCE: 172
gattgtcgca ctttgcatac at            22

<210> SEQ ID NO 173
<211> LENGTH: 21
<212> TYPE: DNA
<213> ORGANISM: Artificial Sequence
<220> FEATURE:
<223> OTHER INFORMATION: Primer

<400> SEQUENCE: 173
gctgcaggat ttcctggtgc a            21

<210> SEQ ID NO 174
<211> LENGTH: 18
<212> TYPE: DNA
<213> ORGANISM: Artificial Sequence
<220> FEATURE:
<223> OTHER INFORMATION: Primer

<400> SEQUENCE: 174
aaccgctcct gctccagc            18

<210> SEQ ID NO 175
<211> LENGTH: 21
<212> TYPE: DNA
<213> ORGANISM: Artificial Sequence
<220> FEATURE:
<223> OTHER INFORMATION: Primer

<400> SEQUENCE: 175
gctgcaggat ttcctggtgc a            21

```
<210> SEQ ID NO 176
<211> LENGTH: 18
<212> TYPE: DNA
<213> ORGANISM: Artificial Sequence
<220> FEATURE:
<223> OTHER INFORMATION: Primer

<400> SEQUENCE: 176
aaccgctcct gctccagc                                                 18

<210> SEQ ID NO 177
<211> LENGTH: 24
<212> TYPE: DNA
<213> ORGANISM: Artificial Sequence
<220> FEATURE:
<223> OTHER INFORMATION: Primer

<400> SEQUENCE: 177
cttccagaca agccaactga ctga                                          24

<210> SEQ ID NO 178
<211> LENGTH: 30
<212> TYPE: DNA
<213> ORGANISM: Artificial Sequence
<220> FEATURE:
<223> OTHER INFORMATION: Primer

<400> SEQUENCE: 178
caacgatttc caacagctta yttccatgga                                    30

<210> SEQ ID NO 179
<211> LENGTH: 24
<212> TYPE: DNA
<213> ORGANISM: Artificial Sequence
<220> FEATURE:
<223> OTHER INFORMATION: Primer

<400> SEQUENCE: 179
cttccagaca agccaactga ctga                                          24

<210> SEQ ID NO 180
<211> LENGTH: 30
<212> TYPE: DNA
<213> ORGANISM: Artificial Sequence
<220> FEATURE:
<223> OTHER INFORMATION: Primer

<400> SEQUENCE: 180
caacgatttc caacagctta yttccatgga                                    30

<210> SEQ ID NO 181
<211> LENGTH: 30
<212> TYPE: DNA
<213> ORGANISM: Artificial Sequence
<220> FEATURE:
<223> OTHER INFORMATION: Primer

<400> SEQUENCE: 181
aaataggcct cgatctttca tactggaaaa                                    30

<210> SEQ ID NO 182
<211> LENGTH: 26
<212> TYPE: DNA
<213> ORGANISM: Artificial Sequence
<220> FEATURE:
<223> OTHER INFORMATION: Primer
```

```
<400> SEQUENCE: 182
ggccaagatt ggtcgayacc atgtaa                                        26

<210> SEQ ID NO 183
<211> LENGTH: 30
<212> TYPE: DNA
<213> ORGANISM: Artificial Sequence
<220> FEATURE:
<223> OTHER INFORMATION: Primer

<400> SEQUENCE: 183
aaataggcct cgatctttca tactggaaaa                                    30

<210> SEQ ID NO 184
<211> LENGTH: 26
<212> TYPE: DNA
<213> ORGANISM: Artificial Sequence
<220> FEATURE:
<223> OTHER INFORMATION: Primer

<400> SEQUENCE: 184
ggccaagatt ggtcgayacc atgtaa                                        26

<210> SEQ ID NO 185
<211> LENGTH: 22
<212> TYPE: DNA
<213> ORGANISM: Artificial Sequence
<220> FEATURE:
<223> OTHER INFORMATION: Primer

<400> SEQUENCE: 185
agtggatcga ggargacgag cc                                            22

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186
ccttggccct atcctcgcc                                                19

<210> SEQ ID NO 187
<211> LENGTH: 23
<212> TYPE: DNA
<213> ORGANISM: Artificial Sequence
<220> FEATURE:
<223> OTHER INFORMATION: Primer

<400> SEQUENCE: 187
cggaagcata catcactggc tca                                           23

<210> SEQ ID NO 188
<211> LENGTH: 19
<212> TYPE: DNA
<213> ORGANISM: Artificial Sequence
<220> FEATURE:
<223> OTHER INFORMATION: Primer

<400> SEQUENCE: 188
ccttggccct atcctcgcc                                                19

<210> SEQ ID NO 189
<211> LENGTH: 17
```

```
<212> TYPE: DNA
<213> ORGANISM: Artificial Sequence
<220> FEATURE:
<223> OTHER INFORMATION: Primer

<400> SEQUENCE: 189
cggccatcgc catcgac                                                      17

<210> SEQ ID NO 190
<211> LENGTH: 23
<212> TYPE: DNA
<213> ORGANISM: Artificial Sequence
<220> FEATURE:
<223> OTHER INFORMATION: Primer

<400> SEQUENCE: 190
cgtaccgatg caaagtggtt gac                                               23

<210> SEQ ID NO 191
<211> LENGTH: 17
<212> TYPE: DNA
<213> ORGANISM: Artificial Sequence
<220> FEATURE:
<223> OTHER INFORMATION: Primer

<400> SEQUENCE: 191
cggccatcgc catcgac                                                      17

<210> SEQ ID NO 192
<211> LENGTH: 23
<212> TYPE: DNA
<213> ORGANISM: Artificial Sequence
<220> FEATURE:
<223> OTHER INFORMATION: Primer

<400> SEQUENCE: 192
cgtaccgatg caaagtggtt gac                                               23

<210> SEQ ID NO 193
<211> LENGTH: 17
<212> TYPE: DNA
<213> ORGANISM: Artificial Sequence
<220> FEATURE:
<223> OTHER INFORMATION: Primer

<400> SEQUENCE: 193
cggccatcgc catcgac                                                      17

<210> SEQ ID NO 194
<211> LENGTH: 23
<212> TYPE: DNA
<213> ORGANISM: Artificial Sequence
<220> FEATURE:
<223> OTHER INFORMATION: Primer

<400> SEQUENCE: 194
cgtaccgatg caaagtggtt gac                                               23

<210> SEQ ID NO 195
<211> LENGTH: 33
<212> TYPE: DNA
<213> ORGANISM: Artificial Sequence
<220> FEATURE:
<223> OTHER INFORMATION: Primer

<400> SEQUENCE: 195
```

```
gcagtcaatt tcaagagaag tatcttaggt atg                                33
```

<210> SEQ ID NO 196
<211> LENGTH: 33
<212> TYPE: DNA
<213> ORGANISM: Artificial Sequence
<220> FEATURE:
<223> OTHER INFORMATION: Primer

<400> SEQUENCE: 196

```
aacttttaca agaatacttc atgcatcaac aga                                33
```

<210> SEQ ID NO 197
<211> LENGTH: 31
<212> TYPE: DNA
<213> ORGANISM: Artificial Sequence
<220> FEATURE:
<223> OTHER INFORMATION: Primer

<400> SEQUENCE: 197

```
gcatttgagt gatgagagta ttaccttttg g                                  31
```

<210> SEQ ID NO 198
<211> LENGTH: 28
<212> TYPE: DNA
<213> ORGANISM: Artificial Sequence
<220> FEATURE:
<223> OTHER INFORMATION: Primer

<400> SEQUENCE: 198

```
cccttgagtc cttctacaaa gattagca                                      28
```

<210> SEQ ID NO 199
<211> LENGTH: 27
<212> TYPE: DNA
<213> ORGANISM: Artificial Sequence
<220> FEATURE:
<223> OTHER INFORMATION: Primer

<400> SEQUENCE: 199

```
ttcaagtctt tatgcatgac caggtga                                       27
```

<210> SEQ ID NO 200
<211> LENGTH: 29
<212> TYPE: DNA
<213> ORGANISM: Artificial Sequence
<220> FEATURE:
<223> OTHER INFORMATION: Primer

<400> SEQUENCE: 200

```
aattgactgc atatgtgcct gatctctac                                     29
```

<210> SEQ ID NO 201
<211> LENGTH: 27
<212> TYPE: DNA
<213> ORGANISM: Artificial Sequence
<220> FEATURE:
<223> OTHER INFORMATION: Primer

<400> SEQUENCE: 201

```
ccgacaaact tttgcttcyc ctcatga                                       27
```

<210> SEQ ID NO 202
<211> LENGTH: 22
<212> TYPE: DNA
<213> ORGANISM: Artificial Sequence
<220> FEATURE:
<223> OTHER INFORMATION: Primer

<400> SEQUENCE: 202
tgcttcggac tagtctgtcc ac                                              22

<210> SEQ ID NO 203
<211> LENGTH: 26
<212> TYPE: DNA
<213> ORGANISM: Artificial Sequence
<220> FEATURE:
<223> OTHER INFORMATION: Primer

<400> SEQUENCE: 203
tttcggaagt acatggttcg aatcga                                          26

<210> SEQ ID NO 204
<211> LENGTH: 26
<212> TYPE: DNA
<213> ORGANISM: Artificial Sequence
<220> FEATURE:
<223> OTHER INFORMATION: Primer

<400> SEQUENCE: 204
ggtagcyarc ccatcggtac tgaaca                                          26

<210> SEQ ID NO 205
<211> LENGTH: 30
<212> TYPE: DNA
<213> ORGANISM: Artificial Sequence
<220> FEATURE:
<223> OTHER INFORMATION: Primer

<400> SEQUENCE: 205
aaaaagaatc ttgatcttgc catttcagca                                      30

<210> SEQ ID NO 206
<211> LENGTH: 22
<212> TYPE: DNA
<213> ORGANISM: Artificial Sequence
<220> FEATURE:
<223> OTHER INFORMATION: Primer

<400> SEQUENCE: 206
gccctaggca cttacctttg ga                                              22

<210> SEQ ID NO 207
<211> LENGTH: 23
<212> TYPE: DNA
<213> ORGANISM: Artificial Sequence
<220> FEATURE:
<223> OTHER INFORMATION: Primer

<400> SEQUENCE: 207
gaactggayg atgcttcagc cga                                             23

<210> SEQ ID NO 208
<211> LENGTH: 23
<212> TYPE: DNA
<213> ORGANISM: Artificial Sequence
<220> FEATURE:
<223> OTHER INFORMATION: Primer

<400> SEQUENCE: 208
ggtacagcca ctttgtcttc acc                                             23

<210> SEQ ID NO 209
<211> LENGTH: 23
<212> TYPE: DNA
<213> ORGANISM: Artificial Sequence
<220> FEATURE:
<223> OTHER INFORMATION: Primer

<400> SEQUENCE: 209

```
gaactggayg atgcttcagc cga                                              23
```

<210> SEQ ID NO 210
<211> LENGTH: 23
<212> TYPE: DNA
<213> ORGANISM: Artificial Sequence
<220> FEATURE:
<223> OTHER INFORMATION: Primer

<400> SEQUENCE: 210

```
ggtacagcca ctttgtcttc acc                                              23
```

<210> SEQ ID NO 211
<211> LENGTH: 880
<212> TYPE: DNA
<213> ORGANISM: Zea mays

<400> SEQUENCE: 211

```
catcgccgtt ccttcctggc gatcgccgct ccctagctat ccggtggcca aagacacggc      60
tagtggtagg ctcgagcgag acgagctctt ggtgaagaga gaatgaatgt aacgttaccg     120
cctcctggtc gtaggggtgt gtgtatgtga ggacaagagg aggagcgaga ggaggagcgc     180
agagcgtggc ggggaaggag ggcgtcatgt gtgcgaggaa tctaggacga cttgttggca     240
gctgggccgg ggtgcgtgcg agatgcaatg caagaacaaa gcggacgggc atctcgctcg     300
gccacgcttc caagtccatc cggggggcgc cactcggccg ccgctcattg aggcccaggc     360
gccaagacgg cggctccacc cacgtcacaa ttggcaacaa gaagcacacg gctgggctg     420
ggacgcgtcg aattttttcac cagaaaatac cgtctgatcc tggcgtttcg tgaacggcaa     480
aacctagcag cagcagcagc attccacggg tcggatgaca tatcatatcc tcgtgcggag     540
cggactctac ggcgagtcca gctgtggctg cggaatattc cggcggaagc gcggggagag     600
cgacggcggc ctccggtggg acccggggcg agcgggagat cgcgaagaa gtgttcggcgc    660
tgatgtcgct ggaatattcg cgccagctgt ggctgccggt gcgacctgct gaccagacga     720
ccaatggcag tggccaccgc ctctcccctct tgctgttgga gttggatcca cggaccactc    780
tccatccaac atccatcaca gattggcgga cgattagccg agactaatcg ctattctcaa     840
cacttttaaa accgtacgtg caaaatgcta aggggccgtt                            880
```

<210> SEQ ID NO 212
<211> LENGTH: 936
<212> TYPE: DNA
<213> ORGANISM: Zea mays

<400> SEQUENCE: 212

```
catcgtcgtt ccttcctggc gatcgccgct tcctagctat ccggtggcca aagacacggc      60
tagtggtagg ctcgagtgag acgagctctt gctgaagaga gaatgaatgt aacgttaccg     120
cctcctggtc gtaggtgtaa taagttgtaa cgcgagcgtc gttagcaagc acagggtttt    180
gtgtatgtga ggacaagagg aggagcgaga ggaggagcgc agagcgtggc ggggaaggag     240
ggcgtcatgt gtgcgaggaa tctaggacga cttgttggca cttggcagct gggccggggt     300
```

```
gcgtgcgaga tgcaatgcaa gaacaaagcg gacgggcatc acgcctccag gtccaacccg      360
ggggcgccac tcggccgccg ctcattgagg cccaggcgcc aagacggcgg ctccacccac      420
atcacaattg caacaagaa gcacacggct ggggttggga cgcgtcgaat ttttcaccag       480
aaaataccgt ctgatcctgg cgtttcgtca gatgctatgc tacgtgaacg gcaaaaccta     540
gcagcagcag cagcactcag actggacaag aggagggaaa tctttgcgtg ggaaccaaac     600
tgaacgcgaa tcgcacgagt cggatgacat atcctcgtcc ggagcggact cgaccgcgag     660
tccagctgtg gctgcggaat attccggcgg aagcgcgggg agaacgacgg cggcctccgg     720
tgggacccgg ggcgagcggg agatgcgcg aagatgttcg gcgctgatgt cgctggaata      780
ttcgcgccag ctgtggctgc cggtgtgacc tgctgaccag acgaccagtg gcagtggcca     840
ccgcctctcc atcacagatt cgcggacgat tagccgagac taatcgctat tctcaacact     900
tttaaaaccg tgcgtgcaga atgctaaggg cgcgtt                               936
```

```
<210> SEQ ID NO 213
<211> LENGTH: 3250
<212> TYPE: DNA
<213> ORGANISM: Zea mays
<220> FEATURE:
<221> NAME/KEY: misc_feature
<222> LOCATION: (1458)..(1737)
<223> OTHER INFORMATION: n is unknown
<220> FEATURE:
<221> NAME/KEY: misc_feature
<222> LOCATION: (3185)..(3188)
<223> OTHER INFORMATION: n is unknown
<220> FEATURE:
<221> NAME/KEY: misc_feature
<222> LOCATION: (3191)..(3191)
<223> OTHER INFORMATION: n is unknown

<400> SEQUENCE: 213
```

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat    240
caaataaaat gggcccactg cagtcaatta acaggcattc aataggattc acattcctgg   300
gcttctatat atggaagttt gcatacaatg ttttggaaat aaaatgaaat ataaattgct    360
tgcatttagt gtaagttaat actcgctccc ttctcgaata tttgtcgtcc gctagttcat   420
ttttgaacta aaacatgata aataaaaaaa cggaaggagt acatgtttgt aacaggagag   480
cccatgaata cttgcttgta acaggtggag cgctaagtat gcttaggaga actttaggca   540
acttgtattc tttagcactt cgacgcagtt tgtatggtaa tatctactga tagacagaat   600
cctggttttg gatttttaat ttttcctgct tttggttaca cctctacagt cccatactcg   660
cagtccaata gtcatggtc tgataataaa ccaattaaga aggactcatg tctcagtcat    720
tatgacttga gcataggagt tgagatcaag aaatatttga gttgcagctt aaggtccaga   780
gaggaaatcc ccatacactt gcttgtaacg gtatgaatgt atgatcattt tttttttcaag   840 gtaacatttt ctagcatctt cacctgtcta cttgactgaa tgcagtatat attagttgta   900
ataactactg gccttctgct gtgcacaaaa ggcgggtatt accacttgca gaaatttgtc    960
gggtaaaggt aattgccagt taccttgtgt tcttcccttg atcaggaaca cctgaggag   1020 gatgcgctgt ggttgaaccg aagccctgtg agcgaagtac tgatgacaga aagagcggaa  1080
```

```
gataagataa gaaaggaacc cttgcgcggc aaggcctggt gacatagagg tagtgcgagg      1140
ctcataccgc cgccgctggc aggttccagg cctgtgcttt tcttgccctg tatcccagt      1200 ctatacttct gcgcacatca gacgagcctc agtgtttcgg cacagtggtg caacagaaaa      1260
ggagagtgct ggtaggtaac gctgaggcgg tgaagaaaga gaggtcagac ggacctggag      1320
gtggcttttt aactggtaaa gagtgaggtc tttcatgccc atcaatctga gcaccgactt      1380
gggtgttgct cctgttcgca ggaagcacaa gaaatggtca gtactccaca ccataagcat      1440
gtcggtggtg tgttggannn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnaaa      1740
aaaaaaaaaa aaaaaagaat gcacaccgac atgctctgta gcacaagcac catactggcg      1800
aactggagag gtctcggctc atcaagcaat cgccttggtg tcggacgggg tcatcaagac      1860
aagacgacta gacgagcact acatatagac gggaacgtac gggaggaagg aaggaaaacg      1920
agagcgagga ctcactgtcc ggtccgccca gcttggtgac ggcgtcgacg aagcgctggt      1980
ggaggtccgg cgtccagcgc agccgcggct tggggtcccg tgacgccgcc ccgtcgtagc      2040
cgtagctccc ctgcatcgtc gttccttcct ggcgatcgcc gcttcctagc tatccggtgg      2100
ccaaagacac ggctagtggt aggctcgagt gagacgagct cttgctgaag agagaatgaa      2160
tgtaacgtta ccgcctcctg gtcgtaggtg taataagttg taacgcgagc gtcgttagca      2220
agcacagggg tttgtgtatg tgaggacaag aggaggagcg agaggaggag cgcagagcgt      2280
ggcggggaag gagggcgtca tgtgtgcgag gaatctagga cgacttgttg gcacttggca      2340
gctgggccgg ggtgcgtgcg agatgcaatg caagaacaaa gcggacgggc atcacgcctc      2400
caggtccaac ccgggggcgc cactcggccg ccgctcattg aggcccaggc gccaagacgg      2460
cggctccacc cacatcacaa ttggcaacaa gaagcacacg gctggggttg ggacgcgtcg      2520
aatttttcac cagaaaatac cgtctgatcc tggcgtttcg tcagatgcta tgctacgtga      2580
acggcaaaac ctagcagcag cagcagcact cagactggac aagaggaggg aaatctttgc      2640
gtgggaacca aactgaacgc gaatcgcacg agtcggatga catatcctcg tccggagcgg      2700
actcgaccgc gagtccagct gtggctgcgg aatattccgg cggaagcgcg gggagaacga      2760
cggcggcctc cggtgggacc cggggcgagc gggagatgcg gcgaagatgt tcggcgctga      2820
tgtcgctgga atattcgcgc cagctgtggc tgccggtgtg acctgctgac cagacgacca      2880
gtggcagtgg ccaccgcctc tccatcacag attcgcggac gattagccga gactaatcgc      2940
tattctcaac acttttaaaa ccgtgcgtgc agaatgctaa gggcgcgttc gtttgcacag      3000
caatagacat ggatttattt cagctcatca aaatctatat aaattaaaga agtaatccgg      3060
ctagaaatta atccggagct tcaatcccta acaaccgaac agggtctaag cctgctagat      3120
tcgagcatct gcgtgactct actttggctc ttctcgtacg atgcgacttg acgatgcatt      3180
tgggnnnncc nttagcgaca ctctcctgat tagtcccacg gaaacgcaac tctaccacta      3240
tcagccgccg                                                             3250
```

<210> SEQ ID NO 214
<211> LENGTH: 3653
<212> TYPE: DNA
<213> ORGANISM: Zea mays

<220> FEATURE:
<221> NAME/KEY: misc_feature
<222> LOCATION: (2001)..(2142)
<223> OTHER INFORMATION: n is unknown
<220> FEATURE:
<221> NAME/KEY: misc_feature
<222> LOCATION: (3588)..(3595)
<223> OTHER INFORMATION: n is unknown

<400> SEQUENCE: 214

```
tcgcatctgc agcttctttt gcacctgatt acagacataa gcacttgtag cgtttatgga    60
agaaagtttt ggagtgcaaa tctcatgaca atgatgtaaa tctatcttgc ctcagtttgt   120
tcttgtagtt tcctttggac ttgaatttga taccttagtg catcgctaag tgctatttct   180
ctgattcaca taagaaatgt gatacaaatg gttagttcaa tcaatgcaga aaagttcaac   240
caaataaaat gggcccactg cagtcaatta acaggcattc ataggattc acattcctgg    300
gcttctatat atggaagttt gcatacaaag ttttgaaat aaaatggaat agaaattgct    360
tgcatttagt gtaagttaat actagctccg ttctcgaata tttgtcgtcc gctagttcat   420
ttttgaacta aaacacgaca aataaaaaaa cggaaggagt acatgtttgt aacaggtgag   480
cccctgaata cttgcttgta acaggtggag cactaagtat gcttagaact ttaggcaact   540
tgtattcttt agcacttcga cgccgtttgt atggtaatat ctactgatag acagaatcct   600
ggttttggat tttttttta tttttcctgt ttttggttac acctacag tcccatactc      660
gcagtccaat aatacatggt ctgataataa accaattaag aaggactcat gtctcagtca   720
ttaggctgtc tccaacaacg tcctctatat tcatcctcta tatctgtcct ttacagtctc   780
ctctaaaaaa tttcatccta tatatctcat ttctctccaa caacgtcctc taaatcacgt   840
cctctatact caaatactca tattaaagac attttttaat tttattttt atacatacgt     900
aattatcata ctctcaaatg tattgtgcat attttagttt tgctaaaccg gttatttaaa   960
gtagtcaaat ggatagagga ccgtttagag aaactctata tatagagaat tcagcagcgt  1020
cctctaaatt taaaggaccg tttagaggac gttgctggag agcgtagagg accgtttggt  1080
cctctatatt tagggtagag aacccttag ggggccttgt tggagccagc cttatgactt    1140
gagcatagga gttgagatca agaaatatgt gagttgcagc ttaaggttca gagaggaaat  1200
ccccatacac ttgcttgtaa cggtatgatc atatcttttc aaggtaacat tttctagcat  1260
cttcagctgt ctacttgact gaatgcagta tatattagtt gtaataaata ctgcccttct  1320
gctgtgcaca aaaggcgggt attaccactt gcagaaattt gtcgggtaaa ggtaattgcc  1380
agttaccttg tgttcttccc ttgatcagga acacctggag gaggatgcgc tgtggttgaa  1440
ccgaagccct gtgagcgaag tactgatgac agaagagcg gaagataaga taagaaagga   1500
acccttgcgc ggcaaggcct ggtgacatag aggtagtgcg aggctcatac cgccgccgct  1560
ggcaggttcc aggcctgtgc ttttcttgcc ctgtatcccc agtctatact tctgcgcaca  1620
tcagacgagc ctcagtgttt cggcacagtg gtgcaacaga aaggagagt gctggtaggt   1680
aacgctgagg cggtgaagaa agagaggtca gacggacctg gaggtggctt tttaactggt  1740
aaagagtgag gtcttcatg cccatcaatc tgagcaccga cttgggtgtt gctcctgttc    1800
gcaggaagca caagaaatgg tcagtactcc acagcgtagg catgtcggtg gtgtgttgga  1860
ggaggcaaga ttcagatgat tattatatga gctcgaaaag ctagagaatg gatgttcaga  1920
cttgagagct ctgatttgag aggaattgca cttgtcgttt tcccaaggcg acgcggcctt  1980
tttccagagt ttttttttt nnnnnnnnnn nnnnnnnnnn nnnnnnnnnn nnnnnnnnnn   2040
```

```
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnaaaaaaaa aaaaaaaaag    2160
aatgcacacc gacatgctct gtagcacaag caccatactg gcgaactgga gaggtctcgg    2220
ctcatcaagc aatcgccttg gtgtcggacg gggtcatcaa gacaagacga ctagacgagc    2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gtcgttcctt cctggcgatc gccgcttcct agctatccgg tggccaaaga cacggctagt    2520
ggtaggctcg agtgagacga gctcttgctg aagagagaat gaatgtaacg ttaccgcctc    2580
ctggtcgtag gtgtaataag ttgtaacgcg agcgtcgtta gcaagcacag gggtttgtgt    2640
atgtgaggac aagaggagga gcgagaggag gagcgcagag cgtggcgggg aaggagggcg    2700
tcatgtgtgc gaggaatcta ggacgacttg ttggcacttg gcagctgggc cggggtgcgt    2760
gcgagatgca atgcaagaac aaagcggacg ggcatcacgc ctccaggtcc aacccggggg    2820
cgccactcgg ccgccgctca ttgaggccca ggcgccaaga cggcggctcc acccacatca    2880
caattggcaa caagaagcac acggctgggg ttgggacgcg tcgaattttt caccagaaaa    2940
taccgtctga tcctggcgtt tcgtcagatg ctatgctacg tgaacggcaa acctagcag    3000 cagcagcagc actcagactg gacaagagga gggaaatctt tgcgtgggaa ccaaactgaa    3060
cgcgaatcgc acgagtcgga tgacatatcc tcgtccggag cggactcgac cgcgagtcca    3120
gctgtggctg cggaatattc cggcggaagc gcggggagaa cgacggcggc ctccggtggg    3180
acccggggcg agcgggagat gcggcgaaga tgttcggcgc tgatgtcgct ggaatattcg    3240
cgccagctgt ggctgccggt gtgacctgct gaccagacga ccagtggcag tggccaccgc    3300
ctctccatca cagattcgcg gacgattagc cgagactaat cgctattctc aacactttta    3360
aaaccgtgcg tgcagaatgc taagggcgcg ttcgtttgca cagcaataga catgggattta    3420 tttcagctca tcaaaatcta tataaattaa agaagtaatc cggctagaaa ttaatccgga    3480
gcttcaatcc ctaacaaccg aacagggtct aagcctgcta gattcgagca tctgcgtgac    3540
tctactttgg ctcttctcgt acgatgcgac ttgacgatgc atttgggnnn nnnnntagcg    3600
acactctcct gattagtccc acggaaacgc aactctacca ctatcagccg ccg            3653
```

<210> SEQ ID NO 215
<211> LENGTH: 3586
<212> TYPE: DNA
<213> ORGANISM: Zea mays
<220> FEATURE:
<221> NAME/KEY: misc_feature
<222> LOCATION: (2001)..(2139)
<223> OTHER INFORMATION: n is unknown

<400> SEQUENCE: 215

```
tcgcatctgc agcttctttt gcacctgatt acagacataa gcacttgtag cgtttatgga     60
agaaagtttt ggagtgcaaa tctcatgaca atgatgtaaa tctatcttgc ctcagttttgt   120 tcttgtagtt tcctttggac ttgaatttga taccttagtg catcgctaag tgctatttct    180
ctgattcaca taagaaatgt gatacaaatg gttagttcaa tcaatgcaga aaagttcaac    240
caaataaaat gggcccactg cagtcaatta acaggcattc aataggattc acattcctgg    300
gcttctatat atggaagttt gcatacaaag ttttgaaat aaaatggaat agaaattgct     360
tgcatttagt gtaagttaat actagctccg ttctcgaata tttgtcgtcc gctagttcat    420
```

```
ttttgaacta aaacacgaca aataaaaaaa cggaaggagt acatgtttgt aacaggtgag    480
cccctgaata cttgcttgta acaggtggag cactaagtat gcttagaact ttaggcaact    540
tgtattcttt agcacttcga cgccgtttgt atggtaatat ctactgatag acagaatcct    600
ggttttggat tttttttta ttttcctgt ttttggttac acctctacag tcccatactc      660
gcagtccaat aatacatggt ctgataataa accaattaag aaggactcat gtctcagtca    720
ttaggctgtc tccaacaacg tcctctatat tcatcctcta tatctgtcct ttacagtctc    780
ctctaaaaaa tttcatccta tatatctcat ttctctccaa caacgtcctc taaatcacgt    840
cctctatact caaatactca tattaaagac attttttaat tttatttttt atacatacgt    900
aattatcata ctctcaaatg tattgtgcat attttagttt tgctaaaccg gttatttaaa    960
gtagtcaaat ggatagagga ccgtttagag aaactctata tatagagaat tcagcagcgt    1020
cctctaaatt taaaggaccg tttagaggac gttgctggag agcgtagagg accgtttggt    1080
cctctatatt tagggtagag aaccctttag ggggccttgt tggagccagc cttatgactt    1140
gagcatagga gttgagatca agaaatatgt gagttgcagc ttaaggttca gagaggaaat    1200
ccccatacac ttgcttgtaa cggtatgatc atatcttttc aaggtaacat tttctagcat    1260
cttcagctgt ctacttgact gaatgcagta tatattagtt gtaataaata ctgcccttct    1320
gctgtgcaca aaaggcgggt attaccactt gcagaaattt gtcgggtaaa ggtaattgcc    1380
agttaccttg tgttcttccc ttgatcagga acacctggag gaggatgcgc tgtggttgaa    1440
ccgaagccct gtgagcgaag tactgatgac agaaagagcg gaagataaga taagaaagga    1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
tcagacgagc ctcagtgttt cggcacagtg gtgcaacaga aaaggagagt gctggtaggt    1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
ggaggcaaga ttcagatgat tattatatga gctcgaaaag ctagagaatg gatgttcaga    1920
cttgagagct ctgatttgag aggaattgca cttgtcgttt tcccaaggcg acgcggcctt    1980
tttccagagt ttttttttt nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnna aaaaaaaaaa aaaaaaaaag    2160
aatgcacacc gacatgctct gtagcacaag caccatactg gcgaactgga gaggtctcgg    2220
ctcatcaagc aatcgccttg gtgtcggacg gggtcatcaa gacaagacga ctagacgagc    2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gtcgttcctt cctggcgatc gccgcttcct agctatccgg tggccaaaga cacggctagt    2520
ggtaggctcg agtgagacga gctccttgctg aagagagaat gaatgtaacg ttaccgcctc    2580
ctggtcgtag gtgtaataag ttgtaacgcg agcgtcgtta gcaagcacag gggtttgtgt    2640
atgtgaggac aagaggagga gcgagaggag gagcgcagag cgtggcgggg aaggagggcg    2700
tcatgtgtgc gaggaatcta ggacgacttg ttggcacttg gcagctgggc cggggtgcgt    2760
```

```
gcgagatgca atgcaagaac aaagcggacg ggcatcacgc ctccaggtcc aacccggggg    2820
cgccactcgg ccgccgctca ttgaggccca ggcgccaaga cggcggctcc acccacatca    2880
caattggcaa caagaagcac acggctgggg ttgggacgcg tcgaattttt caccagaaaa    2940
taccgtctga tcctggcgtt tcgtcagatg ctatgctacg tgaacggcaa aacctagcag    3000
cagcagcagc actcagactg gacaagagga gggaaatctt tgcgtgggaa ccaaactgaa    3060
cgcgaatcgc acgagtcgga tgacatatcc tcgtccggag cggactcgac cgcgagtcca    3120
gctgtggctg cggaatattc cggcggaagc gcggggagaa cgacggcggc ctccggtggg    3180
acccggggcg agcgggagat gcggcgaaga tgttcggcgc tgatgtcgct ggaatattcg    3240
cgccagctgt ggctgccggt gtgacctgct gaccagacga ccagtggcag tggccaccgc    3300
ctctccatca cagattcgcg gacgattagc cgagactaat cgctattctc aacactttta    3360
aaaccgtgcg tgcagaatgc taagggcgcg ttcgtttgca cagcaataga catggattta    3420
tttcagctca tcaaaatcta tataaattaa agaagtaatc cggctagaaa ttaatccgga    3480
gcttcaatcc ctaacaaccg aacagggtct aagcctgcta gattcgagca tctgcgtgac    3540
tctactttgg ctcttctcgt acgatgcgac ttgacgatgc atttgg              3586
```

<210> SEQ ID NO 216
<211> LENGTH: 3588
<212> TYPE: DNA
<213> ORGANISM: Zea mays
<220> FEATURE:
<221> NAME/KEY: misc_feature
<222> LOCATION: (2000)..(2143)
<223> OTHER INFORMATION: n is unknown

<400> SEQUENCE: 216

```
tcgcatctgc agcttctttt gcacctgatt acagacataa gcacttgtag cgtttatgga      60
agaaagtttt ggagtgcaaa tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaac     240
caaataaaat gggcccactg cagtcaatta acaggcattc aataggattc acattcctgg     300
gcttctatat atggaagttt gcatacaaag ttttgaaat aaaatggaat agaaattgct      360
tgcatttagt gtaagttaat actagctccg ttctcgaata tttgtcgtcc gctagttcat     420
ttttgaacta aaacacgaca aataaaaaaa cggaaggagt acatgtttgt aacaggtgag     480
cccctgaata cttgcttgta acaggtggag cactaagtat gcttagaact ttaggcaact     540
tgtattcttt agcacttcga cgccgtttgt atggtaatat ctactgatag acagaatcct     600
ggttttggat ttttttttta tttttcctgt ttttggttac acctctacag tcccatactc     660
gcagtccaat aatacatggt ctgataataa accaattaag aaggactcat gtctcagtca     720
ttaggctgtc tccaacaacg tcctctatat tcatcctcta tatctgtcct ttacagtctc     780
ctctaaaaaa tttcatccta tatatctcat ttctctccaa caacgtcctc taaatcacgt     840
cctctatact caaatactca tattaaagac atttttaat tttatttttt atacatacgt      900
aattatcata ctctcaaatg tattgtgcat attttagttt tgctaaaccg gttatttaaa     960
gtagtcaaat ggatagagga ccgtttagag aaactctata tatagagaat tcagcagcgt    1020
cctctaaatt taaggaccg tttagaggac gttgctggag agcgtagagg accgtttggt     1080
cctctatatt tagggtagag aaccccttag ggggccttgt tggagccagc cttatgactt    1140
gagcatagga gttgagatca agaaatatgt gagttgcagc ttaaggttca gagaggaaat    1200
```

```
ccccatacac ttgcttgtaa cggtatgatc atatctttc aaggtaacat tttctagcat    1260
cttcagctgt ctacttgact gaatgcagta tatattagtt gtaataaata ctgcccttct    1320
gctgtgcaca aaaggcgggt attaccactt gcagaaattt gtcgggtaaa ggtaattgcc    1380
agttaccttg tgttcttccc ttgatcagga cacctggag gaggatgcgc tgtggttgaa     1440
ccgaagccct gtgagcgaag tactgatgac agaagagcg aagataaga taagaaagga     1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
tcagacgagc ctcagtgttt cggcacagtg gtgcaacaga aaggagagt gctggtaggt     1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
ggaggcaaga ttcagatgat tattatatga gctcgaaaag ctagagaatg gatgttcaga    1920
cttgagagct ctgatttgag aggaattgca cttgtcgttt tcccaaggcg acgcggcctt    1980
tttccagagt ttttttttttn nnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnaaaaaaa aaaaaaaaag     2160
aatgcacacc gacatgctct gtagcacaag caccatactg gcgaactgga gaggtctcgg    2220
ctcatcaagc aatcgcctg gtgtcggacg gggtcatcaa gacaagacga ctagacgagc     2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gtcgttcctt cctggcgatc gccgcttcct agctatccgg tggccaaaga cacggctagt    2520
ggtaggctcg agtgagacga gctcttgctg aagagagaat gaatgtaacg ttaccgcctc    2580
ctggtcgtag gtgtaataag ttgtaacgcg agcgtcgtta gcaagcacag gggtttgtgt    2640
atgtgaggac aagaggagga gcgagaggag gagcgcagag cgtggcgggg aaggagggcg    2700
tcatgtgtgc gaggaatcta ggacgacttg ttggcacttg gcagctgggc cggggtgcgt    2760
gcgagatgca atgcaagaac aaagcggacg ggcatcacgc ctccaggtcc aacccggggg    2820
cgccactcgg ccgccgctca ttgaggccca ggcgccaaga cggcggctcc acccacatca    2880
caattggcaa caagaagcac acggctgggg ttggacgcg tcgaatttt caccagaaaa      2940
taccgtctga tcctggcgtt tcgtcagatg ctatgctacg tgaacggcaa aacctagcag    3000
cagcagcagc actcagactg gacaagagga gggaaatctt tgcgtgggaa ccaaactgaa    3060
cgcgaatcgc acgagtcgga tgacatatcc tcgtccggag cggactcgac cgcgagtcca    3120
gctgtggctg cggaatattc cggcggaagc gcggggagaa cgacggcggc ctccggtggg    3180
acccggggcg agcgggagat gcggcgaaga tgttcggcgc tgatgtcgct ggaatattcg    3240
cgccagctgt ggctgccggt gtgacctgct gaccagacga ccagtggcag tggccaccgc    3300
ctctccatca cagattcgcg gacgattagc cgagactaat cgctattctc aacactttta    3360
aaaccgtgcg tgcagaatgc taagggcgcg ttcgtttgca cagcaataga catggattta    3420
tttcagctca tcaaaatcta tataaattaa agaagtaatc cggctagaaa ttaatccgga    3480
gcttcaatcc ctaacaaccg aacagggtct aagcctgcta gattcgagca tctgcgtgac    3540
```

```
tctactttgg ctcttctcgt acgatgcgac ttgacgatgc atttgggc        3588
```

<210> SEQ ID NO 217
<211> LENGTH: 3548
<212> TYPE: DNA
<213> ORGANISM: Zea mays
<220> FEATURE:
<221> NAME/KEY: misc_feature
<222> LOCATION: (1866)..(2143)
<223> OTHER INFORMATION: n is unknown
<220> FEATURE:
<221> NAME/KEY: misc_feature
<222> LOCATION: (3483)..(3489)
<223> OTHER INFORMATION: n is unknown

<400> SEQUENCE: 217

```
tcgcatctgc agcttctttt gcacctgatt acagacataa gcacttgtag cgtttatgga    60
agaaagtttt ggagtgcaaa tctcatgaca atgatgtaaa tctatcttgc ctcagtttgt   120
tcttgtagtt tcctttggac ttgaatttga taccttagtg catcgctaag tgctatttct   180
ctgattcaca taagaaatgt gatacaaatg gttagttcaa tcaatgcaga aaagttcaac   240
caaataaaat gggcccactg cagtcaatta acaggcattc aataggattc acattcctgg   300
gcttctatat atggaagttt gcatacaaag ttttttgaaat aaaatggaat agaaattgct   360
tgcatttagt gtaagttaat actagctccg ttctcgaata tttgtcgtcc gctagttcat   420
ttttgaacta aaacacgaca aataaaaaaa cggaaggagt acatgtttgt aacaggtgag   480
cccctgaata cttgcttgta acaggtggag cactaagtat gcttagaact ttaggcaact   540
tgtattcttt agcacttcga cgccgtttgt atggtaatat ctactgatag acagaatcct   600
ggttttggat tttttttta tttttcctgt ttttggttac acctctacag tcccatactc   660
gcagtccaat aatacatggt ctgataataa accaattaag aaggactcat gtctcagtca   720
ttaggctgtc tccaacaacg tcctctatat tcatcctcta tatctgtcct ttacagtctc   780
ctctaaaaaa tttcatccta tatatctcat ttctctccaa caacgtcctc taaatcacgt   840
cctctatact caaatactca tattaaagac atttttaat tttattttt atacatacgt     900
aattatcata ctctcaaatg tattgtgcat atttagttt tgctaaaccg gttatttaaa    960
gtagtcaaat ggatagagga ccgtttagag aaactctata tatagagaat tcagcagcgt   1020
cctctaaatt taaggaccg tttagaggac gttgctggag agcgtagagg accgtttggt    1080
cctctatatt tagggtagag aacccttag ggggccttgt tggagccagc cttatgactt     1140
gagcatagga gttgagatca agaaatatgt gagttcagc ttaaggttca gagaggaaat     1200
ccccatacac ttgcttgtaa cggtatgatc atatcttttc aaggtaacat tttctagcat   1260
cttcagctgt ctacttgact gaatgcagta tatattagtt gtaataaata ctgcccttct   1320
gctgtgcaca aaaggcgggt attaccactt gcagaaattt gtcgggtaaa ggtaattgcc   1380
agttaccttg tgttcttccc ttgatcagga cacctggag gaggatgcgc tgtggttgaa    1440
ccgaagcct gtgagcgaag tactgatgac agaaagagcg gaagataaga taagaaagga    1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
tcagacgagc ctcagtgttt cggcacagtg gtgcaacaga aaggagagt gctggtaggt     1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
```

```
ggaggnnnnn nnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnaaaaaaa aaaaaaaaag    2160
aatgcagacc gacatgctct gtagcacaag caccatactg gcgaactgga gaggtctcgg    2220
ctcatcaagc aatcgccttg gtgtcggacg gggtcatcaa gacaagacga ctagacgagc    2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gccgttcctt cctggcgatc gccgctccct agctatccgg tggccaaaga cacggctagt    2520
ggtaggctcg agcgagacga gctcttggtg aagagagaat gaatgtaacg ttaccgcctc    2580
ctggtcgtag gggtgtgtgt atgtgaggac aagaggagga gcgagaggag gagcgcagag    2640
cgtggcgggg aaggagggcg tcatgtgtgc gaggaatcta ggacgacttg ttggcagctg    2700
ggccggggtg cgtgcgagat gcaatgcaag aacaaagcgg acgggcatct cgctcggcca    2760
cgcttccaag tccatccggg gggcgccact cggccgccgc tcattgaggc ccaggcgcca    2820
agacggcggc tccacccacg tcacaattgg caacaagaag cacacggctg gggctgggac    2880
gcgtcgaatt tttcaccaga aaataccgtc tgatcctggc gtttcgtgaa cggcaaaacc    2940
tagcagcagc agcagcattc cacgggtcgg atgacatatc atatcctcgt gcggagcgga    3000
ctctacggcg agtccagctg tggctgcgga atattccggc ggaagcgcgg ggagagcgac    3060
ggcggcctcc ggtgggaccc ggggcgagcg ggagatgcgg cgaagatgtt cggcgctgat    3120
gtcgctggaa tattcgcgcc agctgtggct gccggtgcga cctgctgacc agacgaccaa    3180
tggcagtggc caccgcctct ccctcttgct gttggagttg gatccacgga ccactctcca    3240
tccaacatcc atcacagatt ggcggacgat tagccgagac taatcgctat tctcaacact    3300
tttaaaaccg tacgtgcaaa atgctaaggg gccgttcgtt tcttagccgg aatggcggtt    3360
tgtttctcta atttatataa gttttgatta gctgtattga ttcctgatcc aattctgaac    3420
aaacgaacaa aacctgctag attcgagcat ctgcgtgact ctactttggc ccttctcgta    3480
cgnnnnnnnt ggcgttcctc tagcgtcact ttccccgga  aacgcaactc taccactatc    3540
agccgccg                                                              3548
```

<210> SEQ ID NO 218
<211> LENGTH: 3548
<212> TYPE: DNA
<213> ORGANISM: Zea mays
<220> FEATURE:
<221> NAME/KEY: misc_feature
<222> LOCATION: (2003)..(2144)
<223> OTHER INFORMATION: n is unknown
<220> FEATURE:
<221> NAME/KEY: misc_feature
<222> LOCATION: (3446)..(3446)
<223> OTHER INFORMATION: n is unknown
<220> FEATURE:
<221> NAME/KEY: misc_feature
<222> LOCATION: (3490)..(3490)
<223> OTHER INFORMATION: n is unknown

<400> SEQUENCE: 218

```
tcgcatctgc agcttctttt gcacctgatt acagacataa gcacttgtag cgtttatgga        60
agaaagtttt ggagtgcaaa tctcatgaca atgatgtaaa tctatcttgc ctcagtttgt       120
tcttgtagtt tcctttggac ttgaatttga taccttagtg catcgctaag tgctatttct       180
ctgattcaca taagaaatgt gatacaaatg gttagttcaa tcaatgcaga aaagttcaac       240
caaataaaat gggcccactg cagtcaatta acaggcattc aataggattc acattcctgg       300
gcttctatat atggaagttt gcatacaaag ttttttgaaat aaaatggaat agaaattgct       360
tgcatttagt gtaagttaat actagctccg ttctcgaata tttgtcgtcc gctagttcat       420
ttttgaacta aaacacgaca aataaaaaaa cggaaggagt acatgtttgt aacaggtgag       480
cccctgaata cttgcttgta acaggtggag cactaagtat gcttagaact ttaggcaact       540
tgtattcttt agcacttcga cgccgtttgt atggtaatat ctactgatag acagaatcct       600
ggttttggat ttttttttta tttttcctgt ttttggttac acctctacag tcccatactc       660
gcagtccaat aatacatggt ctgataataa accaattaag aaggactcat gtctcagtca       720
ttaggctgtc tccaacaacg tcctctatat tcatcctcta tatctgtcct ttacagtctc       780
ctctaaaaaa tttcatccta tatatctcat ttctctccaa caacgtcctc taaatcacgt       840
cctctatact caaatactca tattaaagac atttttttaat tttatttttt atacatacgt       900
aattatcata ctctcaaatg tattgtgcat attttagttt tgctaaaccg gttatttaaa       960
gtagtcaaat ggatagagga ccgtttagag aaactctata tatagagaat tcagcagcgt      1020
cctctaaatt taaggaccg tttagaggac gttgctggag agcgtagagg accgtttggt      1080
cctctatatt tagggtagag aacccttttag ggggccttgt tggagccagc cttatgactt      1140
gagcatagga gttgagatca agaaatatgt gagttgcagc ttaaggttca gagaggaaat      1200
ccccatacac ttgcttgtaa cggtatgatc atatcttttc aaggtaacat tttctagcat      1260
cttcagctgt ctacttgact gaatgcagta tatattagtt gtaataaata ctgcccttct      1320
gctgtgcaca aaaggcgggt attaccactt gcagaaattt gtcgggtaaa ggtaattgcc      1380
agttaccttg tgttcttccc ttgatcagga acacctggag gaggatgcgc tgtggttgaa      1440
ccgaagccct gtgagcgaag tactgatgac agaaagagcg gaagataaga taagaaagga      1500
acccttgcgc ggcaaggcct ggtgacatag aggtagtgcg aggctcatac cgccgccgct      1560
ggcaggttcc aggcctgtgc ttttcttgcc ctgtatcccc agtctatact tctgcgcaca      1620
tcagacgagc ctcagtgttt cggcacagtg gtgcaacaga aaggagagt gctggtaggt      1680 aacgctgagg cggtgaagaa agagaggtca gacggacctg gaggtggctt tttaactggt      1740
aaagagtgag gtctttcatg cccatcaatc tgagcaccga cttgggtgtt gctcctgttc      1800
gcaggaagca caagaaatgg tcagtactcc acagcgtagg catgtcggtg gtgtgttgga      1860
ggaggcaaga ttcagatgat tattatatga gctcgaaaag ctagagaatg gatgttcaga      1920
cttgagagct ctgatttgag aggaattgca cttgtcgttt tcccaaggcg acgcggcctt      1980
tttccagagt ttttttttttt ttnnnnnnnn nnnnnnnnnn nnnnnnnnnn nnnnnnnnnn      2040
nnnnnnnnnn nnnnnnnnnn nnnnnnnnnn nnnnnnnnnn nnnnnnnnnn nnnnnnnnnn      2100
nnnnnnnnnn nnnnnnnnnn nnnnnnnnnn nnnnnnnnnn nnnnaaaaaa aaaaaaaaag      2160
aatgcagacc gacatgctct gtagcacaag caccatactg gcgaactgga gaggtctcgg      2220
ctcatcaagc aatcgccttg gtgtcggacg gggtcatcaa gacaagacga ctagacgagc      2280
actacatata gacgggaacg tacgggagga aggaaggaaa acgagagcga ggactcactg      2340
tccggtccgc ccagcttggt gacggcgtcg acgaagcgct ggtggaggtc cggcgtccag      2400
```

```
cgcagccgcg gcttggggtc ccgtgacgcc gccccgtcgt agccgtagct cccctgcatc    2460
gccgttcctt cctggcgatc gccgctccct agctatccgg tggccaaaga cacggctagt    2520
ggtaggctcg agcgagacga gctcttggtg aagagagaat gaatgtaacg ttaccgcctc    2580
ctggtcgtag gggtgtgtgt atgtgaggac aagaggagga gcgagaggag gagcgcagag    2640
cgtggcgggg aaggagggcg tcatgtgtgc gaggaatcta ggacgacttg ttggcagctg    2700
ggccggggtc cgtgcgagat gcaatgcaag aacaaagcgg acgggcatct cgctcggcca    2760
cgcttccaag tccatccggg gggcgccact cggccgccgc tcattgaggc ccaggcgcca    2820
agacggcggc tccacccacg tcacaattgg caacaagaag cacacggctg gggctgggac    2880
gcgtcgaatt tttcaccaga aaataccgtc tgatcctggc gtttcgtgaa cggcaaaacc    2940
tagcagcagc agcagcattc cacgggtcgg atgacatatc atatcctcgt gcggagcgga    3000
ctctacggcg agtccagctg tggctgcgga atattccggc ggaagcgcgg ggagagcgac    3060
ggcggcctcc ggtgggaccc ggggcgagcg ggagatgcgg cgaagatgtt cggcgctgat    3120
gtcgctggaa tattcgcgcc agctgtggct gccggtgcga cctgctgacc agacgaccaa    3180
tggcagtggc caccgcctct ccctcttgct gttggagttg gatccacgga ccactctcca    3240
tccaacatcc atcacagatt ggcggacgat agccgagac taatcgctat tctcaacact     3300
tttaaaaccg tacgtgcaaa atgctaaggg gccgttcgtt tcttagccgg aatggcggtt    3360
tgtttctcta atttatataa gttttgatta gctgtattga ttcctgatcc aattctgaac    3420
aaacgaacaa aacctgctag attcgngcat ctgcgtgact ctactttggc ccttctcgta    3480
cgagcttttn ggcgttcctc tagcgtcact ttcccccgga aacgcaactc taccactatc    3540
agccgccg                                                            3548

<210> SEQ ID NO 219
<211> LENGTH: 3482
<212> TYPE: DNA
<213> ORGANISM: Zea mays
<220> FEATURE:
<221> NAME/KEY: misc_feature
<222> LOCATION: (2003)..(2143)
<223> OTHER INFORMATION: n is unknown

<400> SEQUENCE: 219
tcgcatctgc agcttctttt gcacctgatt acagacataa gcacttgtag cgtttatgga      60
agaaagtttt ggagtgcaaa tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaac     240
caaataaaat gggcccactg cagtcaatta acaggcattc aataggattc acattcctgg     300
gcttctatat atggaagttt gcatacaaag tttttgaaat aaaatggaat agaaattgct     360
tgcatttagt gtaagttaat actagctccg ttctcgaata tttgtcgtcc gctagttcat     420
ttttgaacta aaacacgaca aataaaaaaa cggaaggagt acatgtttgt aacaggtgag     480
cccctgaata cttgcttgta acaggtggag cactaagtat gcttagaact ttaggcaact     540
tgtattcttt agcacttcga cgccgtttgt atggtaatat ctactgatag acagaatcct     600
ggttttggat tttttttta ttttcctgt ttttggttac acctctacag tcccatactc       660
gcagtccaat aatacatggt ctgataataa accaattaag aaggactcat gtctcagtca     720
ttaggctgtc tccaacaacg tcctctatat tcatcctcta tatctgtcct ttacagtctc     780
```

```
ctctaaaaaa tttcatccta tatatctcat ttctctccaa caacgtcctc taaatcacgt    840
cctctatact caaatactca tattaaagac attttttaat tttattttt atacatacgt    900 aattatcata ctctcaaatg tattgtgcat attttagttt tgctaaaccg gttatttaaa   960
gtagtcaaat ggatagagga ccgtttagag aaactctata tatagagaat tcagcagcgt  1020
cctctaaatt taaaggaccg tttagaggac gttgctggag agcgtagagg accgtttggt  1080
cctctatatt tagggtagag aacccttag ggggccttgt tggagccagc cttatgactt   1140
gagcatagga gttgagatca agaaatatgt gagttgcagc ttaaggttca gagaggaaat  1200
ccccatacac ttgcttgtaa cggtatgatc atatcttttc aaggtaacat tttctagcat  1260
cttcagctgt ctacttgact gaatgcagta tatattagtt gtaataaata ctgcccttct  1320
gctgtgcaca aaaggcgggt attaccactt gcagaaattt gtcgggtaaa ggtaattgcc  1380
agttaccttg tgttcttccc ttgatcagga acacctggag gaggatgcgc tgtggttgaa  1440
ccgaagccct gtgagcgaag tactgatgac agaaagagcg aagataaga taagaaagga  1500 acccttgcgc ggcaaggcct ggtgacatag aggtagtgcg aggctcatac cgccgccgct  1560
ggcaggttcc aggcctgtgc ttttcttgcc ctgtatcccc agtctatact tctgcgcaca  1620
tcagacgagc ctcagtgttt cggcacagtg gtgcaacaga aaaggagagt gctggtaggt  1680
aacgctgagg cggtgaagaa agagaggtca gacggacctg gaggtggctt tttaactggt  1740
aaagagtgag gtctttcatg cccatcaatc tgagcaccga cttgggtgtt gctcctgttc  1800
gcaggaagca caagaaatgg tcagtactcc acagcgtagg catgtcggtg gtgtgttgga  1860
ggaggcaaga ttcagatgat tattatatga gctcgaaaag ctagagaatg gatgttcaga  1920
cttgagagct ctgatttgag aggaattgca cttgtcgttt tcccaaggcg acgcggcctt  1980
tttccagagt ttttttttt ttnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnaaaaaaa aaaaaaaaag  2160
aatgcagacc gacatgctct gtagcacaag caccatactg gcgaactgga gaggtctcgg  2220
ctcatcaagc aatcgccttg gtgtcggacg gggtcatcaa gacaagacga ctagacgagc  2280
actacatata gacgggaacg tacgggagga aggaaggaaa acgagagcga ggactcactg  2340
tccggtccgc ccagcttggt gacggcgtcg acgaagcgct ggtggaggtc cggcgtccag  2400
cgcagccgcg gcttggggtc ccgtgacgcc gccccgtcgt agccgtagct cccctgcatc  2460
gccgttcctt cctggcgatc gccgctccct agctatccgg tggccaaaga cacggctagt  2520
ggtaggctcg agcgagacga gctcttggtg aagagagaat gaatgtaacg ttaccgcctc  2580
ctggtcgtag gggtgtgtgt atgtgaggac aagaggagga gcgagaggag gagcgcagag  2640
cgtggcgggg aaggagggcg tcatgtgtgc gaggaatcta ggacgacttg ttggcagctg  2700
ggccggggtg cgtgcgagat gcaatgcaag aacaaagcgg acgggcatct cgctcggcca  2760
cgcttccaag tccatccggg gggcgccact cggccgccgc tcattgaggc ccaggcgcca  2820
agacggcggc tccacccacg tcacaattgg caacaagaag cacacggctg gggctgggac  2880
gcgtcgaatt tttcaccaga aaataccgtc tgatcctggc gtttcgtgaa cggcaaaacc  2940
tagcagcagc agcagcattc cacgggtcgg atgacatatc atatcctcgt gcggagcgga  3000
ctctacggcg agtccagctg tggctgcgga atattccggc ggaagcgcgg ggagagcgac  3060
ggcggcctcc ggtgggaccc ggggcgagcg ggagatgcgg cgaagatgtt cggcgctgat  3120
gtcgctggaa tattcgcgcc agctgtggct gccggtgcga cctgctgacc agacgaccaa  3180
```

```
tggcagtggc caccgcctct ccctcttgct gttggagttg gatccacgga ccactctcca    3240
tccaacatcc atcacagatt ggcggacgat tagccgagac taatcgctat tctcaacact    3300
tttaaaaccg tacgtgcaaa atgctaaggg gccgttcgtt tcttagccgg aatggcggtt    3360
tgtttctcta atttatataa gttttgatta gctgtattga ttcctgatcc aattctgaac    3420
aaacgaacaa aacctgctag attcgagcat ctgcgtgact ctactttggc ccttctcgta    3480
cg                                                                  3482
```

<210> SEQ ID NO 220
<211> LENGTH: 2977
<212> TYPE: DNA
<213> ORGANISM: Zea mays
<220> FEATURE:
<221> NAME/KEY: misc_feature
<222> LOCATION: (1593)..(1739)
<223> OTHER INFORMATION: n is unknown
<220> FEATURE:
<221> NAME/KEY: misc_feature
<222> LOCATION: (2846)..(2846)
<223> OTHER INFORMATION: n is unknown

<400> SEQUENCE: 220

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgc gatacaaatg gttagttcag tcaatgcaga aaagttcaac     240
aaaataaaat gggcccactg cagtcaatta acaggcattc aacagcattc acattcctgg     300
gcctctatat atggaagttt gcatacaaag ttttggaaat aaaatggaat agaaattgct     360
tgcatttagt gtaagttaat acccgctccg ttctcgaata tttgtcgcct gctagttcat     420
ttttgaacta aaacacgaca aataaaaaaa acggaaggag tacatgtttg taacaggaga     480 gccccctgaat acttgcttgt aacaggtgga gcgctaagta tgcttaggag aactttaggc     540
aacttgtatt ctttagcact tcgacgccgt ttgtatggta atatctactg atagacagaa     600
tcctggtttt ggaattttt tattttcct gcttttggtt acacctctac agtcccatac       660
tcgcagtcga ataatacatg gtctgataat aaaccaatta aggactcatg tctcagtcat     720
tatgacttga gcataggagt tcagatcgag aaatatttga gttgcagctt aaggttcaga     780
gaggaaaccc ccatacactt gcttgtaacg gtatgatcat ttttttgaa ggtaacattt      840 tctagcatct tcagctgtct acttgactga atgcagtata tattagttgt aataaatact     900
gcccttctgc tgtgcacaaa aggcgggtat taccacttgc agaaatttgt cgggtaaagg     960
taattgccag ttaccttgtg ttcttccctt catcaggaac acctggagga ggatgcgctg    1020
tggttgaact gaagccctgc gagagaagta ctgatgacag aaagagcgga agataagata    1080
agaaaggaaa cccttgcgcg gcagggcctg gtgacataga ggtagtgcga ggctcatacc    1140
gccgccgctg gcaggttcca ggcctgtgct tttcttgccc tgtatcccca gtctatactt    1200
ctgcgcacat cagacgagcg tcagtgtttc ggcacagtgg tgcaacagaa aaggagagtg    1260
ctggtaggta acgctgaggc ggtgaagaaa gagaggtcag acggacctgg aggtggcttt    1320
ttaactggta aagagtgagg tctttcatgc ccatcaatct gagcaccgac ttgggtgttg    1380
ctcctgttcg caggaagcac aagaaatggt cagtactcca cagcgtaggc atgtcggtgg    1440
tgtgttggag gaggcaagat tcagatgatt attatatgag ctcgaaaagc tagagaatgg    1500
```

| | |
|---|---|
| atgttcagac ttgagagctc tgatttgaga gaaattgcac ttgtcgtttt cccaaggcga | 1560 |
| cgcggccttt tccagaggtt tttttttttt ttnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnc | 1740 |
| tgaaaaaaaa atgcacaccg acatgctctg tagcacaagc accataccgg cgaactggag | 1800 |
| aggtctcggc tcatcaagca atcgccttgg tgtcggacgg ggtcatcaag acaaggcgac | 1860 |
| tagaggagca ctacatctac acggggtgaa cggacgggag cagtggcgga cccaggaact | 1920 |
| gatgacagcc ttggcgagaa tacggtgtga tccccacgcc tgtgctcgtg ccacgtgctg | 1980 |
| cttgcttccg tgcactgtgc tcgcgccttg cccattgcag ccggcgagcc agctcaggcc | 2040 |
| accgcctgcg gtgcctggtg agtccgcccc tggacgggag gaaggaagga aaacgagagc | 2100 |
| gaggactcac tgtccggtcc gcccagcttg gtgacggcgt cgacgaagcg ctggtggagg | 2160 |
| tccggcgtcc agcgcagccg cggcttgggg tcccgtgacg ccgccccgtc gtagccgtag | 2220 |
| ctcccctgca tcgccgttcc ttcctggcga tcgccgctcc ctagctatcc ggtggccaaa | 2280 |
| gacacggcta gtggtaggct cgagcgagac gagctcttgc tgaagagaga atgaatgtag | 2340 |
| cgttaccgcc tcctggtcgt aggggtgtgg gtatgtgagg acaagaggag gagcgagagg | 2400 |
| aggagcgcag agcgtggcgg ggaaggaggg cgtcatgtgt gtgaggaatc taggacgact | 2460 |
| tgttggcagc tgggccgggg tgcgtgcgag atgcaatgca agaacaaagc ggacgggcat | 2520 |
| cacgcctcca gtccaaccc gggggcgcca ctcggccgcc gctcattgag gcccaggcgc | 2580 |
| caagacggcg gctccaccca cgtcacaatt ggcaacaaga agcacacggc tggggctggg | 2640 |
| acgcgtcgaa tttttcacca gaaaataccg tcggcgtttc gtcagatgct atgctacgtg | 2700 |
| aacggcaaaa cctagcagca gcagcagcat tcagactgga caagaggagg gaaatctttg | 2760 |
| cgtgggaacc aaactgaacg cgaatcgcac gagtcggatg acatatcctc gtgcggagcg | 2820 |
| gactcgaccg cgagtccagc tgtggntgcg gaatattccg gcggaagcgc ggggagaacg | 2880 |
| acggcggcct ccggtgggac ccggggcgag cgggagatgc ggcgaagatg ttcggcgctg | 2940 |
| atgtcgctgg aatattcgcg ccagctgtgg ctgccgg | 2977 |

```
<210> SEQ ID NO 221
<211> LENGTH: 3064
<212> TYPE: DNA
<213> ORGANISM: Zea mays
<220> FEATURE:
<221> NAME/KEY: misc_feature
<222> LOCATION: (1464)..(1891)
<223> OTHER INFORMATION: n is unknown
<220> FEATURE:
<221> NAME/KEY: misc_feature
<222> LOCATION: (3023)..(3023)
<223> OTHER INFORMATION: n is unknown
<220> FEATURE:
<221> NAME/KEY: misc_feature
<222> LOCATION: (3027)..(3027)
<223> OTHER INFORMATION: n is unknown

<400> SEQUENCE: 221
```

| | |
|---|---|
| tcgcatctgc agcttctttt gcacctgatt acagacataa gcacttgtag cgtttatgga | 60 |
| agaaaggttt ggagtgcaga tctcatgaca atgatgtaaa tctatcttgc ctcagtttgt | 120 |
| tcttgtagtt tcctttggac ttgaatttga taccttagtg catcgctaag tgctatttct | 180 |
| ctgattcaca taagaaatgt gatacaaatg gttagctcaa tcaatgcaga aaagttcaac | 240 |
| caaataaaat gggcccactg cagtcaatta acaggcattc aataggattc acattcctgg | 300 |

```
gcttctatat atggaagttt gcatacaaag ttttggaaat aaaatggaat ataaattgct    360
tgcatttagt gtaagttaat acccgctctg ttctcgaata tttgtcaccc gctagttcat    420
ttttgaacta aaacacgaca aataaaaaaa cggaaggagt acatgtttgt aacaggagag    480
cccctgaata cttgcttgta acaggtggag cgctaagtat gcttaggaga actttaggca    540
acttgtattc tttagcactt cgacgccgtt tgtatggtaa tatctactga tagacagaat    600
cctggttttg gaattttttt tattttcct gcttttggtt acacctctac agtcccatac     660
tcgcagtcga ataatacatg gtctgataat aaaccaatta aggactcatg tctcagtcat    720
tatgacttga gcataggagt tgagatcaag aaatatttga gttgcagctt aaggttcaga    780
gaggaaatcc ccatacacgt gcttgtaacg gtatggtcat tttttttca aggtaacatt     840
ttctagcatc ttcagctgtc tacttgactg aatgcagtat atattagttg taataaatac    900
tggccttctg ctgtgcacaa aaggcgggta ttaccacttg cagaaatttg tcgggtcaag    960
gtaattgcca gttaccttgt gttcttccct tgatcaggaa cacctggagg aggatgcgct   1020
gtggttgaac tgaagccgcc ctgtgagcga agtactgatg acagaaagag cggaagataa   1080
gataagaaag gaacgcttgc gcggcaaggc ctggtgacat agaggtagtg cgaggctcat   1140
accgccgccg ctggcaggtt cgaggcctgt gcttttcttg ccctgtatcc ccagtctata   1200
cttctgcgca catcgacga gcctcagtgt ttcggcacag tggtgcaaca gaaaaggaga    1260
gtgctggtag gtaacgctga ggcggtgaag aaagagaggt cagacggacc tggaggtggc   1320
ttttaactg gtaaagagtg aggtctttca tgcccatcaa tctgagcacc gacttgggtg    1380
ttgctcctgt tcgcaggaag cacaagaaat ggtcagtact ccacagcgta ggcatgtcgg   1440
tggtgtgttg gaggaggcaa gatnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nggacgggag gaaggaagga aaacgagagc   1920
gaggactcac tgtccggtcc gcccagcttg gtgacggcgt cgacgaagcg ctggtggagg   1980
tccggcgtcc agcgcagccg cggcttgggg tcccgtgacg ccgccccgtc gtagccgtag   2040
ctcccctgca tcgccgttcc ttcctggcga tcgccgctcc ctagctatcc ggtggccaaa   2100
gacacggcta gtggtaggct cgagcgagac gagctcttgc tgaagagaga atgaatgtag   2160
cgttaccgcc tcctggtcgt aggggtgtgg gtatgtgagg acaagaggag gagcgagagg   2220
aggagcgcag agcgtggcgg ggaaggaggg cgtcatgtgt gtgaggaatc taggacgact   2280
tgttggcagc tgggccgggg tgcgtgcgag atgcaatgca agaacaaagc ggacgggcat   2340
cacgcctcca ggtccaaccc gggggcgcca ctcgatcggc cgccgctcat tgaggcccag   2400
gcgccaagac ggcggctcca cccacgtcac aattggcaat aagaagcaca cggctggggc   2460
tgggacgcgt cgaatttttc accagaaaat accgtctgat cctggcgttt cgtcagatgc   2520
tatgctacgt gaacggcaaa acctagcagc agcagcactc agactggaca agaggaggga   2580
aatctttgcg tgggaaccaa actgaacgcg aatcgcacgg gtcggatgac atatcatatc   2640
```

```
ctcgtgcgga gcggactcaa cggcgagtcc agctgtggct gcggaatatt ccggcggaag    2700
cgcggggaga gcgacggcgg cctccggtgg gacccggggc gagcgggaga tgcggcgaag    2760
atgttcggcg ctgatgtcgc tggaatattc gcgccagctg tggctgccgg tgcgacctgc    2820
tgaccagacg accagtggca atggccaccg cctctccatc aacctccat cacagattgg     2880 cggacgatta gccgagacta atcgctattc tcaacacttt aaaaaccgtg cgtgcagaat    2940
gctaagcctg ctagattcga gcatctgcgt gactctactt tggctcttct cgtacgatgc    3000
gacctgacga tgcatttggg cgncctntag cgtcacttcc tgattagtcc cccggaaacg    3060
caac                                                                 3064
```

<210> SEQ ID NO 222
<211> LENGTH: 3087
<212> TYPE: DNA
<213> ORGANISM: Zea mays
<220> FEATURE:
<221> NAME/KEY: misc_feature
<222> LOCATION: (1281)..(1735)
<223> OTHER INFORMATION: n is unknown
<220> FEATURE:
<221> NAME/KEY: misc_feature
<222> LOCATION: (3024)..(3025)
<223> OTHER INFORMATION: n is unknown
<220> FEATURE:
<221> NAME/KEY: misc_feature
<222> LOCATION: (3029)..(3029)
<223> OTHER INFORMATION: n is unknown

<400> SEQUENCE: 222

```
tcgcatctgc agcttctttt gcacctgatt acagacataa gcacttgtag cgtttatgga      60
agaaaggttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagctcaa tcaatgcaga aaagttcaac    240
caaataaaat gggcccactg cagtcaatta acaggcattc aataggattc acattcctgg    300
gcttctatat atggaagttt gcatacaaag ttttggaaat aaaatggaat ataaattgct    360
tgcatttagt gtaagttaat acccgctctg ttctcgaata tttgtcaccc gctagttcat    420
ttttgaacta aaacacgaca aataaaaaaa cggaaggagt acatgttgt aacaggagag     480 cccctgaata cttgcttgta acaggtggag cgctaagtat gcttaggaga actttaggca    540
acttgtattc tttagcactt cgacgccgtt tgtatggtaa tatctactga tagacagaat    600
cctggttttg gaattttttt ttattttcc tgcttttggt tacacctcta cagtcccata     660
ctcgcagtcg aataatacat ggtctgataa taaaccaatt aaggactcat gtctcagtca    720
ttatgacttg agcataggag ttgagatcaa gaaatatttg agttgcagct taaggttcag    780
agaggaaatc cccatacacg tgcttgtaac ggtatggtca ttttttttt caaggtaaca     840 ttttctagca tcttcagctg tctacttgac tgaatgcagt atatattagt tgtaataaat    900
actggccttc tgctgtgcac aaaaggcggg tattaccact tgcagaaatt tgtcgggtca    960
aggtaattgc cagttacctt tgttcttcc cttcatcagg aacacctgga ggaggatgcg     1020
ctgtggttga actgaagccg ccctgtgagc gaagtactga tgcagaaag agcggaagat     1080 aagataagaa aggaacgctt gcgcggcaag gcctggtgac atagaggtag tgcgaggctc    1140
ataccgccgc cgctggcagg ttcgaggcct gtgcttttct tgccctgttt ccccattcta    1200
tacttctgcg cacatcagac gagcctcagt gtttcggcac agtggtgcaa caaaaaaga     1260 gagtgctggt aggtaaccct nnnnnnnnnn nnnnnnnnnn nnnnnnnnnn nnnnnnnnnn     1320
```

```
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnaaaaa     1740 aaaaaaaaaa aaagaatgca gaccgacatg ctctgtagca caagcaccat actggcgaac    1800
tggagaggtc tcggctcatc aagcaatcgc cttggtgtcg acggggtca tcaagacaag     1860 acgactagac gagcactaca tatagacggg aacgtacggg aggaaggaag gaaaacgaga    1920
gcgaggactc actgtccggt ccgcccagct tggtgacggc gtcgacgaag cgctggtgga    1980
ggtccggcgt ccagcgcagc cgcggcttgg ggtcccgtga cgccgccccg tcgtagccgt    2040
agctcccctg catcgccgtt ccttcctggc gatcgccgct ccctagctat ccggtggcca    2100 aagcacggc tagtggtagg ctcgagcgag acgagctctt gctgaagaga gaatgaatgt     2160
agcgttaccg cctcctggtc gtagggggtgt gggtatgtga ggacaagagg aggagcgaga   2220
ggaggagcgc agagcgtggc ggggaaggag ggcgtcatgt gtgtgaggaa tctaggacga    2280
cttgttggca gctgggccgg ggtgcgtgcg agatgcaatg caagaacaaa gcggacgggc    2340
atcacgcctc caggtccaac ccgggggcgc cactcgatcg gccgccgctc attgaggccc    2400
aggcgccaag acggcggctc cacccacgtc acaattggca ataagaagca cacggctggg    2460
gctgggacgc gtcgaatttt tcaccagaaa ataccgtctg atcctggcgt ttcgtcagat    2520
gctatgctac gtgaacggca aaacctagca gcagcagcac tcagactgga caagaggagg    2580
gaaatctttg cgtgggaacc aaactgaacg cgaatcgcac gggtcggatg acatatcata    2640
tcctcgtgcg gagcggactc aacggcgagt ccagctgtgg ctgcgaata ttccggcgga     2700 agcgcgggga gagcgacggc ggcctccggt gggacccggg gcgagcggga gatgcggcga    2760
agatgttcgg cgctgatgtc gctggaatat tcgcgccagc tgtggctgcc ggtgcgacct    2820
gctgaccaga cgaccagtgg caatggccac cgcctctcca tccaacctcc atcacagatt    2880
ggcggacgat tagccgagac taatcgctat tctcaacact ttaaaaaccg tgcgtgcaga    2940
atgctaagcc tgctagattc gagcatctgc gtgactctac tttggctctt ctcgtacgat    3000
gcgacctgac gatgcattgg gcgnncctnt agcgtcactt tcctgattag tcccccggaa    3060
acgcaactct accactatca gccgccg                                         3087
```

<210> SEQ ID NO 223
<211> LENGTH: 2956
<212> TYPE: DNA
<213> ORGANISM: Zea mays
<220> FEATURE:
<221> NAME/KEY: misc_feature
<222> LOCATION: (1584)..(1728)
<223> OTHER INFORMATION: n is unknown

<400> SEQUENCE: 223

```
tcgcatctgc agcttctttt gcacctgatt acagacataa gcacttgtag cgtttatgga     60
agaaagtttt ggagtgcaaa tctcatgaca atgatgtaaa tctgtcttgc ctcagtttgt    120
tcttgtagtt tccctttggac ttgaatttga taccttagtg catcgctaag tgctatttct   180
```

```
ctgattcgca taagaaatgc gatacaaatg gttagttcaa tcaatgcaga aaagttcaac    240
aaaataaaat gggcccactg cagtcaatta acaggcattc aacagcattc acattcctgg    300
gcctctatat atggaagttt gcatacaaag ttttggaaat aaaatggaat agaaattgct    360
tgcatttagt gtaagttaat actccatccg ttcttaaata tttgtcggcc gctagtttat    420
ttttgaacta aaacacgaca aataaaaaaa acggagggag tacatgttta taacaggtga    480
gccgaatact tggttgtaac aggtggggcg ctaagtatgc ttaggagaac tttaggcaac    540
ttgtattctg tagcacttcg acgccgtttg tatggtaata tctactgata gacagaatcc    600 tggttttttgg aaaaaaaaaa ttcctgcttt tggttacacc tctacagtcc catactcgca    660
gtcgaataat acatggtctg ataataaacc aattaaggac tcatgtctca gtcattatga    720
cttgagcata ggagttgaga tcgagaaata tttgagttac agcttaaggt tcagacttca    780
gagaggaaat ccccatacac ttgcttgtaa cggtatgatc attttttttc aaggtaacat    840
tttctagcat cttcacctgt ctacttgact gaatgcagta tatattagtt gtaataaata    900
ctgctcttct gctgtgcaga aaaggcgggt attaccactt gcagaaattt gtcgggtaaa    960
ggtaattgcc agttaccttg tgttcttccc ttcatcagga acacctggag gaggatgcgc   1020
tgtggttgaa ccgaagccct gtgagcgaag tactgatgac agaaagagcg aagataaga   1080 taagaaagga acccttgcgc ggcaaggcct ggtgacatag aggtagtgcg aggctcatac   1140
cgccgccgct ggcaggttcc aggcctgtgc ttttcttgcc ctgtatcccc agtctatact   1200
tctgcgcaca tcagacgagc ctcagtgttt cggcacagtg gtgcaacaga aaggagagt   1260 gctgctaacg ctgaggcggt gaagaaagag aggtcggacg gacctggagg tggctttta   1320 actggtaaag agtgaggtct ttcatgccca tcaatctgag caccgacttg ggtgttgctc   1380
ctgttcgcag gaagcacaag aaatggtcag tactccacag cgtaggcatg tcggtgtgtt   1440
cgaggaggca agattcagat gattattata tgagctcgaa aagctagaga atggatgttc   1500
agacttgaga ggtctgattt gagaggaatt gcacttgtcg ttttcccagg gcgacgcggc   1560
ctttttccag aggctttttt tttnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnaa aaaaaaaaa   1740 aagaatgcag accgcatgc tctgtagcac aagcaccata ctggcgaact ggagaggtct   1800
cggctcatca agcaatcgcc ttggtgtcgg acggggtcat caagacaaga cgactagacg   1860
agcactacat atagacggga acgtacggga ggaaggaagg aaaacgagag cgaggactca   1920
ctgtccggtc cgcccagctt ggtgacggcg tcgacgaagc gctggtggag gtccggcgtc   1980
cagcgcagcc gcggcttggg gtcccgtgac gcaaaccaac gtcgtagccg tagctcccct   2040
gcatcgccgt tccttcctgg cgatcgccgc tccctagcta tccggtggcc aaagacacgg   2100
ctagtggtag gctcgagcga gacgagctct tggtgaagag agaatgaatg taacgttacc   2160
gcctcctggt cgtagggggtg tgtgtatgtg aggacaagag gaggagcgag aggaggagcg   2220
cagagcgtgg cggggaagga gggcgtcatg tgtgcgagga atctcggacg acttgttggc   2280
agctgggccg gggtgcgtgc gagatgcaat gcaagaacaa agcggacggg catctcgctc   2340
ggccacgctt ccaagtccaa ccgggggggcg ccactcggcc gccgctcatt gaggcccagg   2400
cgccaagacg gcggctccac ccacatcaca attggcaaca agaagcacac ggctggggct   2460
gggacgcgtc gaattttttca ccagaaaata ccgtcggcgt ttcgtcagat gctatgctac   2520
gtgaacggca aaacctagca gcagcagcac tcagactgga caagaggagg gaaatcttg   2580
```

```
cgtgggaacc aaactgaacg cgaatcgcac gagtcggatg acatatcctc gtccggagcg    2640
gactcggccg cgagtccagc tgtggctgcg gaatattccg gcggaatcgc ggggagaacg    2700
acggcggcct ccgtgtgggac ccggggcgag cgggagatgc ggcgaagatg ttcggcgctg   2760
atgtcgctgg aatattcgcg ccagctgtgg ctgccggtgt gacctgctga ccagacgacc    2820
agtggcagtg gccaccgcct ctgcatcaca gattggcgga cgattagccg agactaattg    2880
ccattctcaa cacttttaaa accgtgcgtg cagaatgcta agcctgctag attcgagcat    2940
ctgcgtgact ctactt                                                    2956

<210> SEQ ID NO 224
<211> LENGTH: 2965
<212> TYPE: DNA
<213> ORGANISM: Zea mays
<220> FEATURE:
<221> NAME/KEY: misc_feature
<222> LOCATION: (1600)..(1902)
<223> OTHER INFORMATION: n is unknown

<400> SEQUENCE: 224
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctggttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag     840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatccccagt    1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca gcgtaggcat    1440
gtcggtggtg tgttggagga ggcaagattc agatgattat tatatgagct cgaaaagcta    1500
gagaatggat gttcagactt gagagctctg atttgagagr aattgcactt gtcgttttcc    1560
```

```
caaggcgacg cggccttttt ccagaggttt tttttttttn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnacgggagg aaggaaggaa    1920
aacgagagcg aggactcact gtccggtccg cccagcttgg tgacggcgtc gacgaagcgc    1980
tggtggaggt ccggcgtcca gcgcagccgc ggcttgggt cccgtgacgc cgccccgtcg    2040
tagccgtagc tcccctgcat cgccgttcct tcctggcgat cgccgctccc tagctatccg    2100
gtggccaaag acacggctag tggtaggctc gagcgagacg agctcttgct gaagagagaa    2160
tgaatgtagc gttaccgcct cctggtcgta ggggtgtggg tatgtgagga caagaggagg    2220
agcgagagga ggagcgcaga gcgtggcggg aaggagggc gtcatgtgtg cgaggaatct    2280
aggacgactt gttggcagct gggccggggt gcgtgcgaga tgcaatgcaa gaacaaagcg    2340
gacgggcatc tcgctcggcc acgcttccaa gtccatccgg ggggcgccac tcggccgccg    2400
ctcattgagg cccaggcgcc aagacggcgg ctccacccac gtcacaattg caacaagaa    2460 gcacacggct ggggctggga cgcgtcgaat ttttcaccag aaaataccgt ctgatcctgg    2520
cgtttcgtga acgcaaaac ctagcagcag cagcagcatt ccacgggtcg gatgacatat    2580
catatcctcg tgcggagcgg actcaacggc gagtccagct gtggctgcgg aatattccgg    2640
cggaagcgcg gggagagcga cggcggcctc cggtgggacc cggggcgagc gggagatgcg    2700
gcgaagatgt tcggcgctga tgtcgctgga atattcgcgc cagctgtggc tgccggtgcg    2760
acctgctgac cagacgacca gtggcaatgg ccaccgcctc tccatccaac ctccatcaca    2820
gattggcgga cgattagccg agactaatcg ctattctcaa cactttaaaa accgtgcgtg    2880
cagaatgcta agcctgctag attcgagcat ctgcgtgact ctactttggc tcttctcgta    2940
cgatgcgacc tgacgatgca tttgg                                         2965

<210> SEQ ID NO 225
<211> LENGTH: 2855
<212> TYPE: DNA
<213> ORGANISM: Zea mays
<220> FEATURE:
<221> NAME/KEY: misc_feature
<222> LOCATION: (1601)..(1748)
<223> OTHER INFORMATION: n is unknown
<220> FEATURE:
<221> NAME/KEY: misc_feature
<222> LOCATION: (2804)..(2806)
<223> OTHER INFORMATION: n is unknown

<400> SEQUENCE: 225
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
```

```
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gattttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt tttttttcaag   840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatccccagt   1200
ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagr aattgcactt gtcgttttcc   1560
caaggcgacg cggcctttc cagaggtttt ttttttttt nnnnnnnnnn nnnnnnnnnn    1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnntg aaaaaaaaat gcacaccgac atgctctgta gcacaagcac cataccggcg   1800
aactggagag gtctcggctc atcaagcaat cgccttggtg tcggacgggg tcatcaagac   1860
aaggcgacta gaggagcact acatctacac ggggtgaacg gacggagca gtggcggacc    1920
caggaactga tgacagcctt ggcgagaata cggtgtgatc cccacgcctg tgctcgtgcc   1980
acgtgctgct tgcttccgtg cactgtgctc gtgccttgcc cattgcagcc ggcgagccag   2040
ctcaggccac cgcctgcggt gcctggtgag tccgccctg gacgggagga aggaaggaaa    2100
acgagagcga ggactcactg tccggtccgc ccagcttggt gacggcgtcg acgaagcgct   2160
ggtgaggtc cggcgtccag cgcagccgcg gcttggggtc ccgtgacgcc gccccgtcgt    2220
agccgtagct cccctgcatc gccgttcctt cctggcgatc gccgctccct agctatccgg   2280
tggccaaaga cacggctagt ggtaggctcg agcgagacga gctcttgctg aagagagaat   2340
gaatgtagcg ttaccgcctc ctggtcgtag gggtgtgggt atgtgaggac aagaggagga   2400
gcgagaggag gagcgcagag cgtggcgggg aaggagggcg tcatgtgtgc gaggaatcta   2460
ggacgacttg ttggcagctg ggccggggtg cgtgcgagat gcaatgcaag aacaaagcgg   2520
acgggcatct cgctcggcca cgcttccaag tccatccggg gggcgccact cggccgccgc   2580
tcattgaggc ccaggcgcca agacggcggc tccacccacg tcacaattgg caacaagaag   2640
cacacggctg gggctgggac gcgtcgaatt tttcaccaga aaataccgtc tgatcctggc   2700
gtttcgtgaa cggcaaaacc tagcagcagc agcagcattc cacgggtcgg atgacatatc   2760
atatcctcgt gcggagcgga ctcaacggcg agtccagctg tggnnncgga atattccggc   2820
```

```
ggaagcgcgg ggagagcgac ggcggcctcc ggtgg                              2855
```

<210> SEQ ID NO 226
<211> LENGTH: 3212
<212> TYPE: DNA
<213> ORGANISM: Zea mays
<220> FEATURE:
<221> NAME/KEY: misc_feature
<222> LOCATION: (1601)..(1805)
<223> OTHER INFORMATION: n is unknown
<220> FEATURE:
<221> NAME/KEY: misc_feature
<222> LOCATION: (3148)..(3150)
<223> OTHER INFORMATION: n is unknown
<220> FEATURE:
<221> NAME/KEY: misc_feature
<222> LOCATION: (3154)..(3154)
<223> OTHER INFORMATION: n is unknown

<400> SEQUENCE: 226

```
tcgcatctgc agcttctttt gcacctgatt acagacataa gcacttgtag cgtttatgga    60
agaaagtttt ggagtgcaga tctcatgaca atgatgtaaa tctatcttgc ctcagtttgt   120
tcttgtagtt tcctttggac ttgaatttga taccttagtg catcgctaag tgctatttct   180
ctgattcaca taagaaatgt gatacaaatg gttagttcaa tcaatgcaga aaagttcaat   240
caaataaaat gggcccactg cagtcaatta acaggcattc aataggattc acattcctgg   300
gcttctatat atggaagttt gcatacaatg ttttggaaat aaaatgaaat ataaattgct   360
tgcatttagt gtaagttaat actcgctccc ttctcgaata tttgtcgtcc gctagttcat   420
ttttgaacta aaacatgata aataaaaaaa cggaaggagt acatgttgt aacaggagag    480
cccatgaata cttgcttgta acaggtggag cgctaagtat gcttaggaga actttaggca   540
acttgtattc tttagcactt cgacgcagtt tgtatggtaa tatctactga tagacagaat   600
cctggttttg gattttaat ttttcctgct tttggttaca cctctacagt cccatactcg     660
cagtccaata gtacatggtc tgataataaa ccaattaaga aggactcatg tctcagtcat   720
tatgacttga gcataggagt tgagatcaag aaatatttga gttgcagctt aaggtccaga   780
gaggaaatcc ccatacactt gcttgtaacg gtatgaatgt atgatcattt ttttttcaag   840
gtaacatttt ctagcatctt cacctgtcta cttgactgaa tgcagtatat attagttgta   900
ataactactg gccttctgct gtgcacaaaa ggcgggtatt accacttgca gaaatttgtc   960
gggtaaaggt aattgccagt taccttgtgt tcttcccttg atcaggaaca cctggaggag  1020
gatgcgctgt ggttgaaccg aagccctgtg agcgaagtac tgatgacaga aagagcggaa  1080
gataagataa gaaaggaacc cttgcgcggc aaggcctggt gacatagagg tagtgcgagg  1140
ctcataccgc cgccgctggc aggttccagg cctgtgcttt tcttgccctg tatccccagt  1200
ctatacttct gcgcacatca gacgagcctc agtgtttcgg cacagtggtg caacagaaaa  1260
ggagagtgct ggtaggtaac gctgaggcgg tgaagaaaga gaggtcagac ggacctggag  1320
gtggcttttt aactggtaaa gagtgaggtc tttcatgccc atcaatctga gcaccgactt  1380
gggtgttgct cctgttcgca ggaagcacaa gaaatggtca gtactccaca gcgtaggcat  1440
gtcggtggtg tgttggagga ggcaagattc agatgattat tatatgagct cgaaaagcta  1500
gagaatggat gttcagactt gagagctctg atttgagagr aattgcactt gtcgttttcc  1560
caaggcgacg cggccttttt ccagaggttt ttttttttt nnnnnnnnnn nnnnnnnnnn    1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnnnnn nnnnnnnnnn  1740
```

```
nnnnnnnnnn nnnnnnnnnn nnnnnnnnnn nnnnnnnnnn nnnnnnnnnn nnnnnnnnnn    1800
nnnnnggaga ggtctcggct catcaagcaa tcgccttggt gtcggacggg gtcatcaaga    1860
caagrcgact agaggagcac tacatctaca cggggtgaac ggacgggagc agtggcggac    1920
ccaggaactg atgacagcct tggcgagaat acggtgtgat ccccacgcct gtgctcgtgc    1980
cacgtgctgc ttgcttccgt gcactgtgct cgtgccttgc ccattgcagc cggcgagcca    2040
gctcaggcca ccgcctgcgg tgcctggtga gtccgcccct ggacgggagg aaggaaggaa    2100
aacgagagcg aggactcact gtccggtccg cccagcttgg tgacggcgtc gacgaagcgc    2160
tggtggaggt ccggcgtcca gcgcagccgc ggcttgggt cccgtgacgc cgccccgtcg     2220
tagccgtagc tcccctgcat cgccgttcct tcctggcgat cgccgctccc tagctatccg    2280
gtggccaaag acacggctag tggtaggctc gagcgagacg agctcttgct gaagagagaa    2340
tgaatgtagc gttaccgcct cctggtcgta ggggtgtggg tatgtgagga caagaggagg    2400
agcgagagga ggagcgcaga gcgtggcggg gaaggagggc gtcatgtgtg cgaggaatct    2460
aggacgactt gttggcagct gggccggggt gcgtgcgaga tgcaatgcaa gaacaaagcg    2520
gacgggcatc tcgctcggcc acgcttccaa gtccatccgg ggggcgccac tcggccgccg    2580
ctcattgagg cccaggcgcc aagacggcgg ctccacccac gtcacaattg caacaagaa    2640
gcacacggct gggctggga cgcgtcgaat ttttcaccag aaaataccgt ctgatcctgg     2700
cgtttcgtga acggcaaaac ctagcagcag cagcagcatt ccacgggtcg gatgacatat    2760
catatcctcg tgcggagcgg actcaacggc gagtccagct gtggctgcgg aatattccgg    2820
cggaagcgcg gggagagcga cggcggcctc cggtgggacc cggggcgagc gggagatgcg    2880
gcgaagatgt tcggcgctga tgtcgctgga atattcgcgc cagctgtggc tgccggtgcg    2940
acctgctgac cagacgacca gtggcaatgg ccaccgcctc tccatccaac ctccatcaca    3000
gattggcgga cgattagccg agactaatcg ctattctcaa cactttaaaa accgtgcgtg    3060
cagaatgcta agcctgctag attcgagcat ctgcgtgact ctactttggc tcttctcgta    3120
cgatgcgacc tgacgatgca tttgggcnnn cctntagcgt cactttcctg attagtcccc    3180
cggaaacgca actctaccac tatcagccgc cg                                  3212
```

<210> SEQ ID NO 227
<211> LENGTH: 3315
<212> TYPE: DNA
<213> ORGANISM: Zea mays
<220> FEATURE:
<221> NAME/KEY: misc_feature
<222> LOCATION: (1601)..(1748)
<223> OTHER INFORMATION: n is unknown

<400> SEQUENCE: 227

```
tcgcatctgc agcttctttt gcacctgatt acagacataa gcacttgtag cgtttatgga     60
agaaagtttt ggagtgcaga tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaat    240
caaataaaat gggcccactg cagtcaatta acaggcattc ataggattc acattcctgg     300
gcttctatat atggaagttt gcatacaatg ttttggaaat aaaatgaaat ataaattgct    360
tgcatttagt gtaagttaat actcgctccc ttctcgaata tttgtcgtcc gctagttcat    420
ttttgaacta aaacatgata aataaaaaaa cggaaggagt acatgtttgt aacaggagag    480
```

```
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gattttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt ttttttcaag    840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatcccagt    1200 ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagg aattgcactt gtcgttttcc   1560
caaggcgacg cggcctttc cagaggtttt ttttttttt nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnntg aaaaaaaaat gcacaccgac atgctctgta gcacaagcac cataccggcg   1800
aactggagag gtctcggctc atcaagcaat cgccttggtg tcggacgggg tcatcaagac   1860
aaggcgacta gaggagcact acatctacac ggggtgaacg gacgggagca gtggcggacc   1920
caggaactga tgacagcctt ggcgagaata cggtgtgatc cccacgcctg tgctcgtgcc   1980
acgtgctgct tgcttccgtg cactgtgctc gcgccttgcc cattgcagcc ggcgagccag   2040
ctcaggccac cgcctgcggt gcctggtgag tccgccctg gacgggagga aggaaggaaa   2100
acgagagcga ggactcactg tccggtccgc ccagcttggt gacggcgtcg acgaagcgct   2160
ggtggaggtc cggcgtccag cgcagccgcg gcttggggtc ccgtgacgcc gccccgtcgt   2220
agccgtagct cccctgcatc gccgttcctt cctggcgatc gccgctccct agctatccgg   2280
tggccaaaga cacggctagt ggtaggctcg agcgagacga gctcttgctg aagagagaat   2340
gaatgtagcg ttaccgcctc ctggtcgtag gggtgtgggt atgtgaggac aagaggagga   2400
gcgagaggag gagcgcagag cgtggcgggg aaggagggcg tcatgtgtgt gaggaatcta   2460
ggacgacttg ttggcagctg gccggggtg cgtgcgagat gcaatgcaag aacaaagcgg   2520
acgggcatca cgcctccagg tccaacccgg gggcgccact cggccgccgc tcattgaggc   2580
ccaggcgcca agacgcggc tccacccacg tcacaattgg caataagaag cacacggctg   2640
gggctgggac gcgtcgaatt tttcaccaga aaataccgtc tgatcctggc gtttcgtcag   2700
atgctatgct acgtgaacgg caaaacctag cagcagcagc agcactcaga ctggacaaga   2760
ggagggaaat ctttgcgtgg gaaccaaact gaacgcgaat cgcacgagtc ggatgacata   2820
tcctcgtccg gagcggactc gaccgcgagt ccagctgtgg ctgcggaata ttccggcgga   2880
```

```
agcgcgggga gaacgacggc ggcctccggt gggacccggg gcgagcggga gatgcggcga    2940
agatgttcgg cgctgatgtc gctggaatat tcgcgccagc tgtggctgcc ggtgtgacct    3000
gctgaccaga cgaccagtgg cagtggccac cgcctctcca tcacagattc gcggacgatt    3060
agccgagact aatcgctatt ctcaacactt ttaaaaccgt gcgtgcagaa tgctaagggc    3120
gcgttcgttt gcacagcaat agacatggat ttatttcagc tcatcaaaat ttatataaat    3180
taaagaagta atccggctag aaattaatcc ggagcttcaa tccctaacaa ccgaacaggg    3240
tctaagcctg ctagattcga gcatctgcgt gactctactt tggctcttct cgtacgatgc    3300
gacttgacga tgcat                                                    3315
```

<210> SEQ ID NO 228
<211> LENGTH: 3271
<212> TYPE: DNA
<213> ORGANISM: Zea mays
<220> FEATURE:
<221> NAME/KEY: misc_feature
<222> LOCATION: (1605)..(1751)
<223> OTHER INFORMATION: n is unknown

<400> SEQUENCE: 228

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag     840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtggcgag    1140
gctcataccg ccgccgctgg caggttccag gcctgtgctt ttcttgccct gtatccccag    1200
tctatacttc tgcgcacatc agacgagcct cagtgtttcg gcacagtggt gcaacagaaa    1260
aggagagtgc tggtaggtaa cgctgagcg gtgaagaaag agaggtcaga cggacctgga    1320
ggtggctttt taactggtaa agagtgaggt cttcatgcc catcaatctg agcaccgact    1380
tgggtgttgc tcctgttcgc aggaagcaca agaaatggtc agtactccac agcgtaggca    1440
tgtcggtggt gtgttggagg aggcaagatt cagatgatta ttatatgagc tcgaaaagct    1500
```

```
agagaatgga tgttcagact tgagagctct gatttgagag gaattgcact tgtcgttttc    1560
ccaaggcgac gcggccttt ccagaggttt tttttttttt ttttnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn naaaaaaaaa tgcacaccga catgctctgt agcacaagca ccataccggc    1800
gaactggaga ggtctcggct catcaagcaa tcgccttggt gtcggacggg gtcatcaaga    1860
caaggcgact agaggagcac tacatctaca cggggtgaac ggacgggagc agtggcggac    1920
ccaggaactg atgacagcct tggcgagaat acggtgtgat ccccacgcct gtgctcgtgc    1980
cacgtgctgc ttgcttccgt gcactgtgct cgcgccttgc ccattgcagc cggcgagcca    2040
gctcaggcca ccgcctgcgg tgcctggtga gtccgcccct ggacgggagg aaggaaggaa    2100
aacgagagcg aggactcact gtccggtccg cccagcttgg tgacggcgtc gacgaagcgc    2160
tggtggaggt ccggcgtcca gcgcagccgc ggcttggggt cccgtgacgc cgccccgtcg    2220
tagccgtagc tcccctgcat cgccgttcct tcctggcgat cgccgctccc tagctatccg    2280
gtggccaaag acacggctag tggtaggctc gagcgagacg agctcttgct gaagagagaa    2340
tgaatgtagc gttaccgcct cctggtcgta ggggtgtggg tatgtgagga caagaggagg    2400
agcgagagga ggagcgcaga gcgtggcggg gaaggagggc gtcatgtgtg tgaggaatct    2460
aggacgactt gttggcagct gggccggggt gcgtgcgaga tgcaatgcaa gaacaaagcg    2520
gacgggcatc acgcctccag gtccaacccg ggggcgccac tcggccgccg ctcattgagg    2580
cccaggcgcc aagacggcgg ctccacccac gtcacaattg gcaataagaa gcacacggct    2640
ggggctggga cgcgtcgaat ttttcaccag aaaataccgt ctgatcctgg cgtttcgtca    2700
gatgctatgc tacgtgaacg gcaaaaccta gcagcagcag cactcagact ggacaagagg    2760
agggaaatct ttgcgtggga accaaactga acgcgaatcg cacgggtcgg atgacatatc    2820
atatcctcgt gcggagcgga ctcaacgcg agtccagctg tggctgcgga atattccggc    2880
ggaagcgcgg ggagagcgac ggcggcctcc ggtgggaccc ggggcgagcg ggagatgcgg    2940
cgaagatgtt cggcgctgat gtcgctggaa tattcgcgcc agctgtggct gccggtgcga    3000
cctgctgacc agacgaccag tggcaatggc caccgcctct ccatccaacc tccatcacag    3060
attggcggac gattagccga gactaatcgc tattctcaac actttaaaaa ccgtgcgtgc    3120
agaatgctaa gcctgctaga ttcgagcatc tgcgtgactc tactttggct cttctcgtac    3180
gatgcgacct gacgatgcat ttgggcgttc ctgtagcgtc actttcctga ttagtccccc    3240
ggaaacgcaa ctctaccact atcagccgcc g                                  3271
```

<210> SEQ ID NO 229
<211> LENGTH: 3251
<212> TYPE: DNA
<213> ORGANISM: Zea mays
<220> FEATURE:
<221> NAME/KEY: misc_feature
<222> LOCATION: (1599)..(1745)
<223> OTHER INFORMATION: n is unknown
<220> FEATURE:
<221> NAME/KEY: misc_feature
<222> LOCATION: (3182)..(3182)
<223> OTHER INFORMATION: n is unknown
<220> FEATURE:
<221> NAME/KEY: misc_feature
<222> LOCATION: (3186)..(3186)
<223> OTHER INFORMATION: n is unknown
<220> FEATURE:
<221> NAME/KEY: misc_feature

```
<222> LOCATION: (3188)..(3189)
<223> OTHER INFORMATION: n is unknown
<220> FEATURE:
<221> NAME/KEY: misc_feature
<222> LOCATION: (3192)..(3193)
<223> OTHER INFORMATION: n is unknown

<400> SEQUENCE: 229
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttaat ttttcctgct tttggttaca cctctacagt cccatactcg       660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt tttttttcaag    840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatcccagt     1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca gcgtaggcat    1440
gtcggtggtg tgttggagga ggcaagattc agatgattat tatatgagct cgaaaagcta    1500
gagaatggat gttcagactt gagagctctg atttgatatg aattgcactt gtcgttttcc    1560
caaggcgaca cggccttttt ccagagtttt tttttttnn nnnnnnnnn nnnnnnnnnn       1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnaaaaa aaaaaaagaa tgcacaccga catgctctgt agcacaagca ccatactggc    1800
gaactggaga ggtctcggct catcaagcaa tcgccttggt gtcggacggg gtcatcaaga    1860
caagacgact agacgagcac tacatataga cgggaacgta cggaggaag gaaggaaaac       1920
gagagcgagg actcactgtc cggtccgccc agcttggtga cggcgtcgac gaagcgctgg    1980
tggaggtccg gcgtccagcg cagccgcggc ttgggtccc gtgacgccgc ccgtcgtag       2040
ccgtagctcc cctgcatcgt cgttccttcc tggcgatcgc cgcttcctag ctatccggtg    2100
```

```
gccaaagaca cggctagtgg taggctcgag tgagacgagc tcttgctgaa gagagaatga    2160
atgtaacgtt accgcctcct ggtcgtaggt gtaataagtt gtaacgcgag cgtcgttagc    2220
aagcacaggg gtttgtgtat gtgaggacaa gaggaggagc gagaggagga gcgcagagcg    2280
tggcggggaa ggagggcgtc atgtgtgcga ggaatctagg acgacttgtt ggcacttggc    2340
agctgggccg gggtgcgtgc gagatgcaat gcaagaacaa agcggacggg catcacgcct    2400
ccaggtccaa cccgggggcg ccactcggcc gccgctcatt gaggcccagg cgccaagacg    2460
gcggctccac ccacatcaca attggcaaca agaagcacac ggctggggtt gggacgcgtc    2520 gaattttttca ccagaaaata ccgtctgatc ctggcgtttc gtcagatgct atgctacgtg    2580
aacggcaaaa cctagcagca gcagcagcac tcagactgga caagaggagg gaaatctttg    2640
cgtgggaacc aaactgaacg cgaatcgcac gagtcggatg acatatcctc gtccggagcg    2700
gactcgaccg cgagtccagc tgtggctgcg gaatattccg gcggaagcgc ggggagaacg    2760
acggcggcct ccggtgggac ccggggcgag cgggagatgc ggcgaagatg ttcggcgctg    2820
atgtcgctgg aatattcgcg ccagctgtgg ctgccggtgt gacctgctga ccagacgacc    2880
agtggcagtg gccaccgcct ctccatcaca gattcgcgga cgattagccg agactaatcg    2940
ctattctcaa cacttttaaa accgtgcgtg cagaatgcta agggcgcgtt cgtttgcaca    3000
gcaatagaca tggatttatt tcagctcatc aaaatctata taaattaaag aagtaatccg    3060
gctagaaatt aatccggagc ttcaatccct aacaaccgaa cagggtctaa gcctgctaga    3120
ttcgagcatc tgcgtgactc tactttggct cttctcgtac gatgcgactt gacgatgcat    3180
tngggncnnc cnntagcgac actctcctga ttagtcccac ggaaacgcaa ctctaccact    3240
atcagccgcc g                                                          3251

<210> SEQ ID NO 230
<211> LENGTH: 3102
<212> TYPE: DNA
<213> ORGANISM: Zea mays
<220> FEATURE:
<221> NAME/KEY: misc_feature
<222> LOCATION: (1599)..(1743)
<223> OTHER INFORMATION: n is unknown

<400> SEQUENCE: 230
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tccttttggac ttgaatttga taccttagtg catcgctaag tgctatttct    180
ctgattcaca taagaaatgt gatacaaatg gttagttcaa tcaatgcaga aaagttcaat     240
caaataaaat gggcccactg cagtcaatta acaggcattc ataggattc acattcctgg     300 gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag     840
```

```
gtaacatttt ctagcatctt cacctgtcta cttgactgaa tgcagtatat attagttgta   900
ataactactg gccttctgct gtgcacaaaa ggcgggtatt accacttgca gaaatttgtc   960
gggtaaaggt aattgccagt taccttgtgt tcttcccttg atcaggaaca cctggaggag  1020
gatgcgctgt ggttgaaccg aagccctgtg agcgaagtac tgatgacaga aagagcggaa  1080
gataagataa gaaaggaacc cttgcgcggc aaggcctggt gacatagagg tagtgcgagg  1140
ctcataccgc cgccgctggc aggttccagg cctgtgcttt tcttgccctg tatccccagt  1200
ctatacttct gcgcacatca gacgagcctc agtgtttcgg cacagtggtg caacagaaaa  1260
ggagagtgct ggtaggtaac gctgaggcgg tgaagaaaga gaggtcagac ggacctggag  1320
gtggcttttt aactggtaaa gagtgaggtc tttcatgccc atcaatctga gcaccgactt  1380
gggtgttgct cctgttcgca ggaagcacaa gaaatggtca gtactccaca gcgtaggcat  1440
gtcggtggtg tgttggagga ggcaagattc agatgattat tatatgagct cgaaaagcta  1500
gagaatggat gttcagactt gagagctctg atttgagagg aattgcactt gtcgttttcc  1560
caaggcgacg cggccttttt ccagaggctt ttttttttnn nnnnnnnnn nnnnnnnnnn   1620
nnnnnnnnnn nnnnnnnnnn nnnnnnnnnn nnnnnnnnnn nnnnnnnnnn nnnnnnnnnn  1680
nnnnnnnnnn nnnnnnnnnn nnnnnnnnnn nnnnnnnnnn nnnnnnnnnn nnnnnnnnnn  1740
nnnaaaaaaa aaaaaaagaa tgcagaccga catgctctgt agcacaagca ccatactggc  1800
gaactggaga ggtctcggct catcaagcaa tcgccttggt gtcggacggg gtcatcaaga  1860
caagacgact agacgagcac tacatataga cgggaacgta cgggaggaag gaaggaaaac  1920
gagagcgagg actcactgtc cggtccgccc agcttggtga cggcgtcgac gaagcgctgg  1980
tggaggtccg gcgtccagcg cagccgcggc ttgggtccc gtgacgccgc ccgtcgtag   2040
ccgtagctcc cctgcatcgt cgttccttcc tggcgatcgc cgcttcctag ctatccggtg  2100
gccaaagaca cggctagtgg taggctcgag tgagacgagc tcttgctgaa gagagaatga  2160
atgtaacgtt accgcctcct ggtcgtaggt gtaataagtt gtaacgcgag cgtcgttagc  2220
aagcacaggg gtttgtgtat gtgaggacaa gaggaggagc gagaggagga gcgcagagcg  2280
tggcggggaa ggagggcgtc atgtgtgcga ggaatctagg acgacttgtt ggcacttggc  2340
agctgggccg gggtgcgtgc gagatgcaat gcaagaacaa agcggacggg catcacgcct  2400
ccaggtccaa cccgggggcg ccactcggcc gccgctcatt gaggcccagg cgccaagacg  2460
gcggctccac ccacatcaca attggcaaca agaagcacac ggctggggtt gggacgcgtc  2520
gaattttca ccagaaaata ccgtcggcgt ttcgtcagat gctatgctac gtgaacggca  2580
aaacctagca gcagcagcac tcagactgga cgagaggagg gaaatctttg cgtgggaacc  2640
aaactgaacg cgaatcgcac gagtcggatg acatatcctc gtccggagcg gactcgaccg  2700
cgagtccagc tgtggctgcg gaatattccg gcggaagcgc ggggagaacg acggcggcct  2760
ccggtgggaa ccggggcgag cgggagatgc ggcgaagatg ttcggcgctg atgtcgctgg  2820
aatattcgcg ccagctgtgg ctgccggtgt gacctgctga ccagtggcag tggccaccgc  2880
ctctccatca cagattggcg gacgattagc cgagactaat cgctattctc aacactttta  2940
aaaccgtgcg tgcagaatga taaccctgct agattcgagc atctgcgtga ctctactctg  3000
gctcttctcg tacgatgcga cttgacgatg catttgcgcg cctttagcgt cactttcctg  3060
attagtccca cggaaacgca actctaccac tatcagccgc ca                     3102
```

<210> SEQ ID NO 231

<211> LENGTH: 3251
<212> TYPE: DNA
<213> ORGANISM: Zea mays
<220> FEATURE:
<221> NAME/KEY: misc_feature
<222> LOCATION: (1598)..(1740)
<223> OTHER INFORMATION: n is unknown
<220> FEATURE:
<221> NAME/KEY: misc_feature
<222> LOCATION: (3186)..(3192)
<223> OTHER INFORMATION: n is unknown

<400> SEQUENCE: 231

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt tttttttcaag    840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga agagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatccccagt    1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca gcgtaggcat    1440
gtcggtggtg tgttggagga ggcaagattc agatgattat tatatgagct cgaaaagcta    1500
gagaatggat gttcagactt gagagctctg atttgagagg aattgcactt gtcgttttcc    1560
caaggcgacg cggcctttt ccagagtttt ttttttnnn nnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
aaaaaaaaaa aaaaaagaa tgcacaccga catgctctgt agcacaagca ccatactggc    1800
gaactggaga ggtctcggct catcaagcaa tcgccttggt gtcggacggg gtcatcaaga    1860
caagacgact agacgagcac tacatataga cgggaacgta cgggaggaag gaaggaaaac    1920
gagagcgagg actcactgtc cggtccgccc agcttggtga cggcgtcgac gaagcgctgg    1980
```

-continued

```
tggaggtccg gcgtccagcg cagccgcggc ttggggtccc gtgacgccgc cccgtcgtag    2040
ccgtagctcc cctgcatcgt cgttccttcc tggcgatcgc cgcttcctag ctatccggtg    2100
gccaaagaca cggctagtgg taggctcgag tgagacgagc tcttgctgaa gagagaatga    2160
atgtaacgtt accgcctcct ggtcgtaggt gtaataagtt gtaacgcgag cgtcgttagc    2220
aagcacaggg gtttgtgtat gtgaggacaa gaggaggagc gagaggagga gcgcagagcg    2280
tggcggggaa ggagggcgtc atgtgtgcga ggaatctagg acgacttgtt ggcacttggc    2340
agctgggccg gggtgcgtgc gagatgcaat gcaagaacaa agcggacggg catcacgcct    2400
ccaggtccaa cccgggggcg ccactcggcc gccgctcatt gaggcccagg cgccaagacg    2460
gcggctccac ccacatcaca attggcaaca agaagcacac ggctggggtt gggacgcgtc    2520 gaattttca ccagaaaata ccgtctgatc ctggcgtttc gtcagatgct atgctacgtg    2580
aacggcaaaa cctagcagca gcagcagcac tcagactgga caagaggagg gaaatctttg    2640
cgtgggaacc aaactgaacg cgaatcgcac gagtcggatg acatatcctc gtccggagcg    2700
gactcgaccg cgagtccagc tgtggctgcg gaatattccg gcggaagcgc ggggagaacg    2760
acggcggcct ccggtgggac ccggggcgag cgggagatgc ggcgaagatg ttcggcgctg    2820
atgtcgctgg aatattcgcg ccagctgtgg ctgccggtgt gacctgctga ccagacgacc    2880
agtggcagtg gccaccgcct ctccatcaca gattcgcgga cgattagccg agactaatcg    2940
ctattctcaa cacttttaaa accgtgcgtg cagaatgcta agggcgcgtt cgtttgcaca    3000
gcaatagaca tggatttatt tcagctcatc aaaatctata taaattaaag aagtaatccg    3060
gctagaaatt aatccggagc ttcaatccct aacaaccgaa cagggtctaa gcctgctaga    3120
ttcgagcatc tgcgtgactc tactttggct cttctcgtac gatgcgactt gacgatgcat    3180
ttgggnnnnn nngtagcgac actctcctga ttagtcccac ggaaacgcaa ctctaccact    3240
atcagccgcc g                                                         3251
```

<210> SEQ ID NO 232
<211> LENGTH: 3034
<212> TYPE: DNA
<213> ORGANISM: Zea mays
<220> FEATURE:
<221> NAME/KEY: misc_feature
<222> LOCATION: (1599)..(1742)
<223> OTHER INFORMATION: n is unknown

<400> SEQUENCE: 232

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc ataggattc acattcctgg     300 gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga acttaggca     540 acttgtattc tttagcactt cgacgcagtt tgtatggtaa tatctactga tagacagaat     600
cctggttttg gatttttaat ttttcctgct tttggttaca cctctacagt cccatactcg     660
```

```
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt ttttttcaag    840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatccccagt   1200
ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagg aattgcactt gtcgttttcc   1560
caaggcgacg cggccttttt ccagaggctt ttttttttnn nnnnnnnnn nnnnnnnnn    1620 nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnaaaaaaaa aaaaaaagaa tgcagaccga catgctctgt agcacaagca ccatactggc   1800
gaactggaga ggtctcggct catcaagcaa tcgccttggt gtcggacggg gtcatcaaga   1860
caagacgact agacgagcac tacatataga cgggaacgta cgggaggaag gaaggaaaac   1920
gagagcgagg actcactgtc cggtccgccc agcttggtga cggcgtcgac gaagcgctgg   1980
tggaggtccg cgcgtccagcg cagccgcggc ttggggtccc gtgacgccgc ccgtcgtag   2040 ccgtagctcc cctgcatcgt cgttccttcc tggcgatcgc cgcttcctag ctatccggtg   2100
gccaaagaca cggctagtgg taggctcgag tgagacgagc tcttgctgaa gagagaatga   2160
atgtaacgtt accgcctcct ggtcgtaggt gtaataagtt gtaacgcgag cgtcgttagc   2220
aagcacaggg gtttgtgtat gtgaggacaa gaggaggagc gagaggagga gcgcagagcg   2280
tggcggggaa ggagggcgtc atgtgtgcga ggaatctagg acgacttgtt ggcacttggc   2340
agctgggccg gggtgcgtgc gagatgcaat gcaagaacaa agcggacggg catcacgcct   2400
ccaggtccaa cccgggggcg ccactcggcc gccgctcatt gaggcccagg cgccaagacg   2460
gcggctccac ccacatcaca attggcaaca agaagcacac ggctgggggtt gggacgcgtc   2520 gaatttttca ccagaaaata ccgtcggcgt ttcgtcagat gctatgctac gtgaacggca   2580
aaacctagca gcagcagcac tcagactgga cgagaggagg gaaatctttg cgtgggaacc   2640
aaactgaacg cgaatcgcac gagtcggatg acatatcctc gtccggagcg gactcgaccg   2700
cgagtccagc tgtggctgcg gaatattccg gcggaagcgc ggggagaacg acggcggcct   2760
ccggtgggaa ccggggcgag cgggagatgc ggcgaagatg ttcggcgctg atgtcgctgg   2820
aatattcgcg ccagctgtgg ctgccggtgt gacctgctga ccagtggcag tggccaccgc   2880
ctctccatca cagattggcg gacgattagc cgagactaat cgctattctc aacactttta   2940
aaaccgtgcg tgcagaatga taaccctgct agattcgagc atctgcgtga ctctactctg   3000
gctcttctcg tacgatgcga cttgacgatg catt                              3034
```

<210> SEQ ID NO 233
<211> LENGTH: 3139
<212> TYPE: DNA
<213> ORGANISM: Zea mays
<220> FEATURE:
<221> NAME/KEY: misc_feature
<222> LOCATION: (1722)..(1744)
<223> OTHER INFORMATION: n is unknown

<400> SEQUENCE: 233

```
tcgcatctgc agcttctttt gcacctgatt acagacataa gcacttgtag cgtttatgga        60
agaaagtttt ggagtgcaga tctcatgaca atgatgtaaa tctatcttgc ctcagtttgt       120
tcttgtagtt tcctttggac ttgaatttga taccttagtg catcgctaag tgctatttct       180
ctgattcaca taagaaatgt gatacaaatg gttagttcaa tcaatgcaga aaagttcaat       240
caaataaaat gggcccactg cagtcaatta acaggcattc aataggattc acattcctgg       300
gcttctatat atggaagttt gcatacaatg ttttggaaat aaaatgaaat ataaattgct       360
tgcatttagt gtaagttaat actcgctccc ttctcgaata tttgtcgtcc gctagttcat       420
ttttgaacta aacatgata  aataaaaaaa cggaaggagt acatgtttgt aacaggagag       480
cccatgaata cttgcttgta acaggtggag cgctaagtat gcttaggaga actttaggca       540
acttgtattc tttagcactt cgacgcagtt tgtatggtaa tatctactga tagacagaat       600
cctggttttg gattttaat  ttttcctgct tttggttaca cctctacagt cccatactcg       660
cagtccaata gtacatggtc tgataataaa ccaattaaga aggactcatg tctcagtcat       720
tatgacttga gcataggagt tgagatcaag aaatatttga gttgcagctt aaggtccaga       780
gaggaaatcc ccatacactt gcttgtaacg gtatgaatgt atgatcattt tttttttcaag      840
gtaacatttt ctagcatctt cacctgtcta cttgactgaa tgcagtatat attagttgta       900
ataactactg gccttctgct gtgcacaaaa ggcgggtatt accacttgca gaaatttgtc       960
gggtaaaggt aattgccagt taccttgtgt tcttcccttg atcaggaaca cctggaggag      1020
gatgcgctgt ggttgaaccg aagccctgtg agcgaagtac tgatgacaga aagagcggaa      1080
gataagataa gaaaggaacc cttgcgcggc aaggcctggt gacatagagg tagtgcgagg      1140
ctcataccgc cgccgctggc aggttcsagg cctgtgcttt tcttgccctg tatcccagt       1200
ctatacttct gcgcacatca gacgagcgtc agtgtttcgg cacagtggtg caacagaaaa      1260
ggagagtgct ggtaggtaac gctgaggcgg tgaagaaaga gaggtcagac ggacctggag      1320
gtggctttt  aactggtaaa gagtgaggtc tttcatgccc atcaatctga gcaccgactt      1380
gggtgttgct tctgttcgca ggaagcacaa gaaatggtca gtactccaca gcgtaggcat      1440
gtcggtgtgt tcgaggaggc aagattcaga tgattattat atgagctcga aaagctagag      1500
aatggatgtt cagacttgag atctctgatt tgagaggaat tgcacttgtc gttttcccag      1560
ggcgacgcgg cctttttcca gaggcatttt ttttcaactg ccttttggtc atgtcaacgg      1620
aactgccttt tcctctgact gcatgctata gacttggcaa tggcagaagc gcaaagccag      1680
gcagcgaagg attcggactg caactggccg tcgttttaca annnnnnnnn nnnnnnnnnn      1740
nnnnaaaaaa aaaagaatgc agaccgacat gctctgtagc acaagcacca tacttgcgaa      1800
ctgcagaggt gtcgggtcat caagcaatcg ccttggtgtc ggacggggtg gggtcatcaa      1860
gacaagacga ctagaggagc actacatcta cacgggggg  aacggacggg aggaaggaag      1920
gaaaacgaga gcgaggactc actgtccggt ccgcccagct tggtgacggc gtcgacgaag      1980
```

| | |
|---|---|
| cgctggtgga ggaccggcgt ccagcgcagc cgcggcttgg ggtcccgtga cgccgccccg | 2040 |
| tcgtagccgt agctcccctg catcgtcgtt ccttcctggc gatcgccgct ccctagctat | 2100 |
| ccggtggcca agacacggc tagtgctgaa gagagaatga atgtaacgtt accgcctcct | 2160 |
| ggtcgtaggt gtaataagtt gtaacgcgag tgtcgttaga agcacagggg tgtgtgtatg | 2220 |
| tgaggacaag aggaggagcg agaggaggag cgcagagcgt ggcggggaag gagggcgtca | 2280 |
| tgtgtgtgag gaatctagga cgacttgttg gcagctgggc cggggtgcgt gcagatgca | 2340 |
| atgcaagaac aaagcatcac gcctccaagt ccaaccgggg ggcgccactc ggccgccgct | 2400 |
| cattgaggcc caggcgccaa gacggcggct ccacccacat cacaattggc aacaagaagc | 2460 |
| acacggctgg ggctgggacg cgtcgaattt ttcaccagaa aataccgtcg gcgtttcgtc | 2520 |
| agatgctatg ctacgtgaac ggcaaaacct agcagcagca gcagcagcac tcagactgga | 2580 |
| caagaggagg gaaatctttg cgtgggaacc aaactgaacg cgaatcgcac gagtcggatg | 2640 |
| acatatcctc gtccggagcg gactcggccg cgagtccagc tgtggctgcg gaatattccg | 2700 |
| gcggaagcgc ggggagaacg acggcggcct ccggtggac ccggggcgag cgggagatgc | 2760 |
| ggcgaagatg ttcggcgctg atgtcgctgg aatattcgcg ccagctgtgg ctgccggtgt | 2820 |
| gacctgctga ccagacgacc agtggcagtg gccaccgcct ctccatcaca gattcgcgga | 2880 |
| cgattagccg agactaatcg ctattctcaa cacttttaaa accgtgcgtg cagaatgcta | 2940 |
| agggcgcgtt cgtttgcaca gcaatagaca ttgatttatt tcagctcatc aaaatctata | 3000 |
| taaattaaag aagtaatccg gctagaaatt aatccggagc ttcaatccct aacaaccgaa | 3060 |
| cagggtctaa gcctgctaga ttcgagcatc tgcgtgactc tactttggct cttctcgtac | 3120 |
| gatgcgactt gacgatgca | 3139 |

<210> SEQ ID NO 234
<211> LENGTH: 3052
<212> TYPE: DNA
<213> ORGANISM: Zea mays
<220> FEATURE:
<221> NAME/KEY: misc_feature
<222> LOCATION: (1563)..(1708)
<223> OTHER INFORMATION: n is unknown
<220> FEATURE:
<221> NAME/KEY: misc_feature
<222> LOCATION: (2987)..(2990)
<223> OTHER INFORMATION: n is unknown
<220> FEATURE:
<221> NAME/KEY: misc_feature
<222> LOCATION: (2994)..(2994)
<223> OTHER INFORMATION: n is unknown

<400> SEQUENCE: 234

| | |
|---|---|
| tcgcatctgc agcttctttt gcacctgatt acagacataa gcacttgtag cgtttatgga | 60 |
| agaaagtttt ggagtgcaga tctcatgaca atgatgtaaa tctatcttgc ctcagtttgt | 120 |
| tcttgtagtt tcctttggac ttgaatttga taccttaatg catcgctaag tgctatttct | 180 |
| ctgattcaca taagaaatgc gatacaaatg gttagttcaa tcaatgcaga aaagttcaac | 240 |
| caaataaaat gggcccactg cagtcaatta acaggcattc aataggattc acattcctgg | 300 |
| gcttctatat atggaagttt gcatacaaag ttttggaaat aaaatggaat agaaattgct | 360 |
| tgcatttagt gtaagttaat acccgctagt tcattttta actaaaacac gacaaataaa | 420 |
| aaaatggagg agtacatctt tgtaacaggt gagcctgaat acttgtttgt agcaggtggg | 480 |
| gcgctaagta tgcttaggag aagtttaggc aacttgtatt ctgtagcatt tcgacgccgt | 540 |
| ttgtatggta atatctactg ataggcagaa tcctggttgg attttttttc ctgcttttgt | 600 |

```
ttacacctat acagtcccat actcgcagtc gaataataca tggtctgatg ataaaccaat    660
taagaaggac tcatgtctca gtcattatga cttgagcata ggagttgaga tcaagaaata    720
tttgagttgc agcttaaggt ccagagagga aatccccata cacttgcttg taacggtatg    780
aatgtatgat cattttttt tcaaggtaac attttctagc atcttcacct gtctacttga     840
ctgaatgcag tatatattag ttgtaataac tactggcctt ctgctgtgca caaaaggcgg    900
gtattaccac ttgcagaaat ttgtcgggta aggtaattg ccagttacct tgtgttcttc    960
ccttgatcag gaacacctgg aggaggatgc gctgtggttg aaccgaagcc ctgtgagcga    1020
agtactgatg acagaaagag cggaagataa gataagaaag gaacccttgc gcggcaaggc    1080
ctggtgacat agaggtagtg cgaggctcat accgccgccg ctggcaggtt ccaggcctgt    1140
gcttttcttg ccctgtatcc ccagtctata cttctgcgca catcagacga gcctcagtgt    1200
ttcggcacag tggtgcaaca gaaaaggaga gtgctggtag gtaacgctga ggcggtgaag    1260
aaagagaggt cagacggacc tggaggtggc ttttaactg gtaaagagtg aggtctttca     1320
tgcccatcaa tctgagcacc gacttgggtg ttgctcctgt tcgcaggaag cacaagaaat    1380
ggtcagtact ccacagcgta ggcatgtcgg tggtgtgttg gaggaggcaa gattcagatg    1440
attattatat gagctcgaaa agctagagaa tggatgttca gacttgagag ctctgatttg    1500
agaggaattg cacttgtcgt tttcccaagg cgacgcggcc ttttttccaga gtttttttt    1560 ttnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnaa aaaaaaaaa agaatgcaga ccgacatgct     1740
ctgtagcaca agcaccatac tggcgaactg gagaggtctc ggctcatcaa gcaatcgcct    1800
tggtgtcgga cggggtcatc aagacaagac gactagacga gcactacata tagacgggaa    1860
cgtacgggag gaaggaagga aaacgagagc gaggactcac tgtccggtcc gcccagcttg    1920
gtgacggcgt cgacgaagcg ctggtggagg tccggcgtcc agcgcagccg cggcttgggg    1980
tcccgtgacg ccgccccgtc gtagccgtag ctcccctgca tcgccgttcc ttcctggcga    2040
tcgccgctcc ctagctatcc ggtggccaaa gacacggcta gtggtaggct cgagcgagac    2100
gagctcttgg tgaagagaga atgaatgtaa cgttaccgcc tcctggtcgt aggggtgtgt    2160
gtatgtgagg acaagaggag gagcgagagg aggagcgcag agcgtggcgg ggaaggaggg    2220
cgtcatgtgt gtgaggaatc taggacgact tgttggcagc tgggccgggg tgcgtgcgag    2280
atgcaatgca agaacaaagc ggacgggcat cacgcctcca ggtccaaccc ggggcgcca    2340 ctcggccgcc gctcattgag gcccaggcgc caagacggcg gctccaccca cgtcacaatt    2400
ggcaataaga agcacggc tggggctggg acgcgtcgaa ttttcacca gaaaataccg       2460 tctgatcctg gcgtttcgtc agatgctatg ctacgtgaac ggcaaaacct agcagcagca    2520
gcactcagac tggacaagag gagggaaatc tttgcgtggg aaccaaactg aacgcgaatc    2580
gcacgggtcg gatgacatat catatcctcg tgcggagcgg actcaacggc gagtccagct    2640
gtggctgcgg aatattccgg cggaagcgcg gggagagcga cggcggcctc cggtgggacc    2700
cggggcgagc gggagatgcg gcgaagatgt tcggcgctga tgtcgctgga atattcgcgc    2760
cagctgtggc tgccggtgcg acctgctgac cagacgacca gtggcaatgg ccaccgcctc    2820
tccatccaac ctccatcaca gattggcgga cgattagccg agactaatcg ctattctcaa    2880
cactttaaaa accgtgcgtg cagaatgcta agcctgctag attcgagcat ctgcgtgact    2940
```

```
ctactttggc tcttctcgta cgatgcgacc tgacgatgca tttgggnnnn cctntagcgt      3000
cactttcctg attagtcccc cggaaacgca actctaccac tatcagccgc cg              3052
```

<210> SEQ ID NO 235
<211> LENGTH: 3219
<212> TYPE: DNA
<213> ORGANISM: Zea mays
<220> FEATURE:
<221> NAME/KEY: misc_feature
<222> LOCATION: (1554)..(1701)
<223> OTHER INFORMATION: n is unknown
<220> FEATURE:
<221> NAME/KEY: misc_feature
<222> LOCATION: (3155)..(3157)
<223> OTHER INFORMATION: n is unknown
<220> FEATURE:
<221> NAME/KEY: misc_feature
<222> LOCATION: (3161)..(3161)
<223> OTHER INFORMATION: n is unknown

<400> SEQUENCE: 235

```
tcgcatctgc agcttctttt gcacctgatt acagacataa gcacttgtag cgtttatgga        60
agaaagtttt ggagtgcaga tctcatgaca atgatgtaaa tctatcttgc ctcagtttgt       120
tcttgtagtt tcctttggac ttgaatttga taccttagtg catcgctaag tgctatttct       180
ctgattcaca taagaaatgt gatacaaatg gttagctcaa tcaatgcaga aaagttcaac       240
caaataaaat gggcccactg cagtcaatta acaggcattc aataggattc acattcctgg       300
gcttctatat atggaagttt gcatacaaag ttttggaaat aaaatggaat agaaattgct       360
tgcatttagt gtaagttaat acccgctagt tcattttta actaaaacac gacaaataaa        420
aaaatggagg agtacatctt tgtaacaggt gagcctgaat acttgtttgt agcaggtggg       480
gcgctaagta tgcttaggag aagtttaggc aacttgtatt ctgtagcatt tcgacgccgt       540
ttgtatggta atatctactg ataggcagaa tcctggttgg atttttttc ctgcttttgt        600 ttacacctat acagtcccat actcgcagtc gaataataca tggtctgatg ataaaccaat       660
taagaaggac tcatgtctca gtcattatga cttgagcata ggagttcaga tcgagaaata       720
tttgagttgc agcttaaggt tcagagagga aatcccatac acttgcttgt aacgatatga       780
tcattttttt tcaaggtaac atttttctagc atcttcagct gtctacttga ctgaatgcag      840
tatatattag ttgtaataaa tactgccctt ctgctgtgca caaaaggcgg gtattaccac       900
ttgcagaaat ttgtcgggta aggtaattg ccagttacct tgtgttcttc ccttcatcag        960
gaacacctgg aggaggatgc gctgtggttg aactgaagcc ctgcgagaga agtactgatg      1020
acagaaagag cggaagataa gataagaaag gaaacccttg cgcggcaagg cctggtgaca      1080
tagaggtagt gcgaggctca taccgccgct ggcaggttcc aggcctgtgc ttttcttgcc      1140
ctgtatcccc agtctatact tctgcgcaca tcagacgagc ctcagtgttt cggcacagtg      1200
gtgcaacaga aaggagagt gctggtaggt aacgctgagg cggtgaagaa agagaggtca       1260
gacggacctg gaggtggctt tttaactggt aaagagtgag gtctttcatg cccatcaatc      1320
tgagcaccga cttgggtgtt gctcctgttc gcaggaagca caagaaatgg tcagtactcc      1380
acagcgtagg catgtcggtg gtgtgttgga ggaggcaaga ttcagatgat tattatatga      1440
gctcgaaaag ctagagaatg gatgttcaga cttgagagct ctgatttgag aggaattgca      1500
cttgtcgttt tcccaaggcg acgcggcctt ttccagaggt ttttttttt tttnnnnnn       1560 nnnnnnnnn nnnnnnnnn nnnnnnnnn nnnnnnnnn nnnnnnnnn nnnnnnnnn          1620 nnnnnnnnn nnnnnnnnn nnnnnnnnn nnnnnnnnn nnnnnnnnn nnnnnnnnn          1680
```

```
nnnnnnnnnn nnnnnnnnnn ntgaaaaaaa aatgcacacc gacatgctct gtagcacaag    1740
caccataccg gcgaactgga gaggtctcgg ctcatcaagc aatcgccctt ggtgtcggac    1800
ggggtcatca agacaaggcg actagaggag cactacatct acacggggtg aacggacggg    1860
agcagtggcg gacccaggaa ctgatgacag ccttggcgag aatacggtgt gatccccacg    1920
cctgtgctcg tgccacgtgc tgcttgcttc cgtgcactgt gctcgcgcct tgcccattgc    1980
agccggcgag ccagctcagg ccaccgcctg cggtgcctgg tgagtccgcc cctggacggg    2040
aggaaggaag gaaaacgaga gcgaggactc actgtccggt ccgcccagct tggtgacggc    2100
gtcgacgaag cgctggtgga ggtccggcgt ccagcgcagc cgcggcttgg ggtcccgtga    2160
cgccgccccg tcgtagccgt agctcccctg catcgccgtt ccttcctggc gatcgccgct    2220
ccctagctat ccggtggcca agacacggc tagtggtagg ctcgagcgag acgagctctt    2280
gctgaagaga gaatgaatgt agcgttaccg cctcctggtc gtaggggtgt gggtatgtga    2340
ggacaagagg aggagcgaga ggaggagcgc agagcgtggc ggggaaggag ggcgtcatgt    2400
gtgtgaggaa tctaggacga cttgttggca gctgggccgg ggtgcgtgcg agatgcaatg    2460
caagaacaaa gcggacgggc atcacgcctc caggtccaac ccgggggcgc cactcgatcg    2520
gccgccgctc attgaggccc aggcgccaag acggcggctc cacccacgtc acaattggca    2580
ataagaagca cacggctggg gctgggacgc gtcgaatttt tcaccagaaa ataccgtctg    2640
atcctggcgt ttcgtcagat gctatgctac gtgaacggca aaacctagca gcagcagcac    2700
tcagactgga caagaggagg gaaatctttg cgtgggaacc aaactgaacg cgaatcgcac    2760
gggtcggatg acatatcata tcctcgtgcg gagcggactc aacggcgagt ccagctgtgg    2820
ctgcggaata ttccggcgga agcgcgggga gagcgacggc ggcctccggt gggacccggg    2880
gcgagcggga gatgcggcga agatgttcgg cgctgatgtc gctggaatat tcgcgccagc    2940
tgtggctgcc ggtgcgacct gctgaccagt ggcaatggcc accgcctctc catccaacct    3000
ccatcacaga ttggcggacg attagccgag actaatcgct attctcaaca ctttaaaaac    3060
cgtgcgtgca gaatgctaag cctgctagat tcgagcatct gcgtgactct actttggctc    3120
ttctcgtacg atgcgacctg acgatgcatt tgggnnncct ntagcgtcac tttcctgatt    3180
agtcccccgg aaacgcaact ctaccactat cagccgccg                          3219
```

<210> SEQ ID NO 236  
<211> LENGTH: 3099  
<212> TYPE: DNA  
<213> ORGANISM: Zea mays  
<220> FEATURE:  
<221> NAME/KEY: misc_feature  
<222> LOCATION: (1555)..(1701)  
<223> OTHER INFORMATION: n is unknown

<400> SEQUENCE: 236

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttaatg catcgctaag tgctatttct     180
ctgattcaca taagaaatgc gatacaaatg gttagttcaa tcaatgcaga aaagttcaac     240
caaataaaat gggcccactg cagtcaatta acaggcattc aataggattc acattcctgg     300
gcttctatat atggaagttt gcatacaaag ttttggaaat aaaatggaat agaaattgct     360
tgcatttagt gtaagttaat acccgctagt tcatttttta actaaaacac gacaaataaa     420
```

```
aaaatggagg agtacatctt tgtaacaggt gagcctgaat acttgtttgt agcaggtggg    480
gcgctaagta tgcttaggag aagtttaggc aacttgtatt ctgtagcatt tcgacgccgt    540
ttgtatggta atatctactg ataggcagaa tcctggttgg attttttttc ctgcttttgt    600
ttacacctat acagtcccat actcgcagtc gaataataca tggtctgatg ataaaccaat    660
taagaaggac tcatgtctca gtcattatga cttgagcata ggagttcaga tcgagaaata    720
tttgagttgc agcttaaggt tcagagagga aatcccatac acttgcttgt aacgatatga    780
tcattttttt tcaaggtaac attttctagc atcttcagct gtctacttga ctgaatgcag    840
tatatattag ttgtaataaa tactgcccct ctgctgtgca caaaaggcgg gtattaccac    900
ttgcagaaat ttgtcgggta aggtaattg ccagttacct tgtgttcttc ccttcatcag    960
gaacacctgg aggaggatgc gctgtggttg aactgaagcc ctgcgagaga agtactgatg    1020
acagaaagag cggaagataa gataagaaag gaaacccttg cgcggcaagg cctggtgaca    1080
tagaggtagt gcgaggctca taccgccgct ggcaggttcc aggcctgtgc tttcttgcc    1140 ctgtatcccc agtctatact tctgcgcaca tcagacgagc tcagtgtttt cggcacagtg    1200
gtgcaacaga aaaaggagag tgctggactg ctggtaacgc tgaggcggtg aagaaagaga    1260
ggtcagacgg acctggaggt ggcttttaa ctggtaaaga gtgaggtctt tcatgcccat    1320
caatctgagc accgacttgg gtgttgcttc tgttcgcagg aagcacaaga aatggtcagt    1380
actccacagc gtaggcatgt cggtgtgttc gaggaggcaa gattcagatg attattatat    1440
gagctcgaaa agctagagaa tggatgttca gacttgagat ctctgatttg agaggaattg    1500
cacttgtcgt tttcccargg cgacgcggcc tttttccaga ggcattttt ttcannnnn    1560 nnnnnnnnn nnnnnnnnn nnnnnnnnn nnnnnnnnn nnnnnnnnn nnnnnnnnn    1620 nnnnnnnnn nnnnnnnnn nnnnnnnnn nnnnnnnnn nnnnnnnnn nnnnnnnnn    1680 nnnnnnnnn nnntnnnnn ngaaaaaaa aagaatgcag accgacatgc tctgtagcac    1740
aagcaccata cttgcgaact gcagaggtgt cgggtcatca agcaatcgcc ttggtgtcgg    1800
acggggtggg gtcatcaaga caagacgact agaggagcac tacatctaca cggggggaa    1860 cggacgggag gaaggaagga aaacgagagc gaggactcac tgtccggtcc gcccagcttg    1920
gtgacggcgt cgacgaagcg ctggtggagg accggcgtcc agcgcagccg cggcttgggg    1980
tcccgtgacg ccgccccgtc gtagccgtag ctcccctgca tcgtcgttcc ttcctggcga    2040
tcgccgctcc ctagctatcc ggtggccaaa gacacggcta gtgctgaaga gagaatgaat    2100
gtaacgttac cgcctcctgg tcgtaggtgt aataagttgt aacgcgagtg tcgttagaag    2160 cacagggtg tgtgtatgtg aggacaagag gaggagcgag aggaggagcg cagagcgtgg    2220
cggggaagga gggcgtcatg tgtgtgagga atctaggacg acttgttggc agctgggccg    2280
gggtgcgtgc gagatgcaat gcaagaacaa agcatcacgc ctccaagtcc aaccgggggg    2340
cgccactcgg ccgccgctca ttgaggccca ggcgccaaga cggcggctcc acccacatca    2400
caattggcaa caagaagcac acggctgggg ctggacgcg tcgaattttt caccagaaaa    2460
taccgtcggc gtttcgtcag atgctatgct acgtgaacgg caaaacctag cagcagcagc    2520
agcactcaga ctgacaaga ggagggaaat ctttgcgtgg gaaccaaact gaacgcgaat    2580
cgcacgagtc ggatgacata tcctcgtccg gagcggactc ggccgcgagt ccagctgtgg    2640
ctgcggaata ttccggcgga agcgcgggga gaacgacggc ggcctccggt gggacccggg    2700
gcgagcggga gatgcggcga agatgttcgg cgctgatgtc gctggaatat tcgcgccagc    2760
tgtggctgcc ggtgtgacct gctgaccaga cgaccagtgg cagtggccac cgcctctcca    2820
```

```
tcacagattc gcggacgatt agccgagact aatcgctatt ctcaacactt ttaaaaccgt   2880
gcgtgcagaa tgctaagggc gcgttcgttt gcacagcaat agacatggat ttatttcagc   2940
tcatcaaaat ctatataaat taaagaagta atccggctag aaattaatcc ggagcttcaa   3000
tccctaacaa ccgaacaggg tctaagcctg ctagattcga gcatctgcgt gactctactt   3060
tggctcttct cgtacgatgc gacttgacga tgcatttgg                          3099
```